US008067551B2

(12) United States Patent
Gerngross et al.

(10) Patent No.: US 8,067,551 B2
(45) Date of Patent: Nov. 29, 2011

(54) COMBINATORIAL DNA LIBRARY FOR PRODUCING MODIFIED N-GLYCANS IN LOWER EUKARYOTES

(75) Inventors: Tillman U. Gerngross, Hanover, NH (US); Stefan Wildt, Lebanon, NH (US); Byung-Kwon Choi, Norwich, VT (US); Juergen Hermann Nett, Enfield, NH (US); Piotr Bobrowicz, Enfield, NH (US); Stephen R Hamilton, Enfield, NH (US); Robert C. Davidson, Enfield, NH (US)

(73) Assignee: Glycofi, Inc., Lebanon, NH (US)

( * ) Notice: Subject to any disclaimer, the term of this patent is extended or adjusted under 35 U.S.C. 154(b) by 0 days.

(21) Appl. No.: 12/291,373

(22) Filed: Nov. 7, 2008

(65) Prior Publication Data

US 2009/0155847 A1   Jun. 18, 2009

Related U.S. Application Data

(63) Continuation of application No. 10/371,877, filed on Feb. 20, 2003, now Pat. No. 7,449,308, which is a continuation-in-part of application No. 09/892,591, filed on Jun. 27, 2001, now Pat. No. 7,029,872.

(60) Provisional application No. 60/214,358, filed on Jun. 28, 2000, provisional application No. 60/215,638, filed on Jun. 30, 2000, provisional application No. 60/279,997, filed on Mar. 30, 2001.

(51) Int. Cl.
C07K 14/00 (2006.01)

(52) U.S. Cl. .................................. 530/395; 514/2

(58) Field of Classification Search .................. None
See application file for complete search history.

(56) References Cited

U.S. PATENT DOCUMENTS

| | | |
|---|---|---|
| 4,414,329 A | 11/1983 | Wegner |
| 4,617,274 A | 10/1986 | Wegner |
| 4,683,293 A | 7/1987 | Craig |
| 4,775,622 A | 10/1988 | Hitzeman et al. |
| 4,808,537 A | 2/1989 | Stroman et al. |
| 4,812,405 A | 3/1989 | Lair et al. |
| 4,818,700 A | 4/1989 | Cregg et al. |
| 4,837,148 A | 6/1989 | Cregg |
| 4,855,231 A | 8/1989 | Stroman et al. |
| 4,857,467 A | 8/1989 | Sreekrishna et al. |
| 4,879,231 A | 11/1989 | Stroman et al. |
| 4,882,279 A | 11/1989 | Cregg |
| 4,885,242 A | 12/1989 | Cregg |
| 4,925,796 A | 5/1990 | Bergh et al. |
| 4,929,555 A | 5/1990 | Cregg et al. |
| 4,935,349 A | 6/1990 | McKnight et al. |
| 5,002,876 A | 3/1991 | Sreekrishna et al. |
| 5,004,688 A | 4/1991 | Craig et al. |
| 5,032,516 A | 7/1991 | Cregg |
| 5,032,519 A | 7/1991 | Paulson et al. |
| 5,047,335 A | 9/1991 | Paulson et al. |
| 5,122,465 A | 6/1992 | Cregg et al. |
| 5,135,854 A | 8/1992 | MacKay et al. |
| 5,166,329 A | 11/1992 | Cregg |
| 5,272,066 A | 12/1993 | Bergh et al. |
| 5,324,663 A | 6/1994 | Lowe |
| 5,595,900 A | 1/1997 | Lowe |
| 5,602,003 A | 2/1997 | Pierce et al. |
| 5,683,899 A | 11/1997 | Stuart |
| 5,707,828 A | 1/1998 | Sreekrishna et al. |
| 5,766,910 A | 6/1998 | Fukuda et al. |
| 5,834,251 A | 11/1998 | Maras et al. |
| 5,849,904 A | 12/1998 | Gerardy-Schahn et al. |
| 5,854,018 A | 12/1998 | Hitzeman et al. |
| 5,861,293 A | 1/1999 | Kojiri et al. |
| 5,910,570 A | 6/1999 | Elhammer et al. |
| 5,945,314 A | 8/1999 | Prieto et al. |
| 5,945,322 A | 8/1999 | Gotschlich |
| 5,955,347 A | 9/1999 | Lowe |
| 5,955,422 A | 9/1999 | Lin |
| 5,962,294 A | 10/1999 | Paulson et al. |
| 6,017,743 A | 1/2000 | Tsuji et al. |
| 6,069,235 A | 5/2000 | Davis et al. |
| 6,096,512 A | 8/2000 | Elhammer et al. |
| 6,204,431 B1 | 3/2001 | Prieto et al. |
| 6,300,113 B1 | 10/2001 | Landry |
| 6,410,246 B1 | 6/2002 | Zhu et al. |

(Continued)

FOREIGN PATENT DOCUMENTS

EP    1054062    11/2000

(Continued)

OTHER PUBLICATIONS

Montesino, R., et al., "Characterization of the oligosaccharides assembled on the *Pichia pastoris*-expressed recombinant aspartic protease", 1999 Oxford University Press.

(Continued)

*Primary Examiner* — Anand Desai

(57) ABSTRACT

The present invention relates to eukaryotic host cells having modified oligosaccharides which may be modified further by heterologous expression of a set of glycosyltransferases, sugar transporters and mannosidases to become host-strains for the production of mammalian, e.g., human therapeutic glycoproteins. The invention provides nucleic acid molecules and combinatorial libraries which can be used to successfully target and express mammalian enzymatic activities such as those involved in glycosylation to intracellular compartments in a eukaryotic host cell. The process provides an engineered host cell which can be used to express and target any desirable gene(s) involved in glycosylation. Host cells with modified oligosaccharides are created or selected. N-glycans made in the engineered host cells have a $Man_5GlcNAc_2$ core structure which may then be modified further by heterologous expression of one or more enzymes, e.g., glycosyltransferases, sugar transporters and mannosidases, to yield human-like glycoproteins. For the production of therapeutic proteins, this method may be adapted to engineer cell lines in which any desired glycosylation structure may be obtained.

17 Claims, 45 Drawing Sheets

U.S. PATENT DOCUMENTS

| | | |
|---|---|---|
| 6,602,684 B1 | 8/2003 | Umana et al. |
| 6,946,292 B2 | 9/2005 | Kanda et al. |
| 7,029,872 B2 | 4/2006 | Gerngross |
| 7,064,191 B2 | 6/2006 | Shinkawa et al. |
| 7,214,775 B2 | 5/2007 | Hanai et al. |
| 7,259,007 B2 | 8/2007 | Bobrowicz |
| 7,326,681 B2 | 2/2008 | Gerngross |
| 7,332,299 B2 | 2/2008 | Hamilton |
| 7,365,163 B2 | 4/2008 | Hanna |
| 7,449,308 B2 | 11/2008 | Gerngross |
| 7,465,577 B2 | 12/2008 | Bobrowicz |
| 7,514,253 B2 | 4/2009 | Nett |
| 7,517,670 B2 | 4/2009 | Umana |
| 7,598,055 B2 | 10/2009 | Bobrowicz |
| 7,625,756 B2 | 12/2009 | Hamilton |
| 7,629,163 B2 | 12/2009 | Gerngross |
| 2002/0137134 A1 | 9/2002 | Gerngross |
| 2003/0157108 A1 | 8/2003 | Presta |
| 2003/0175884 A1 | 9/2003 | Umana et al. |
| 2004/0018590 A1 | 1/2004 | Gerngross et al. |
| 2004/0171826 A1 | 9/2004 | Hamilton |
| 2004/0191256 A1 | 9/2004 | Raju |
| 2004/0229306 A1 | 11/2004 | Nett |
| 2004/0230042 A1 | 11/2004 | Hamilton |
| 2005/0079605 A1 | 4/2005 | Umana et al. |
| 2005/0170452 A1 | 8/2005 | Wildt et al. |
| 2005/0208617 A1 | 9/2005 | Bobrowicz et al. |
| 2005/0260729 A1 | 11/2005 | Hamilton |
| 2005/0265988 A1 | 12/2005 | Choi et al. |
| 2006/0024292 A1 | 2/2006 | Gerngross et al. |
| 2006/0024304 A1 | 2/2006 | Gerngross et al. |
| 2006/0029604 A1 | 2/2006 | Gerngross et al. |
| 2006/0034828 A1 | 2/2006 | Gerngross et al. |
| 2006/0034829 A1 | 2/2006 | Gerngross et al. |
| 2006/0034830 A1 | 2/2006 | Gerngross et al. |
| 2006/0040353 A1 | 2/2006 | Davidson et al. |
| 2006/0078963 A1 | 4/2006 | Gerngross |
| 2006/0148035 A1 | 7/2006 | Gerngross |
| 2006/0160179 A1 | 7/2006 | Bobrowicz et al. |
| 2006/0177898 A1 | 8/2006 | Gerngross |
| 2006/0211085 A1 | 9/2006 | Bobrowicz et al. |
| 2006/0257399 A1 | 11/2006 | Gerngross et al. |
| 2006/0265988 A1 | 11/2006 | Fujito et al. |
| 2006/0286637 A1 | 12/2006 | Hamilton |
| 2007/0037248 A1 | 2/2007 | Bobrowicz et al. |
| 2007/0105127 A1 | 5/2007 | Gerngross |
| 2007/0154591 A1 | 7/2007 | Andersen |
| 2008/0274162 A1 | 11/2008 | Nessa et al. |

FOREIGN PATENT DOCUMENTS

| | | |
|---|---|---|
| EP | 1176195 | 1/2002 |
| EP | 1211310 | 6/2002 |
| EP | 1239047 | 9/2002 |
| EP | 0905232 | 3/2005 |
| EP | 1522590 | 4/2005 |
| EP | 1297172 | 11/2005 |
| JP | 8-336387 | 12/1996 |
| JP | 11-103158 | 4/1999 |
| WO | WO 96/21038 | 7/1996 |
| WO | WO 98/05768 | 2/1998 |
| WO | WO 99/31224 | 6/1999 |
| WO | WO 99/40208 | 8/1999 |
| WO | WO 99/54342 | 10/1999 |
| WO | WO 01/14522 | 8/2000 |
| WO | WO 00/61739 | 10/2000 |
| WO | WO 01/25406 | 4/2001 |
| WO | WO 01/36432 | 5/2001 |
| WO | WO 01/60860 | 8/2001 |
| WO | WO 02/00856 | 1/2002 |
| WO | WO 02/00879 | 1/2002 |
| WO | WO 02/079255 | 10/2002 |
| WO | WO 02/097060 | 12/2002 |
| WO | WO 03/011878 | 2/2003 |
| WO | WO 03/025148 | 3/2003 |
| WO | WO 03/031464 | 4/2003 |
| WO | WO 03/056914 | 7/2003 |
| WO | WO 2004/003194 | 1/2004 |
| WO | WO 2004/074497 | 7/2004 |
| WO | WO 2004/074458 | 9/2004 |
| WO | WO 2004/074461 | 9/2004 |
| WO | WO 2004/074498 | 9/2004 |
| WO | WO 2004/074499 | 9/2004 |
| WO | WO 2004/104165 | 12/2004 |
| WO | WO 2005/065019 | 7/2005 |
| WO | WO 2005/090552 | 9/2005 |
| WO | WO 2005/100584 | 10/2005 |
| WO | WO 2005/106010 | 11/2005 |
| WO | WO 2006/014679 | 2/2006 |
| WO | WO 2006/014683 | 2/2006 |
| WO | WO 2006/014685 | 2/2006 |
| WO | WO 2006/014725 | 2/2006 |
| WO | WO 2006/014726 | 2/2006 |
| WO | WO 2006/071280 | 7/2006 |
| WO | WO 2006/071856 | 7/2006 |
| WO | WO 2007/028144 | 3/2007 |
| WO | WO 2007/029054 | 3/2007 |

OTHER PUBLICATIONS

Reichner, J., et al., "Recycling cell surface glycoproteins undergo limited oligosaccharide reprocessing in LEC1 mutant Chinese hamster ovary cells", 1998 Oxford University Press.

File History of U.S. Appl. No. 11/249,061.

Puglielli et al., J. Biol. Chem., vol. 274 (1999), pp. 35596-35600, "Reconstitution, identification, and purification of the rat liver Golgi membrane . . . ".

Guillen et al., PNAS, vol. 95 (1998), pp. 7888-7892, "Mammalian Golgi apparatus UDP-N-acetylglucosamine transporter: . . . ".

Chiba et al., J. Biol. Chem., vol. 273 (1998), pp. 26298-26304, "Production of human compatible high mannose-type (Man5GlcNAc2) sugar chains in Saccharomyces cerevisiae".

Berninsone et al., J. Biol. Chem., vol. 272 (1997), pp. 12616-12619, "Functional expression of the murine Golgi CMP-sialic acid transporter in Saccharomyces cerevisiae".

Berninsone et al., J. Biol. Chem., vol. 270 (1995), pp. 14564-14567, "Regulation of yeast Golgi glycosylation".

Nakayama et al., The EMBO Journal, vol. 11 (1992), pp. 2511-2519, "OCH1 encodes a novel membrane bound mannosyltransferase: . . . ".

Nikawa et al., Gene, vol. 171 (1996), pp. 107-111, "Structural and functional conservation of human and yeast HCP1 genes which can suppres the growth defect . . . ".

Kalsner et al., Glycoconjugate Journal, vol. 12 (1995), pp. 360-370, "Insertion into Aspergilus nidulans of functional UDP-GlcNAc: alpha3-D-mannoside beta-1,2-N-acetylglucosaminyl-transferase 1 . . . ".

Martinet et al., Biotechnol. Letters, vol. 20 (1998), pp. 1171-1177, "Modification of the protein glycosylation pathway . . . ".

Kainuma et al., Glycobiology, vol. 9 (1999), pp. 133-141, "Coexpression of alpha1,2 galactosyltransferase and UDP-galactose transporter . . . ".

Jarvis et al., Curr. Opin. in Biotech., vol. 9 (1998), pp. 528-533, "Engineering N-glycosylation pathways in the baculovirus-insert cell system".

Ishida et al., J. Biochem., vol. 126 (1999), pp. 68-77, "Molecular cloning and functional expression of the human Golgi . . . ".

Ichishima et al., Biochem. Journal, vol. 339 (1999), pp. 589-597, "Molecular and enzymic properties of recombinant 1,2-alpha-mannosidase . . . ".

Harkki et al., Bio-Tech., vol. 7 (1989), pp. 596-603, "A novel fungal expression system: Secretion of active calf chymosin . . . ".

Eckhardt et al., Eur. J. Biochem., vol. 248 (1997), pp. 187-192, "Molecular cloning of the hamster CMP-sialic acid transporter".

Graham et al., J. Cell Biol., vol. 114 (1991), pp. 207-218, "Compartmental organization of Golgi-specific protein modification . . . ".

Eades et al., Gene, vol. 255 (2000), pp. 25-34, "Characterization of the Class I alpha-mannosidase gene family in the filamentous . . . ".

Dente, Prog. Clin. Biol. Res., vol. 300 (1989), pp. 85-98, "Human alpha-I-acid glycoprotein genes".

Cereghino et al., FEMS Microbiol. Rev., vol. 24 (2000), pp. 45-66, "Heterologous protein expression in the methylotrophic yeast . . . ".

Chandrasekaran et al., Cancer Res., vol. 44 (1984), pp. 4059-4068, "Purification and properties of alpha-D-mannose: . . . ".

Bretthauer et al., Biotech. Appl. Biochem., vol. 30 (1999), pp. 193-200, "Glycosylation of Pichia pastoris-derived proteins".
Bonneaud et al., Yeast, vol. 7 (1991), pp. 609-615, "A family of low and high copy replicative, integrative and single-stranded . . .".
Berninsone et al., J. Biol. Chem., vol. 269 (1994), pp. 207-211, "The Golgi guanosine diphosphatase is required for transport . . .".
Beaudet et al., Methods in Enzymology, vol. 292 (1998), pp. 397-413, High-level expression of mouse Mdr3 P-glycoprotein in yeast . . . .
Bardor et al., Trends in Plant Science, vol. 4 (1999), pp. 376-380, "Analysis of the N-glycosylation of recombinant glycoproteins . . .".
Aoki et al., J. Biochem., vol. 126 (1999), pp. 940-950, "Expression and activity of chimeric molecules between human UDP-galactose . . .".
Andersen et al., Curr. Opin. in Biotech., vol. 5 (1994), pp. 546-549, "The effect of cell-culture conditions on the oligosaccharide structures . . .".
Altmann et al., Glycoconjugate Journal, vol. 16 (1999), pp. 109-123, "Insect cells as hosts for the expression of recombinant glycoproteins".
Altmann et al., Glycoconjugate Journal, vol. 12 (1995), pp. 150-155, "Processing of asparagine-linked oligosaccharides in insect cells: . . .".
Wiggins et al., PNAS, vol. 95 (1998), pp. 7945-7950, "Activity of the yeast MNN1 alpha-1,3-mannosyltransferase require a motif . . .".
Choi et al., PNAS, vol. 100 (2003), pp. 5022-5027, "Use of combinatorial genetic libraries to humanize N-linked glycosylation . . .".
Abeijon et al., PNAS, vol. 93 (1996), pp. 5963-5968, "Molecular cloning of the Golgi apparatus uridine . . .".
Khatra et al., Eur. J. Biochem., vol. 44 (1974), pp. 537-560, "Some kinetic properties of human-milk galactosyl transferase".
Nakanishi-Shindo et al., J. Biol. Chem., vol. 268 (1993), pp. 26338-26345, "Structure of the N-linked oligosaccharides that show the complete loss . . .".
Yoshida et al., Glycobiology, vol. 9 (1999), pp. 53-58, "Expression and characterization of rat UDP-N-acetylglucoasamine: . . .".
Yoshida et al., Biochem. J., vol. 290 (1993), pp. 349-354, "1,2-alpha-D-mannosidase from *Penicillium citrinum*: . . .".
Yoko-o et al., FEBS Letters, vol. 489 (2001), pp. 75-80, "Schizosaccharomyces pombe och1+ encodes alpha-1,6-mannosyltransferase that is involved . . .".
Yang et al., Biotechnol. & Bioeng., vol. 68 (2000), pp. 370-380, "Effects of ammonia on CHO cell growth, erythropoietin production, . . .".
Werner et al., Drug Res., vol. 48 (1998), pp. 870-880, "Appropriate mammalian expression systems . . .".
Ware et al., Thrombosis and Haemostasis, vol. 69 (1993), pp. 1194-1194, "Expression of human platelet glycoprotein 1β-Alpha in transgenic mice".
Weikert et al., Nature Biotech., vol. 17 (1999), pp. 1116-1121, "Engineering Chinese hamster ovary cells to maximize sialic acid . . .".
Takeuchi, Trends in Glycoscience & Glycotech., vol. 9 (1997), pp. S29-S35, "Trial for molecular breeding of yeast for the production of glycoprotein therapeutics".
Berka, Abstract Papers Amer. Chem. Soc., vol. 203 (1992), pp. 121-BIOT, "The filamentous fungus Aspergillus niger var. awamori as host . . .".
Svetina et al., J. of Biotech., vol. 76 (2000), pp. 245-251, "Expression of catalytic subunit of bovine enterokinase . . .".
Staub et al., Nature Biotech., vol. 18 (2000), pp. 333-338, "High-yield production of a human therapeutic protein . . .".
Sommers et al., J. Cell. Biol., vol. 91, Abstract A406-A406 (1981), "Transport of sugar nucleotides into rat liver Golgi".
Sommers et al., J. Biol. Chem., vol. 257 (1982), pp. 10811-10817, "Transport of sugar nucleotides into rat liver Golgi".
Sikorski et al., Genetics, vol. 122 (1989), p. 19-27, "A system of shuttle vectors and yeast host strains designed for efficient . . .".
Segawa et al., FEBS Letters, vol. 451 (1999), pp. 295-298, "Schizosaccharomyces pombe UDP-galactose transporter: . . .".
Schwientek et al., J. Biol. Chem., vol. 270 (1995), pp. 5483-5489, "Golgi localization in yeast is mediated by the membrane . . .".

Schneikert et al., Glycobiology, vol. 4 (1994), pp. 445-450, "Characterization of a novel mouse recombinant processing alpha-mannosidase".
Schachter, Glycobiology, vol. 1 (1991), pp. 453-461, "The 'yellow-brick road' to branched complex N-glycans".
Ruther et al., Cell, vol. 53 (1988), pp. 847-856, "c-fos Expression interferes with thymus development in transgenic mice".
Romero et al., Biochem. Journal, vol. 321 (1997), pp. 289-295, "Ktr1p is an alpha-1,2-mannosyltransferase of *Saccharomyces cerevisiae*".
Raju, Analytical Biochem., vol. 283 (2000), pp. 123-124, "Analysis of Glycoconjugates".
Ren et al., Biochem., vol. 34 (1995), pp. 2489-2495, "Purification and properties of a Golgi-derived (alpha1,2)-mannosidase-I from Baculovirus-infected Lepidopteran . . .".
Perez et al., Methods in Enzymology, vol. 138 (1987), pp. 709-715, "Transport of sugar nucleotides into the lumen of vesciles derived from rat liver . . .".
Moens et al., Arch. Microbiol., vol. 168 (1997), pp. 169-175, "Glycoproteins in prokaryotes".
McGarvey et al., Biotech., vol. 13 (1995), pp. 1484-1487, "Expression of the rabies virus glycoprotein . . .".
Maruyama et al., Carbohydrate Res., vol. 251 (1994), pp. 89-98, "A 1,2-alpha-D-mannosidase from a *Bacillus sp*.: . . .".
Maras et al., J. of Biotech., vol. 77 (2000), p. 255-263, "Molecular cloning and enzymatic characterization of a Trichoderma reesei . . .".
Maras et al., Eur. J. Biochem., vol. 249 (1997), pp. 701-707, "In vitro conversion of the carbohydrate moiety of fungal glycoproteins . . .".
Malissard et al., Biochem. & Biophys. Res. Comm., vol. 267 (2000), pp. 169-173, "Expression of functional soluble forms of human beta-1,4-galactosyltransferase I, . . .".
Krezdorn et al., Eur. J. Biochem., vol. 220 (1994), pp. 809-817, "Human beta1,4 galactosyltransferase and alpha2,6 sialyltransferase . . .".
Adachi et al., XP002293645, Database accession No. AK029913 Abstract, Database EMBL, Dec. 21, 2002, "Mus musculus adult male testis cDNA, . . .".
Alani et al., Genetics, vol. 116 (1987), pp. 541-545, "A method for gene disruption that allows repeated use of URA3 . . .".
Yamashita et al., Biochem. & Biophys. Res. Comm., vol. 96 (1980), pp. 1335-1342, "An alpha-mannosidase purified from Aspergillus saitoi . . .".
Lussier et al., Biochimica et Biophysica Acta, vol. 1426 (1999), pp. 323-334, "The KTR and MNN1 mannosyltransferase families . . .".
Bianchi et al., Current Genetics, vol. 12 (1987), pp. 185-192, "Transformation of the yeast Kluyveromyces lactis by new vectors . . .".
Boehm et al., Yeast, vol. 15 (1999), pp. 563-572, "Disruption of the KEX1 gene in Pichia pastoris allows expression . . .".
Bretthauer et al., Trends in Biochem., vol. 21 (2003), pp. 459-462, "Genetic engineering of Pichia pastoris to humanize . . .".
Brockhausen et al., Biochem. Cell Biol., vol. 66 (1988), pp. 1134-1151, "Control of glycoprotein synthesis".
Callewaert et al., FEBS Letters, vol. 503 (2001), pp. 173-178, "Use of HDEL-tagged Trichoderma reesei mannosyl oligosaccharide . . .".
Cereghino et al., Gene, vol. 263 (2001), pp. 159-169, "New selectable marker/auxotrophic hose strain combinations . . .".
Chui et al., PNAS, vol. 98 (2001), pp. 1142-1147, "Genetic remodeling of protein glycosylation in vivo . . .".
Chui et al., Cell, vol. 90 (1997), pp. 157-167, "Alphamannosidase-II deficiency results in dyserythropoiesis and unveils . . .".
Daniel et al., Glycobiology, vol. 4 (1994), pp. 551-566, "Mammalian alpha-mannosidases—multiple forms but a common purpose?".
Davidson et al., Microbiology, vol. 148 (2002), pp. 2607-2615, "A PCR-based strategy to generate integrative targeting alleles . . .".
Duvet et al., Biochem. J., vol. 335 (1998), pp. 389-396, "Cytosolic deglycosylation process of newly synthesized glycoproteins . . .".
Foster et al., Gene, vol. 154 (1995), pp. 183-196, "Cloning and sequence analysis of GmII, a Drosophila melanogaster homologue . . .".
Gleeson, Histochem. Cell Biol., vol. 109 (1998), pp. 517-532, "Targeting of proteins to the Golgi apparatus".

Gonzalez et al., Molecular Biol. & Evolution, vol. 17 (2000), pp. 292-300, XP002293609 ISSN: 0737-4038, "The alpha-mannosidases: Phylogeny and . . . ".
Grard et al., Biochem. J., vol. 316 (1996), pp. 787-792, "Oligomannosides or oligosaccharide-lipds as potential substrates . . . ".
Hamilton et al., Science, vol. 301 (2003), pp. 1244-1246, "Production of complex human glycoproteins in yeast".
Harris et al., "Caenorhabditis elegans cosmid F58H1", XP002293610, Protein F58H1.1, abstract, Database EMBL Jul. 13, 1996.
Jarvis et al., Glycobiology, vol. 7 (1997), pp. 113-127, "Isolation and characterization of a class II alpha-mannosidase cDNA . . . ".
Genbank Accession No. NM 000528, dated Sep. 25, 2005.
Kawar et al., J. Biol. Chem., vol. 276 (2001), pp. 16335-16340, "Insect cells encode a class II α-mannosidase . . . ".
Lal et al., J. Biol. Chem., vol. 269 (1994), pp. 9872-9881, "Isolation and expression of murine and rabbit cDNAs encoding . . . ".
Lal et al., Glycobiology, vol. 8 (1998), pp. 981-995, "Substrate specificities of recombinant murine Golgi alpha1,2-mannosidase IA and IB . . . ".
Liao et al., J. Biol. Chem., vol. 271 (1996), pp. 28348-28358, "Cloning, expression, purification, and characterization of the human broad . . . ".
Lehle et al., Biochem. Biophys. Acta, vol. 350 (1974), pp. 225-235, "Membrane-bound mannosyl transferase in yeast . . . ".
Lu et al., Appl. Microbiol. Biotechnol., vol. 49 (1998), pp. 141-146, "Cloning an disruption of the beta-isopropylmalate . . . ".
McClure, Int. J. Food Microbiol., vol. 23 (1994), pp. 265-275, "Modeling the growth, survival and death of microorganisms . . . ".
Merkle et al., Biochim. Biophys. Acta, vol. 1336 (1997), pp. 132-146, "Cloning, expression, purification and chraracterization . . . ".
Miele et al., Biotechnol. Appl. Biochem., vol. 25 (1997), pp. 151-157, "Glycosylation properties of the Pichia pastoris-expressed . . . ".
Moremen, Biochim. Biophys. Acta, vol. 1573 (2002), pp. 225-235, "Golgi alpha-mannosidase II deficiency in vertebrate systems . . . ".
Moremen et al., J. Biol. Chem., vol. 260 (1985), pp. 6654-6662, "Biosynthesis and modification of Golgi mannosidase II . . . ".
Moremen et al., J. Biol. Chem., vol. 261 (1986), pp. 10945-10951, "Topology of mannosidase II in rat liver Golgi membranes . . . ".
Moremen, PNAS, vol. 86 (1989), pp. 5276-5280, "Isolation of rat liver Golgi mannosidase II clone by mixed oligonucleotide-primed . . . ".
Moremen et al., J. Cell Biol., vol. 115 (1991), pp. 1521-1534, "Isolation, characterization, and expression of cDNAs encoding . . . ".
Moremen et al., Glycobiology, vol. 4 (1994), pp. 113-125, "Glycosidases of the asparagine-linked oligosaccharide . . . ".
Nakayama et al., FEBS Lett., vol. 412 (1997), pp. 547-550, "Substrate specificity of α-1,6-mannosylatransferase that initiates . . . ".
Ogawa et al., Eur. J. Biochem., vol. 242 (1996), pp. 446-453, "Structure and transcriptional regulation of human alpha-mannosidase IIX . . . ".
Oh-eda et al., Eur. J. Biochem., vol. 268 (2001), pp. 1280-1288, "Overexpression of the Golgi-localized enzyme α-mannosidase IIx . . . ".
Papac et al, Glycobiology, vol. 8 (1998), pp. 445-454, "A high-throughput microscale method to release N-linked oligo-qjsaccharides . . . ".
Rabouille et al., J. Cell Sci., vol. 112 (1999), pp. 3319-3330, "The Drosophila GMII gene encodes Golgi alpha-mannosidase II".
Romero et al., J. Biol. Chem., vol. 275 (2000), pp. 11071-11074, "Mutation of Arg273 to Leu alters the specificity of the yeast . . . ".
Sato et al., "Arabidopsis thaliana DNA chromosome 5, BAC clone F2G14 (Essa project)", XP002293613. database accession No. AL 3921146, gene "F2G14_70" encoding "alpha-mannisodase-like protein . . . ", Abstract, database EMBL Aug. 7, 2000.
Soderholm et al., Biotechniques, vol. 31 (2001), pp. 306-312, "Vector for pop-in/pop-out gene replacement in Pichia pastoris".
Stix, Scientific Amer., Jan. 2004, pp. 32-33, "Supercharging protein manufacture".
Swiss Prot P11655, dated Oct. 1989.
Swiss Prot P32906, dated Oct. 1993.
Swiss Prot P39107, dated Feb. 1995.
Swiss Prot P50108, dated Oct. 1996.
Swiss Prot P53008, dated Oct. 1996.
Umaña et al., Nature Biotechnol., vol. 17 (1999), pp. 176-180, "Engineered glycoforms of an antineuroblastoma IgG1 with optimized . . . ".
Yang et al., Glycobiology, vol. 9 (1999), pp. 1347-1356, "Glycosylation and proteolytic processing of 70 kDa C-terminal recombinant . . . ".
Yip et al., PNAS, vol. 91 (1994), pp. 2723-2727, "Cloning and analysis of the Saccharomyces cerevisiae MNN9 and MNN1 genes . . . ".
Genbank Accession No. AF005034, dated Jul. 10, 1997.
Genbank Accession No. AF106080, dated Apr. 17, 1999.
Genbank Accession No. AK116684, dated Nov. 30, 2002.
Genbank Accession No. D55649, dated Feb. 7, 2003.
Genbank Accession No. NM 073594, dated Aug. 19, 2005.
Genbank Accession No. U31520, dated Dec. 13, 1995.
Genbank Accession No. X77652, dated Apr. 24, 1995.
Genbank Accession No. XM 218816, dated Apr. 15, 2005.
Genbank Accession No. NM 002406, dated Sep. 23, 2005.
Genbank Accession No. CAA98114, dated Aug. 9, 2005.
Genbank Accession No. NM 008548 (Genbank AN 6678787), dated Apr. 7, 2003.
Genbank Accession No. NM006715, dated Oct. 18, 2005.
Genbank Accession No. X61172, dated Apr. 18, 2005.
Genbank Accession No. NM121499, dated Nov. 4, 2005.
Strasser et a., Biochem. J., vol. 387 (2005), pp. 385-391, "Molecular basis of N-acetylglucosaminyltransferase 1 deficiency . . . ".
Voet et al., Biochemistry, Section 10-3. Glycoproteins (1990), pp. 266-267.
Tatara et al., J. Biol. Chem., vol. 278 (2003), pp. 25289-25294, "Identification of catalytic residues of Ca2+-independent 1,2-α-D-mannosidase . . . ".
Fujita et al., Biochem. & Biophys. Res. Comm., vol. 238 (1997), pp. 779-783, "Five crucial carboxyl residues of 1,2-α-mannosidase from Aspergillus saitoi . . . ".
Merriam & Webster online dictionary, © 2006-2007 Merriam-Webster, Incorporated, definition of Domain, pp. 1-2.
Lee et al., Biotech. Prog., vol. 13 (1997), pp. 368-373, "Sequential & integration for the regulated insertion of cloned genes . . . ".
Weng et al., Glycobiol., vol. 6 (1996), pp. 861-868, "Evaluation of the early processing routes of N-linked oligosaccharides of glycoproteins . . . ".
Zhu et al., Arch. Biochem. & Biophysics, vol. 352 (1998), pp. 1-8, "Structural studies of α-N-acetylgalactosaminidase: . . . ".
Vervecken et al., Applied & Environ. Microbiol., vol. 70 (2004), pp. 2639-2646, "In vivo synthesis of mammalian-like, hybrid-type N-glycans . . . ".
Minowa et al., J. Biol. Chem., vol. 273 (1998), pp. 11556-11562, "cDNA cloning and expression of bovine UDP-N-acetylglucosamine: . . . ".
Fukuta et al., Glycobiol., vol. 10 (2000), pp. 421-430, "Remodeling of sugar chain structures of human interferon-γ".
Duman et al., Biotech. Applied Biochem., vol. 28 (1998), pp. 39-45, "O-Mannosylation of Pichia pastoris cellular and recombinant proteins".
Li et al, Nature Biotech., vol. 24 (2006), pp. 210-215, "Optimization of humanized IgGs in glycoengineered Pichia pastoris".
Lifely et al., Glycobiology, vol. 5 (1995), pp. 813-822, "Glycosylation and biological activity of CAMPATH-1H expressed in different cell lines . . . ".
Yamane-Ohnucki et al., Biotech. Bioengin., vol. 87 (2004), pp. 614-622, "Establishment of FUT8 knockout Chinese hamster ovary cells: . . . ".
Maras et al., Glycoconj. Journal, vol. 16 (1999), pp. 99-107, "Filamentous fungi as productio norganisms for glycoproteins . . . ".
EP 1297172 B1—Glycode Opposition Brief (French), dated Jul. 26, 2006.
EP 1297172 B1—Glycode Opposition Brief (English translation), dated Aug. 25, 2006.
EP 1297172 B1—Novozyme Opposition Brief, dated Aug. 4, 2006.
EP 1297172 B1—Patentee's Reply to the Notice of Opinion, dated Mar. 22, 2007.
EP 1297172 B1—EPO Non-Binding Opinion, dated Jun. 29, 2007.

Pakula et al., Microbiol., vol. 146 (2000), pp. 223-232, "Monitoring the kinetics of glycoprotein synthesis and secretion in the filamentous fungus Trichoderma reesei: . . . ".
Lowder et al., Western J. Med., vol. 143 (1985), pp. 810-816, "Monoclonal antibodies—therapeutic and diagnostics uses in malignancy".
Hard et al., Eur. J. Biochem., vol. 193 (1990), pp. 263-271, "Isolation and structure determination of the intact sialylated N-linked carbohydrate chains . . . ".
Maras et al., Eur. J. Biochem., vol. 245 (1997), pp. 617-625, "Structural characterization of N-linked oligosaccharides from cellobiohydrolase I . . . ".
Maras et al., FEBS Letters, vol. 452 (1999), pp. 365-370, "In vivo synthesis of complex N-glycans by expression of human N-acetylglucosaminyltransferase I . . . ".
Salovuori et al., Bio/Technol., vol. 5 (1987), pp. 152-156, "Low molecular weight high-mannose type glycans in secreted protein . . . ".
Applicants' Response of Apr. 18, 2008 to Office Action re U.S. Appl. No. 11/187,066.
Applicants' Response of Apr. 11, 2008 to Office Action re U.S. Appl. No. 11/187,196.
Applicants' Response of Apr. 11, 2008 to Office Action re U.S. Appl. No. 11/187,113.
Wikipidia, Signal Peptide, pp. 1-3 (2008).
Kaletta et al., FEBS Letters, vol. 434 (1998), pp. 377-381, "The peptide HDEF as a new retention signal is necessary and sufficient to direct proteins to the endoplasmic reticulum".
Chapman et al., Arch. Biochem. Biophys., vol. 260 (1988), pp. 320-333 (abstract), "Effects of glucose starvation and puromycin treatment on lipid-linked oligosaccharide precursors . . . ".
Schweintek et al., J. Biol. Chem., vol. 271 (1996), p. 3398-3405, "Golgi localization and in vivo activity of a mammalian glycosyltransferase . . . ".
Davies et al., Biotech. & Engineer., vol. 74 (2001), pp. 288-294, "Expression of GnTIII in a recombinant anti-CD20 CHO production cell line: . . . ".
Gerngross et al., Nature Biotech., vol. 22 (2004), pp. 1409-1414, "Advances in the production of human therapeutic proteins in yeasts and filamentous fungi".
Kim et al., PNAS USA, vol. 95 (1998), pp. 2997-3002, "Noninvasive measurement of the pH of the endoplasmic reticulum . . . ".
Bobrowicz et al., Glycobiology, vol. 14 (2004), pp. 757-766, "Engineering of an artificial glycosylation pathway blocked in core oligosaccharide assembly . . . ".
Rothman et al., Molec. Immunol., vol. 26 (1989), pp. 1113-1123, "Antibody-dependent cytotoxicity mediated by natural killer cells . . . ".
Ripka et al., Arch. of Biochem. & Biophys., vol. 249 (1986), pp. 533-545, "Two Chinese hamster ovary glycosylation mutants affected in the conversion of GdP-mannose to GDP-fucose".
Shields et al., J. Biol. Chem., vol. 276 (2001), pp. 6591-6604, "High resolution mapping of the binding site on human IgG1 for FcγRI, FcγRII, FcγRIII, and FcRn . . . ".
Shields et al., J. Biol. Chem., vol. 277 (2002), pp. 26733-26740, "Lack of fucose on human IgG1 N-linked oligosaccharide improves binding to human FcγRIII . . . ".
Tremblay et al., J. Biol. Chem., vol. 275 (2000), pp. 31655-31660, "Characterization of a cDNA encoding a novel human Golgi γ1,2-mannosidase (IC) . . . ".
Tremblay et al., Glycobiology, vol. 9 (1999), pp. 1073-1078, "Cloning and expression of a specific human α1,2-mannosidase that trims Man9GlcNAc2 isomer B . . . ".
Shitara et al., J. Immunol. Methods, vol. 167 (1994), pp. 271-278, "A new vector for the hig level expression of chimeric antibodies in myeloma cells".
Shinkawa et al., J. Biol. Chem., vol. 278 (2003), pp. 3466-3473, "The absence of fucose but not the presence of galactose or bisecting N-acetylglucosamine . . . ".
Xie et al., Nature Biotech., vol. 15 (1997), pp. 768-771, "Direct demonstration of MuSK involvement in acetylcholine receptor clustering . . . ".

Wildt et al., Nature Rev. Microbiol., vol. 3 (2005), pp. 119-128, "The humanization of N-glycosylation pathways in yeast".
Mimura et al., Molecular Immunol., vol. 37 (2000), pp. 697-706, "The influence of glycosylation on the thermal stability and effector function expression of human IgG1-Fc: . . . ".
Pena et al., J. of Bacteriol., vol. 177 (1995), pp. 1017-1022, "Proton pumping and the internal pH of yeast cells, measured with pyranine . . . ".
Allison et al., Molecular & Cellular Biol., vol. 9 (1989), pp. 4977-4985, "Mutations in the signal sequence of prepro-α-factor . . . ".
Kojima et al., J. Biol. Chem., vol. 271 (1996), pp. 19457-19463, "Characterization of mouse ST8Sia II (STX) as a neural cell adhesion molecule-specific polysialic acid synthase".
Llopis et al., PNAS USA, vol. 95 (1998), pp. 6803-6808, "Measurement of cytosolic, mitochondrial, and Golgi pH in single living cells . . . ".
Spiro, J. Biol. Chem., vol. 275 (2000), pp. 35657-35660, "Glucose residues as key determinants in the biosynthesis and quality control . . . ".
Spiro et al., J. Biol. Chem., vol. 272 (1997), pp. 29356-29363, "Molecular cloning and expression of rat liver endo-α-mannosidase, . . . ".
Hamilton et al., Science, vol. 313 (2006), pp. 1441-1443, "Humanization of yeast to produce complex terminally sialylated glycoproteins".
Abdel-Salam et al., "Expression of mouse anticreatine kinase (MAK33) monoclonal antibody in the yeast Hansenula Polymorpha", App. Microbiol. Biotechnol. 56:157-164 (2001).
Al-Rawi et al., "Synthesis and biochemical properties of reversible inhibitors of UDP-N-acetylglucosamine 2-epimerase. Angew.", Chem. Int. Ed. Engl. vol. 43, No. 33, pp. 4366-4370, (2004).
Altschul et al., "Basic Local Alignment Search Tool", J. Mol. Biol. 215:403-410 (1990).
Altschul et al., "Gapped BLAST and PSI-BLAST: a new generation of protein database search program", Nucleic Acids Res. 25:3389-3402 (1997).
Bause and Burbach, "Purification and Enzymatic Properties of Endo-α1,2-Mannosidase from Pig Liver Involved in Oligosaccharide Processing," Biol. Chem. 377:639-646 (1996).
Boeke et al., "A positive selection for mutants lacking orotidine-5'-phosphate decarboxylase activity in yeast: 5-fluoro-orotic acid resistance", Mol. Gen. Genet. 197:345-346 (1984).
Borreback et al., "Human Momoclonal antibodies produced by primary in vitro immunization of peripheral blood lymphocytes", Proc. Natl. Acad. Sci. USa, 85:3995-3999 (1988).
Boutin, "Myristoylation," Cell. Signal. 9(1):15-35 (1997).
Bucket et al., "Cloning and nucleotide sequence of heavy and light chain cDNAs from a creatine-kinase-specific monoclonal antibody", Gene, 51:13-19 (1987).
Cadwell and Joyce, Randomization of Genes by PCR Mutagenesis:, PCR Methods Applic. 2:28-33 (1992).
Cabanes-Macheteau et al., "N-Glycosylation of a mouse IgG expressed in transgenic tobacco plants," Glycobiology, vol. 9, No. 4., pp. 365-372 (1999).
Chen et al., "Effect of retinoic acid on the structure of N-glycans on the surface of human hepatocarcinoma cells and its enzymatic mechanism", J. Cancer Res. Clin. Oncol. vol. 121, No. 7, pp. 397-401, (1995).
Cole, et al., "Modelling the growth, survival and death of microorganisms in foods: the UK food micromodel approach," J. Cell Biochem 23(3-4) 265-275 (1994).
D'Agostaro et al., "Molecular cloning and expression of cDNA encoding the rate UDP-N-acetylglucosamine:alpha-6-D-mannoside beta-1,2-N-acetylglucosaminyltransferase II", J. Biol. Chem, vol. 270, No. 25, pp. 15211-15221 (1995).
Dempski and Imperiali, "Oligosaccharyl transferase: gatekeeper to the secretory pathway," Curr. Opin. in Chem. Biol. 6:844-850 (2002).
Dennis et al., "Protein glycosylation in development and disease", Bioessays, 21(5):412-21 (1999).
Gavel et al., "Sequence differences between glycosylated and non-glycosylated Asn-X-Thr/Ser acceptor sites: implications for protein engineering", Protein Eng., 3:433-43 (1990).

Gleeson et al., "Control of glycoprotein synthesis", J. Biol. Chem. vol. 258, No. 10, pp. 1662-1673, (1983).

Goochee et al., "The Olgosaccharides of Glycoproteins: Bioprocess Factors Affecting Oligosaccharide Structure and Their Effect on Glycoprotein Properties", Biotechnology, 9(12):1347-1355 (1999).

Grasziano et al., "Construction and Characterization of a Humanized Anti-γ-Ig Receptor Type I (FcγRI) Monoclonal Antibody", J. Immunol., 155(10):4996-5002 (1995).

Haworth, Robert S., et al., "Intracellular pH in Schizosaccharomyces pombe-Comparison with *Saccharomyces cerevisiae*", Molecular and Cellular Biochemistry, vol. 124, pp. 131-140 (1993).

Hayes et al., "Carbohydrate Compositions of the Rabbit Plasminogen Isozymes", J. Arch. Biochem. Biophys., 171:651-655 (1975).

Hernandez et al., "Structure of the Phosphorylated N-linked Oligosaccharides from the mnn9 and mnn10 Mutants of *Saccharomyces cerevisiae*", The Journal of Biological Chemistry, 264(23):13648-13659 (1989).

Herscovics, Processing glycosidases of *Saccharomyces cerevisiae*, Biochim. Biophys. Acta 1426:275-285 (1999).

Hiraizumi et al., "Characterization of Endomannosidase Inhibitors and Evaluation of Their Effect on *N*-Linked Olligosaccharide Processing during Glycoprotein Biosynthesis," *J. Biol. Chem.* 268(13):9927-9935 (1993).

Hiraizumi et al., "Ligand Affinity Chromatographic Purification of Rat Liver Golgi Endomannosidase," *J. Biol. Chem.* 269(7)4697-4700 (1994).

Huffaker et al., "Yeast mutants deficient in protein glycosylation", Proc. Natl. Acad. Sci. USA, 80(24):7466-70 (1983).

Inamori et al., Molecular Cloning and Characterization of Human GnT-IX, a Novel β1,6-N-Acetylglucosaminyltransferase that is specifically expressed in the Brain, J. Biol. Chem., vol. 278, No. 44, pp. 43102-43109 (2003).

Ishida et al., "Molecular Cloning and Characterization of a Novel Isoform of the Human UDP-Galactose Transporter, and of Related Complementary DNAs Belonging to the Nucleotide-Sugar Transporter Gene Family", J. Biochem., (Tokyo) 120(6):1074-1078 (1996).

Jefferis, "Glycosylation of Human IgG Antibodies", Biopharma, 14:19-26 (2001).

Jungmann et al., Multi-protein complexes in the cis Golgi of *Saccharomyces cerevisiae* with alpha-1,6-mannosyltransferase activity, EMBO J., vol. 17, No. 2, pp. 423-434, (1998).

Kyte and Doolittle, "A Simple Method for Displaying the Hydropathic Character of a Protein," *J. Mol. Biol.* 157:105-132, (1982).

Leung et al., "A method for random mutagenesis of a defined DNA segment using a modified polymerase chain reacation", Techniqure, 1:11-15 (1989).

Lopez, et al., "Microheterogeneity of the oligosaccharides carried by the recombinant bovine lactoferrin expressed in mamestra brassicae cells," Glycobiology., vol. 7, No. 5, pp. 635-651 (1997).

Lubas and Spiro, "Evaluation of the Role of Rat Liver Golgi Endo-α-D-mannosidase in Processing *N*-linked Oligosaccharides," *J. Biol. Chem.* 263(8):3990-3998 (1988).

Madden et al., "Applications of Network BLAST Server", Meth. Enzymol., 266:131-141 (1996).

Makoto, T., et al., "Trial for Molecular Breeding of Yeast for the production of glycoprotein therapeutics", Trends in Glycoscience and Glycotechnology, vol. 9 (suppl.):S29-S35 (1997).

Moore and Spiro, "Characterization of the Endomannosidase Pathway for the Processing of *N*-Linked Oligosaccharides in Glucosidase II-deficient and Parent Mouse Lymphoma Cells," *J. Biol. Chem* 267(12):8443-8451 (1992).

Morin-Ganet et al., "Morphogenesis and Dynamics of the Yeast Golgi Apparatus", Traffic, 1(1):56-68 (2000).

Narasimhan et al., "Control of Glycoprotein Synthesis", J. Biol. Chem., 257:10235:42 (1982).

Neiman et al., "*Saccharomyces cerevisiae* HOC1, a Supressor of pkc 1, Encodes a Putative glycosyltransferase", Genetics, 145(3):637-645 (1997).

Ogunjimi et al., "High-level secretory expression of immunologically active intact antibody from the yeast pichia pastoris", Biotechnology Letters, 21:561-567 (1999).

Orlandi et al., "Cloning immunolglobulin variable domains for expression by the polymerase chain reaction", Proc. Natl., Acad. Sci. USA, 86:3833 (1988).

Pearson, "Rapid and Sensitive Sequence Comparison with FASTA", Methods Enzymol. 183:63-98 (1990).

Ragu et al., "Species-specific variation in glycosylation of IgG: evidence for the species-specific sialyation and branch-specific galactosylation and importance for engineering recombinant glycoprotein therapeutics", Glycobiology, 10(5):477-486 (2000).

Raschke et al., "Genetic Control of Yeast Mannan Structure", J. Biol. Chem. 248(13):4660-66 (1973).

Ray et al., A Novel Glycosylation Phenotype Expressed by Lec23, a Chinese Hamster Ovary Mutant Deficient in α-Glucosidase I, *J. Biol. Chem.* 255(34):22818-22825 (1991).

Recinos et al., "Sequences of cDNAs encoding immunoglobulin heavy-and ligh-chain variable regions from two anti-dioxin monoclonal antibodies", Gene, 149:385-386 (1994).

Recinos et al., "Sequences of cDNAs encoding immunoglobulin heavy-and ligh-chain variable regions from two anti-dioxin monoclonal antibodies", Gene, 158:311-312 (1995).

Reichner et al., Recycling cell surface glycoproteins undergo limited ligosaccharide reprocessing in LEC1 mutant Chinese hamster ovary cells, Glycobiology, vol. 8, No. 12, pp. 1173-1182 (1998).

Reidhaar-Olson et al., "Combinatorial Cassett Mutagenesis as a proble of the informational content of protein sequences", Science, 241:53-57 (1988).

Reitman et al., "A Lectin-resistant Mouse Lymphoma Cell Line Is Deficient in Glucosidase II, a Glycoprotein-processing Enzyme," *J. Biol. Chem.* 257(17):10357-10363, (1982).

Roth et al., "The role of glucosidase II and endomannosidase in glucose trimming of asparagines-linked oligosaccharides," *Biochimie* 85:287-294, (2003).

Rothstein et al., "Targeting, Disruption, Replacement and Allele Rescue: Integrative DNA Transformation in Yeast", Methods in Enzymology, 194:281 (1991).

Sakamoto et al., Molecular Cloning and Expression of CDNA Encoding Chicken UDP-N-acetyl-D-glucosamine (GlcNAc): GlcNAc β1-6(GlcNAc β1-2)-Man α1-R[GlcNAc) to Man]β1,4N-acetylglucosaminyltransferase VI, J. Biol. Chem. vol. 275, No. 46, pp. 36029-26034 (2000).

Sambrook et al., "Hybridization of Radiolabeled Probes to immobilized nucleic acids", Molecular Cloning: A Laboratory Manual, 2d ed., Cold Spring Harbor Laboratory Press, Cold Spring Harbor, N.Y., pp. 9.51, (1989).

Sasai et al., "UDP-GlcNAc concentration is an important factor in the biosynthesis of β1,6-branched oligosaccharides: regulation based on the kinetic properties of N-acetylglucosaminytransferase V", Glycobiology, vol. 12, No. 2, pp. 119-127 (2002).

Shiha et al., "Functional characterization of human blood coagulation factor XIa using hybridoma antibodies", J. Biol. Chem. vol. 260, No. 19, pp. 10714-10719 (1985).

Spiro et al., "Definition of the Lectin-like Properties of the Molecular Chaperone, Calreticulin, and Demonstration of Its Copurification with Endomannosidase from Rat Liver Golgi," *J. Biol. Chem.* 271(19):11588-11594 (1996).

Spiro and Spiro, "Use of recombinant endomannosidase for evaluation of the processing of *N*-linked oligosaccharides of glycoproteins and their oligosaccharide-lipid precursors," *Glycobiology* 10(5):521-529 (2000).

Spiro et al., "Glucose residues as key determinants in the biosynthesis and quality control . . . ," J. Biol. Chem., vol. 275, pp. 35657-35660 (2000).

Spiro et al., "Molecular cloning and expression of rat liver endo-α-mannosidase . . . ," J. Biol. Chem., vol. 272, pp. 29356-29363 (1997).

Suzuki et al., "Characterizaion of alpha-1,6-mannosyltransferase responsible for the synthesis of branched side chains in candida albicans mannan.", Eur J. Biochem, vol. 240, No. 1, pp. 37-44, (1996).

Teixeira et al., "Antifungal susceptibility and pathogenic potential of environmental isolated filamentous fungi compared with colonizing agents in immunocompromised patients", Mycopathologia., vol. 160, No. 2, pp. 129-135, (2005).

Terness et al., "Idiotypic vaccine for treatment of human B-cell lymphoma", Hum. Immunol., 56:17-27 (1997).

Tremblay et al., "Molecular cloning, chromosomal mapping and tissue-specific expression of a novel human α-1,2-mannosidase gene involved in N-glycan maturation", Glycobiology, 8(6):585-595 (1998).

Tsuji-Hayashi et al., "A potential endogenous ligand of annexin IV in the Exocrine pancreas", The Journal of Biological Chemistry, 277(49):47493-47499 (2002).

Tsujikawa et al., "Secretion of a variant of human single-chain urokinase-type plasminogen activator without an N-glycosylation site in the methylotrophic yeast, pichia patoris and characterization of the secreated product:", Yeast, vol. 12, No. 6, pp. 541-553 (1996).

Umana et al., "Tetracycline-Regulated Overexpression of glycosyltransferase in Chinese hamster ovary cells", Biotechnol. Bioeng., 65(5):542-549 (1999).

Welschof et al., "Amino acid sequence based PCR primers for amplification of rearranged human heavy and light chain immunolglobulin variable region genes", J. Immunol. Methods, 179:203-214 (1995).

Yoshida et al., "Molecular cloning and nucleotide sequence of the genomic DNA for 1-2-alpha-D-mannosidase gene, msdC from *Penicillium citriunum*," Biochem. Biophys. Acta. vol. 1263, No. 2 pp. 159-162 (1995).

Zerangue et al, "Analysis of endoplasmic reticulum trafficking singals by combinatorial screening in mammalian cells", Proc. Natl. Acad. Sci. USA, vol. 98, No. 5, pp. 2431-2436 (2001).

Zhang and Madden, "PowerBLAST: a new network BLAST application for interactive or automated sequence analysis and annotation", Genome Res. 7:649-656 (1997).

Zuber et al., "Golgi Apparatus Immunolocalization of Endomannosidase Suggests Post-Endoplasmic Reticulum Glucose Trimming: Implications for Quality Control," *Mol. Bio. of the Cell*, 11:4227-4240 (2000).

File History of U.S. Appl. No. 11/249,061, submitted 2010.

Opposition Brief filed by Novartis against EP1597379 (Feb. 15, 2010).

Opposition Brief filed by Novozymes A/S for EP1297172 B1 (2007).

Further submission by Patentee in opposition proceeding against EP 1297172B1 (2007).

Opinion of the Opposition Division for EP1297172B1 (2007).

Grounds of Appeal for EP 1297172 B1 (2008).

Response by Glycode to Grounds of Appeal for EP 1297172 B1 (2008) (English Translation of French Document).

Preliminary Opinion of Appeal Board for EP 1297171 B1 (2010).

O'Brian et al., "Mass Spectrometry of Cardiac Calsequestrin Characterizes Microheterogeneity Unique to Heart and Indicative of Complex Intracellular Transit", The Journal of Biological Chemistry, vol. 277, No. 40, pp. 37154-37160 (2002).

Abecassis, et al., "High efficiency family shuffling based on multistep PCR and in vivo DNA recombination in yeast: statistical and functional analysis of a combinatorial library between human cytochrome P450 1A1 and 1A2", Nucleic Acids Research, vol. 28, No. 20, pp. 1-10 (2000).

Brockhausen, et al., "The biosynthesis of highly branched N-glycans: studies on the sequential pathway and functional role of N-acetylglucosaminyltransferases I, II, III, IV, V and VI", Biochimie, vol. 70, pp. 1521-1533 (1988).

Carmirand, et al., "Glycoprotein Biosynthesis in *Saccharomyces cerevisiae*", The Journal of Biological Chemistry, vol. 266, No. 23, pp. 15120-15127 (1991).

Dorland, et al., "Investigation by 360-MHZ $^1$H-Nuclear-Magnetic-Resonance Spectroscopy and Methylation Analysis of the Single Glycan Chain of Chicken Ovotransferrin", Eur. J. Biochem. vol. 100, pp. 569-574 (1979).

Gabius, "The Sugar Code, Fundamentals of glycosciences", Wiley-VCH, pp. 152 (2009).

Gawlitzek, et al., "Characterization of changes in the glycosylation pattern of recombinant proteins from BHL-21 cells due to different culture conditions", Journal of Biotechnology, vol. 42, pp. 117-131 (1995).

George, et al., "Use of fetal bovine serum substitutes for the protection of the mouse zona pellucida against hardening during cryoprotectant addition", Human Reproduction, vol. 18, No. 11, pp. 1898-1900 (1993).

Gleeson, et al., "Glycopinion Mini-Review, Targeting of proteins to the Golgi apparatus", Glycoconjugate Journal, vol. 11, pp. 381-394 (1994).

Langeland, et al., "A Clinical and Immunological Study of Allergy to Hen's Egg White", Allergy, vol. 38, pp. 131-139 (1983).

Lussier, et al., "Localization and Targeting of the *Saccharomyces cerevisiae* Kre2p/Mnt1p α1,2-Mannosyltransferase to a medial-Golgi Compartment", The Journal of Cell Biology, vol. 131, No. 4, pp. 913-927 (1995).

Lussier, et al., "Functional Characterization of the *YUR1*, *KTR1*, and *KTR2* Genes as Members of the Yeast *KRE2/MNT1* Mannosyltransferase", The Journal of Biological Chemistry, vol. 271, No. 18, pp. 11001-11008 (1996).

Mille, et al., "Identification of New Family of Genes Involved in β-1,2-Mannosylation of Glycans in *Picha pastoris* and *Candida albicans*", Journal of Biological Chernistry, vol. 283, No. 15, pp. 9274-9736 (2008).

Misaizu, et al., "Role of Antennary Structure of N-Linked Sugar Chains in Renal Handling of Recombinant Human Erythopoietin", Blood, vol. 86, No. 11, pp. 4097-4104 (1995).

Nagasu, et al., "Isolation of New Temperature-Sensitive Mutants of *Saccharomyces cerevisiae* Deficient in Mannose Outer Chain Elongation", Yeast, vol. 8, pp. 535-547 (1992).

Petrenko, et al., "A library of organic landscapes on filamentous phage", Protein Engineering, vol. 9, No. 9, pp. 797-801 (1996).

Sasaki, et al., "Carbohydrate Structure of Erythropoietin Expressed in Chinese Hamster Ovary Cells by a Human Erythropoietin cDNA", The Journal of Biological Chemistry, vol. 262, No. 25, pp. 12059-12076 (1987).

Takeuchi, et al., "Comparative Study of the Asparagine-linked Sugar Chains of Human Erythropoietins Purified from Urine and the Culture Medium of Recombinant Chinese Hamster Ovary Cells", The Journal of Biological Chemistry, vol. 263, No. 8, pp. 3657-3663 (1988).

Tsuda, et al., "Comparative Structural Study of N-Linked Oligosaccharides of Urinary and Recombinanat Erythropoietins", Biochemistry, vol. 27, pp. 5646-5654 (1988).

Vowels, et al., "A Role for the Lumenal Domain in Golgi Localization of the *Saccharomyces cerevisiae* Guanosine Diphosphatase", Molecular Biology, vol. 9, pp. 1351-1365 (1998).

Yet, et al., "The Covalent Structure of Individual N-Linked Glycopeptides from Ovomucoid and Asialofetuin", The Journal of Biological Chemistry, vol. 263, No. 1 pp. 111-117 (1988).

Yoshida, et al., Overproduction of 1,2-α-Mannosidase, a Glycochain Processing Enzyme, by *Aspergillus oryzae*, Biosci. Biotechnol. Biochem. vol. 62, No. 2, pp. 309-315 (1998).

Yoshida, et al., "Tissue specific expression and chromosomal mapping of a human UDP-N-acetylglucisomaine:α1,3-D-mannoside β1,4-N-acetylglucosaminyltransferase", Glycobiology, vol. 9, No. 3, pp. 303-310 (1999).

Yoshida, et al., "A novel second isoenyzme of the human UDP-N-acetylglucosamine:α1,3-D-mannoside β1 ,4-N-acetylglucosaminyltransferase family: cDNA cloning, expression, and chromosomal assignment", Glycoconjugate Journal, vol. 15, pp. 1115-1123 (1998).

Notice of Opposition filed by Lonza against EP1597381 (Sep. 15, 2010).

Notice of Opposition filed by Strawman against EP1597381 (Sep. 16, 2010).

Notice of Opposition filed by Glycode against EP1522590 (May 26, 2010).

Notice of Opposition filed by Novartis against EP1522590 (May 26, 2010).

English Translation of WO 01/14522 (Mar. 1, 2001).

Roberts, "Drosophia Melanogaster GMII gene, exons 1-5" XP002293614, Database accession No. AJ132715, Abstract, Database EMBL (Nov. 14, 2006).

Satoh et al., *Ciona intestinalis* cDNA, clone: ciego014e11, full insert sequence XP002293611, Database accession No. AK116684, the whole document, Database EMBL (Nov. 30, 2002).

Shinn et al., "*Arabidopsis thaliana* AT5g14950/F2G14_70 mRNA, complete cds." XP002293612, Database accession No. AY052707, Abstract, Database EMBL., (Sep. 5, 2001).

Schlegel et al., (Derwen) XP002293375, "Human prostate expression marker cDNA 29377" (Aug. 23, 2001).

Montesino et al., Glycobiol., pp. 1037-1043, "Characterization of the oligosaccharides assembled on the *Pichia pastoris*-expressed recombinant aspartic protease" (Oct. 9, 1999).

Swarnakar et al., XP-002293374, Database accession No. AAG79783, abstract, "Carbohydrate-associated protein (CHOP)-5" (Dec. 5, 2002).

Carninci et al., XP-002293371, Database accession No. AK030141, "*Mus musculus* adult male testis cDNA, RIKEN full-length enriched library, . . . " (Dec. 5, 2002).

Tang et al., XP-002293373, Database accession No. AD121896, "Novel human protein cDNA #155" (Mar. 27, 2003).

Tang et al., XP-002293372, Database accession No. AD121180, "Novel human protein #155" (Mar. 27, 2003).

Juranic et al., Food Chemistry, vol. 93 (2005), pp. 39-45, "Antiproliferative acation of water extracts of seeds or pulp . . . " (Nov. 2005).

M. musculus alpha-1,2-mannosidase IA open reading frame. The transmembrane and catalytic domains are highlighted in bold respectively. The sequence of the primers used to generate the N-terminal truncations are highlighted by underlining and the start of each respective protein fragment indicated by an arrow.

```
  1  atgcccgtggggggcctgttgccgctcttcagtagcccggggcggcagtggcctgggcggcttggcggcggagaagggg
  1▷ M  P  V  G  G  L  L  P  L  F  S  S  P  G  G  G  L  G  S  G  L  G  G  L  G  G  G  R  K  G
 97  tctgccccgctgcttccgcctcaccgagaagttcgtgctgctgctcttcagcgccttcatcacgctcttcgggcaatc
 33▷ S  G  P  A  A  F  R  L  T  E  K  F  V  L  L  V  F  S  A  F  I  T  L  C  F  G  A  I
184  ttcttcctgcctgactcctccagctgctcaggggtctgtcagctccactccaacctgccttgcagccgcggagcacaagcccggctcg
 62▷ F  F  L  P  D  S  S  K  L  L  S  G  V  L  F  H  S  N  P  A  L  Q  P  P  A  E  H  K  P  G  L
                   d65 primer ─────────▶
278  gggcgcgtgcggaggatgccgccggggagagtccgcaccgcgaggaagccgcctgggacctgggactgaagcaactagcca
 93▷ G  A  R  A  E  D  A  A  E  G  R  V  R  H  R  E  E  G  A  P  G  D  P  G  A  G  L  E  D  N  L  A
                        d105 primer ─────────▶
374  ggatccgcgaaacaccacgagcgggctctcagggaagccaaggagctgcaggagctgccgaggagatccaagagacattctgctggagaagg
125▷ R  I  R  E  N  H  E  R  A  L  R  E  A  K  E  T  L  Q  K  L  P  E  E  I  Q  R  D  I  L  L  E  K
470  aaaggtggccccaggaccagctgcgtgacaaggatcgtgtttaggggcttgccccaagtggacttcctgcccccccgtcgggtgagaaccgggagc
157▷ E  K  V  A  Q  D  Q  L  R  D  K  D  L  F  R  G  L  P  K  V  D  F  L  P  P  V  G  V  E  N  R  E
                                                                           d187 primer ─────────
566  ccgctgacgcgccaccatccgtgagaaggggcaaagatcaaggagatgatgacccatgcttgaataattataacgctatgcgtgggc
189▷ P  A  D  A  T  I  R  E  K  R  A  K  I  K  E  M  M  T  H  A  W  N  N  Y  K  R  Y  A  W  G
655  ttgaacgaactgaaactatatcaaagaaggagccattcaagcagtttgtttggcaccatcaaaggagctcaatagtagatg
219▷ L  N  E  L  K  P  I  S  K  E  G  H  S  S  L  F  G  N  I  K  G  A  T  I  V  D
737  ccctggataccctttcattatgggcatgaagactgaattcaagaagctaaatcgtggattaaaaatatttagatttaa
```

FIG.3

```
 246▸ A  L  D  T  L  F  I  M  G  M  K  T  E  F  Q  E  A  K  S  W  I  K  K  Y  L  D  F  N
 819  tgtgaatgctgaagtttctgtttttgaagtcaacatacgcttcgtcgtggactgctgcagctctactatttgtccggagag
 273▸ V  N  A  E  V  S  V  F  E  V  N  I  R  F  V  G  G  L  L  S  A  Y  Y  L  S  G  E
 901  gagatatttcgaaagaaagtggactggaactgggtaaaattgctacctgcatttcatactccctgaatacctggcat
 301▸ E  I  F  R  K  K  A  V  E  L  G  V  K  L  L  P  A  F  H  T  P  S  G  I  P  W  A
 983  tcgtgaatatgaaagtgggatcggaggaactggctgccctggcctctggaggcagcagtatcctggccgaatttgaactct
 328▸ L  L  N  M  K  S  G  I  G  R  N  W  P  W  A  S  G  G  S  S  I  L  A  E  F  G  T  L
1065  gcatttagagtttatgcacttgtccacttatcagggagaccagtctttgccgaaaaggttatgaaaattcgaacagtgttg
 355▸ H  L  E  F  M  H  L  S  H  L  S  G  D  P  V  F  A  E  K  V  M  K  I  R  T  V  L
1147  aacaactggacaaaccagaaggcctttatcctacctatctgaaccccagtagtgacagtgggtcaacatcatgtgtcgg
 383▸ N  K  L  D  K  P  E  G  L  Y  P  N  Y  L  N  P  S  S  G  Q  W  G  Q  H  H  V  S
1229  ttgggggacttggagcagcttttctgttcaggccatcagatggctcaagtgttaatgtctgcaagacagatctcgaagccaagaa
 410▸ V  G  G  L  G  D  S  F  Y  E  Y  L  L  K  A  W  L  M  S  D  K  T  D  L  E  A  K  K
1311  gatgtattttgatgctgttcaggccatcgaacacagtgggctgcacttgcagggaggcatgtttgcactgggcagatggagctc
 437▸ M  Y  F  D  A  V  Q  A  I  E  T  H  L  I  R  K  S  S  G  G  L  T  Y  I  A  E  W
1393  aagggggcctcctggaacacaagatgggccacctgaactcggactgaattgccgactctgtcatgaatcttataatcgtacatgt
 465▸ K  G  G  L  L  E  H  K  M  G  H  L  T  C  F  A  G  G  M  F  A  L  G  A  D  G  A
1475  cggaagccgggcccacactacctgaactcggattgcgttcgatttgatggcggtgtggaagcttgccacgaggcaaaatgaaaatgtattacatctta
 492▸ P  E  A  R  A  Q  H  Y  L  E  L  G  A  E  I  A  R  T  C  H  E  S  Y  N  R  T  Y  V
1557  gaagttgggaccggaagcgttcgatttgatggcggtgtggaagcttgccacgaggcaaaatgaaaatgtattacatctta
 519▸ K  L  G  P  E  A  F  R  F  D  G  G  V  E  A  I  A  T  R  Q  N  E  K  Y  Y  I  L
1639  cggcccgaggtcatcgagacatacatgtacatgtggcgactgactcacgaccccaagtacaggacctgggcctgggagttgagagttatga
 547▸ R  P  E  V  I  E  T  Y  M  Y  M  W  R  L  T  H  D  P  K  Y  R  T  W  A  W  E  A
1721  tggggctctagaaagtcactgcagggtgaacggagcactcaggcttacattgcccgtgagagttatga
 574▸ V  E  A  L  E  S  H  C  R  V  N  G  G  Y  S  G  L  R  D  V  Y  I  A  R  E  S  Y  D
1803  cgatgtccagcaaggttcttcctgctggagactttcttaaccgacgaactgaagtatttgacttgcgatgatgaccttccta
 601▸ D  V  Q  Q  S  F  F  L  A  E  T  L  K  Y  L  Y  L  I  F  S  D  D  D  L  L  P  L
1885  gaacactggatcttcaacaccgaggctcatccttcctatactccgtgaacagaggaggaaattgatgcagaagaaatga
 629▸ E  H  W  I  F  N  T  E  A  H  P  F  P  I  L  R  E  Q  K  K  E  I  D  G  K  E  K
```

FIG. 3 cont.

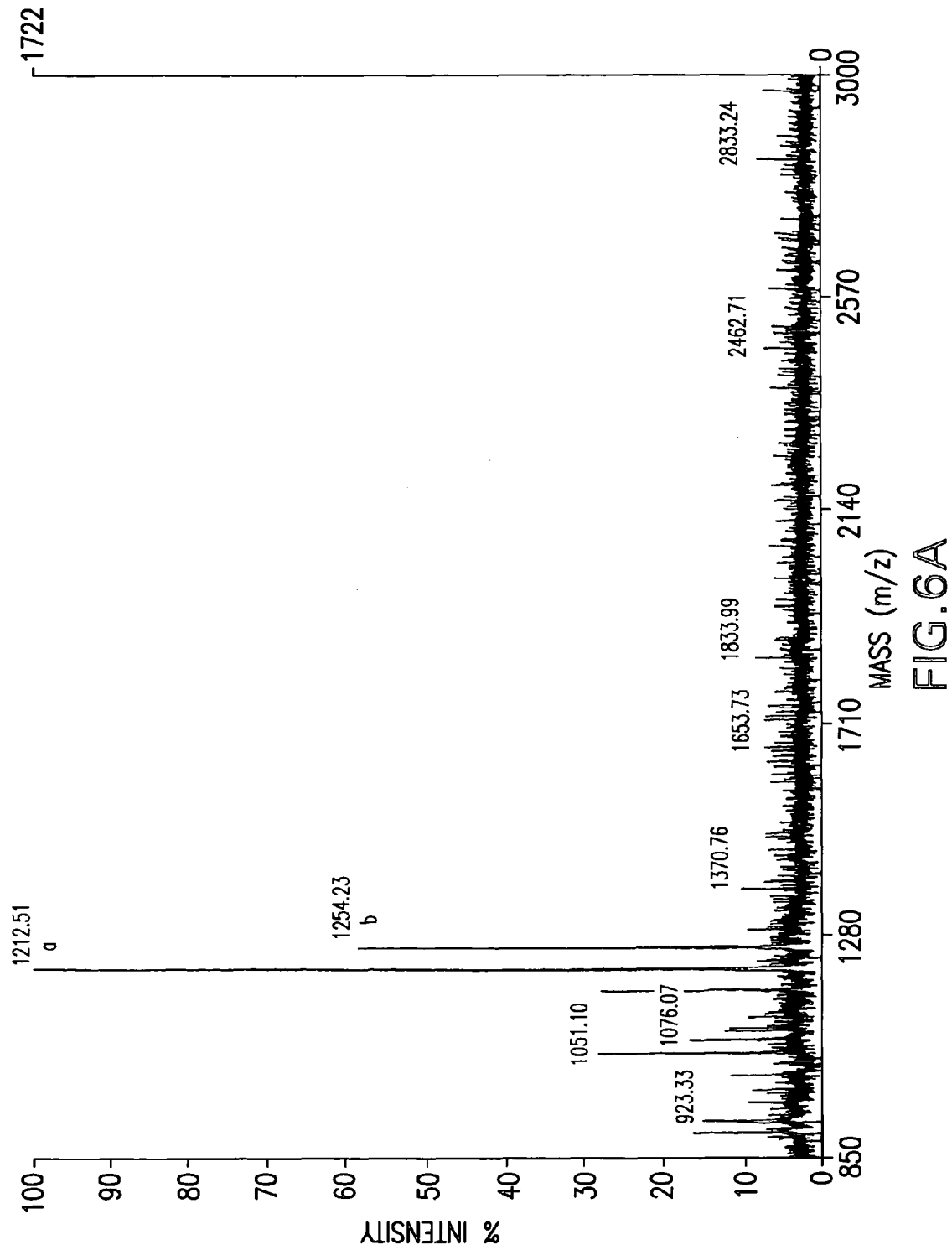

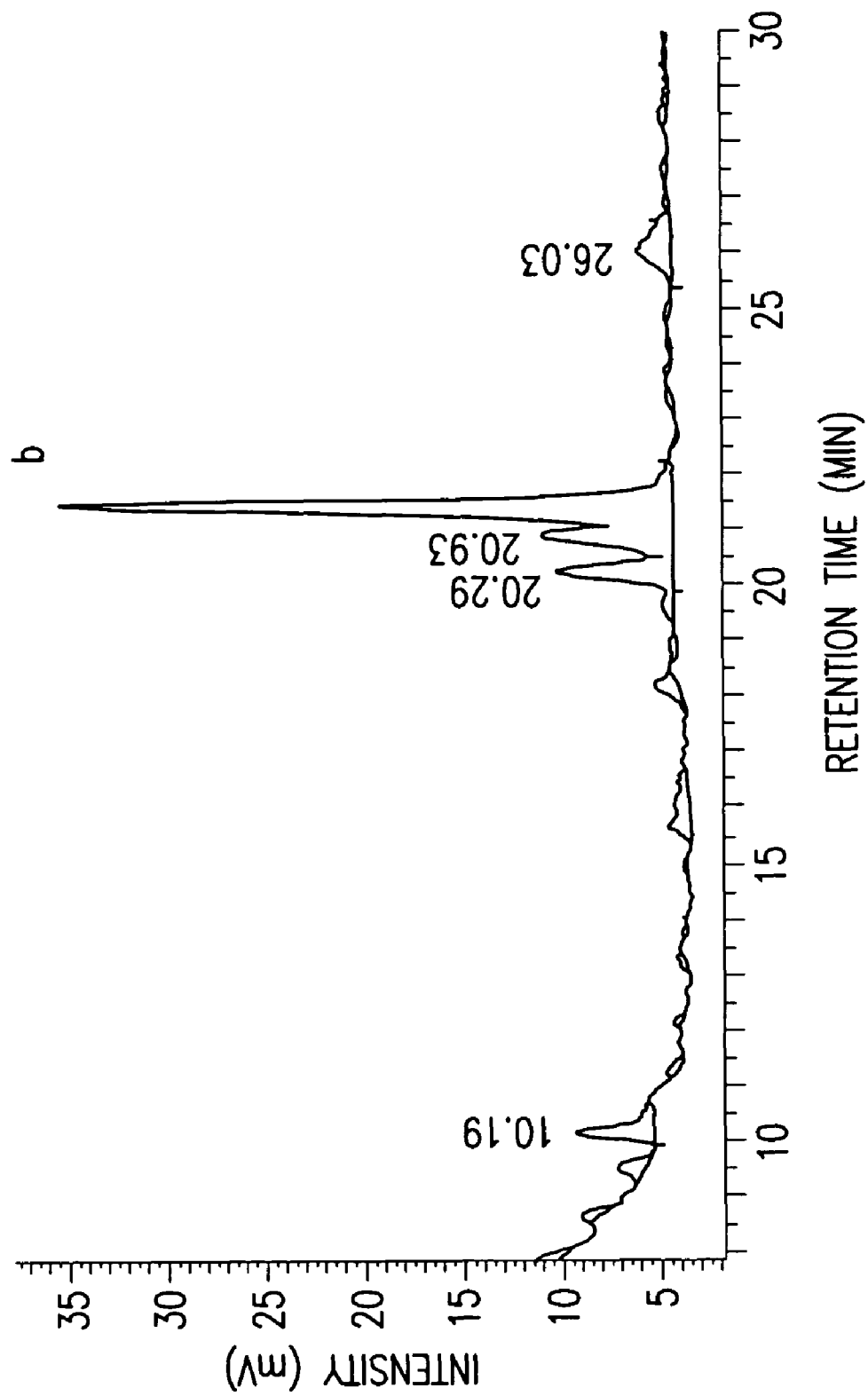

US 8,067,551 B2

COMBINATORIAL DNA LIBRARY FOR PRODUCING MODIFIED N-GLYCANS IN LOWER EUKARYOTES

CROSS-REFERENCE TO RELATED APPLICATIONS

This application is a continuation application of U.S. application Ser. No. 10/371,877, filed Feb. 20, 2003 now U.S. Pat. No. 7,449,308 which is a continuation-in-part of U.S. application Ser. No. 09/892,591, filed Jun. 27, 2001, now issued as U.S. Pat. No. 7,029,872, which claims benefit of U.S. Provisional Application Ser. No. 60/214,358, filed Jun. 28, 2000, U.S. Provisional Application No. 60/215,638, filed Jun. 30, 2000, and U.S. Provisional Application No. 60/279,997, filed Mar. 30, 2001; each of which is incorporated herein by reference in its entirety.

STATEMENT AS TO FEDERALLY SPONSORED RESEARCH

This invention was funded, at least in part, with a government grant from the National Institutes of Health (NHI Phase I Grant No. 1R43GM66690-1) and a grant from the Department of Commerce, NIST-ATP Cooperative Agreement Number 70NANB2H3046. The United States Government may therefore have certain rights in this invention.

FIELD OF THE INVENTION

The present invention is directed to methods and compositions by which non-human eukaryotic host cells, such as fungi or other eukaryotic cells, can be genetically modified to produce glycosylated proteins (glycoproteins) having patterns of glycosylation similar to those of glycoproteins produced by animal cells, especially human cells, which are useful as human or animal therapeutic agents.

BACKGROUND OF THE INVENTION

Glycosylation Pathways in Humans and Lower Eukaryotes

After DNA is transcribed and translated into a protein, further post-translational processing involves the attachment of sugar residues, a process known as glycosylation. Different organisms produce different glycosylation enzymes (glycosyltransferases and glycosidases), and have different substrates (nucleotide sugars) available, so that the glycosylation patterns as well as composition of the individual oligosaccharides, even of the same protein, will be different depending on the host system in which the particular protein is being expressed. Bacteria typically do not glycosylate proteins, and if so only in a very unspecific manner (Moens and Vanderleyden, 1997 Arch Microbiol 168(3):169-175). Lower eukaryotes such as filamentous fungi and yeast add primarily mannose and mannosylphosphate sugars. The resulting glycan is known as a "high-mannose" type glycan or a mannan. Plant cells and insect cells (such as Sf9 cells) glycosylate proteins in yet another way. By contrast, in higher eukaryotes such as humans, the nascent oligosaccharide side chain may be trimmed to remove several mannose residues and elongated with additional sugar residues that typically are not found in the N-glycans of lower eukaryotes. See, e.g., R. K. Bretthauer, et al. Biotechnology and Applied Biochemistry, 1999, 30, 193-200; W. Martinet, et al. Biotechnology Letters, 1998, 20, 1171-1177; S. Weikert, et al. Nature Biotechnology, 1999, 17, 1116-1121; M. Malissard, et al. Biochemical and Biophysical Research Communications, 2000, 267, 169-173; Jarvis, et al., Current Opinion in Biotechnology, 1998, 9:528-533; and M. Takeuchi, 1 Trends in Glycoscience and Glycotechnology, 1997, 9, S29-S35.

Synthesis of a mammalian-type oligosaccharide structure begins with a set of sequential reactions in the course of which sugar residues are added and removed while the protein moves along the secretory pathway in the host organism. The enzymes which reside along the glycosylation pathway of the host organism or cell determine the resulting glycosylation patterns of secreted proteins. Thus, the resulting glycosylation pattern of proteins expressed in lower eukaryotic host cells differs substantially from the glycosylation pattern of proteins expressed in higher eukaryotes such as humans and other mammals (Bretthauer, 1999). The structure of a typical fungal N-glycan is shown in FIG. 1A.

The early steps of human glycosylation can be divided into at least two different phases: (i) lipid-linked $Glc_3Man_9GlcNAc_2$ oligosaccharides are assembled by a sequential set of reactions at the membrane of the endoplasmic reticulum (ER) and (ii) the transfer of this oligosaccharide from the lipid anchor dolichyl pyrophosphate onto de novo synthesized protein. The site of the specific transfer is defined by an asparagine (Asn) residue in the sequence Asn-Xaa-Ser/Thr where Xaa can be any amino acid except proline (Gavel, 1990). Further processing by glucosidases and mannosidases occurs in the ER before the nascent glycoprotein is transferred to the early Golgi apparatus, where additional mannose residues are removed by Golgi specific alpha ($\alpha$)-1,2-mannosidases. Processing continues as the protein proceeds through the Golgi. In the medial Golgi, a number of modifying enzymes, including N-acetylglucosaminyl Transferases (GnTI, GnTII, GnTIII, GnTIV and GnTV), mannosidase II and fucosyltransferases, add and remove specific sugar residues. Finally, in the trans-Golgi, galactosyltransferases (GalT) and sialyltransferases (ST) produce a glycoprotein structure that is released from the Golgi. It is this structure, characterized by bi-, tri- and tetra-antennary structures, containing galactose, fucose, N-acetylglucosamine and a high degree of terminal sialic acid, that gives glycoproteins their human characteristics. The structure of a typical human N-glycan is shown in FIG. 1B. In nearly all eukaryotes, glycoproteins are derived from a common lipid-linked oligosaccharide precursor $Glc_3Man_9GlcNAc_2$-dolichol-pyrophosphate. Within the endoplasmic reticulum, synthesis and processing of dolichol pyrophosphate bound oligosaccharides are identical between all known eukaryotes. However, further processing of the core oligosaccharide by fungal cells, e.g., yeast, once it has been transferred to a peptide leaving the ER and entering the Golgi, differs significantly from humans as it moves along the secretory pathway and involves the addition of several mannose sugars.

In yeast, these steps are catalyzed by Golgi residing mannosyl-transferases, like Och1p, Mnt1p and Mnn1p, which sequentially add mannose sugars to the core oligosaccharide. The resulting structure is undesirable for the production of human-like proteins and it is thus desirable to reduce or eliminate mannosyltransferase activity. Mutants of S. cerevisiae, deficient in mannosyl-transferase activity (for example och1 or mnn9 mutants) have been shown to be non-lethal and display reduced mannose content in the oligosaccharide of yeast glycoproteins. Other oligosaccharide processing enzymes, such as mannosylphosphate transferase, may also have to be eliminated depending on the host's particular endogenous glycosylation pattern.

Sugar Nucleotide Precursors

The N-glycans of animal glycoproteins typically include galactose, fucose, and terminal sialic acid. These sugars are not found on glycoproteins produced in yeast and filamentous fungi. In humans, the full range of nucleotide sugar precursors (e.g. UDP-N-acetylglucosamine, UDP-N-acetylgalactosamine, CMP-N-acetylneuraminic acid, UDP-galactose, GDP-fucose, etc.) are synthesized in the cytosol and transported into the Golgi, where they are attached to the core oligosaccharide by glycosyltransferases. (Sommers and Hirschberg, 1981 *J. Cell Biol.* 91(2): A406-A406; Sommers and Hirschberg 1982 *J. Biol. Chem.* 257(18): 811-817; Perez and Hirschberg 1987 *Methods in Enzymology* 138: 709-715).

Glycosyl transfer reactions typically yield a side product which is a nucleoside diphosphate or monophosphate. While monophosphates can be directly exported in exchange for nucleoside triphosphate sugars by an antiport mechanism, diphosphonucleosides (e.g. GDP) have to be cleaved by phosphatases (e.g. GDPase) to yield nucleoside monophosphates and inorganic phosphate prior to being exported. This reaction is important for efficient glycosylation; for example, GDPase from *Saccharomyces cerevisiae* (*S. cerevisiae*) has been found to be necessary for mannosylation. However that GDPase has 90% reduced activity toward UDP (Berninsone et al., 1994 *J. Biol. Chem.* 269(1):207-211). Lower eukaryotes typically lack UDP-specific diphosphatase activity in the Golgi since they do not utilize UDP-sugar precursors for Golgi-based glycoprotein synthesis. *Schizosaccharomyces pombe*, a yeast found to add galactose residues to cell wall polysaccharides (from UDP-galactose) has been found to have specific UDPase activity, indicating the potential requirement for such an enzyme (Beminsone et al., 1994). UDP is known to be a potent inhibitor of glycosyltransferases and the removal of this glycosylation side product may be important to prevent glycosyl-transferase inhibition in the lumen of the Golgi (Khatara et al., 1974). See Beminsone, P., et al. 1995. *J. Biol. Chem.* 270(24): 14564-14567; Beaudet, L., et al. 1998 *Abc Transporters: Biochemical, Cellular, and Molecular Aspects.* 292: 397-413.

Sequential Processing of N-Glycans by Compartmentalized Enzyme Activities

Sugar transferases and glycosidases (e.g., mannosidases) line the inner (luminal) surface of the ER and Golgi apparatus and thereby provide a "catalytic" surface that allows for the sequential processing of glycoproteins as they proceed through the ER and Golgi network. The multiple compartments of the cis, medial, and trans Golgi and the trans-Golgi Network (TGN), provide the different localities in which the ordered sequence of glycosylation reactions can take place. As a glycoprotein proceeds from synthesis in the ER to full maturation in the late Golgi or TGN, it is sequentially exposed to different glycosidases, mannosidases and glycosyltransferases such that a specific carbohydrate structure may be synthesized. Much work has been dedicated to revealing the exact mechanism by which these enzymes are retained and anchored to their respective organelle. The evolving picture is complex but evidence suggests that stem region, membrane spanning region and cytoplasmic tail, individually or in concert, direct enzymes to the membrane of individual organelles and thereby localize the associated catalytic domain to that locus (see, e.g., Gleeson, P. A. (1998) *Histochem. Cell Biol.* 109, 517-532).

In some cases, these specific interactions were found to function across species. For example, the membrane spanning domain of α2,6-ST from rats, an enzyme known to localize in the trans-Golgi of the animal, was shown to also localize a reporter gene (invertase) in the yeast Golgi (Schwientek, 1995). However, the very same membrane spanning domain as part of a full-length α2,6-ST was retained in the ER and not further transported to the Golgi of yeast (Krezdorn, 1994). A full length GalT from humans was not even synthesized in yeast, despite demonstrably high transcription levels. In contrast, the transmembrane region of the same human GalT fused to an invertase reporter was able to direct localization to the yeast Golgi, albeit it at low production levels. Schwientek and co-workers have shown that fusing 28 amino acids of a yeast mannosyltransferase (MNT1), a region containing a cytoplasmic tail, a transmembrane region and eight amino acids of the stem region, to the catalytic domain of human GalT are sufficient for Golgi localization of an active GalT. Other galactosyltransferases appear to rely on interactions with enzymes resident in particular organelles because, after removal of their transmembrane region, they are still able to localize properly.

Improper localization of a glycosylation enzyme may prevent proper functioning of the enzyme in the pathway. For example, *Aspergillus nidulans*, which has numerous α-1,2-mannosidases (Eades and Hintz, 2000 *Gene* 255(1):25-34), does not add GlcNAc to $Man_5GlcNAc_2$ when transformed with the rabbit GnTI gene, despite a high overall level of GnTI activity (Kalsner et al., 1995). GnTI, although actively expressed, may be incorrectly localized such that the enzyme is not in contact with both of its substrates: UDP-GlcNAc and a productive $Man_5GlcNAc_2$ substrate (not all $Man_5GlcNAc_2$ structures are productive; see below). Alternatively, the host organism may not provide an adequate level of UDP-GlcNAc in the Golgi or the enzyme may be properly localized but nevertheless inactive in its new environment. In addition, $Man_5GlcNAc_2$ structures present in the host cell may differ in structure from $Man_5GlcNAc_2$ found in mammals. Maras and coworkers found that about one third of the N-glycans from cellobiohydrolase I (CBHI) obtained from *T. reesei* can be trimmed to $Man_5GlcNAc_2$ by *A. saitoi* 1,2 mannosidase in vitro. Fewer than 1% of those N-glycans, however, could serve as a productive substrate for GnTI. The mere presence of $Man_5GlcNAc_2$, therefore, does not assure that further processing to $Man_5GlcNAc_2$ can be achieved. It is formation of a productive, GnTI-reactive $Man_5GlcNAc_2$ structure that is required. Although $Man_5GlcNAc_2$ could be produced in the cell (about 27 mol %), only a small fraction could be converted to $Man_5GlcNAc_2$ (less than about 5%, see Chiba WO 01/14522).

To date, there is no reliable way of predicting whether a particular heterologously expressed glycosyltransferase or mannosidase in a lower eukaryote will be (1), sufficiently translated (2), catalytically active or (3) located to the proper organelle within the secretory pathway. Because all three of these are necessary to affect glycosylation patterns in lower eukaryotes, a systematic scheme to achieve the desired catalytic function and proper retention of enzymes in the absence of predictive tools, which are currently not available, would be desirable.

Production of Therapeutic Glycoproteins

A significant number of proteins isolated from humans or animals are post-translationally modified, with glycosylation being one of the most significant modifications. An estimated 70% of all therapeutic proteins are glycosylated and thus currently rely on a production system (i.e., host cell) that is able to glycosylate in a manner similar to humans. Several studies have shown that glycosylation plays an important role in determining the (1) immunogenicity, (2) pharmacokinetic properties, (3) trafficking, and (4) efficacy of therapeutic proteins. It is thus not surprising that substantial efforts by the pharmaceutical industry have been directed at developing processes to obtain glycoproteins that are as "humanoid" or "human-like" as possible. To date, most glycoproteins are made in a mammalian host system. This may involve the genetic engineering of such mammalian cells to enhance the degree of sialylation (i.e., terminal addition of sialic acid) of proteins expressed by the cells, which is known to improve pharmacokinetic properties of such proteins. Alternatively, one may improve the degree of sialylation by in vitro addition of such sugars using known glycosyltransferases and their respective nucleotide sugars (e.g., 2,3-sialyltransferase and CMP-sialic acid).

While most higher eukaryotes carry out glycosylation reactions that are similar to those found in humans, recombinant human proteins expressed in the above mentioned host systems invariably differ from their "natural" human counterpart (Raju, 2000). Extensive development work has thus been directed at finding ways to improve the "human character" of proteins made in these expression systems. This includes the optimization of fermentation conditions and the genetic modification of protein expression hosts by introducing genes encoding enzymes involved in the formation of human-like glycoforms (Werner, 1998; Weikert, 1999; Andersen, 1994; Yang, 2000). Inherent problems associated with all mammalian expression systems have not been solved.

Fermentation processes based on mammalian cell culture (e.g., CHO, murine, or human cells), for example, tend to be very slow (fermentation times in excess of one week are not uncommon), often yield low product titers, require expensive nutrients and cofactors (e.g., bovine fetal serum), are limited by programmed cell death (apoptosis), and often do not enable expression of particular therapeutically valuable proteins. More importantly, mammalian cells are susceptible to viruses that have the potential to be human pathogens and stringent quality controls are required to assure product safety. This is of particular concern as many such processes require the addition of complex and temperature sensitive media components that are derived from animals (e.g., bovine calf serum), which may carry agents pathogenic to humans such as bovine spongiform encephalopathy (BSE) prions or viruses. Moreover, the production of therapeutic compounds is preferably carried out in a well-controlled sterile environment. An animal farm, no matter how cleanly kept, does not constitute such an environment, thus constituting an additional problem in the use of transgenic animals for manufacturing high volume therapeutic proteins.

Most, if not all, currently produced therapeutic glycoproteins are therefore expressed in mammalian cells and much effort has been directed at improving (i.e., "humanizing") the glycosylation pattern of these recombinant proteins. Changes in medium composition as well as the co-expression of genes encoding enzymes involved in human glycosylation have been successfully employed (see, for example, Weikert, 1999).

Glycoprotein Production Using Eukaryotic Microorganisms

The lack of a suitable mammalian expression system is a significant obstacle to the low-cost and safe production of recombinant human glycoproteins for therapeutic applications. It would be desirable to produce recombinant proteins similar to their mammalian, e.g., human, counterparts in lower eukaryotes (fungi and yeast). Production of glycoproteins via the fermentation of microorganisms would offer numerous advantages over existing systems. For example, fermentation-based processes may offer (a) rapid production of high concentrations of protein; (b) the ability to use sterile, well-controlled production conditions; (c) the ability to use simple, chemically defined (and protein-free) growth media; (d) ease of genetic manipulation; (e) the absence of contaminating human or animal pathogens such as viruses; (f) the ability to express a wide variety of proteins, including those poorly expressed in cell culture owing to toxicity etc.; and (g) ease of protein recovery (e.g. via secretion into the medium). In addition, fermentation facilities for yeast and fungi are generally far less costly to construct than cell culture facilities. Although the core oligosaccharide structure transferred to a protein in the endoplasmic reticulum is basically identical in mammals and lower eukaryotes, substantial differences have been found in the subsequent processing reactions which occur in the Golgi apparatus of fungi and mammals. In fact, even amongst different lower eukaryotes there exist a great variety of glycosylation structures. This has historically prevented the use of lower eukaryotes as hosts for the production of recombinant human glycoproteins despite otherwise notable advantages over mammalian expression systems.

Therapeutic glycoproteins produced in a microorganism host such as yeast utilizing the endogenous host glycosylation pathway differ structurally from those produced in mammalian cells and typically show greatly reduced therapeutic efficacy. Such glycoproteins are typically immunogenic in humans and show a reduced half-life (and thus bioactivity) in vivo after administration (Takeuchi, 1997). Specific receptors in humans and animals (i.e., macrophage mannose receptors) can recognize terminal mannose residues and promote the rapid clearance of the foreign glycoprotein from the bloodstream. Additional adverse effects may include changes in protein folding, solubility, susceptibility to proteases, trafficking, transport, compartmentalization, secretion, recognition by other proteins or factors, antigenicity, or allergenicity.

Yeast and filamentous fungi have both been successfully used for the production of recombinant proteins, both intracellular and secreted (Cereghino, J. L. and J. M. Cregg 2000 *FEMS Microbiology Reviews* 24(1): 45-66; Harkki, A., et al. 1989 *Bio-Technology* 7(6): 596; Berka, R. M., et al. 1992 *Abstr. Papers Amer. Chem. Soc.* 203: 121-BIOT; Svetina, M., et al. 2000 *J. Biotechnol.* 76(2-3): 245-251). Various yeasts, such as *K. lactis, Pichia pastoris, Pichia methanolica*, and *Hansenula polymorpha*, have played particularly important roles as eukaryotic expression systems because they are able to grow to high cell densities and secrete large quantities of recombinant protein. Likewise, filamentous fungi, such as *Aspergillus niger, Fusarium* sp, *Neurospora crassa* and others, have been used to efficiently produce glycoproteins at the industrial scale. However, as noted above, glycoproteins expressed in any of these eukaryotic microorganisms differ substantially in N-glycan structure from those in animals. This has prevented the use of yeast or filamentous fungi as hosts for the production of many therapeutic glycoproteins.

Although glycosylation in yeast and fungi is very different than in humans, some common elements are shared. The first step, the transfer of the core oligosaccharide structure to the nascent protein, is highly conserved in all eukaryotes including yeast, fungi, plants and humans (compare FIGS. 1A and 1B). Subsequent processing of the core oligosaccharide, however, differs significantly in yeast and involves the addition of several mannose sugars. This step is catalyzed by mannosyltransferases residing in the Golgi (e.g. OCH1, MNT1, MNN1, etc.), which sequentially add mannose sugars to the core oligosaccharide. The resulting structure is undesirable for the production of humanoid proteins and it is thus desirable to reduce or eliminate mannosyltransferase activity. Mutants of *S. cerevisiae* deficient in mannosyltransferase activity (e.g. och1 or mnn9 mutants) have shown to be non-lethal and display a reduced mannose content in the oligosaccharide of yeast glycoproteins. Other oligosaccharide processing enzymes, such as mannosylphosphate transferase, may also have to be eliminated depending on the host's particular endogenous glycosylation pattern. After reducing undesired endogenous glycosylation reactions, the formation of complex N-glycans has to be engineered into the host system. This requires the stable expression of several enzymes and sugar-nucleotide transporters. Moreover, one has to localize these enzymes so that a sequential processing of the maturing glycosylation structure is ensured.

Several efforts have been made to modify the glycosylation pathways of eukaryotic microorganisms to provide glycoproteins more suitable for use as mammalian therapeutic agents. For example, several glycosyltransferases have been separately cloned and expressed in S. cerevisiae (GalT, GnTI), Aspergillus nidulans (GnTI) and other fungi (Yoshida et al., 1999, Kalsner et al., 1995 Glycoconj. J. 12(3):360-370, Schwientek et al., 1995). However, N-glycans resembling those made in human cells were not obtained.

Yeasts produce a variety of mannosyltransferases (e.g., 1,3-mannosyltransferases such as MNN1 in S. cerevisiae; Graham and Emr, 1991 J. Cell. Biol. 114(2):207-218), 1,2-mannosyltransferases (e.g. KTR/KRE family from S. cerevisiae), 1,6-mannosyltransferases (e.g., OCH1 from S. cerevisiae), mannosylphosphate transferases and their regulators (e.g., MNN4 and MNN6 from S. cerevisiae) and additional enzymes that are involved in endogenous glycosylation reactions. Many of these genes have been deleted individually giving rise to viable organisms having altered glycosylation profiles. Examples are shown in Table 1.

Although Japanese Patent Application Publication No. 8-336387 discloses methods to obtain an och1 mutant of P. pastoris displaying a reduced mannosylation phenotype, it provides no data on whether the initiating 1,6 mannosyltransferase activity presumed to be encoded by OCH1 is reduced or eliminated. It is well-established in the field of fungal genetics that homologs of genes often do not play the same role in their respective host organism. For example, the Neurospora rca-1 gene complements an Aspergillus flbD sporulation mutant but has no identifiable role in Neurospora sporulation. Shen, W. C. et al., Genetics 1998; 148(3):1031-41. More recently, Contreras (WO 02/00856 A2) shows that, in an och1 mutant of P. pastoris, at least 50% of the cell wall glycans cannot be trimmed to $Man_5GlcNAc_2$ with a Trichoderma reesei α-1,2-mannosidase (see FIG. 11 of WO 02/00856 A2). As the wild-type displays a very similar glycosylation pattern (FIG. 10, Panel 2 of WO 02/00856 A2), it appears that the OCH1 gene of P. pastoris may not encode the initiating 1,6-mannosyltransferase activity and is thus different from its genetic homolog in S. cerevisiae. Thus, to date, there is no evidence that initiating α-1,6-mannosyltransferase activity is eliminated in och1 mutants of P. pastoris, which further supports the notion that the glycosylation pathways of S. cerevisiae and P. pastoris are significantly different.

Martinet et al. (Biotechnol. Lett. 1998, 20(12), 1171-1177) reported the expression of α-1,2-mannosidase from T. reesei

TABLE 1

Examples of yeast strains having altered mannosylation

| Strain | N-glycan (wild type) | Mutation | N-glycan (mutant) | Reference |
|---|---|---|---|---|
| S. pombe | $Man_{>9}GlcNAc_2$ | OCH1 | $Man_8GlcNAc_2$ | Yoko-o et al., 2001 FEBS Lett. 489(1): 75-80 |
| S. cerevisiae | $Man_{>9}GlcNAc_2$ | OCH1/MNN1 | $Man_8GlcNAc_2$ | Nakanishi-Shindo et al,. 1993 J. Biol. Chem. 268(35): 26338-26345 |
| S. cerevisiae | $Man_{>9}GlcNAc_2$ | OCH1/MNN1/MNN4 | $Man_8GlcNAc_2$ | Chiba et al., 1998 J. Biol. Chem. 273, 26298-26304 |
| P. pastoris | Hyperglycosylated | OCH1 (complete deletion) | Not hyperglycosylated | Welfide, Japanese Application Publication No. 8-336387 |
| P. pastoris | $Man_{>8}GlcNAc_2$ | OCH1 (disruption) | $Man_{>8}GlcNAc_2$ | Contreras et al. WO 02/00856 A2 |

Japanese Patent Application Publication No. 8-336387 discloses the deletion of an OCH1 homolog in Pichia pastoris. In S. cerevisiae, OCH1 encodes a 1,6-mannosyltransferase, which adds a mannose to the glycan structure $Man_8GlcNAc_2$ to yield $Man_9GlcNAc_2$. The $Man_9GlcNAc_2$ structure, which contains three 1,6 mannose residues, is then a substrate for further 1,2-, 1,6-, and 1,3-mannosyltransferases in vivo, leading to the hypermannosylated glycoproteins that are characteristic for S. cerevisiae and which typically may have 30-40 mannose residues per N-glycan. Because the Och1p initiates the transfer of 1,6 mannose to the $Man_8GlcNAc_2$ core, it is often referred to as the "initiating 1,6 mannosyltransferase" to distinguish it from other 1,6 mannosyltransferases acting later in the Golgi. In an och1 mnn1 mnn4 mutant strain of S. cerevisiae, proteins glycosylated with $Man_8GlcNAc_2$ accumulate and hypermannosylation does not occur. However, $Man_8GlcNAc_2$ is not a substrate for mammalian glycosyltransferases, such as human UDP-GlcNAc transferase I, and accordingly, the use of that mutant strain, in itself, is not useful for producing mammalian-like proteins, i.e., with complex or hybrid glycosylation patterns.

in P. pastoris. Some mannose trimming from the N-glycans of a model protein was observed. However, the model protein had no N-glycans with the structure $Man_5GlcNAc_2$, which would be necessary as an intermediate for the generation of complex N-glycans. Accordingly, that system is not useful for producing proteins with complex or hybrid glycosylation patterns.

Similarly, Chiba et al. (1998) expressed α-1,2-mannosidase from Aspergillus saitoi in the yeast Saccharomyces cerevisiae. A signal peptide sequence (His-Asp-Glu-Leu) (SEQ ID NO:5) was engineered into the exogenous mannosidase to promote its retention in the endoplasmic reticulum. In addition, the yeast host was a mutant lacking enzyme activities associated with hypermannosylation of proteins: 1,6-mannosyltransferase (och1); 1,3-mannosyltransferase (mnn1); and a regulator of mannosylphosphate transferase (mnn4). The N-glycans of the triple mutant host consisted primarily of the structure $Man_8GlcNAc_2$, rather than the high mannose forms found in wild-type S. cerevisiae. In the presence of the engineered mannosidase, the N-glycans of a model protein (carboxypeptidase Y) were trimmed to give a mixture consisting of 27 mole % Man$_5$GlcNAc$_2$, 22 mole % Man$_6$GlcNAc$_2$, 22 mole % Man$_7$GlcNAc$_2$, and 29 mole % Man$_8$GlcNAc$_2$. Trimming of cell wall glycoproteins was less efficient, with only 10 mole % of the N-glycans having the desired Man$_5$GlcNAc$_2$ structure.

Even if all the Man$_5$GlcNAc$_2$ glycans were the correct Man$_5$GlcNAc$_2$ form that can be converted to GlcNAcMan$_5$GlcNAc$_2$ by GnTI, the above system would not be efficient for the production of proteins having human-like glycosylation patterns. If several glycosylation sites are present in a desired protein, the probability (P) of obtaining such a protein in a correct form follows the relationship P=(F)$^n$, where n equals the number of glycosylation sites, and F equals the fraction of desired glycoforms. A glycoprotein with three glycosylation sites would have a 0.1% chance of providing the appropriate precursors for complex and hybrid N-glycan processing on all of its glycosylation sites. Thus, using the system of Chiba to make a glycoprotein having a single N-glycosylation site, at least 73 mole % would have an incorrect structure. For a glycoprotein having two or three N-glycosylation sites, at least 93 or 98 mole % would have an incorrect structure, respectively. Such low efficiencies of conversion are unsatisfactory for the production of therapeutic agents, particularly as the separation of proteins having different glycoforms is typically costly and difficult.

Chiba et al. (WO 01/14522) have shown high levels of Man$_5$GlcNAc$_2$ structures on recombinant fibroblast growth factor (FGF), a secreted soluble glycoprotein produced in *S. cerevisiae*. It is not clear, however, that the detected Man$_5$GlcNAc$_2$ was produced inside the host cell (i.e. in vivo) because the α-1,2 mannosidase was targeted by fusion with an HDEL (SEQ ID NO:5) localization tag, a mechanism, which is known to be leaky (Pelham H. R. (1998) *EMBO J.* 7, 913-918). It is more likely that FGF was secreted into the medium, where it was then processed by α-1,2 mannosidase which had escaped the HDEL (SEQ ID NO:5) retrieval mechanism and leaked into the medium. As mentioned above, an intracellular protein (CPY), expressed in the same strain, contained mostly glycans (more than 73%) that were Man$_6$GlcNAc$_2$ and larger. The majority of the Man$_5$GlcNAc$_2$ structures on FGF are, thus, likely to have been produced ex vivo. It is further unclear whether the Man$_5$GlcNAc$_2$ structures that were produced were productive substrates for GnTI.

As the above work demonstrates, one can trim Man$_8$GlcNAc$_2$ structures to a Man$_5$GlcNAc$_2$ isomer in *S. cerevisiae*, although high efficiency trimming greater than 50% in vivo has yet to be determined, by engineering a fungal mannosidase from *A. saitoi* into the endoplasmic reticulum (ER). The shortcomings of this approach are two-fold: (1) it is not clear whether the Man$_5$GlcNAc$_2$ structures formed are in fact formed in vivo (rather than having been secreted and further modified by mannosidases outside the cell); and (2) it is not clear whether any Man$_5$GlcNAc$_2$ structures formed, if in fact formed in vivo, are the correct isoform to be a productive substrate for subsequent N-glycan modification by GlcNAc transferase I (Maras et al., 1997, *Eur. J. Biochem.* 249, 701-707).

With the objective of providing a more human-like glycoprotein derived from a fungal host, U.S. Pat. No. 5,834,251 discloses a method for producing a hybrid glycoprotein derived from *Trichoderma reseei*. A hybrid N-glycan has only mannose residues on the Manα1-6 arm of the core mannose structure and one or two complex antennae on the Manα1-3 arm. While this structure has utility, the method has the disadvantage that numerous enzymatic steps must be performed in vitro, which is costly and time-consuming. Isolated enzymes are expensive to prepare and need costly substrates (e.g. UDP-GlcNAc). The method also does not allow for the production of complex glycans on a desired protein.

Intracellular Mannosidase Activity Involved in N-Glycan Trimming

Alpha-1,2-mannosidase activity is required for the trimming of Man$_8$GlcNAc$_2$ to form Man$_5$GlcNAc$_2$, which is a major intermediate for complex N-glycan formation in mammals. Previous work has shown that truncated murine, fungal and human α-1,2-mannosidase can be expressed in the methylotropic yeast *P. pastoris* and display Man$_8$GlcNAc$_2$ to Man$_5$GlcNAc$_2$ trimming activity (Lal et al., *Glycobiology* 1998 October; 8(10):981-95; Tremblay et al., *Glycobiology* 1998 June; 8(6):585-95, Callewaert et al., 2001). However, to date, no reports exist that show the high level in vivo trimming of Man$_8$GlcNAc$_2$ to Man$_5$GlcNAc$_2$ on a secreted glycoprotein from *P. pastoris*.

While it is useful to engineer strains that are able to produce Man$_5$GlcNAc$_2$ as the primary N-glycan structure, any attempt to further modify these high mannose precursor structures to more closely resemble human glycans requires additional in vivo or in vitro steps. Methods to further humanize glycans from fungal and yeast sources in vitro are described in U.S. Pat. No. 5,834,251 (supra). As discussed above, however, if Man$_5$GlcNAc$_2$ is to be further humanized in vivo, one has to ensure that the generated Man$_5$GlcNAc$_2$ structures are, in fact, generated intracellularly and not the product of mannosidase activity in the medium. Complex N-glycan formation in yeast or fungi will require high levels of Man$_5$GlcNAc$_2$ to be generated within the cell because only intracellular Man$_5$GlcNAc$_2$ glycans can be further processed to hybrid and complex N-glycans in vivo. In addition, one has to demonstrate that the majority of Man$_5$GlcNAc$_2$ structures generated are in fact a substrate for GnTI and thus allow the formation of hybrid and complex N-glycans.

Moreover, the mere presence of an α-1,2-mannosidase in the cell does not, by itself, ensure proper intracellular trimming of Man$_8$GlcNAc$_2$ to Man$_5$GlcNAc$_2$. (See, e.g., Contreras et al. WO 02/00856 A2, in which an HDEL (SEQ ID NO:5) tagged mannosidase of *T. reesei* is localized primarily in the ER and co-expressed with an influenza haemagglutinin (HA) reporter protein on which virtually no Man$_5$GlcNAc$_2$ could be detected. See also Chiba et al., 1998 (supra), in which a chimeric α-1,2-mannosidase/Och1p transmembrane domain fusion localized in the ER, early Golgi and cytosol of *S. cerevisiae*, had no mannosidase trimming activity). Accordingly, mere localization of a mannosidase in the ER or Golgi is insufficient to ensure activity of the respective enzyme in that targeted organelle. (See also, Martinet et al. (1998), supra, showing that α-1,2-mannosidase from *T. reesei*, while localizing intracellularly, increased rather than decreased the extent of mannosylation). To date, there is no report that demonstrates the intracellular localization of an active heterologous α-1,2-mannosidase in either yeast or fungi using a transmembrane localization sequence.

Accordingly, the need exists for methods to produce glycoproteins characterized by a high intracellular Man$_5$GlcNAc$_2$ content which can be further processed into human-like glycoprotein structures in non-human eukaryotic host cells, and particularly in yeast and filamentous fungi.

SUMMARY OF THE INVENTION

Host cells and cell lines having genetically modified glycosylation pathways that allow them to carry out a sequence of enzymatic reactions which mimic the processing of glycoproteins in mammals, especially in humans, have been developed. Recombinant proteins expressed in these engineered hosts yield glycoproteins more similar, if not substantially identical, to their mammalian, e.g., human counterparts. Host cells of the invention, e.g., lower eukaryotic micro-organisms and other non-human, eukaryotic host cells grown in culture, are modified to produce N-glycans such as $Man_5GlcNAc_2$ or other structures produced along human glycosylation pathways. This is achieved using a combination of engineering and/or selection of strains which: do not express certain enzymes which create the undesirable structures characteristic of the fungal glycoproteins; which express heterologous enzymes selected either to have optimal activity under the conditions present in the host cell where activity is to be achieved; or combinations thereof; wherein the genetically engineered eukaryote expresses at least one heterologous enzyme activity required to produce a "human-like" glycoprotein. Host cells of the invention may be modified further by heterologous expression of one or more activities such as glycosyltransferases, sugar transporters and mannosidases, to become strains for the production of mammalian, e.g., human therapeutic glycoproteins.

The present invention thus provides a glycoprotein production method using (1) a lower eukaryotic host such as a unicellular or filamentous fungus, or (2) any non-human eukaryotic organism that has a different glycosylation pattern from humans, to modify the glycosylation composition and structures of the proteins made in a host organism ("host cell") so that they resemble more closely carbohydrate structures found in mammalian, e.g., human proteins. The process allows one to obtain an engineered host cell which can be used to express and target any desirable gene(s), e.g., one involved in glycosylation, by methods that are well-established in the scientific literature and generally known to the artisan in the field of protein expression. Host cells with modified oligosaccharides are created or selected. N-glycans made in the engineered host cells have a $Man_5GlcNAc_2$ core structure which may then be modified further by heterologous expression of one or more enzymes, e.g., glycosyltransferases, glycosidases, sugar transporters and mannosidases, to yield human-like glycoproteins. For the production of therapeutic proteins, this method may be adapted to engineer cell lines in which any desired glycosylation structure may be obtained.

Accordingly, in one embodiment, the invention provides a method for producing a human-like glycoprotein in a non-human eukaryotic host cell. The host cell of the invention is selected or engineered to be depleted in 1,6-mannosyl-transferase activities which would otherwise add mannose residues onto the N-glycan on a glycoprotein. One or more enzymes (enzymatic activities) are introduced into the host cell which enable the production of a $Man_5GlcNAc_2$ carbohydrate structure at a high yield, e.g., at least 30 mole percent. In a more preferred embodiment, at least 10% of the $Man_5GlcNAc_2$ produced within the host cell is a productive substrate for GnTI and thus for further glycosylation reactions in vivo and/or in vitro that produce a finished N-glycan that is similar or identical to that formed in mammals, especially humans.

In another embodiment, a nucleic acid molecule encoding one or more enzymes for production of a $Man_5GlcNAc_2$ carbohydrate structure is introduced into a host cell selected or engineered to be depleted in 1,6-mannosyltransferase activities. In one preferred embodiment, at least one enzyme introduced into the host cell is selected to have optimal activity at the pH of the subcellular location where the carbohydrate structure is produced. In another preferred embodiment, at least one enzyme is targeted to a host subcellular organelle where the enzyme will have optimal activity, e.g., by means of a chimeric protein comprising a cellular targeting signal peptide not normally associated with the enzyme.

The invention further provides isolated nucleic acid molecules and vectors comprising such molecules which encode an initiating α1,6-mannosyl-transferase activity isolated from P. pastoris or from K. lactis. These nucleic acid molecules comprise sequences that are homologous to the OCH1 gene in S. cerevisiae. These and homologous sequences are useful for constructing host cells which will not hypermannosylate the N-glycan of a glycoprotein.

In another embodiment, the host cell is engineered to express a heterologous glycosidase, e.g., by introducing into the host one or more nucleic acid molecules encoding the glycosidase. Preferably, a nucleic acid molecule encodes one or more mannosidase activities involved in the production of $Man_5GlcNAc_2$ from $Man_8GlcNAc_2$ or $Man_9GlcNAc_2$. In a preferred embodiment, at least one of the encoded mannosidase activities has a pH optimum within 1.4 pH units of the average pH optimum of other representative enzymes in the organelle in which the mannosidase activity is localized, or has optimal activity at a pH of between about 5.1 and about 8.0, preferably between about 5.5 and about 7.5. Preferably, the heterologous enzyme is targeted to the endoplasmic reticulum, the Golgi apparatus or the transport vesicles between ER and Golgi of the host organism, where it trims N-glycans such as $Man_8GlcNAc_2$ to yield high levels of $Man_5GlcNAc_2$. In one embodiment, the enzyme is targeted by forming a fusion protein between a catalytic domain of the enzyme and a cellular targeting signal peptide, e.g., by the in-frame ligation of a DNA fragment encoding a cellular targeting signal peptide with a DNA fragment encoding a glycosylation enzyme or catalytically active fragment thereof.

In yet another embodiment, the glycosylation pathway of a host is modified to express a sugar nucleotide transporter. In a preferred embodiment, a nucleotide diphosphatase enzyme is also expressed. The transporter and diphosphatase improve the efficiency of engineered glycosylation steps, by providing the appropriate substrates for the glycosylation enzymes in the appropriate compartments, reducing competitive product inhibition, and promoting the removal of nucleoside diphosphates.

The present invention also provides a combinatorial nucleic acid library useful for making fusion constructs which can target a desired protein or polypeptide fragment, e.g., an enzyme involved in glycosylation or a catalytic domain thereof, to a selected subcellular region of a host cell. In one preferred embodiment, the combinatorial nucleic acid library comprises (a) nucleic acid sequences encoding different cellular targeting signal peptides and (b) nucleic acid sequences encoding different polypeptides to be targeted. Nucleic acid sequences of or derived from (a) and (b) are ligated together to produce fusion constructs, at least one of which encodes a functional protein domain (e.g., a catalytic domain of an enzyme) ligated in-frame to a heterologous cellular targeting signal peptide, i.e., one which it normally does not associate with.

The invention also provides a method for modifying the glycosylation pathway of a host cell (e.g., any eukaryotic host cell, including a human host cell) using enzymes involved in modifying N-glycans including glycosidases and glycosyltransferases; by transforming the host cell with a nucleic acid (e.g., a combinatorial) library of the invention to produce a genetically mixed cell population expressing at least one and preferably two or more distinct chimeric glycosylation enzymes having a catalytic domain ligated in-frame to a cellular targeting signal peptide which it normally does not associate with. A host cell having a desired glycosylation phenotype may optionally be selected from the population. Host cells modified using the library and associated methods of the invention are useful, e.g., for producing glycoproteins having a glycosylation pattern similar or identical to those produced in mammals, especially humans.

In another aspect, the combinatorial library of the present invention enables production of one or a combination of catalytically active glycosylation enzymes, which successfully localize to intracellular compartments in which they function efficiently in the glycosylation/secretory pathway. Preferred enzymes convert $Man_5(\alpha\text{-}1,2\text{-}Man)_{3\text{-}9}GlcNAc_2$ to $Man_5GlcNAc_2$ at high efficiency in vivo. In addition, the invention provides eukaryotic host strains, and in particular, yeasts, fungal, insect, plant, plant cells, algae and insect cell hosts, capable of producing glycoprotein intermediates or products with $Man_5GlcNAc_2$ and/or $GlcNAcMan_5GlcNAc_2$ as the predominant N-glycan.

The present invention also provides recombinant molecules derived from a combinatorial nucleic acid library; vectors, including expression vectors, comprising such recombinant molecules; proteins encoded by the recombinant molecules and vectors; host cells transformed with the recombinant molecules or vectors; glycoproteins produced from such transformed hosts; and methods for producing, in vivo, glycoprotein intermediates or products with predominantly $Man_5GlcNAc_2$ or $GlcNAcMan_5GlcNAc_2$ N-glycans covalently attached to appropriate glycosylation sites using the combinatorial library.

Further aspects of this invention include methods, compositions and kits for diagnostic and therapeutic uses in which presence or absence of $Man_5GlcNAc_2$ and/or $GlcNAcMan_5GlcNAc_2$ on a glycoprotein may be detected.

BRIEF DESCRIPTION OF THE DRAWINGS

FIG. 2A diagrams the insertion of a targeting peptide fragment into pCR2.1-TOPO (Invitrogen, Carlsbad, Calif.). FIG. 2B shows the generated targeting peptide sub-library having restriction sites NotI-AscI. FIG. 2C diagrams the insertion of a catalytic domain region into pJN347, a modified pUC19 vector. FIG. 2D shows the generated catalytic domain sub-library having restriction sites NotI, AscI and PacI. FIG. 2E depicts one particular fusion construct generated from the targeting peptide sub-library and the catalytic domain sub-library.

FIG. 3 (SEQ ID NOS 45-46 respectively, in order of appearance) illustrates the M. musculus α-1,2-mannosidase IA open reading frame. The sequences of the PCR primers used to generate N-terminal truncations are underlined.

FIG. 5A depicts the standard $Man_5GlcNAc_2$ [a] glycan (Glyko, Novato, Calif.) and $Man_5GlcNAc_2+Na^+$ [b]. FIG. 5B shows PNGase—released glycans from K3 wild type. The N-glycans shown are as follows: $Man_9GlcNAc_2$ [d]; $Man_{10}GlcNAc_2$ [e]; $Man_{11}GlcNAc_2$ [f]; $Man_{12}GlcNAc_2$ [g] FIG. 5C depicts the och1 deletion resulting in the production of $Man_8GlcNAc_2$ [c] as the predominant N-glycan. FIGS. 5D and 5E show the production of $Man_5GlcNAc_2$ [b] after in vivo trimming of $Man_8GlcNAc_2$ with a chimeric α-1,2-mannosidase. The predominant N-glycan is indicated by a peak with a mass (m/z) of 1253 consistent with its identification as $Man_5GlcNAc_2$ [b].

FIG. 6A shows the standard $Man_5GlcNAc_2$ [a] and $Man_5GlcNAc_2+Na^+$ [b] as the standard (Glyko, Novato, Calif.). FIG. 6B shows PNGase—released glycans from IFN-β wildtype. FIG. 6C depicts the och1 knock-out producing $Man_8GlcNAc_2$ [c]; $Man_9GlcNAc_2$ [d]; $Man_{10}GlcNAc_2$ [e]; $Man_{11}GlcNAc_2$ [f]; $Man_{12}GlcNAc_2$ [g]; and no production of $Man_5GlcNAc_2$ [b]. FIG. 6D shows relatively small amount of $Man_5GlcNAc_2$ [b] among other intermediate N-glycans $Man_8GlcNAc_2$ [c] to $Man_{12}GlcNAc_2$ [g]. FIG. 6E shows a significant amount of $Man_5GlcNAc_2$ [b] relative to the other glycans $Man_8GlcNAc_2$ [c] and $Man_9GlcNAc_2$ [d] produced by pGC5 (Saccharomyces MNS1(m)/mouse mannosidase IB Δ99). FIG. 6F shows predominant production of $Man_5GlcNAc_2$ [b] on the secreted glycoprotein IFN-β by pFB8 (Saccharomyces SEC12 (m)/mouse mannosidase IA Δ187). The N-glycan is indicated by a peak with a mass (m/z) of 1254 consistent with its identification as $Man_5GlcNAc_2$ [b].

FIG. 10A depicts a P. pastoris strain (YSH-3) with a human GnTI but without the UDP-GlcNAc transporter resulting in some production of $GlcNAcMan_5GlcNAc_2$ [b] but a predominant production of $Man_5GlcNAc_2$ [a]. FIG. 10B depicts the addition of UDP-GlcNAc transporter from K. lactis in a strain (PBP-3) with the human GnTI, which resulted in the predominant production of $GlcNAcMan_5GlcNAc_2$ [b]. The single prominent peak of mass (m/z) at 1457 is consistent with its identification as $GlcNAcMan_5GlcNAc_2$ [b] as shown in FIG. 10B.

FIG. 12A shows the N-glycans released from wild-type cells, which includes high-mannose type N-glycans. FIG. 12B shows the N-glycans released from och1 mnn1 deleted cells, revealing a distinct peak of mass (m/z) at 1908 consistent with its identification as $Man_9GlcNAc_2$ [d]. FIG. 12C shows the N-glycans released from och1 mnn1 deleted cells after in vitro α-1,2-mannosidase digest corresponding to a peak consistent with $Man_5GlcNAc_2$.

DETAILED DESCRIPTION OF THE INVENTION

Figure 1A:
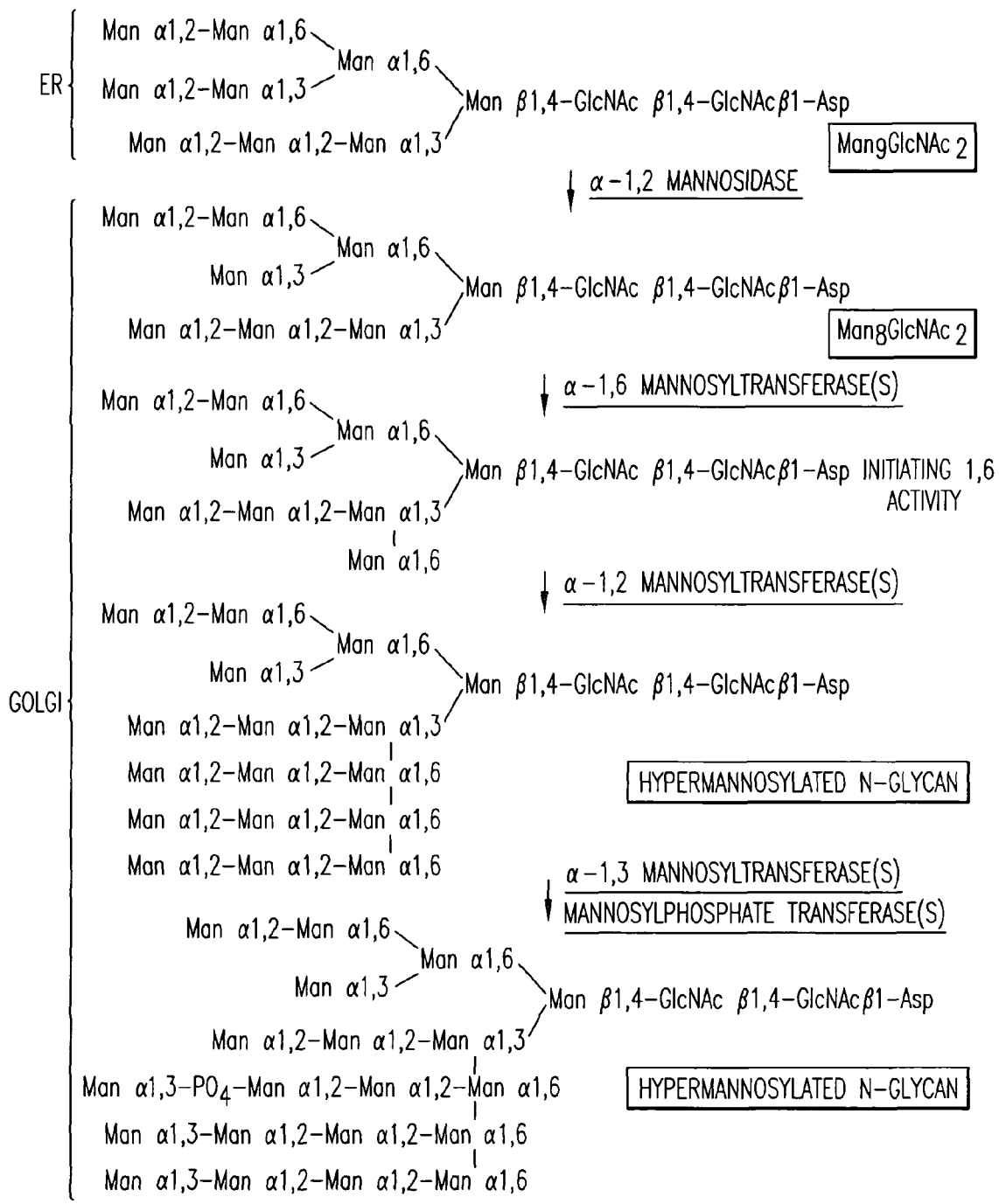
FIG. 1A is a schematic diagram of a typical fungal N-glycosylation pathway.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well-known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane Antibodies: A Laboratory Manual Cold Spring Harbor Laboratory Press, Cold Spring Harbor, N.Y. (1990); Introduction to Glycobiology, Maureen E. Taylor, Kurt Drickamer, Oxford Univ. Press (2003); Worthington Enzyme Manual, Worthington Biochemical Corp. Freehold, N.J.; Handbook of Biochemistry: Section A Proteins Vol I 1976 CRC Press; Handbook of Biochemistry: Section A Proteins Vol II 1976 CRC Press; Essentials of Glycobiology, Cold Spring Harbor Laboratory Press (1999). The nomenclatures used in connection with, and the laboratory procedures and techniques of, molecular and cellular biology, protein biochemistry, enzymology and medicinal and pharmaceutical chemistry described herein are those well known and commonly used in the art.

All publications, patents and other references mentioned herein are incorporated by reference.

The following terms, unless otherwise indicated, shall be understood to have the following meanings:

As used herein, the term "N-glycan" refers to an N-linked oligosaccharide, e.g., one that is attached by an asparagine-N-acetylglucosamine linkage to an asparagine residue of a polypeptide. N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). The term "trimannose core" used with respect to the N-glycan also refers to the structure $Man_3GlcNAc_2$ ("$Man_3$"). N-glycans differ with respect to the number of branches (antennae) comprising peripheral sugars (e.g., fucose and sialic acid) that are added to the $Man_3$ core structure. N-glycans are classified according to their branched constituents (e.g., high mannose, complex or hybrid).

A "high mannose" type N-glycan has five or more mannose residues. A "complex" type N-glycan typically has at least one GlcNAc attached to the 1,3 mannose arm and at least one GlcNAc attached to the 1,6 mannose arm of the trimannose core. Complex N-glycans may also have galactose ("Gal") residues that are optionally modified with sialic acid or derivatives ("NeuAc", where "Neu" refers to neuraminic acid and "Ac" refers to acetyl). A complex N-glycan typically has at least one branch that terminates in an oligosaccharide such as, for example: NeuNAc-; NeuAca2-6GalNAca1-; NeuAca2-3Galb1-3GalNAca1-; NeuAca2-3/6Galb1-4GlcNAcb1-; GlcNAca1-4Galb1-(mucins only); Fuca1-2Galb1-(blood group H). Sulfate esters can occur on galactose, GalNAc, and GlcNAc residues, and phosphate esters can occur on mannose residues. NeuAc (Neu: neuraminic acid; Ac:acetyl) can be O-acetylated or replaced by NeuG1 (N-glycolylneuraminic acid). Complex N-glycans may also have intrachain substitutions comprising "bisecting" GlcNAc and core fucose ("Fuc"). A "hybrid" N-glycan has at least one GlcNAc on the terminal of the 1,3 mannose arm of the trimannose core and zero or more mannoses on the 1,6 mannose arm of the trimannose core.

The term "predominant" or "predominantly" used with respect to the production of N-glycans refers to a structure which represents the major peak detected by matrix assisted laser desorption ionization time of flight mass spectrometry (MALDI-TOF) analysis.

Abbreviations used herein are of common usage in the art, see, e.g., abbreviations of sugars, above. Other common abbreviations include "PNGase", which refers to peptide N-glycosidase F (EC 3.2.2.18); "GlcNAc Tr" or "GnT," which refers to N-acetylglucosaminyl Transferase enzymes; "NANA" refers to N-acetylneuraminic acid.

As used herein, a "humanized glycoprotein" or a "human-like glycoprotein" refers alternatively to a protein having attached thereto N-glycans having less than four mannose residues, and synthetic glycoprotein intermediates (which are also useful and can be manipulated further in vitro or in vivo) having at least five mannose residues. Preferably, glycoproteins produced according to the invention contain at least 30 mole %, preferably at least 40 mole % and more preferably 50-100 mole % of the $Man_5GlcNAc_2$ intermediate, at least transiently. This may be achieved, e.g., by engineering a host cell of the invention to express a "better", i.e., a more efficient glycosylation enzyme. For example, a mannosidase is selected such that it will have optimal activity under the conditions present at the site in the host cell where proteins are glycosylated and is introduced into the host cell preferably by targeting the enzyme to a host cell organelle where activity is desired.

The term "enzyme", when used herein in connection with altering host cell glycosylation, refers to a molecule having at least one enzymatic activity, and includes full-length enzymes, catalytically active fragments, chimerics, complexes, and the like. A "catalytically active fragment" of an enzyme refers to a polypeptide having a detectable level of functional (enzymatic) activity.

A lower eukaryotic host cell, when used herein in connection with glycosylation profiles, refers to any eukaryotic cell which ordinarily produces high mannose containing N-glycans, and thus is meant to include some animal or plant cells and most typical lower eukaryotic cells, including uni- and multicellular fungal and algal cells.

As used herein, the term "secretion pathway" refers to the assembly line of various glycosylation enzymes to which a lipid-linked oligosaccharide precursor and an N-glycan substrate are sequentially exposed, following the molecular flow of a nascent polypeptide chain from the cytoplasm to the endoplasmic reticulum (ER) and the compartments of the Golgi apparatus. Enzymes are said to be localized along this pathway. An enzyme X that acts on a lipid-linked glycan or an N-glycan before enzyme Y is said to be or to act "upstream" to enzyme Y; similarly, enzyme Y is or acts "downstream" from enzyme X.

The term "targeting peptide" as used herein refers to nucleotide or amino acid sequences encoding a cellular targeting signal peptide which mediates the localization (or retention) of an associated sequence to sub-cellular locations, e.g., organelles.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The term includes single and double stranded forms of DNA. A nucleic acid molecule of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non-native promoter sequence can be substituted (e.g., by homologous recombination) for the native promoter of a gene in the genome of a human cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site, a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences (Pearson, 1990, herein incorporated by reference). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., supra, page 9.51, hereby incorporated by reference. For purposes herein, "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled artisan that hybridization at 65° C. will occur at different rates depending on a number of factors including the length and percent identity of the sequences which are hybridizing.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product. See, e.g., Leung, D. W., et al., *Technique*, 1, pp. 11-15 (1989) and Caldwell, R. C. & Joyce G. F., *PCR Methods Applic.*, 2, pp. 28-33 (1992)); and "oligonucleotide-directed mutagenesis" (a process which enables the generation of site-specific mutations in any cloned DNA segment of interest. See, e.g., Reidhaar-Olson, J. F. & Sauer, R. T., et al., *Science*, 241, pp. 53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a nucleic acid such as a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" as used herein encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) when it exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well-known in the art. As thus defined, "isolated" does not necessarily require that the protein, polypeptide, peptide or oligopeptide so described has been physically removed from its native environment.

The term "polypeptide fragment" as used herein refers to a polypeptide that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well-known in the art, and include radioactive isotopes such as $^{125}$I, $^{32}$P, $^{35}$S, and 3H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well-known in the art. See Ausubel et al., 1992, hereby incorporated by reference.

A "polypeptide mutant" or "mutein" refers to a polypeptide whose sequence contains an insertion, duplication, deletion, rearrangement or substitution of one or more amino acids compared to the amino acid sequence of a native or wild type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein. For instance, a mutein may have an increased or decreased neuron or NgR binding activity. In a preferred embodiment of the present invention, a MAG derivative that is a mutein (e.g., in MAG Ig-like domain 5) has decreased neuronal growth inhibitory activity compared to endogenous or soluble wild-type MAG.

A mutein has at least 70% overall sequence homology to its wild-type counterpart. Even more preferred are muteins having 80%, 85% or 90% overall sequence homology to the wild-type protein. In an even more preferred embodiment, a mutein exhibits 95% sequence identity, even more preferably 97%, even more preferably 98% and even more preferably 99% overall sequence identity. Sequence homology may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the left-hand direction is the amino terminal direction and the right hand direction is the carboxy-terminal direction, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences). In a preferred embodiment, a homologous protein is one that exhibits 60% sequence homology to the wild type protein, more preferred is 70% sequence homology. Even more preferred are homologous proteins that exhibit 80%, 85% or 90% sequence homology to the wild type protein. In a yet more preferred embodiment, a homologous protein exhibits 95%, 97%, 98% or 99% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A preferred algorithm when comparing a inhibitory molecule sequence to a database containing a large number of sequences from different organisms is the computer program BLAST (Altschul, S. F. et al. (1990) *J. Mol. Biol.* 215:403-410; Gish and States (1993) *Nature Genet.* 3:266-272; Madden, T. L. et al. (1996) *Meth. Enzymol.* 266:131-141; Altschul, S. F. et al. (1997) *Nucleic Acids Res.* 25:3389-3402; Zhang, J. and Madden, T. L. (1997) *Genome Res.* 7:649-656), especially blastp or tblastn (Altschul et al., 1997). Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in-frame with a nucleic acid sequence encoding a different protein or peptide and then expressing the fusion protein. Alternatively, a fusion protein can be produced chemically by crosslinking the polypeptide or a fragment thereof to another protein.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Methods for Producing Host Cells Having $Man_5GlcNAc_2$ Modified Oligosaccharides for the Generation of Human-Like N-Glycans The invention provides a method for producing a glycoprotein having human-like glycosylation in a non-human eukaryotic host cell. As described in more detail below, a eukaryotic host cell that does not naturally express, or which is engineered not to express, one or more enzymes involved in production of high mannose structures is selected as a starting host cell. Such a selected host cell is engineered to express one or more enzymes or other factors required to produce human-like glycoproteins. A desired host strain can be engineered one enzyme or more than one enzyme at a time. In addition, a nucleic acid molecule encoding one or more enzymes or activities may be used to engineer a host strain of the invention. Preferably, a library of nucleic acid molecules encoding potentially useful enzymes (e.g., chimeric enzymes comprising a catalytically active enzyme fragment ligated in-frame to a heterologous subcellular targeting sequence) is created (e.g., by ligation of sub-libraries comprising enzymatic fragments and subcellular targeting sequences), and a strain having one or more enzymes with optimal activities or producing the most "human-like" glycoproteins may be selected by transforming target host cells with one or more members of the library.

In particular, the methods described herein enable one to obtain, in vivo, Man$_5$GlcNAc$_2$ structures in high yield, at least transiently, for the purpose of further modifying it to yield complex N-glycans. A successful scheme to obtain suitable Man$_5$GlcNAc$_2$ structures in appropriate yields in a host cell, such as a lower eukaryotic organism, generally involves two parallel approaches: (1) reducing high mannose structures made by endogenous mannosyltransferase activities, if any, and (2) removing 1,2-α-mannose by mannosidases to yield high levels of suitable Man$_5$GlcNAc$_2$ structures which may be further reacted inside the host cell to form complex, human-like glycoforms.

Accordingly, a first step involves the selection or creation of a eukaryotic host cell, e.g., a lower eukaryote, capable of producing a specific precursor structure of Man$_5$GlcNAc$_2$ that is able to accept in vivo GlcNAc by the action of a GlcNAc transferase I ("GnTI"). In one embodiment, the method involves making or using a non-human eukaryotic host cell depleted in a 1,6 mannosyltransferase activity with respect to the N-glycan on a glycoprotein. Preferably, the host cell is depleted in an initiating 1,6 mannosyltransferase activity (see below). Such a host cell will lack one or more enzymes involved in the production of high mannose structures which are undesirable for producing human-like glycoproteins.

One or more enzyme activities are then introduced into such a host cell to produce N-glycans within the host cell characterized by having at least 30 mol % of the Man$_5$GlcNAc$_2$ ("Man$_5$") carbohydrate structures. Man$_5$GlcNAc$_2$ structures are necessary for complex N-glycan formation: Man$_5$GlcNAc$_2$ must be formed in vivo in a high yield (e.g., in excess of 30%), at least transiently, as subsequent mammalian- and human-like glycosylation reactions require Man$_5$GlcNAc$_2$ or a derivative thereof.

This step also requires the formation of a particular isomeric structure of Man$_5$GlcNAc$_2$ within the cell at a high yield. While Man$_5$GlcNAc$_2$ structures are necessary for complex N-glycan formation, their presence is by no means sufficient. That is because Man$_5$GlcNAc$_2$ may occur in different isomeric forms, which may or may not serve as a substrate for GlcNAc transferase I. As most glycosylation reactions are not complete, a particular glycosylated protein generally contains a range of different carbohydrate structures (i.e. glycoforms) on its surface. Thus, the mere presence of trace amounts (i.e., less than 5%) of a particular structure like Man$_5$GlcNAc$_2$ is of little practical relevance for producing mammalian- or human-like glycoproteins. It is the formation of a GlcNAc transferase I-accepting Man$_5$GlcNAc$_2$ intermediate (FIG. 1B) in high yield (i.e., above 30%), which is required. The formation of this intermediate is necessary to enable subsequent in vivo synthesis of complex N-glycans on glycosylated proteins of interest (target proteins).

Accordingly, some or all of the Man$_5$GlcNAc$_2$ produced by the selected host cell must be a productive substrate for enzyme activities along a mammalian glycosylation pathway, e.g., can serve as a substrate for a GlcNAc transferase I activity in vivo, thereby forming the human-like N-glycan intermediate GlcNAcMan$_5$GlcNAc$_2$ in the host cell. In a preferred embodiment, at least 10%, more preferably at least 30% and most preferably 50% or more of the Man$_5$GlcNAc$_2$ intermediate produced in the host cell of the invention is a productive substrate for GnTI in vivo. It is understood that if, for example, GlcNAcMan$_5$GlcNAc$_2$ is produced at 10% and Man$_5$GlcNAc$_2$ is produced at 25% on a target protein, that the total amount of transiently produced Man$_5$GlcNAc$_2$ is 35% because GlcNAcMan$_5$GlcNAc$_2$ is a product of Man$_5$GlcNAc$_2$.

One of ordinary skill in the art can select host cells from nature, e.g., existing fungi or other lower eukaryotes that produce significant levels of Man$_5$GlcNAc$_2$ in vivo. As yet, however, no lower eukaryote has been shown to provide such structures in vivo in excess of 1.8% of the total N-glycans (see e.g. Maras et al., 1997). Alternatively, such host cells may be genetically engineered to produce the Man$_5$GlcNAc$_2$ structure in vivo. Methods such as those described in U.S. Pat. No. 5,595,900 may be used to identify the absence or presence of particular glycosyltransferases, mannosidases and sugar nucleotide transporters in a target host cell or organism of interest.

Inactivation of Undesirable Host Cell Glycosylation Enzymes

The methods of the invention are directed to making host cells which produce glycoproteins having altered, and preferably human-like, N-glycan structures. In a preferred embodiment, the methods are directed to making host cells in which oligosaccharide precursors are enriched in Man$_5$GlcNAc$_2$. Preferably, a eukaryotic host cell is used that does not express one or more enzymes involved in the production of high mannose structures. Such a host cell may be found in nature or may be engineered, e.g., starting with or derived from one of many such mutants already described in yeasts. Thus, depending on the selected host cell, one or a number of genes that encode enzymes known to be characteristic of non-human glycosylation reactions will have to be deleted. Such genes and their corresponding proteins have been extensively characterized in a number of lower eukaryotes (e.g., S. cerevisiae, T. reesei, A. nidulans etc.), thereby providing a list of known glycosyltransferases in lower eukaryotes, their activities and their respective genetic sequence. These genes are likely to be selected from the group of mannosyltransferases e.g. 1,3 mannosyltransferases (e.g. MNN1 in S. cerevisiae) (Graham, 1991), 1,2 mannosyltransferases (e.g. KTR/KRE family from S. cerevisiae), 1,6 mannosyltransferases (OCH1 from S. cerevisiae), mannosylphosphate transferases and their regulators (MNN4 and MNN6 from S. cerevisiae) and additional enzymes that are involved in aberrant, i.e. non human, glycosylation reactions. Many of these genes have in fact been deleted individually giving rise to viable phenotypes with altered glycosylation profiles. Examples are shown in Table 1.

Preferred lower eukaryotic host cells of the invention, as described herein to exemplify the required manipulation steps, are hypermannosylation-minus (och1) mutants of Pichia pastoris or K. lactis. Like other lower eukaryotes, P. pastoris processes Man$_9$GlcNAc$_2$ structures in the ER with an α-1,2-mannosidase to yield Man$_8$GlcNAc$_2$ (FIG. 1A). Through the action of several mannosyltransferases, this structure is then converted to hypermannosylated structures (Man$_{>9}$GlcNAc$_2$), also known as mannans. In addition, it has been found that P. pastoris is able to add non-terminal phosphate groups, through the action of mannosylphosphate transferases, to the carbohydrate structure. This differs from the reactions performed in mammalian cells, which involve the removal rather than addition of mannose sugars. It is of particular importance to eliminate the ability of the eukaryotic host cell, e.g., fungus, to hypermannosylate an existing Man$_8$GlcNAc$_2$ structure. This can be achieved by either selecting for a host cell that does not hypermannosylate or by genetically engineering such a cell.

Genes that are involved in the hypermannosylation process have been identified, e.g., in *Pichia pastoris*, and by creating mutations in these genes, one can reduce the production of "undesirable" glycoforms. Such genes can be identified by homology to existing mannosyltransferases or their regulators (e.g., OCH1, MNN4, MNN6, MNN1) found in other lower eukaryotes such as *C. albicans, Pichia angusta* or *S. cerevisiae* or by mutagenizing the host strain and selecting for a glycosylation phenotype with reduced mannosylation. Based on homologies amongst known mannosyltransferases and mannosylphosphate transferases, one may either design PCR primers (SEQ ID NOS 7, 8, 47, & 4 left to right, respectively, in order of appearance)(examples of which are shown in Table 2), or use genes or gene fragments encoding such enzymes as probes to identify homologs in DNA libraries of the target or a related organism. Alternatively, one may identify a functional homolog having mannosyltransferase activity by its ability to complement particular glycosylation phenotypes in related organisms.

After ligation of the chromosomal DNA and the vector, one may transform the DNA library into a strain of *S. cerevisiae* with a specific mutation and select for the correction of the corresponding phenotype. After sub-cloning and sequencing the DNA fragment that is able to restore the wild-type phenotype, one may use this fragment to eliminate the activity of the gene product encoded by OCH1 in *P. pastoris* using in vivo mutagenesis and/or recombination techniques well-known to those skilled in the art.

Alternatively, if the entire genomic sequence of a particular host cell, e.g., fungus, of interest is known, one may identify such genes simply by searching publicly available DNA databases, which are available from several sources, such as NCBI, Swissprot. For example, by searching a given genomic sequence or database with sequences from a known 1,6 mannosyltransferase gene (e.g., OCH1 from *S. cerevisiae*), one can identify genes of high homology in such a host cell genome which may (but do not necessarily) encode proteins that have 1,6-mannosyltransferase activity. Nucleic acid

TABLE 2

PCR Primers

| PCR primer A | PCR primer B | Target Gene(s) in P. pastoris | Homologs |
|---|---|---|---|
| ATGGCGAAGGCAGA TGGCAGT (SEQ ID NO: 1) | TTAGTCCTTCCAAC TTCCTTC (SEQ ID NO: 2) | 1,6-mannosyltransferase | OCH1 *S. cerevisiae*, *Pichia albicans* |
| TAYTGGMGNGTNGA RCYNGAYATHAA (SEQ ID NO: 3) | GCRTCNCCCCANCK YTCRTA (SEQ ID NO: 4) | 1,2 mannosyltransferases | KTR/KRE family, *S. cerevisiae* |

Legend: M = A or C, R = A or G, W = A or T, S = C or G, Y = C or T, K = G or T, V = A or C or G, H = A or C or T, D = A or G or T, B = C or G or T, N = G or A or T or C.

To obtain the gene or genes encoding 1,6-mannosyltransferase activity in *P. pastoris*, for example, one would carry out the following steps: OCH1 mutants of *S. cerevisiae* are temperature sensitive and are slow growers at elevated temperatures. One can thus identify functional homologs of OCH1 in *P. pastoris* by complementing an OCH1 mutant of *S. cerevisiae* with a *P. pastoris* DNA or cDNA library. Mutants of *S. cerevisiae* are available, e.g., from Stanford University and are commercially available from ResGen, an Invitrogen Corp. (Carlsbad, Calif.). Mutants that display a normal growth phenotype at elevated temperature, after having been transformed with a *P. pastoris* DNA library, are likely to carry an OCH1 homolog of *P. pastoris*. Such a library can be created by partially digesting chromosomal DNA of *P. pastoris* with a suitable restriction enzyme and, after inactivating the restriction enzyme, ligating the digested DNA into a suitable vector, which has been digested with a compatible restriction enzyme.

Suitable vectors include, e.g., pRS314, a low copy (CEN6/ARS4) plasmid based on pBluescript containing the Trp1 marker (Sikorski, R. S., and Hieter, P., 1989, *Genetics* 122, pg 19-27) and pFL44S, a high copy (2μ) plasmid based on a modified pUC19 containing the URA3 marker (Bonneaud, N., et al., 1991, Yeast 7, pg. 609-615). Such vectors are commonly used by academic researchers and similar vectors are available from a number of different vendors (e.g., Invitrogen (Carlsbad, Calif.); Pharmacia (Piscataway, N.J.); New England Biolabs (Beverly, Mass.)). Further examples include pYES/GS, 2μ origin of replication based yeast expression plasmid from Invitrogen, or Yep24 cloning vehicle from New England Biolabs.

sequence homology alone is not enough to prove, however, that one has identified and isolated a homolog encoding an enzyme having the same activity. To date, for example, no data exist to show that an OCH1 deletion in *P. pastoris* eliminates the crucial initiating 1,6-mannosyltransferase activity. (Martinet et al. Biotech. Letters 20(12) (December 1998): 1171-1177; Contreras et al. WO 02/00856 A2). Thus, no data prove that the *P. pastoris* OCH1 gene homolog actually encodes that function. That demonstration is provided for the first time herein.

Homologs to several *S. cerevisiae* mannosyltransferases have been identified in *P. pastoris* using these approaches. Homologous genes often have similar functions to genes involved in the mannosylation of proteins in *S. cerevisiae* and thus their deletion may be used to manipulate the glycosylation pattern in *P. pastoris* or, by analogy, in any other host cell, e.g., fungus, plant, insect or animal cells, with similar glycosylation pathways.

The creation of gene knock-outs, once a given target gene sequence has been determined, is a well-established technique in the art and can be carried out by one of ordinary skill in the art (see, e.g., R. Rothstein, (1991) Methods in Enzymology, vol. 194, p. 281). The choice of a host organism may be influenced by the availability of good transformation and gene disruption techniques.

If several mannosyltransferases are to be knocked out, the method developed by Alani and Kleckner, (Genetics 116: 541-545 (1987)), for example, enables the repeated use of a selectable marker, e.g., the URA3 marker in yeast, to sequentially eliminate all undesirable endogenous mannosyltransferase activity. This technique has been refined by others but basically involves the use of two repeated DNA sequences, flanking a counter selectable marker. For example: URA3 may be used as a marker to ensure the selection of a transformants that have integrated a construct. By flanking the URA3 marker with direct repeats one may first select for transformants that have integrated the construct and have thus disrupted the target gene. After isolation of the transformants, and their characterization, one may counter select in a second round for those that are resistant to 5-fluoroorotic acid (5-FOA). Colonies that are able to survive on plates containing 5-FOA have lost the URA3 marker again through a crossover event involving the repeats mentioned earlier. This approach thus allows for the repeated use of the same marker and facilitates the disruption of multiple genes without requiring additional markers. Similar techniques for sequential elimination of genes adapted for use in another eukaryotic host cells with other selectable and counter-selectable markers may also be used.

Eliminating specific mannosyltransferases, such as 1,6 mannosyltransferase (OCH1) or mannosylphosphate transferases (MNN6, or genes complementing lbd mutants) or regulators (MNN4) in *P. pastoris* enables one to create engineered strains of this organism which synthesize primarily $Man_8GlcNAc_2$ and which can be used to further modify the glycosylation pattern to resemble more complex glycoform structures, e.g., those produced in mammalian, e.g., human cells. A preferred embodiment of this method utilizes DNA sequences encoding biochemical glycosylation activities to eliminate similar or identical biochemical functions in *P. pastoris* to modify the glycosylation structure of glycoproteins produced in the genetically altered *P. pastoris* strain.

Methods used to engineer the glycosylation pathway in yeasts as exemplified herein can be used in filamentous fungi to produce a preferred substrate for subsequent modification. Strategies for modifying glycosylation pathways in *A. niger* and other filamentous fungi, for example, can be developed using protocols analogous to those described herein for engineering strains to produce human-like glycoproteins in yeast. Undesired gene activities involved in 1,2 mannosyltransferase activity, e.g., KTR/KRE homologs, are modified or eliminated. A filamentous fungus, such as *Aspergillus*, is a preferred host because it lacks the 1,6 mannosyltransferase activity and as such, one would not expect a hypermannosylating gene activity, e.g. OCH1, in this host. By contrast, other desired activities (e.g., α-1,2-mannosidase, UDP-GlcNAc transporter, glycosyltransferase (GnT), galactosyltransferase (GalT) and sialyltransferase (ST)) involved in glycosylation are introduced into the host using the targeting methods of the invention.

Engineering or Selecting Hosts Having Diminished Initiating α-1,6 Mannosyltransferase Activity In a preferred embodiment, the method of the invention involves making or using a host cell which is diminished or depleted in the activity of an initiating α-1,6-mannosyltransferase, i.e., an initiation specific enzyme that initiates outer chain mannosylation on the α-1,3 arm of the $Man_3GlcNAc_2$ core structure. In *S. cerevisiae*, this enzyme is encoded by the OCH1 gene. Disruption of the OCH1 gene in *S. cerevisiae* results in a phenotype in which N-linked sugars completely lack the poly-mannose outer chain. Previous approaches for obtaining mammalian-type glycosylation in fungal strains have required inactivation of OCH1 (see, e.g., Chiba, 1998). Disruption of the initiating α-1,6-mannosyltransferase activity in a host cell of the invention may be optional, however (depending on the selected host cell), as the Ochlp enzyme requires an intact $Man_8GlcNAc_2$ for efficient mannose outer chain initiation. Thus, host cells selected or produced according to this invention which accumulate oligosaccharides having seven or fewer mannose residues may produce hypoglycosylated N-glycans that will likely be poor substrates for Ochlp (see, e.g., Nakayama, 1997).

The OCH1 gene was cloned from *P. pastoris* (Example 1) and *K. lactis* (Example 16), as described. The nucleic acid and amino acid sequences of the OCH1 gene from *K. lactis* are set forth in SEQ ID NOS: 41 and 42. Using gene-specific primers, a construct was made from each clone to delete the OCH1 gene from the genome of *P. pastoris* and *K. lactis* (Examples 1 and 16, respectively). Host cells depleted in initiating α-1, 6-mannosyltransferase activity and engineered to produce N-glycans having a $Man_5GlcNAc_2$ carbohydrate structure were thereby obtained (see, e.g., FIGS. 5 and 6; Examples 11 and 16).

Thus, in another embodiment, the invention provides an isolated nucleic acid molecule having a nucleic acid sequence comprising or consisting of at least forty-five, preferably at least 50, more preferably at least 60 and most preferably 75 or more nucleotide residues of the *K. lactis* OCH1 gene (SEQ ID NO: 41), and homologs, variants and derivatives thereof. The invention also provides nucleic acid molecules that hybridize under stringent conditions to the above-described nucleic acid molecules. Similarly, isolated polypeptides (including muteins, allelic variants, fragments, derivatives, and analogs) encoded by the nucleic acid molecules of the invention are provided. Also provided are vectors, including expression vectors, which comprise the above nucleic acid molecules of the invention, as described further herein. Similarly, host cells transformed with the nucleic acid molecules or vectors of the invention are provided.

Host Cells of the Invention

A preferred host cell of the invention is a lower eukaryotic cell, e.g., yeast, a unicellular and multicellular or filamentous fungus. However, a wide variety of host cells are envisioned as being useful in the methods of the invention. Plant cells or insect cells, for instance, may be engineered to express a human-like glycoprotein according to the invention (Examples 17 and 18). Likewise, a variety of non-human, mammalian host cells may be altered to express more human-like or otherwise altered glycoproteins using the methods of the invention. As one of skill in the art will appreciate, any eukaryotic host cell (including a human cell) may be used in conjunction with a library of the invention to express one or more chimeric proteins which is targeted to a subcellular location, e.g., organelle, in the host cell where the activity of the protein is modified, and preferably is enhanced. Such a protein is preferably—but need not necessarily be—an enzyme involved in protein glycosylation, as exemplified herein. It is envisioned that any protein coding sequence may be targeted and selected for modified activity in a eukaryotic host cell using the methods described herein.

Lower eukaryotes that are able to produce glycoproteins having the attached N-glycan $Man_5GlcNAc_2$ are particularly useful because (a) lacking a high degree of mannosylation (e.g. greater than 8 mannoses per N-glycan, or especially 30-40 mannoses), they show reduced immunogenicity in humans; and (b) the N-glycan is a substrate for further glycosylation reactions to form an even more human-like glycoform, e.g., by the action of GlcNAc transferase I (FIG. 1B; β1,2 GnTI) to form $GlcNAcMan_5GlcNAc_2$. A yield is obtained of greater than 30 mole %, more preferably a yield of 50-100 mole %, glycoproteins with N-glycans having a $Man_5GlcNAc_2$ structure. In a preferred embodiment, more than 50% of the $Man_5GlcNAc_2$ structure is shown to be a substrate for a GnTI activity and can serve as such a substrate in vivo.

Preferred lower eukaryotes of the invention include but are not limited to: *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reseei, Chrysosporium lucknowense, Fusarium* sp. *Fusarium gramineum, Fusarium venenatum* and *Neurospora crassa.*

In each above embodiment, the method is directed to making a host cell in which the oligosaccharide precursors are enriched in $Man_5GlcNAc_2$. These structures are desirable because they may then be processed by treatment in vitro, for example, using the method of Maras and Contreras, U.S. Pat. No. 5,834,251. In a preferred embodiment, however, precursors enriched in $Man_5GlcNAc_2$ are processed by at least one further glycosylation reaction in vivo—with glycosidases (e.g., α-mannosidases) and glycosyltransferases (e.g., GnTI)—to produce human-like N-glycans. Oligosaccharide precursors enriched in $Man_5GlcNAc_2$, for example, are preferably processed to those having $GlcNAcMan_XGlcNAc_2$ core structures, wherein X is 3, 4 or 5, and is preferably 3. N-glycans having a $GlcNAcMan_XGlcNAc_2$ core structure where X is greater than 3 may be converted to $GlcNAcMan_3GlcNAc_2$, e.g., by treatment with an α-1,3 and/or α-1,6 mannosidase activity, where applicable. Additional processing of $GlcNAcMan_3GlcNAc_2$ by treatment with glycosyltransferases (e.g., GnTII) produces $GlcNAc_2Man_3GlcNAc_2$ core structures which may then be modified, as desired, e.g., by ex vivo treatment or by heterologous expression in the host cell of additional glycosylation enzymes, including glycosyltransferases, sugar transporters and mannosidases (see below), to become human-like N-glycans.

Preferred human-like glycoproteins which may be produced according to the invention include those which comprise N-glycans having seven or fewer, or three or fewer, mannose residues; and which comprise one or more sugars selected from the group consisting of galactose, GlcNAc, sialic acid, and fucose.

Formation of Complex N-Glycans

Formation of complex N-glycan synthesis is a sequential process by which specific sugar residues are removed and attached to the core oligosaccharide structure. In higher eukaryotes, this is achieved by having the substrate sequentially exposed to various processing enzymes. These enzymes carry out specific reactions depending on their particular location within the entire processing cascade. This "assembly line" consists of ER, early, medial and late Golgi, and the trans Golgi network all with their specific processing environment. To re-create the processing of human glycoproteins in the Golgi and ER of lower eukaryotes, numerous enzymes (e.g. glycosyltransferases, glycosidases, phosphatases and transporters) have to be expressed and specifically targeted to these organelles, and preferably, in a location so that they function most efficiently in relation to their environment as well as to other enzymes in the pathway.

Because one goal of the methods described herein is to achieve a robust protein production strain that is able to perform well in an industrial fermentation process, the integration of multiple genes into the host cell chromosome involves careful planning. As described above, one or more genes which encode enzymes known to be characteristic of non-human glycosylation reactions are preferably deleted. The engineered cell strain is transformed with a range of different genes encoding desired activities, and these genes are transformed in a stable fashion, thereby ensuring that the desired activity is maintained throughout the fermentation process.

Any combination of the following enzyme activities may be engineered singly or multiply into the host using methods of the invention: sialyltransferases, mannosidases, fucosyltransferases, galactosyltransferases, GlcNAc transferases, ER and Golgi specific transporters (e.g. syn- and antiport transporters for UDP-galactose and other precursors), other enzymes involved in the processing of oligosaccharides, and enzymes involved in the synthesis of activated oligosaccharide precursors such as UDP-galactose and CMP-N-acetylneuraminic acid. Preferably, enzyme activities are introduced on one or more nucleic acid molecules (see also below). Nucleic acid molecules may be introduced singly or multiply, e.g., in the context of a nucleic acid library such as a combinatorial library of the invention. It is to be understood, however, that single or multiple enzymatic activities may be introduced into a host cell in any fashion, including but not limited to protein delivery methods and/or by use of one or more nucleic acid molecules without necessarily using a nucleic acid library or combinatorial library of the invention.

Expression of Glycosyltransferases to Produce Complex N-Glycans:

With DNA sequence information, the skilled artisan can clone DNA molecules encoding GnT activities (e.g., Examples 3 and 4). Using standard techniques well-known to those of skill in the art, nucleic acid molecules encoding GnTI, II, III, IV or V (or encoding catalytically active fragments thereof) may be inserted into appropriate expression vectors under the transcriptional control of promoters and other expression control sequences capable of driving transcription in a selected host cell of the invention, e.g., a fungal host such as *Pichia* sp., *Kluyveromyces* sp. and *Aspergillus* sp., as described herein, such that one or more of these mammalian GnT enzymes may be actively expressed in a host cell of choice for production of a human-like complex glycoprotein (e.g., Examples 15, 17 and 18).

Several individual glycosyltransferases have been cloned and expressed in *S. cerevisiae* (GalT, GnTI), *Aspergillus nidulans* (GnTI) and other fungi, without however demonstrating the desired outcome of "humanization" on the glycosylation pattern of the organisms (Yoshida, 1995; Schwientek, 1995; Kalsner, 1995). It was speculated that the carbohydrate structure required to accept sugars by the action of such glycosyltransferases was not present in sufficient amounts, which most likely contributed to the lack of complex N-glycan formation.

A preferred method of the invention provides the functional expression of a GnT, such as GnTI, in the early or medial Golgi apparatus as well as ensuring a sufficient supply of UDP-GlcNAc (e.g., by expression of a UDP-GlcNAc transporter; see below).

Methods for Providing Sugar Nucleotide Precursors to the Golgi Apparatus:

For a glycosyltransferase to function satisfactorily in the Golgi, the enzyme requires a sufficient concentration of an appropriate nucleotide sugar, which is the high-energy donor of the sugar moiety added to a nascent glycoprotein. In humans, the full range of nucleotide sugar precursors (e.g. UDP-N-acetylglucosamine, UDP-N-acetylgalactosamine, CMP-N-acetylneuraminic acid, UDP-galactose, etc.) are generally synthesized in the cytosol and transported into the Golgi, where they are attached to the core oligosaccharide by glycosyltransferases.

To replicate this process in non-human host cells such as lower eukaryotes, sugar nucleoside specific transporters have to be expressed in the Golgi to ensure adequate levels of nucleoside sugar precursors (Sommers, 1981; Sommers, 1982; Perez, 1987). Nucleotide sugars may be provided to the appropriate compartments, e.g., by expressing in the host microorganism an exogenous gene encoding a sugar nucleotide transporter. The choice of transporter enzyme is influenced by the nature of the exogenous glycosyltransferase being used. For example, a GlcNAc transferase may require a UDP-GlcNAc transporter, a fucosyltransferase may require a GDP-fucose transporter, a galactosyltransferase may require a UDP-galactose transporter, and a sialyltransferase may require a CMP-sialic acid transporter.

The added transporter protein conveys a nucleotide sugar from the cytosol into the Golgi apparatus, where the nucleotide sugar may be reacted by the glycosyltransferase, e.g. to elongate an N-glycan. The reaction liberates a nucleoside diphosphate or monophosphate, e.g. UDP, GDP, or CMP. Nucleoside monophosphates can be directly exported from the Golgi in exchange for nucleoside triphosphate sugars by an antiport mechanism. Accumulation of a nucleoside diphosphate, however, inhibits the further activity of a glycosyltransferase. As this reaction appears to be important for efficient glycosylation, it is frequently desirable to provide an expressed copy of a gene encoding a nucleotide diphosphatase. The diphosphatase (specific for UDP or GDP as appropriate) hydrolyzes the diphosphonucleoside to yield a nucleoside monophosphate and inorganic phosphate.

Suitable transporter enzymes, which are typically of mammalian origin, are described below. Such enzymes may be engineered into a selected host cell using the methods of the invention (see also Examples 7-10).

Figure 1B:
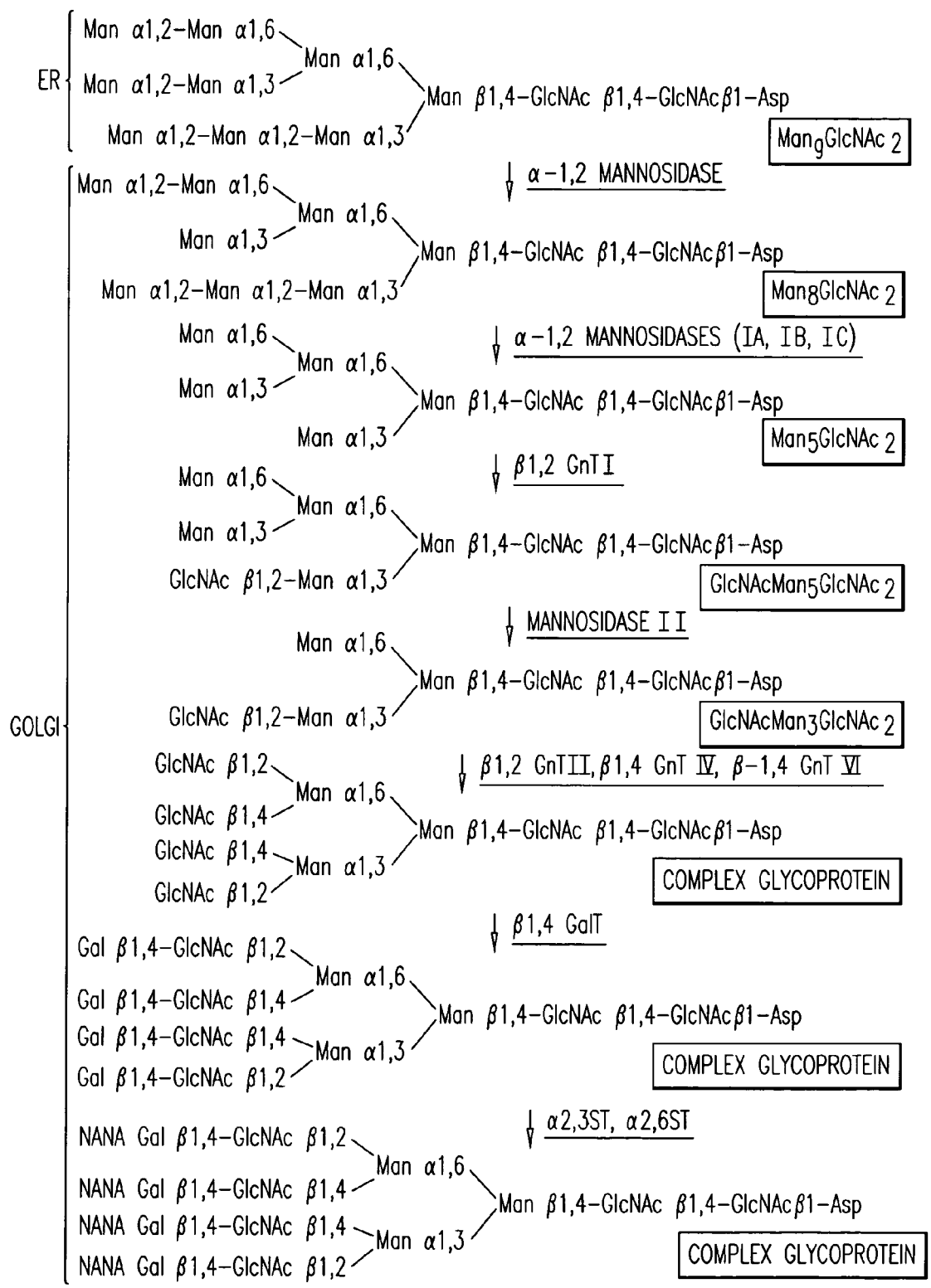
FIG. 1B is a schematic diagram of a typical human N-glycosylation pathway.

In another example, α 2,3- or α 2,6-sialyltransferase caps galactose residues with sialic acid in the trans-Golgi and TGN of humans leading to a mature form of the glycoprotein (FIG. 1B). To reengineer this processing step into a metabolically engineered yeast or fungus will require (1) α 2,3- or α 2,6-sialyltransferase activity and (2) a sufficient supply of CMP-N-acetyl neuraminic acid, in the late Golgi of yeast (Example 6). To obtain sufficient α 2,3-sialyltransferase activity in the late Golgi, for example, the catalytic domain of a known sialyltransferase (e.g. from humans) has to be directed to the late Golgi in fungi (see above). Likewise, transporters have to be engineered to allow the transport of CMP-N-acetyl neuraminic acid into the late Golgi. There is currently no indication that fungi synthesize or can even transport sufficient amounts of CMP-N-acetyl neuraminic acid into the Golgi. Consequently, to ensure the adequate supply of substrate for the corresponding glycosyltransferases, one has to metabolically engineer the production of CMP-sialic acid into the fungus.

UDP-N-Acetylglucosamine

The cDNA of human UDP-N-acetylglucosamine transporter, which was recognized through a homology search in the expressed sequence tags database (dbEST), has been cloned (Ishida, 1999 *J. Biochem.* 126(1): 68-77). The mammalian Golgi membrane transporter for UDP-N-acetylglucosamine was cloned by phenotypic correction with cDNA from canine kidney cells (MDCK) of a recently characterized *Kluyveromyces lactis* mutant deficient in Golgi transport of the above nucleotide sugar (Guillen, 1998). Results demonstrate that the mammalian Golgi UDP-GlcNAc transporter gene has all of the necessary information for the protein to be expressed and targeted functionally to the Golgi apparatus of yeast and that two proteins with very different amino acid sequences may transport the same solute within the same Golgi membrane (Guillen, 1998).

Accordingly, one may incorporate the expression of a UDP-GlcNAc transporter in a host cell by means of a nucleic acid construct which may contain, for example: (1) a region by which the transformed construct is maintained in the cell (e.g. origin of replication or a region that mediates chromosomal integration), (2) a marker gene that allows for the selection of cells that have been transformed, including counterselectable and recyclable markers such as ura3 or T-urf13 (Soderholm, 2001) or other well characterized selection-markers (e.g., his4, bla, Sh ble etc.), (3) a gene or fragment thereof encoding a functional UDP-GlcNAc transporter (e.g. from *K. lactis*, (Abeijon, (1996) *Proc. Natl. Acad. Sci. USA*. 93:5963-5968), or from *H. sapiens* (Ishida, 1996), and (4) a promoter activating the expression of the above mentioned localization/catalytic domain fusion construct library.

GDP-Fucose

The rat liver Golgi membrane GDP-fucose transporter has been identified and purified by Puglielli, L. and C. B. Hirschberg (Puglielli, 1999 *J. Biol. Chem.* 274(50):35596-35600). The corresponding gene has not been identified, however, N-terminal sequencing can be used for the design of oligonucleotide probes specific for the corresponding gene. These oligonucleotides can be used as probes to clone the gene encoding for GDP-fucose transporter.

UDP-Galactose

Two heterologous genes, gmal2(+) encoding alpha 1,2-galactosyltransferase (alpha 1,2 GalT) from *Schizosaccharomyces pombe* and (hUGT2) encoding human UDP-galactose (UDP-Gal) transporter, have been functionally expressed in *S. cerevisiae* to examine the intracellular conditions required for galactosylation. Correlation between protein galactosylation and UDP-galactose transport activity indicated that an exogenous supply of UDP-Gal transporter, rather than alpha 1,2 GalT played a key role for efficient galactosylation in *S. cerevisiae* (Kainuma, 1999 *Glycobiology* 9(2): 133-141). Likewise, an UDP-galactose transporter from *S. pombe* was cloned (Aoki, 1999 *J. Biochem.* 126(5): 940-950; Segawa, 1999 *Febs Letters* 451(3): 295-298).

CMP-N-Acetylneuraminic Acid (CMP-Sialic Acid).

Human CMP-sialic acid transporter (hCST) has been cloned and expressed in Lec 8 CHO cells (Aoki, 1999; Eckhardt, 1997). The functional expression of the murine CMP-sialic acid transporter was achieved in *Saccharomyces cerevisiae* (Berninsone, 1997). Sialic acid has been found in some fungi, however it is not clear whether the chosen host system will be able to supply sufficient levels of CMP-Sialic acid. Sialic acid can be either supplied in the medium or alternatively fungal pathways involved in sialic acid synthesis can also be integrated into the host genome.

Expression of Diphosphatases:

When sugars are transferred onto a glycoprotein, either a nucleoside diphosphate or monophosphate is released from the sugar nucleotide precursors. While monophosphates can be directly exported in exchange for nucleoside triphosphate sugars by an antiport mechanism, diphosphonucleosides (e.g. GDP) have to be cleaved by phosphatases (e.g. GDPase) to yield nucleoside monophosphates and inorganic phosphate prior to being exported. This reaction appears to be important for efficient glycosylation, as GDPase from *S. cerevisiae* has been found to be necessary for mannosylation. However, the enzyme only has 10% of the activity towards UDP (Berninsone, 1994). Lower eukaryotes often do not have UDP-specific diphosphatase activity in the Golgi as they do not utilize UDP-sugar precursors for glycoprotein synthesis in the Golgi. *Schizosaccharomyces pombe*, a yeast which adds galactose residues to cell wall polysaccharides (from UDP-galactose), was found to have specific UDPase activity, further suggesting the requirement for such an enzyme (Berninsone, 1994). UDP is known to be a potent inhibitor of glycosyltransferases and the removal of this glycosylation side product is important to prevent glycosyltransferase inhibition in the lumen of the Golgi (Khatara et al. 1974).

Methods for Altering N-Glycans in a Host By Expressing a Targeted Enzymatic Activity from a Nucleic Acid Molecule The present invention further provides a method for producing a human-like glycoprotein in a non-human host cell comprising the step of introducing into the cell one or more nucleic acid molecules which encode an enzyme or enzymes for production of the Man$_5$GlcNAc$_2$ carbohydrate structure. In one preferred embodiment, a nucleic acid molecule encoding one or more mannosidase activities involved in the production of Man$_5$GlcNAc$_2$ from Man$_8$GlcNAc$_2$ or Man$_9$GlcNAc$_2$ is introduced into the host. The invention additionally relates to methods for making altered glycoproteins in a host cell comprising the step of introducing into the host cell a nucleic acid molecule which encodes one or more glycosylation enzymes or activities. Preferred enzyme activities are selected from the group consisting of UDP-GlcNAc transferase, UDP-galactosyltransferase, GDP-fucosyltransferase, CMP-sialyltransferase, UDP-GlcNAc transporter, UDP-galactose transporter, GDP-fucose transporter, CMP-sialic acid transporter, and nucleotide diphosphatases. In a particularly preferred embodiment, the host is selected or engineered to express two or more enzymatic activities in which the product of one activity increases substrate levels of another activity, e.g., a glycosyltransferase and a corresponding sugar transporter, e.g., GnTI and UDP-GlcNAc transporter activities. In another preferred embodiment, the host is selected or engineered to expresses an activity to remove products which may inhibit subsequent glycosylation reactions, e.g. a UDP- or GDP-specific diphosphatase activity.

Preferred methods of the invention involve expressing one or more enzymatic activities from a nucleic acid molecule in a host cell and comprise the step of targeting at least one enzymatic activity to a desired subcellular location (e.g., an organelle) by forming a fusion protein comprising a catalytic domain of the enzyme and a cellular targeting signal peptide, e.g., a heterologous signal peptide which is not normally ligated to or associated with the catalytic domain. The fusion protein is encoded by at least one genetic construct ("fusion construct") comprising a nucleic acid fragment encoding a cellular targeting signal peptide ligated in the same translational reading frame ("in-frame") to a nucleic acid fragment encoding an enzyme (e.g., glycosylation enzyme), or catalytically active fragment thereof.

The targeting signal peptide component of the fusion construct or protein is preferably derived from a member of the group consisting of: membrane-bound proteins of the ER or Golgi, retrieval signals, Type II membrane proteins, Type I membrane proteins, membrane spanning nucleotide sugar transporters, mannosidases, sialyltransferases, glucosidases, mannosyltransferases and phosphomannosyltransferases.

The catalytic domain component of the fusion construct or protein is preferably derived from a glycosidase, mannosidase or a glycosyltransferase activity derived from a member of the group consisting of GnTI, GnTII, GnTIII, GnTIV, GnTV, GnTVI, GalT, Fucosyltransferase and Sialyltransferase. The catalytic domain preferably has a pH optimum within 1.4 pH units of the average pH optimum of other representative enzymes in the organelle in which the enzyme is localized, or has optimal activity at a pH between 5.1 and 8.0. In a preferred embodiment, the catalytic domain encodes a mannosidase selected from the group consisting of *C. elegans* mannosidase IA, *C. elegans* mannosidase IB, *D. melanogaster* mannosidase IA, *H. sapiens* mannosidase IB, *P. citrinum* mannosidase I, mouse mannosidase IA, mouse mannosidase IB, *A. nidulans* mannosidase IA, *A. nidulans* mannosidase IB, *A. nidulans* mannosidase IC, mouse mannosidase II, *C. elegans* mannosidase II, *H. sapiens* mannosidase II, and mannosidase III.

Selecting a Glycosylation Enzyme: pH Optima and Subcellular Localization

In one embodiment of the invention, a human-like glycoprotein is made efficiently in a non-human eukaryotic host cell by introducing into a subcellular compartment of the cell a glycosylation enzyme selected to have a pH optimum similar to the pH optima of other enzymes in the targeted subcellular compartment. For example, most enzymes that are active in the ER and Golgi apparatus of *S. cerevisiae* have pH optima that are between about 6.5 and 7.5 (see Table 3). Because the glycosylation of proteins is a highly evolved and efficient process, the internal pH of the ER and the Golgi is likely also in the range of about 6-8. All previous approaches to reduce mannosylation by the action of recombinant mannosidases in fungal hosts, however, have introduced enzymes that have a pH optimum of around pH 5.0 (Martinet et al., 1998, and Chiba et al., 1998). At pH 7.0, the in vitro determined activity of those mannosidases is reduced to less than 10%, which is likely insufficient activity at their point of use, namely, the ER and early Golgi, for the efficient in vivo production of Man$_5$GlcNAc$_2$ on N-glycans.

Accordingly, a preferred embodiment of this invention targets a selected glycosylation enzyme (or catalytic domain thereof), e.g., an α-mannosidase, to a subcellular location in the host cell (e.g., an organelle) where the pH optimum of the enzyme or domain is within 1.4 pH units of the average pH optimum of other representative marker enzymes localized in the same organelle(s). The pH optimum of the enzyme to be targeted to a specific organelle should be matched with the pH optimum of other enzymes found in the same organelle to maximize the activity per unit enzyme obtained. Table 3 summarizes the activity of mannosidases from various sources and their respective pH optima. Table 4 summarizes their typical subcellular locations.

TABLE 3

Mannosidases and their pH optimum.

| Source | Enzyme | pH optimum | Reference |
|---|---|---|---|
| *Aspergillus saitoi* | α-1,2-mannosidase | 5.0 | Ichishima et al., 1999 Biochem. J. 339(Pt 3): 589-597 |
| *Trichoderma reesei* | α-1,2-mannosidase | 5.0 | Maras et al., 2000 J. Biotechnol. 77(2-3): 255-263 |
| *Penicillium citrinum* | α-D-1,2-mannosidase | 5.0 | Yoshida et al., 1993 Biochem. J. 290(Pt 2): 349-354 |

TABLE 3-continued

Mannosidases and their pH optimum.

Figure 11:
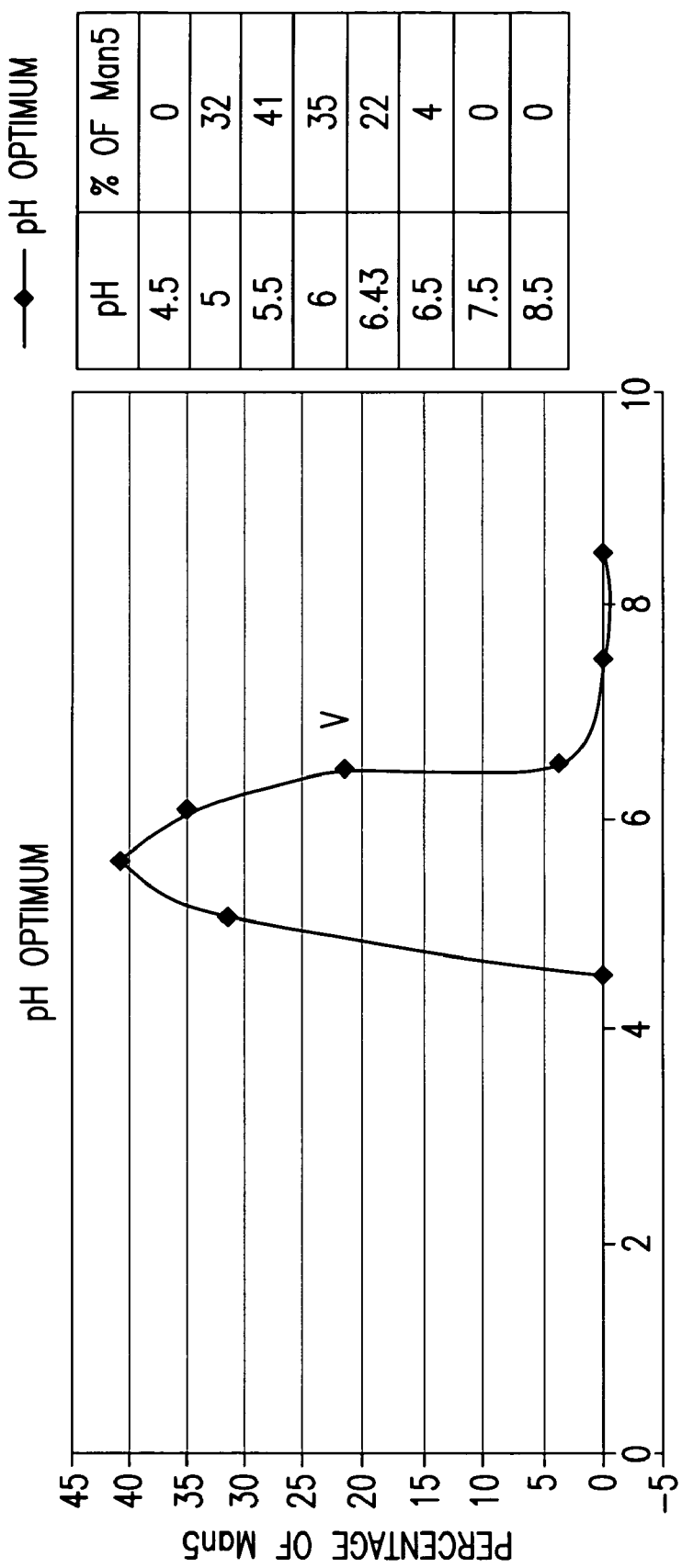
FIG. 11 shows a pH optimum of a heterologous mannosidase enzyme encoded by pBB27-2 (*Saccharomyces* MNN10 (s)/*C. elegans* mannosidase IB Δ31) expressed in *P. pastoris*.

| Source | Enzyme | pH optimum | Reference |
|---|---|---|---|
| C. elegans | α-1,2-mannosidase | 5.5 | see FIG. 11 |
| Aspergillus nidulans | α-1,2-mannosidase | 6.0 | Eades and Hintz, 2000 |
| Homo sapiens IA (Golgi) | α-1,2-mannosidase | 6.0 | |
| Homo sapiens IB (Golgi) | α-1,2-mannosidase | 6.0 | |
| Lepidopteran insect cells | Type I α-1,2-Man$_6$-mannosidase | 6.0 | Ren et al., 1995 Biochem. 34(8): 2489-2495 |
| Homo sapiens | α-D-mannosidase | 6.0 | Chandrasekaran et al., 1984 Cancer Res. 44(9): 4059-68 |
| Xanthomonas manihotis | α-1,2,3-mannosidase | 6.0 | U.S. Pat. No. 6,300,113 |
| Mouse IB (Golgi) | α-1,2-mannosidase | 6.5 | Schneikert and Herscovics, 1994 Glycobiology. 4(4): 445-50 |
| Bacillus sp. (secreted) | α-D-1,2-mannosidase | 7.0 | Maruyama et al., 1994 Carbohydrate Res. 251: 89-98 |

In a preferred embodiment, a particular enzyme or catalytic domain is targeted to a subcellular location in the host cell by means of a chimeric fusion construct encoding a protein comprising a cellular targeting signal peptide not normally associated with the enzymatic domain. Preferably, an enzyme or domain is targeted to the ER, the early, medial or late Golgi of the trans Golgi apparatus of the host cell.

In a more preferred embodiment, the targeted glycosylation enzyme is a mannosidase, glycosyltransferase or a glycosidase. In an especially preferred embodiment, mannosidase activity is targeted to the ER or cis Golgi, where the early reactions of glycosylation occur. While this method is useful for producing a human-like glycoprotein in a non-human host cell, it will be appreciated that the method is also useful more generally for modifying carbohydrate profiles of a glycoprotein in any eukaryotic host cell, including human host cells.

Targeting sequences which mediate retention of proteins in certain organelles of the host cell secretory pathway are well-known and described in the scientific literature and public databases, as discussed in more detail below with respect to libraries for selection of targeting sequences and targeted enzymes. Such subcellular targeting sequences may be used alone or in combination to target a selected glycosylation enzyme (or catalytic domain thereof) to a particular subcellular location in a host cell, i.e., especially to one where the enzyme will have enhanced or optimal activity based on pH optima or the presence of other stimulatory factors.

When one attempts to trim high mannose structures to yield Man$_5$GlcNAc$_2$ in the ER or the Golgi apparatus of a host cell such as S. cerevisiae, for example, one may choose any enzyme or combination of enzymes that (1) has a sufficiently close pH optimum (i.e. between pH 5.2 and pH 7.8), and (2) is known to generate, alone or in concert, the specific isomeric Man$_5$GlcNAc$_2$ structure required to accept subsequent addition of GlcNAc by GnTI. Any enzyme or combination of enzymes that is shown to generate a structure that can be converted to GlcNAcMan$_5$GlcNAc$_2$ by GnTI in vitro would constitute an appropriate choice. This knowledge may be obtained from the scientific literature or experimentally.

For example, one may determine whether a potential mannosidase can convert Man$_8$GlcNAc$_2$-2AB (2-aminobenzamide) to Man$_5$GlcNAc$_2$-AB and then verify that the obtained Man$_5$GlcNAc$_2$-2AB structure can serve a substrate for GnTI and UDP-GlcNAc to give GlcNAcMan$_5$GlcNAc$_2$ in vitro. Mannosidase IA from a human or murine source, for example, would be an appropriate choice (see, e.g., Example 11). Examples described herein utilize 2-aminobenzamide labeled N-linked oligomannose followed by HPLC analysis to make this determination.

TABLE 4

Cellular location and pH optima of various glycosylation-related enzymes of S. cerevisiae.

| Gene | Activity | Location | pH optimum | Reference(s) |
|---|---|---|---|---|
| KTR1 | α-1,2 mannosyltransferase | Golgi | 7.0 | Romero et al., 1997 Biochem. J. 321(Pt 2): 289-295 |
| MNS1 | α-1,2-mannosidase | ER | 6.5 | |
| CWH41 | glucosidase I | ER | 6.8 | |
| — | mannosyltransferase | Golgi | 7-8 | Lehele and Tanner, 1974 Biochim. Biophys. Acta 350(1): 225-235 |
| KRE2 | α-1,2 mannosyltransferase | Golgi | 6.5-9.0 | Romero et al., 1997 |

Accordingly, a glycosylation enzyme such as an α-1,2-mannosidase enzyme used according to the invention has an optimal activity at a pH of between 5.1 and 8.0. In a preferred embodiment, the enzyme has an optimal activity at a pH of between 5.5 and 7.5. The C. elegans mannosidase enzyme, for example, works well in the methods of the invention and has an apparent pH optimum of about 5.5). Preferred mannosidases include those listed in Table 3 having appropriate pH optima, e.g. Aspergillus nidulans, Homo sapiens IA (Golgi), Homo sapiens IB (Golgi), Lepidopteran insect cells (IPLB-SF21AE), Homo sapiens, mouse IB (Golgi), Xanthomonas manihotis, Drosophila melanogaster and C. elegans.

The experiment which illustrates the pH optimum for an α-1,2-mannosidase enzyme is described in Example 14. A chimeric fusion protein BB27-2 (Saccharomyces MNN10 (s)/C. elegans mannosidase IB A31), which leaks into the medium was subjected to various pH ranges to determine the optimal activity of the enzyme. The results of the experiment show that the α-1,2-mannosidase has an optimal pH of about 5.5 for its function (FIG. 11).

In a preferred embodiment, a single cloned mannosidase gene is expressed in the host organism. However, in some cases it may be desirable to express several different mannosidase genes, or several copies of one particular gene, in order to achieve adequate production of $Man_5GlcNAc_2$. In cases where multiple genes are used, the encoded mannosidases preferably all have pH optima within the preferred range of about 5.1 to about 8.0, or especially between about 5.5 and about 7.5. Preferred mannosidase activities include α-1,2-mannosidases derived from mouse, human, *Lepidoptera, Aspergillus nidulans*, or *Bacillus* sp., *C. elegans, D. melanogaster, P. citrinum, X. laevis* or *A. nidulans*.

In Vivo Alteration of Host Cell Glycosylation Using a Combinatorial DNA Library

Certain methods of the invention are preferably (but need not necessarily be) carried out using one or more nucleic acid libraries. An exemplary feature of a combinatorial nucleic acid library of the invention is that it comprises sequences encoding cellular targeting signal peptides and sequences encoding proteins to be targeted (e.g., enzymes or catalytic domains thereof, including but not limited to those which mediate glycosylation).

In one embodiment, a combinatorial nucleic acid library comprises: (a) at least two nucleic acid sequences encoding different cellular targeting signal peptides; and (b) at least one nucleic acid sequence encoding a polypeptide to be targeted. In another embodiment, a combinatorial nucleic acid library comprises: (a) at least one nucleic acid sequence encoding a cellular targeting signal peptide; and (b) at least two nucleic acid sequences encoding a polypeptide to be targeted into a host cell. As described further below, a nucleic acid sequence derived from (a) and a nucleic acid sequence derived from (b) are ligated to produce one or more fusion constructs encoding a cellular targeting signal peptide functionally linked to a polypeptide domain of interest. One example of a functional linkage is when the cellular targeting signal peptide is ligated to the polypeptide domain of interest in the same translational reading frame ("in-frame").

In a preferred embodiment, a combinatorial DNA library expresses one or more fusion proteins comprising cellular targeting signal peptides ligated in-frame to catalytic enzyme domains. The encoded fusion protein preferably comprises a catalytic domain of an enzyme involved in mammalian- or human-like modification of N-glycans. In a more preferred embodiment, the catalytic domain is derived from an enzyme selected from the group consisting of mannosidases, glycosyltransferases and other glycosidases which is ligated in-frame to one or more targeting signal peptides. The enzyme domain may be exogenous and/or endogenous to the host cell. A particularly preferred signal peptide is one normally associated with a protein that undergoes ER to Golgi transport.

The combinatorial DNA library of the present invention may be used for producing and localizing in vivo enzymes involved in mammalian- or human-like N-glycan modification. The fusion constructs of the combinatorial DNA library are engineered so that the encoded enzymes are localized in the ER, Golgi or the trans-Golgi network of the host cell where they are involved in producing particular N-glycans on a glycoprotein of interest. Localization of N-glycan modifying enzymes of the present invention is achieved through an anchoring mechanism or through protein-protein interaction where the localization peptide constructed from the combinatorial DNA library localizes to a desired organelle of the secretory pathway such as the ER, Golgi or the trans Golgi network.

An example of a useful N-glycan, which is produced efficiently and in sufficient quantities for further modification by human-like (complex) glycosylation reactions is $Man_5GlcNAc_2$. A sufficient amount of $Man_5GlcNAc_2$ is needed on a glycoprotein of interest for further human-like processing in vivo (e.g., more than 30 mole %). The $Man_5GlcNAc_2$ intermediate may be used as a substrate for further N-glycan modification to produce $GlcNAcMan_5GlcNAc_2$ (FIG. 1B; see above). Accordingly, the combinatorial DNA library of the present invention may be used to produce enzymes which subsequently produce $GlcNAcMan_5GlcNAc_2$, or other desired complex N-glycans, in a useful quantity.

A further aspect of the fusion constructs produced using the combinatorial DNA library of the present invention is that they enable sufficient and often near complete intracellular N-glycan trimming activity in the engineered host cell. Preferred fusion constructs produced by the combinatorial DNA library of the invention encode a glycosylation enzyme, e.g., a mannosidase, which is effectively localized to an intracellular host cell compartment and thereby exhibits very little and preferably no extracellular activity. The preferred fusion constructs of the present invention that encode a mannosidase enzyme are shown to localize where the N-glycans are modified, namely, the ER and the Golgi. The fusion enzymes of the present invention are targeted to such particular organelles in the secretory pathway where they localize and act upon N-glycans such as $Man_8GlcNAc_2$ to produce $Man_5GlcNAc_2$ on a glycoprotein of interest.

Figure 5:
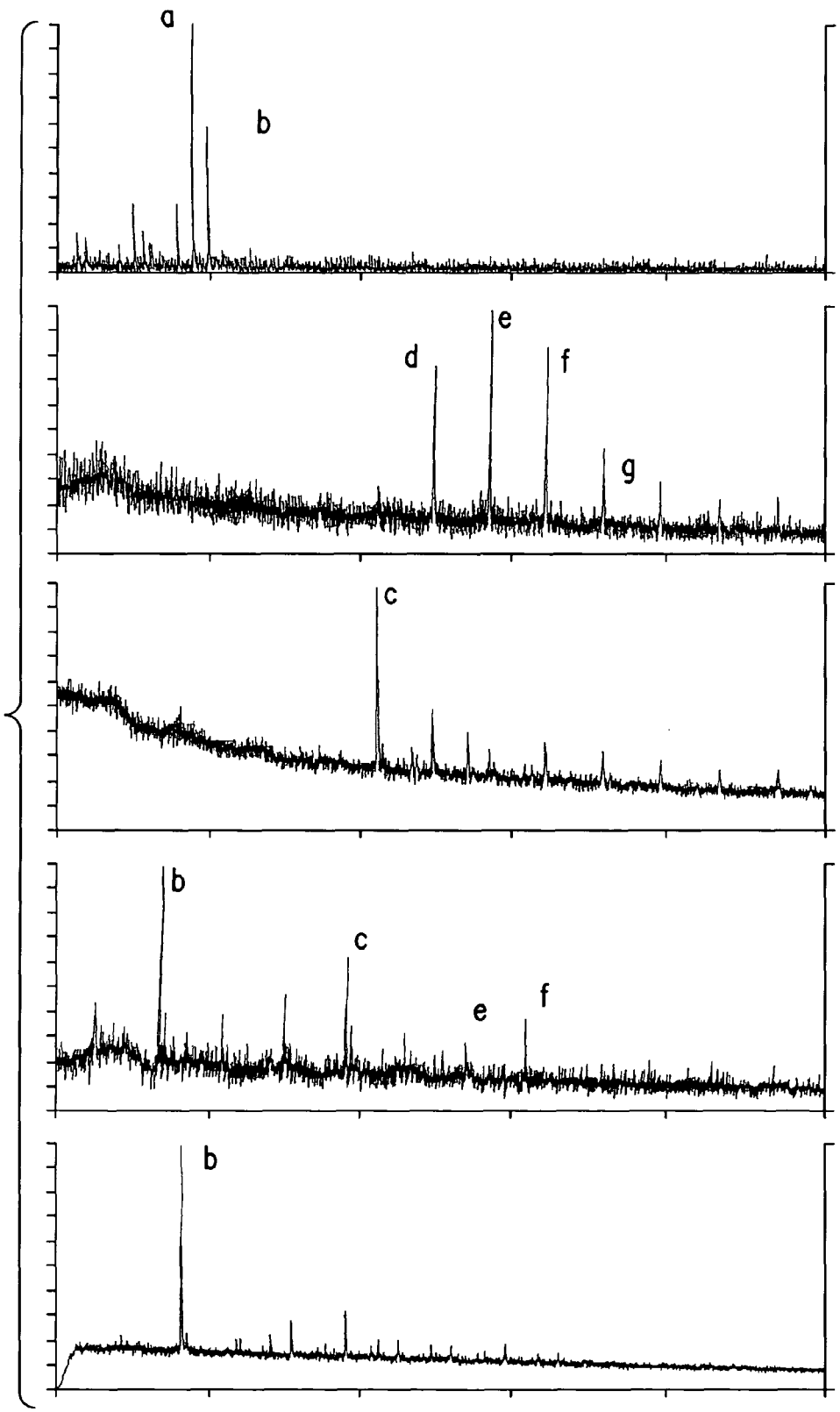
FIGS. 5A-5E show MALDI-TOF analysis demonstrating production of kringle 3 domain of human plasminogen (K3) glycoproteins having $Man_5GlcNAc_2$ as the predominant N-glycan structure in P. pastoris.
Figure 5A:
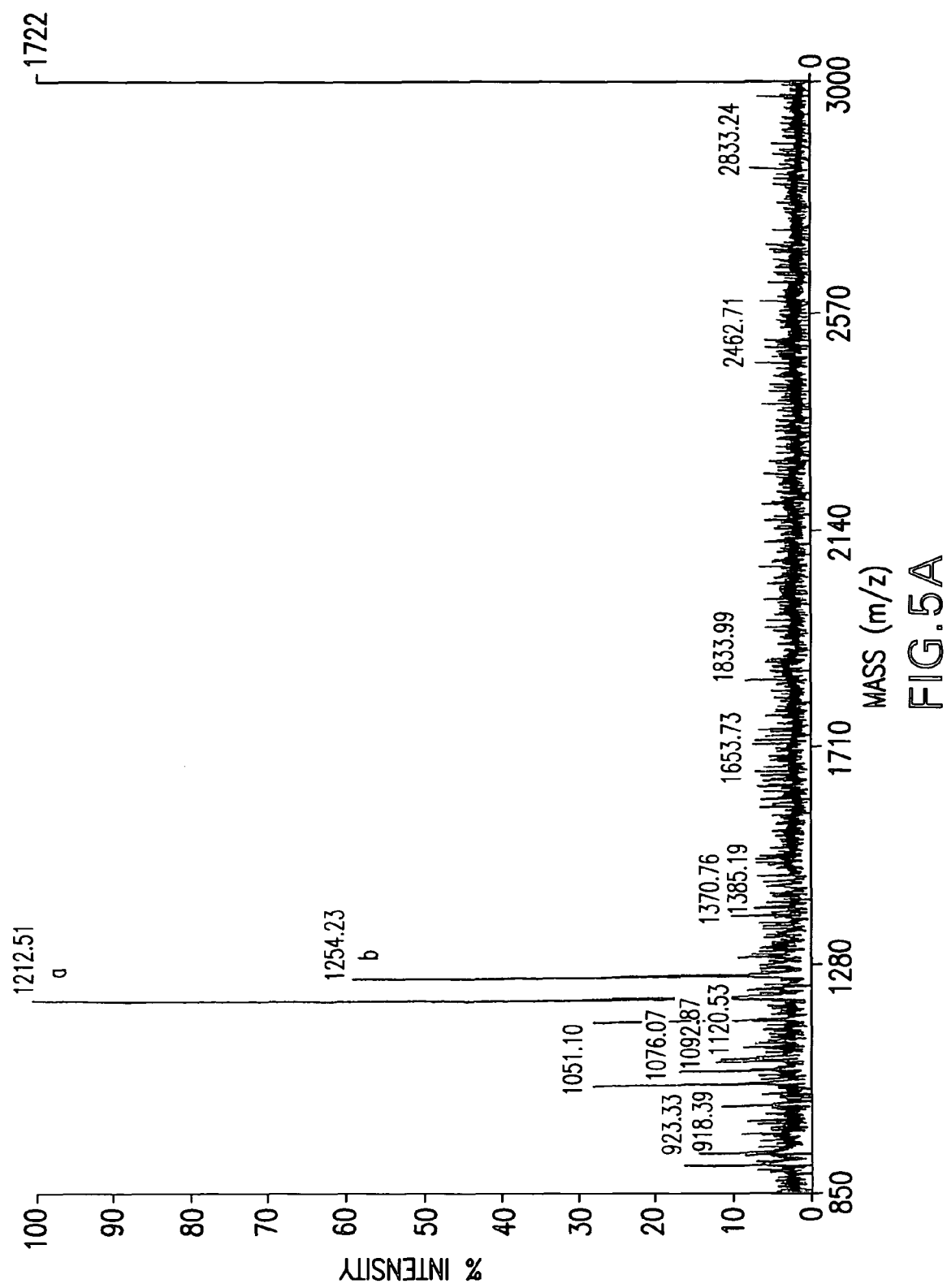
Figure 5B:
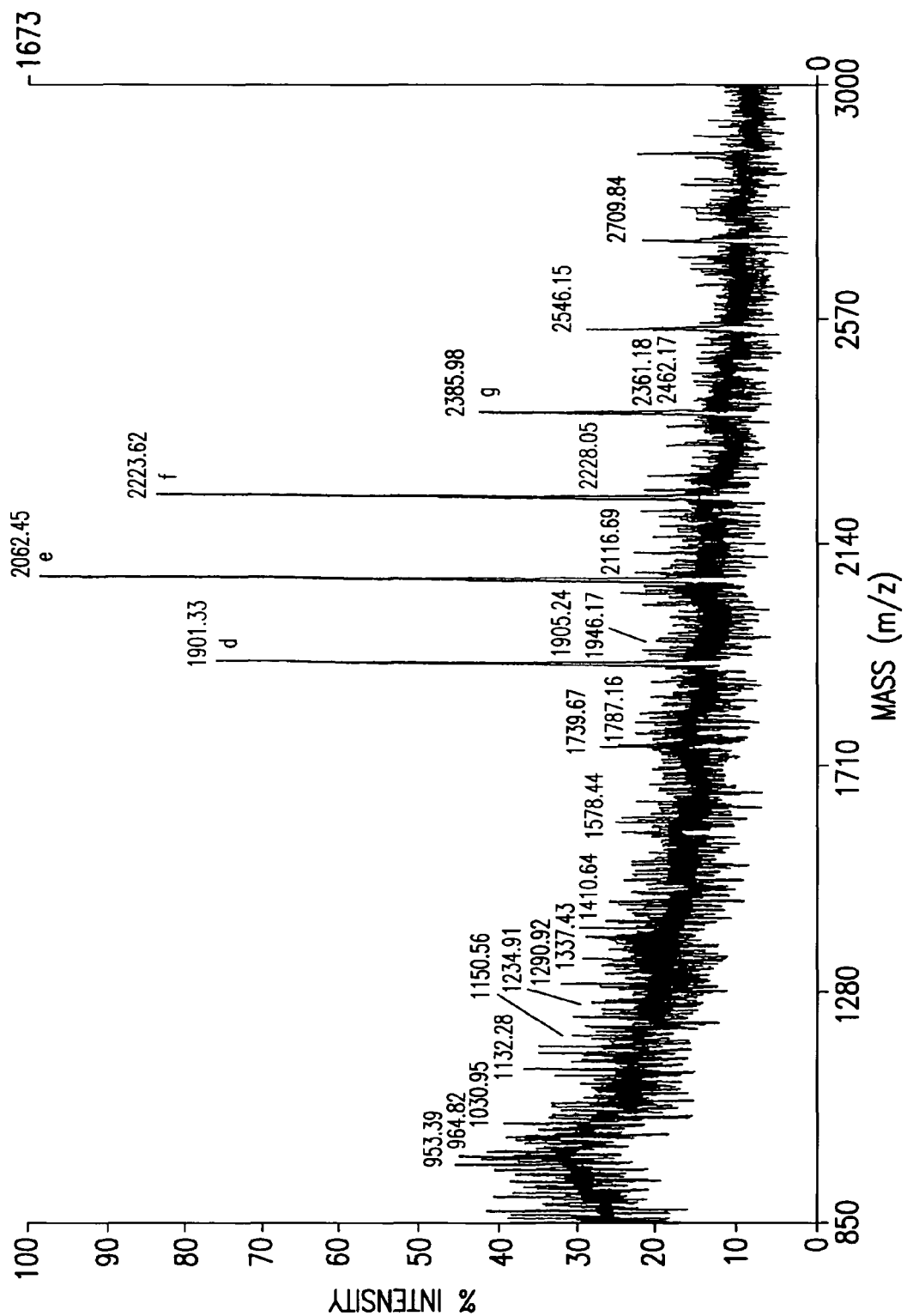
Figure 6:
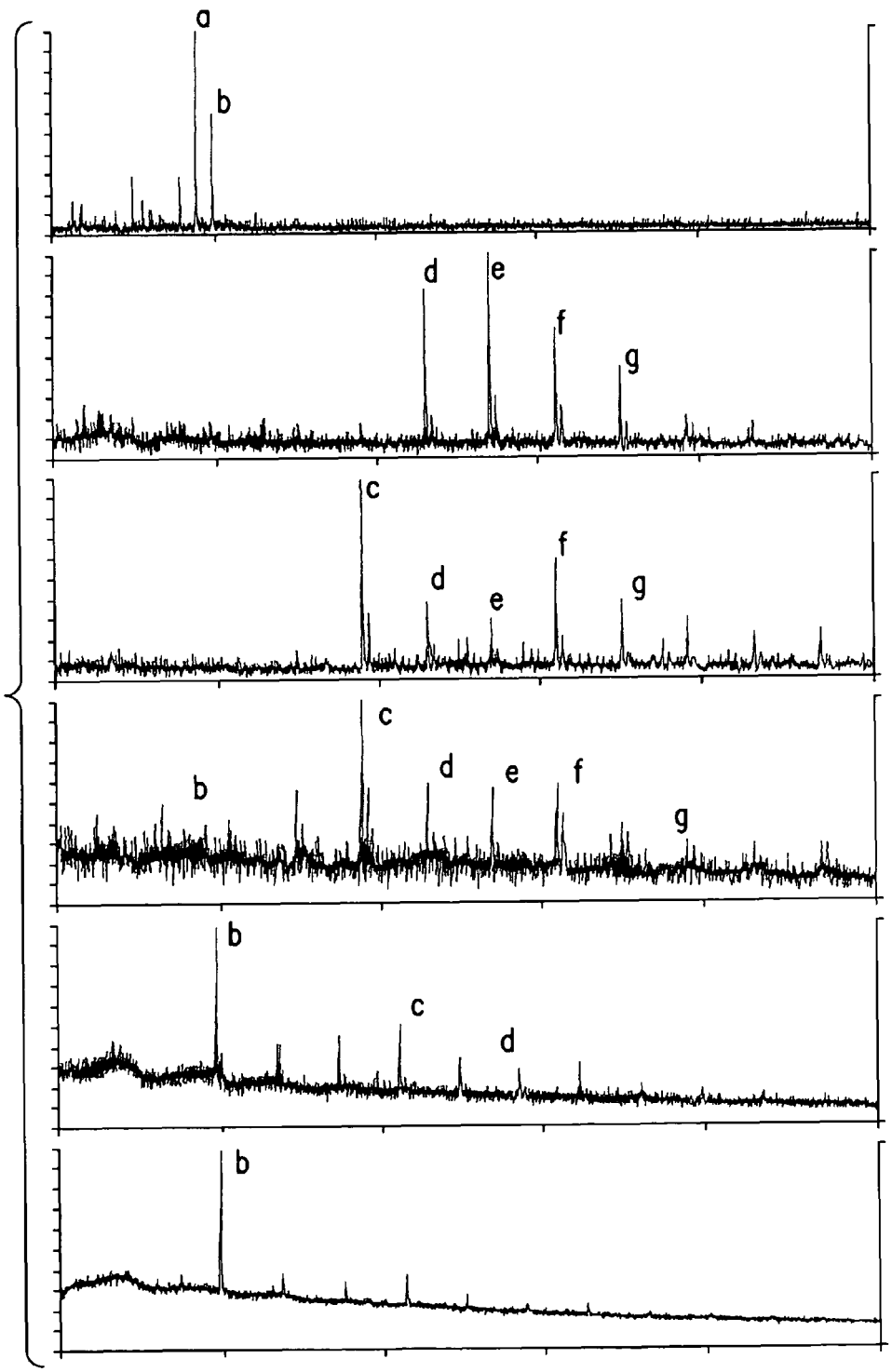
FIGS. 6A-6F show MALDI-TOF analysis demonstrating production of IFN-β glycoproteins having $Man_5GlcNAc_2$ as the predominant N-glycan structure in P. pastoris.
Figure 6B:
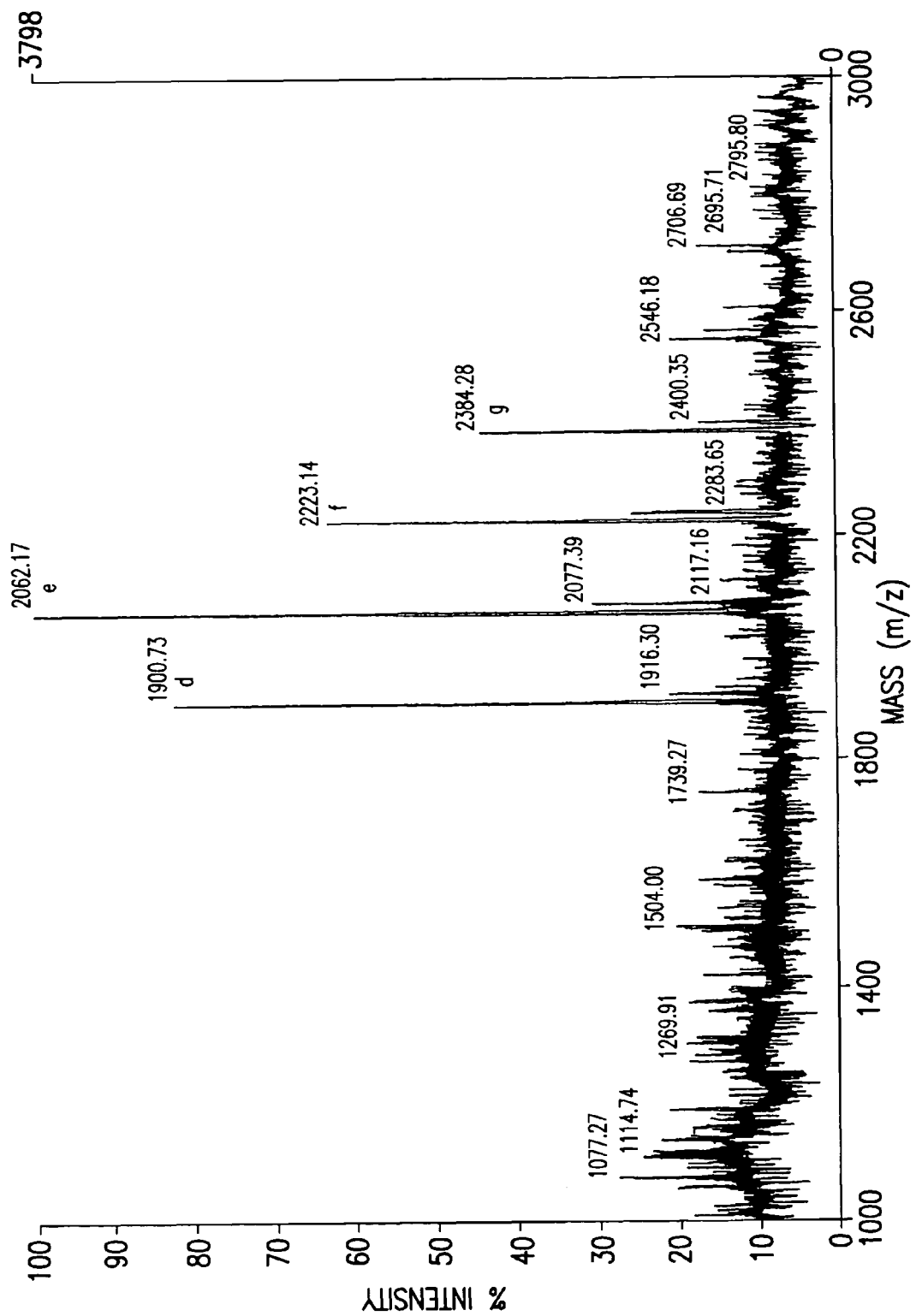
Figure 6C:
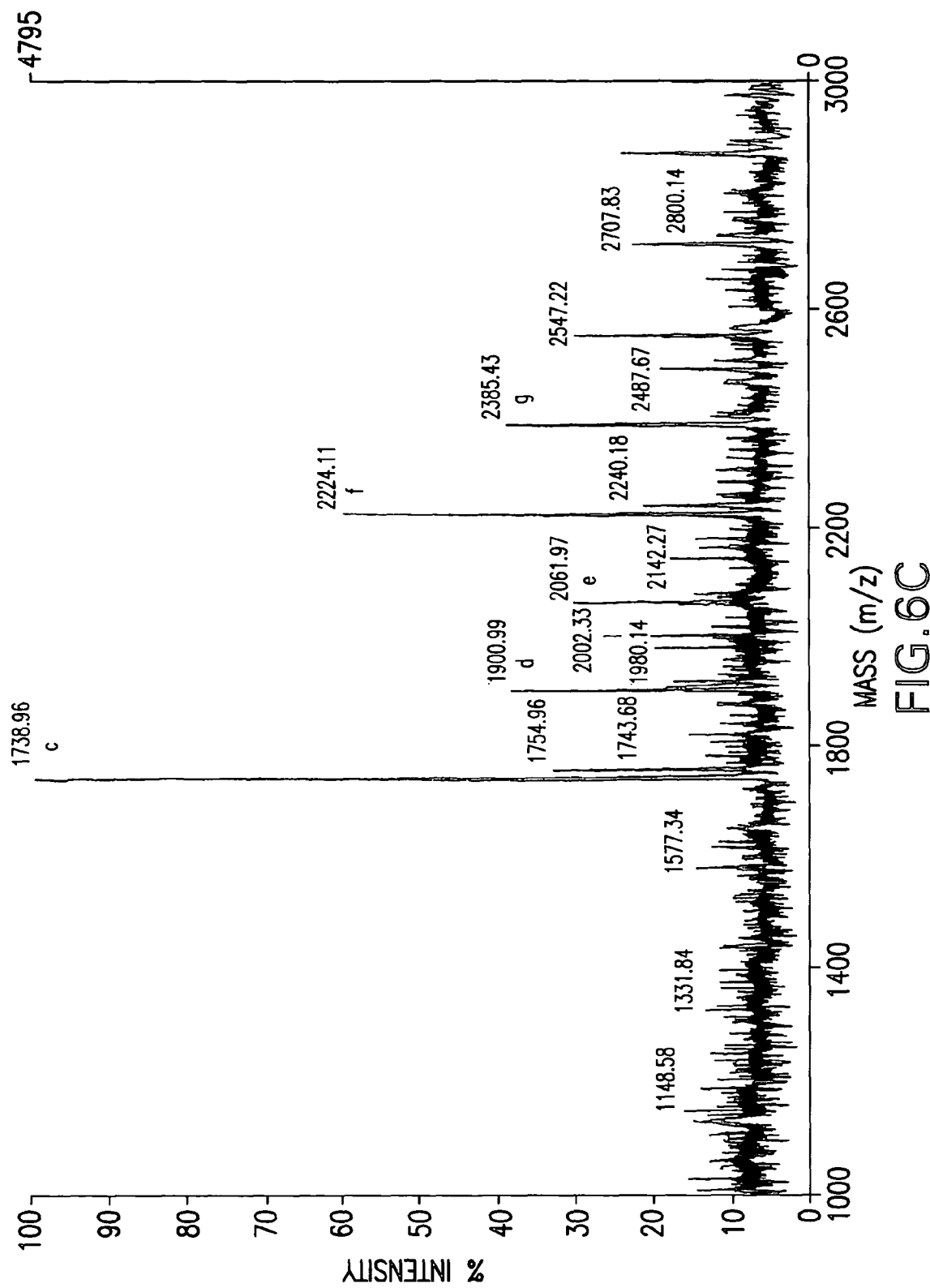
Figure 6D:
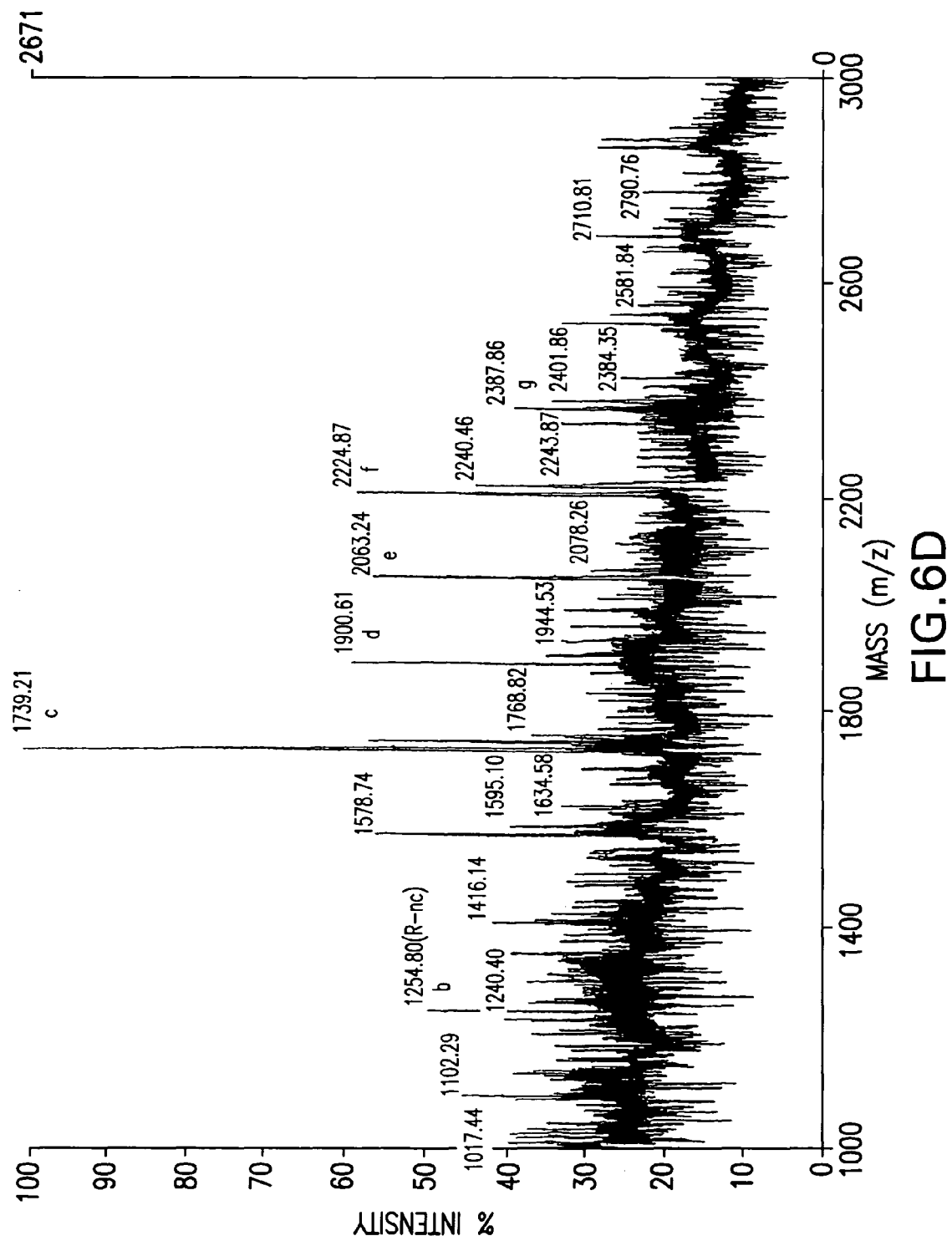
Figure 6E:
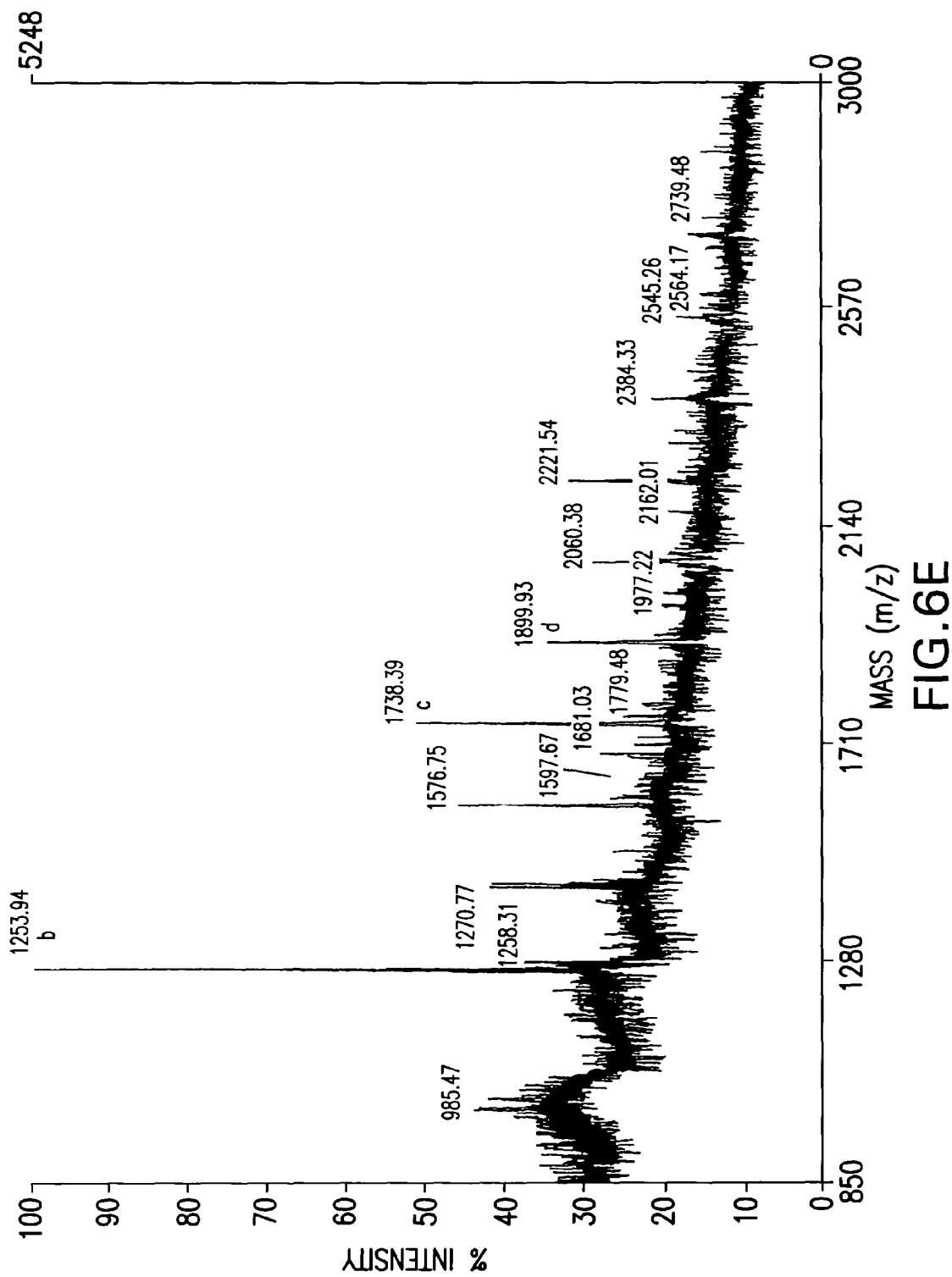

Enzymes produced by the combinatorial DNA library of the present invention can modify N-glycans on a glycoprotein of interest as shown for K3 or IFN-β proteins expressed in *P. pastoris*, as shown in FIG. 5 and FIG. 6, respectively (see also Examples 2 and 11). It is, however, appreciated that other types of glycoproteins, without limitation, including erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II and α-feto proteins may be glycosylated in this way.

Constructing a Combinatorial DNA Library of Fusion Constructs:

A combinatorial DNA library of fusion constructs features one or more cellular targeting signal peptides ("targeting peptides") generally derived from N-terminal domains of native proteins (e.g., by making C-terminal deletions). Some targeting peptides, however, are derived from the C-terminus of native proteins (e.g. SEC12). Membrane-bound proteins of the ER or the Golgi are preferably used as a source for targeting peptide sequences. These proteins have sequences encoding a cytosolic tail (ct), a transmembrane domain (tmd) and a stem region (sr) which are varied in length. These regions are recognizable by protein sequence alignments and comparisons with known homologs and/or other localized proteins (e.g., comparing hydrophobicity plots).

The targeting peptides are indicated herein as short (s), medium (m) and long (l) relative to the parts of a type II membrane. The targeting peptide sequence indicated as short (s) corresponds to the transmembrane domain (tmd) of the membrane-bound protein. The targeting peptide sequence indicated as long (l) corresponds to the length of the transmembrane domain (tmd) and the stem region (sr). The targeting peptide sequence indicated as medium (m) corresponds to the transmembrane domain (tmd) and approximately half the length of the stem region (sr). The catalytic domain regions are indicated herein by the number of nucleotide deletion with respect to its wild-type glycosylation enzyme.

Sub-Libraries

In some cases a combinatorial nucleic acid library of the invention may be assembled directly from existing or wild-type genes. In a preferred embodiment, the DNA library is assembled from the fusion of two or more sub-libraries. By the in-frame ligation of the sub-libraries, it is possible to create a large number of novel genetic constructs encoding useful targeted protein domains such as those which have glycosylation activities.

Catalytic Domain Sub-Libraries Encoding Glycosylation Activities

One useful sub-library includes DNA sequences encoding enzymes such as glycosidases (e.g., mannosidases), glycosyltransferases (e.g., fucosyl-transferases, galactosyltransferases, glucosyltransferases), GlcNAc transferases and sialyltransferases. Catalytic domains may be selected from the host to be engineered, as well as from other related or unrelated organisms. Mammalian, plant, insect, reptile, algal or fungal enzymes are all useful and should be chosen to represent a broad spectrum of biochemical properties with respect to temperature and pH optima. In a preferred embodiment, genes are truncated to give fragments some of which encode the catalytic domains of the enzymes. By removing endogenous targeting sequences, the enzymes may then be redirected and expressed in other cellular loci.

The choice of such catalytic domains may be guided by the knowledge of the particular environment in which the catalytic domain is subsequently to be active. For example, if a particular glycosylation enzyme is to be active in the late Golgi, and all known enzymes of the host organism in the late Golgi have a certain pH optimum, or the late Golgi is known to have a particular pH, then a catalytic domain is chosen which exhibits adequate, and preferably maximum, activity at that pH, as discussed above.

Targeting Peptide Sequence Sub-Libraries

Another useful sub-library includes nucleic acid sequences encoding targeting signal peptides that result in localization of a protein to a particular location within the ER, Golgi, or trans Golgi network. These targeting peptides may be selected from the host organism to be engineered as well as from other related or unrelated organisms. Generally such sequences fall into three categories: (1) N-terminal sequences encoding a cytosolic tail (ct), a transmembrane domain (tmd) and part or all of a stem region (sr), which together or individually anchor proteins to the inner (lumenal) membrane of the Golgi; (2) retrieval signals which are generally found at the C-terminus such as the HDEL (SEQ ID NO:5) or KDEL (SEQ ID NO:6) tetrapeptide; and (3) membrane spanning regions from various proteins, e.g., nucleotide sugar transporters, which are known to localize in the Golgi.

In the first case, where the targeting peptide consists of various elements (ct, tmd and sr), the library is designed such that the ct, the tmd and various parts of the stem region are represented. Accordingly, a preferred embodiment of the sub-library of targeting peptide sequences includes ct, tmd, and/or sr sequences from membrane-bound proteins of the ER or Golgi. In some cases it may be desirable to provide the sub-library with varying lengths of sr sequence. This may be accomplished by PCR using primers that bind to the 5' end of the DNA encoding the cytosolic region and employing a series of opposing primers that bind to various parts of the stem region.

Still other useful sources of targeting peptide sequences include retrieval signal peptides, e.g. the tetrapeptides HDEL (SEQ ID NO:5) or KDEL (SEQ ID NO:6), which are typically found at the C-terminus of proteins that are transported retrograde into the ER or Golgi. Still other sources of targeting peptide sequences include (a) type II membrane proteins, (b) the enzymes listed in Table 3, (c) membrane spanning nucleotide sugar transporters that are localized in the Golgi, and (d) sequences referenced in Table 5 (The HDEL signal in column 1, cell 8 is shown in (SEQ ID NO:5).

TABLE 5

Sources of useful compartmental targeting sequences

| Gene or Sequence | Organism | Function | Location of Gene Product |
|---|---|---|---|
| MNSI | A. nidulans | α-1,2-mannosidase | ER |
| MNSI | A. niger | α-1,2-mannosidase | ER |
| MNSI | S. cerevisiae | α-1,2-mannosidase | ER |
| GLSI | S. cerevisiae | glucosidase | ER |
| GLSI | A. niger | glucosidase | ER |
| GLSI | A. nidulans | glucosidase | ER |
| HDEL at C-terminus | Universal in fungi | retrieval signal | ER |
| SEC12 | S. cerevisiae | COPII vesicle protein | ER/Golgi |
| SEC12 | A. niger | COPII vesicle protein | ER/Golgi |
| OCH1 | S. cerevisiae | 1,6-mannosyltransferase | Golgi (cis) |
| OCH1 | P. pastoris | 1,6-mannosyltransferase | Golgi (cis) |
| MNN9 | S. cerevisiae | 1,6-mannosyltransferase complex | Golgi |
| MNN9 | A. niger | undetermined | Golgi |
| VAN1 | S. cerevisiae | undetermined | Golgi |
| VAN1 | A. niger | undetermined | Golgi |
| ANP1 | S. cerevisiae | undetermined | Golgi |
| HOCI | S. cerevisiae | undetermined | Golgi |
| MNN10 | S. cerevisiae | undetermined | Golgi |
| MNN10 | A. niger | undetermined | Golgi |
| MNN11 | S. cerevisiae | undetermined | Golgi (cis) |

TABLE 5-continued

Sources of useful compartmental targeting sequences

| Gene or Sequence | Organism | Function | Location of Gene Product |
|---|---|---|---|
| MNN11 | A. niger | undetermined | Golgi (cis) |
| MNT1 | S. cerevisiae | 1,2-mannosyltransferase | Golgi (cis, medial |
| KTR1 | P. pastoris | undetermined | Golgi (medial) |
| KRE2 | P. pastoris | undetermined | Golgi (medial) |
| KTR3 | P. pastoris | undetermined | Golgi (medial) |
| MNN2 | S. cerevisiae | 1,2-mannosyltransferase | Golgi (medial) |
| KTR1 | S. cerevisiae | undetermined | Golgi (medial) |
| KTR2 | S. cerevisiae | undetermined | Golgi (medial) |
| MNN1 | S. cerevisiae | 1,3-mannosyltransferase | Golgi (trans) |
| MNN6 | S. cerevisiae | Phosphomannosyltransferase | Golgi (trans) |
| 2,6 ST | H. sapiens | 2,6-sialyltransferase | trans Golgi network |
| UDP-Gal T | S. pombe | UDP-Gal transporter | Golgi |

In any case, it is highly preferred that targeting peptide sequences are selected which are appropriate for the particular enzymatic activity or activities to function optimally within the sequence of desired glycosylation reactions. For example, in developing a modified microorganism capable of terminal sialylation of nascent N-glycans, a process which occurs in the late Golgi in humans, it is desirable to utilize a sub-library of targeting peptide sequences derived from late Golgi proteins. Similarly, the trimming of $Man_8GlcNAc_2$ by an α-1,2-mannosidase, to give $Man_5GlcNAc_2$ is an early step in complex N-glycan formation in humans (FIG. 1B). It is therefore desirable to have this reaction occur in the ER or early Golgi of an engineered host microorganism. A sub-library encoding ER and early Golgi retention signals is used.

A series of fusion protein constructs (i.e., a combinatorial DNA library) is then constructed by functionally linking one or a series of targeting peptide sequences to one or a series of sequences encoding catalytic domains. In a preferred embodiment, this is accomplished by the in-frame ligation of a sub-library comprising DNA encoding targeting peptide sequences (above) with a sub-library comprising DNA encoding glycosylation enzymes or catalytically active fragments thereof (see below).

The resulting library comprises synthetic genes encoding targeting peptide sequence-containing fusion proteins. In some cases it is desirable to provide a targeting peptide sequence at the N-terminus of a fusion protein, or in other cases at the C-terminus. In some cases, targeting peptide sequences may be inserted within the open reading frame of an enzyme, provided the protein structure of individual folded domains is not disrupted. Each type of fusion protein is constructed (in a step-wise directed or semi-random fashion) and optimal constructs may be selected upon transformation of host cells and characterization of glycosylation patterns in transformed cells using methods of the invention.

Generating Additional Sequence Diversity

The method of this embodiment is most effective when a nucleic acid, e.g., a DNA library transformed into the host contains a large diversity of sequences, thereby increasing the probability that at least one transformant will exhibit the desired phenotype. Single amino acid mutations, for example, may drastically alter the activity of glycoprotein processing enzymes (Romero et al., 2000). Accordingly, prior to transformation, a DNA library or a constituent sub-library may be subjected to one or more techniques to generate additional sequence diversity. For example, one or more rounds of gene shuffling, error prone PCR, in vitro mutagenesis or other methods for generating sequence diversity, may be performed to obtain a larger diversity of sequences within the pool of fusion constructs.

Expression Control Sequences

In addition to the open reading frame sequences described above, it is generally preferable to provide each library construct with expression control sequences, such as promoters, transcription terminators, enhancers, ribosome binding sites, and other functional sequences as may be necessary to ensure effective transcription and translation of the fusion proteins upon transformation of fusion constructs into the host organism.

Suitable vector components, e.g., selectable markers, expression control sequences (e.g., promoter, enhancers, terminators and the like) and, optionally, sequences required for autonomous replication in a host cell, are selected as a function of which particular host cell is chosen. Selection criteria for suitable vector components for use in a particular mammalian or a lower eukaryotic host cell are routine. Preferred lower eukaryotic host cells of the invention include Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp. Fusarium gramineum, Fusarium venenatum and Neurospora crassa. Where the host is Pichia pastoris, suitable promoters include, for example, the AOX1, AOX2, GAPDH and P40 promoters.

Selectable Markers

It is also preferable to provide each construct with at least one selectable marker, such as a gene to impart drug resistance or to complement a host metabolic lesion. The presence of the marker is useful in the subsequent selection of transformants; for example, in yeast the URA3, HIS4, SUC2, G418, BLA, or SH BLE genes may be used. A multitude of selectable markers are known and available for use in yeast, fungi, plant, insect, mammalian and other eukaryotic host cells.

Transformation

The nucleic acid library is then transformed into the host organism. In yeast, any convenient method of DNA transfer may be used, such as electroporation, the lithium chloride method, or the spheroplast method. In filamentous fungi and plant cells, conventional methods include particle bombardment, electroporation and agrobacterium mediated transformation. To produce a stable strain suitable for high-density culture (e.g., fermentation in yeast), it is desirable to integrate the DNA library constructs into the host chromosome. In a preferred embodiment, integration occurs via homologous recombination, using techniques well-known in the art. For example, DNA library elements are provided with flanking sequences homologous to sequences of the host organism. In this manner, integration occurs at a defined site in the host genome, without disruption of desirable or essential genes.

In an especially preferred embodiment, library DNA is integrated into the site of an undesired gene in a host chromosome, effecting the disruption or deletion of the gene. For example, integration into the sites of the OCH1, MNN1, or MNN4 genes allows the expression of the desired library DNA while preventing the expression of enzymes involved in yeast hypermannosylation of glycoproteins. In other embodiments, library DNA may be introduced into the host via a nucleic acid molecule, plasmid, vector (e.g., viral or retroviral vector), chromosome, and may be introduced as an autonomous nucleic acid molecule or by homologous or random integration into the host genome. In any case, it is generally desirable to include with each library DNA construct at least one selectable marker gene to allow ready selection of host organisms that have been stably transformed. Recyclable marker genes such as ura3, which can be selected for or against, are especially suitable.

Screening and Selection Processes

After transformation of the host strain with the DNA library, transformants displaying a desired glycosylation phenotype are selected. Selection may be performed in a single step or by a series of phenotypic enrichment and/or depletion steps using any of a variety of assays or detection methods. Phenotypic characterization may be carried out manually or using automated high-throughput screening equipment. Commonly, a host microorganism displays protein N-glycans on the cell surface, where various glycoproteins are localized.

One may screen for those cells that have the highest concentration of terminal GlcNAc on the cell surface, for example, or for those cells which secrete the protein with the highest terminal GlcNAc content. Such a screen may be based on a visual method, like a staining procedure, the ability to bind specific terminal GlcNAc binding antibodies or lectins conjugated to a marker (such lectins are available from E.Y. Laboratories Inc., San Mateo, Calif.), the reduced ability of specific lectins to bind to terminal mannose residues, the ability to incorporate a radioactively labeled sugar in vitro, altered binding to dyes or charged surfaces, or may be accomplished by using a Fluorescence Assisted Cell Sorting (FACS) device in conjunction with a fluorophore labeled lectin or antibody (Guillen, 1998).

Accordingly, intact cells may be screened for a desired glycosylation phenotype by exposing the cells to a lectin or antibody that binds specifically to the desired N-glycan. A wide variety of oligosaccharide-specific lectins are available commercially (e.g., from EY Laboratories, San Mateo, Calif.). Alternatively, antibodies to specific human or animal N-glycans are available commercially or may be produced using standard techniques. An appropriate lectin or antibody may be conjugated to a reporter molecule, such as a chromophore, fluorophore, radioisotope, or an enzyme having a chromogenic substrate (Guillen et al., 1998. *Proc. Natl. Acad. Sci. USA* 95(14): 7888-7892)).

Screening may then be performed using analytical methods such as spectrophotometry, fluorimetry, fluorescence activated cell sorting, or scintillation counting. In other cases, it may be necessary to analyze isolated glycoproteins or N-glycans from transformed cells. Protein isolation may be carried out by techniques known in the art. In a preferred embodiment, a reporter protein is secreted into the medium and purified by affinity chromatography (e.g. Ni-affinity or glutathione-S-transferase affinity chromatography). In cases where an isolated N-glycan is preferred, an enzyme such as endo-β-N-acetylglucosaminidase (Genzyme Co., Boston, Mass.; New England Biolabs, Beverly, Mass.) may be used to cleave the N-glycans from glycoproteins. Isolated proteins or N-glycans may then be analyzed by liquid chromatography (e.g. HPLC), mass spectroscopy, or other suitable means. U.S. Pat. No. 5,595,900 teaches several methods by which cells with desired extracellular carbohydrate structures may be identified. In a preferred embodiment, MALDI-TOF mass spectrometry is used to analyze the cleaved N-glycans.

Prior to selection of a desired transformant, it may be desirable to deplete the transformed population of cells having undesired phenotypes. For example, when the method is used to engineer a functional mannosidase activity into cells, the desired transformants will have lower levels of mannose in cellular glycoprotein. Exposing the transformed population to a lethal radioisotope of mannose in the medium depletes the population of transformants having the undesired phenotype, i.e. high levels of incorporated mannose (Hufaker T C and Robbins P W., *Proc Natl Acad Sci USA*. 1983 December; 80(24):7466-70). Alternatively, a cytotoxic lectin or antibody, directed against an undesirable N-glycan, may be used to deplete a transformed population of undesired phenotypes (e.g., Stanley P and Siminovitch L. *Somatic Cell Genet.* 1977 July; 3(4):391-405). U.S. Pat. No. 5,595,900 teaches several methods by which cells with a desired extracellular carbohydrate structures may be identified. Repeatedly carrying out this strategy allows for the sequential engineering of more and more complex glycans in lower eukaryotes.

To detect host cells having on their surface a high degree of the human-like N-glycan intermediate GlcNAcMan$_3$GlcNAc$_2$, for example, one may select for transformants that allow for the most efficient transfer of GlcNAc by GlcNAc Transferase from UDP-GlcNAc in an in vitro cell assay. This screen may be carried out by growing cells harboring the transformed library under selective pressure on an agar plate and transferring individual colonies into a 96-well microtiter plate. After growing the cells, the cells are centrifuged, the cells resuspended in buffer, and after addition of UDP-GlcNAc and GnT II, the release of UDP is determined either by HPLC or an enzyme linked assay for UDP. Alternatively, one may use radioactively labeled UDP-GlcNAc and GnT II, wash the cells and then look for the release of radioactive GlcNAc by N-actylglucosaminidase. All this may be carried manually or automated through the use of high throughput screening equipment. Transformants that release more UDP, in the first assay, or more radioactively labeled GlcNAc in the second assay, are expected to have a higher degree of GlcNAcMan$_3$GlcNAc$_2$ on their surface and thus constitute the desired phenotype. Similar assays may be adapted to look at the N-glycans on secreted proteins as well.

Alternatively, one may use any other suitable screen such as a lectin binding assay that is able to reveal altered glycosylation patterns on the surface of transformed cells. In this case the reduced binding of lectins specific to terminal mannoses may be a suitable selection tool. *Galantus nivalis* lectin binds specifically to terminal α-1,3 mannose, which is expected to be reduced if sufficient mannosidase II activity is present in the Golgi. One may also enrich for desired transformants by carrying out a chromatographic separation step that allows for the removal of cells containing a high terminal mannose content. This separation step would be carried out with a lectin column that specifically binds cells with a high terminal mannose content (e.g., *Galantus nivalis* lectin bound to agarose, Sigma, St. Louis, Mo.) over those that have a low terminal mannose content.

In addition, one may directly create such fusion protein constructs, as additional information on the localization of active carbohydrate modifying enzymes in different lower eukaryotic hosts becomes available in the scientific literature. For example, it is known that human β1,4-GalTr can be fused to the membrane domain of MNT, a mannosyltransferase from *S. cerevisiae*, and localized to the Golgi apparatus while retaining its catalytic activity (Schwientek et al., 1995). If *S. cerevisiae* or a related organism is the host to be engineered one may directly incorporate such findings into the overall strategy to obtain complex N-glycans from such a host. Several such gene fragments in *P. pastoris* have been identified that are related to glycosyltransferases in *S. cerevisiae* and thus could be used for that purpose.

Figure 2:
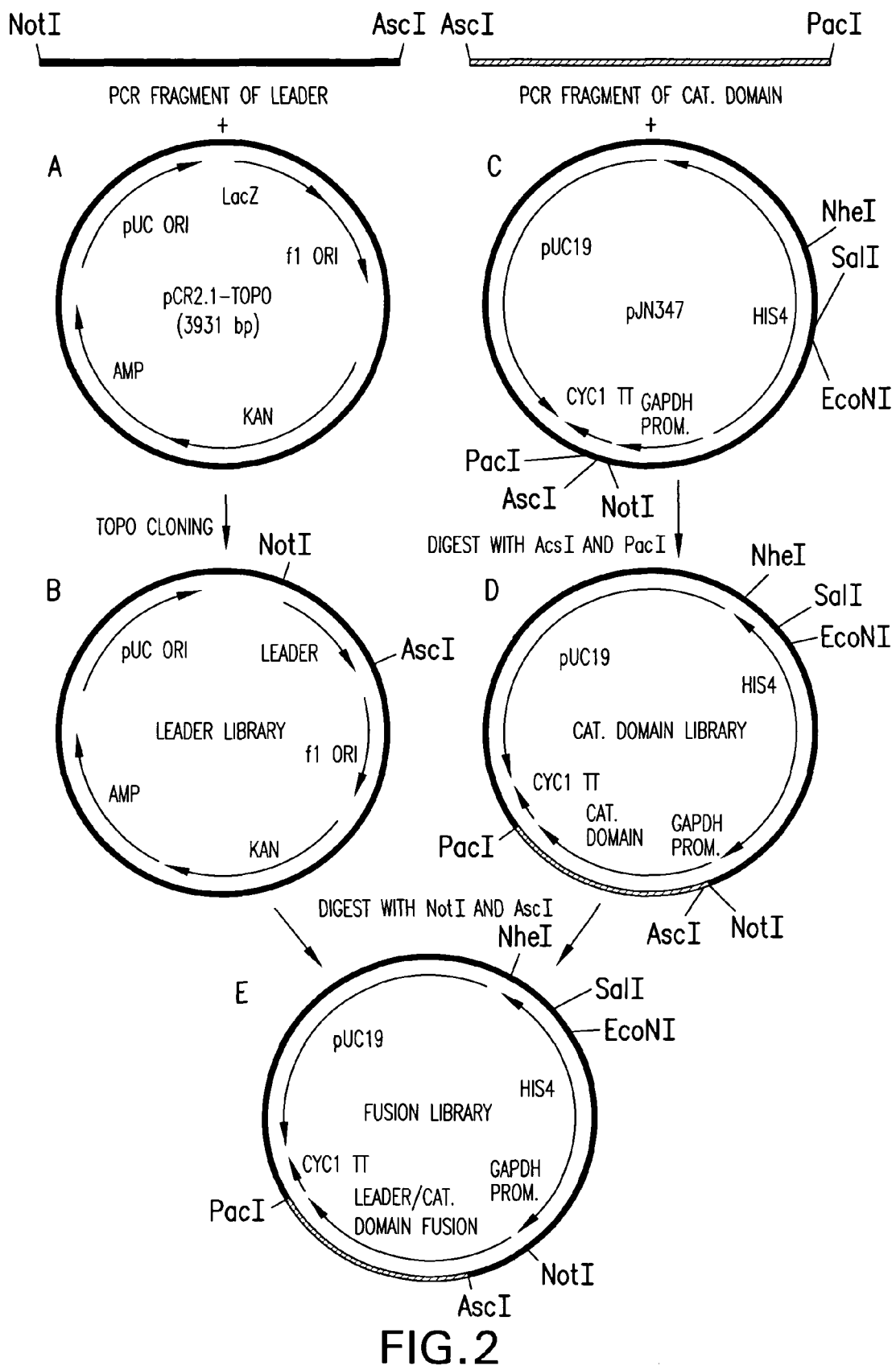
FIG. 2 depicts construction of a combinatorial DNA library of fusion constructs.

Alteration of Host Cell Glycosylation Using Fusion Constructs From Combinatorial Libraries The construction of a preferred combinatorial DNA library is illustrated schematically in FIG. 2 and described in Example 11. The fusion construct may be operably linked to a multitude of vectors, such as expression vectors well-known in the art. A wide variety of such fusion constructs were assembled using representative activities as shown in Table 6. Combinations of targeting peptide/catalytic domains may be assembled for use in targeting mannosidase, glycosyltransferase and glycosidase activities in the ER, Golgi and the trans Golgi network according to the invention. Surprisingly, the same catalytic domain may have no effect to a very profound effect on N-glycosylation patterns, depending on the type of targeting peptide used (see, e.g., Table 7, Example 11).

Mannosidase Fusion Constructs

Figure 6F:
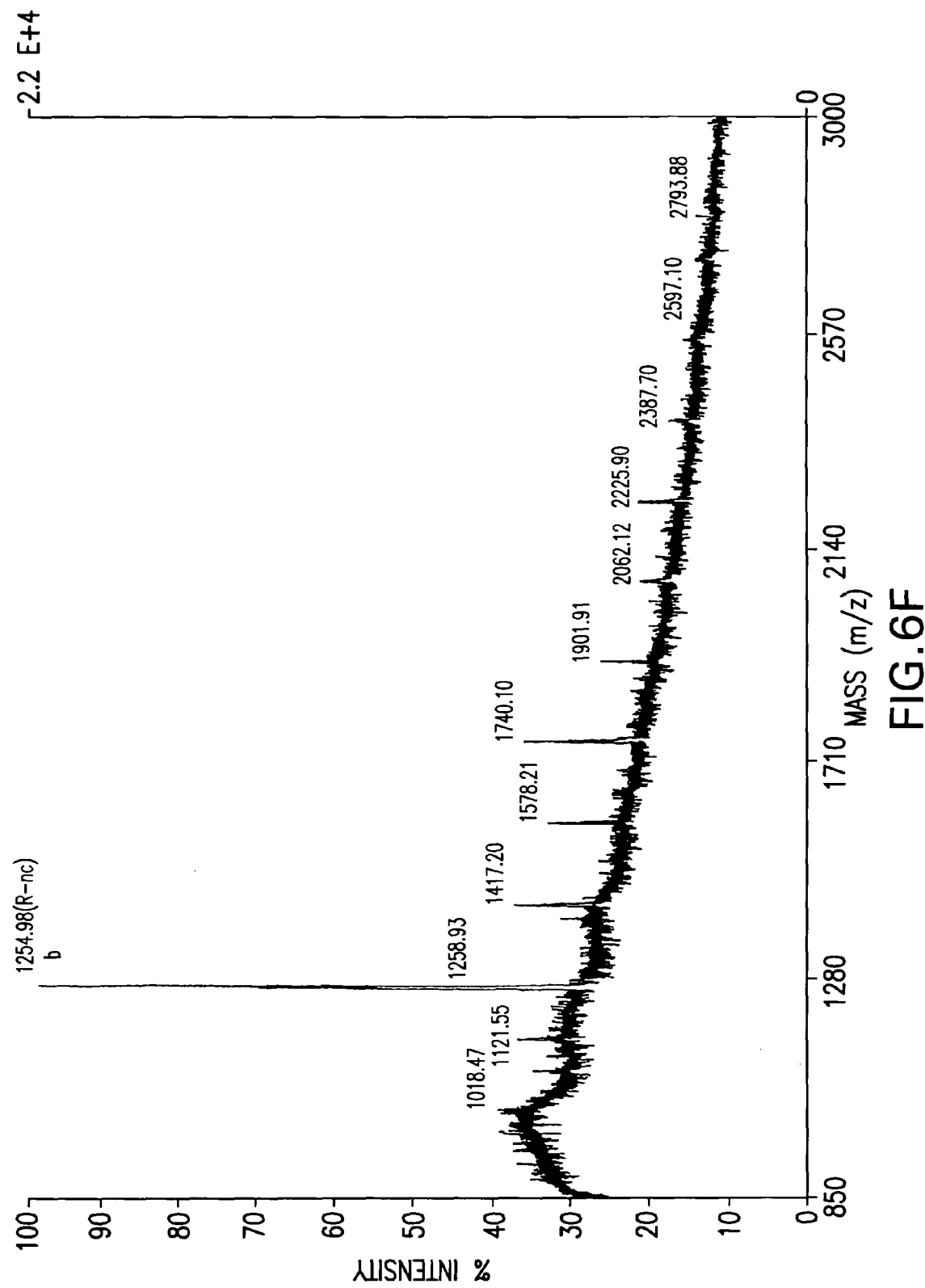
Figure 7:
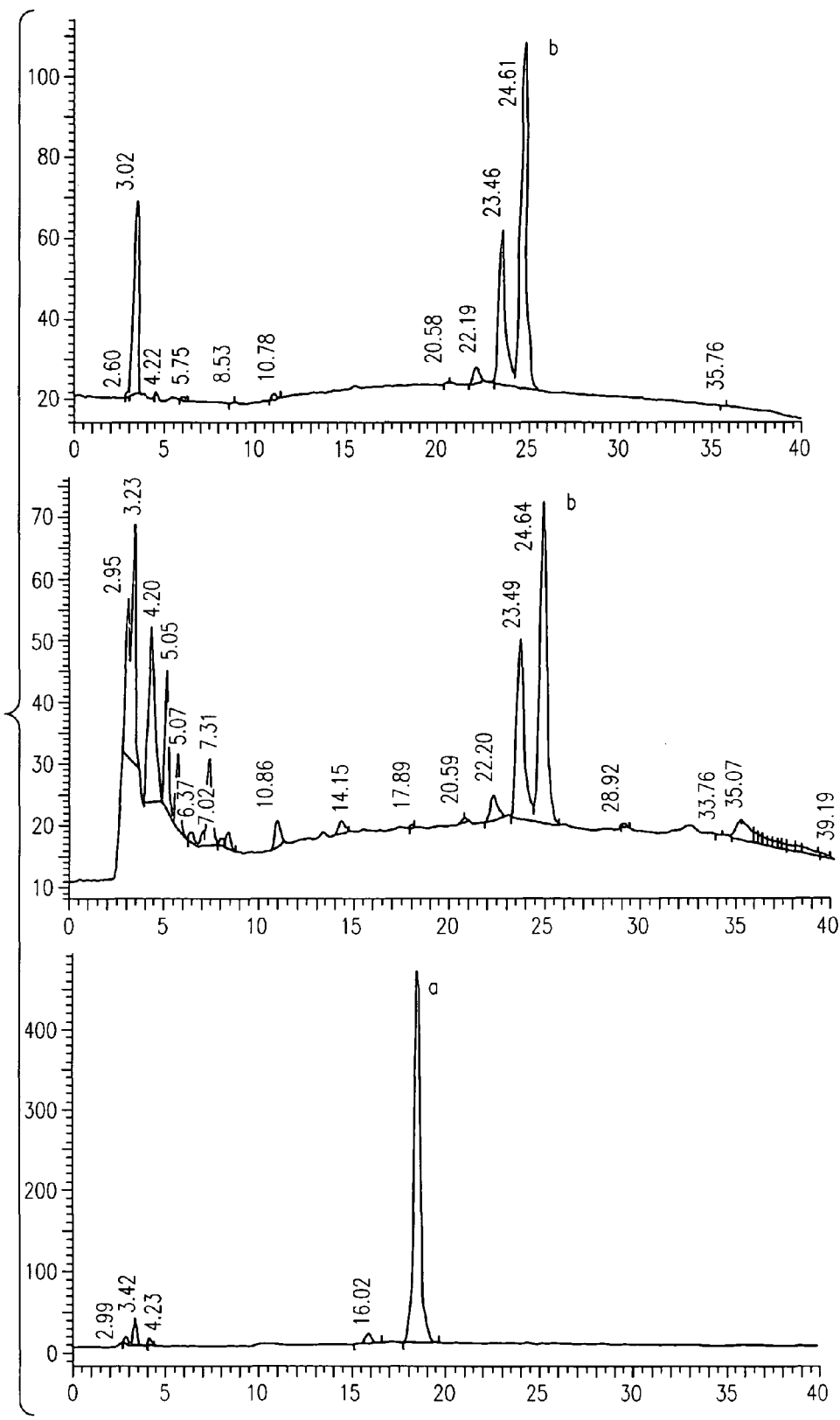
FIG. 7 shows a high performance liquid chromatogram for: (A) $Man_9GlcNAc_2$ standard labeled with 2-AB (negative control); (B) supernatant of medium P. pastoris, Δoch1 transformed with pFB8 mannosidase, which demonstrates a lack of extracellular mannosidase activity in the supernatant; and (C) $Man_9GlcNAc_2$ standard labeled with 2-AB after exposure to T. reesei mannosidase (positive control).
Figure 7A:
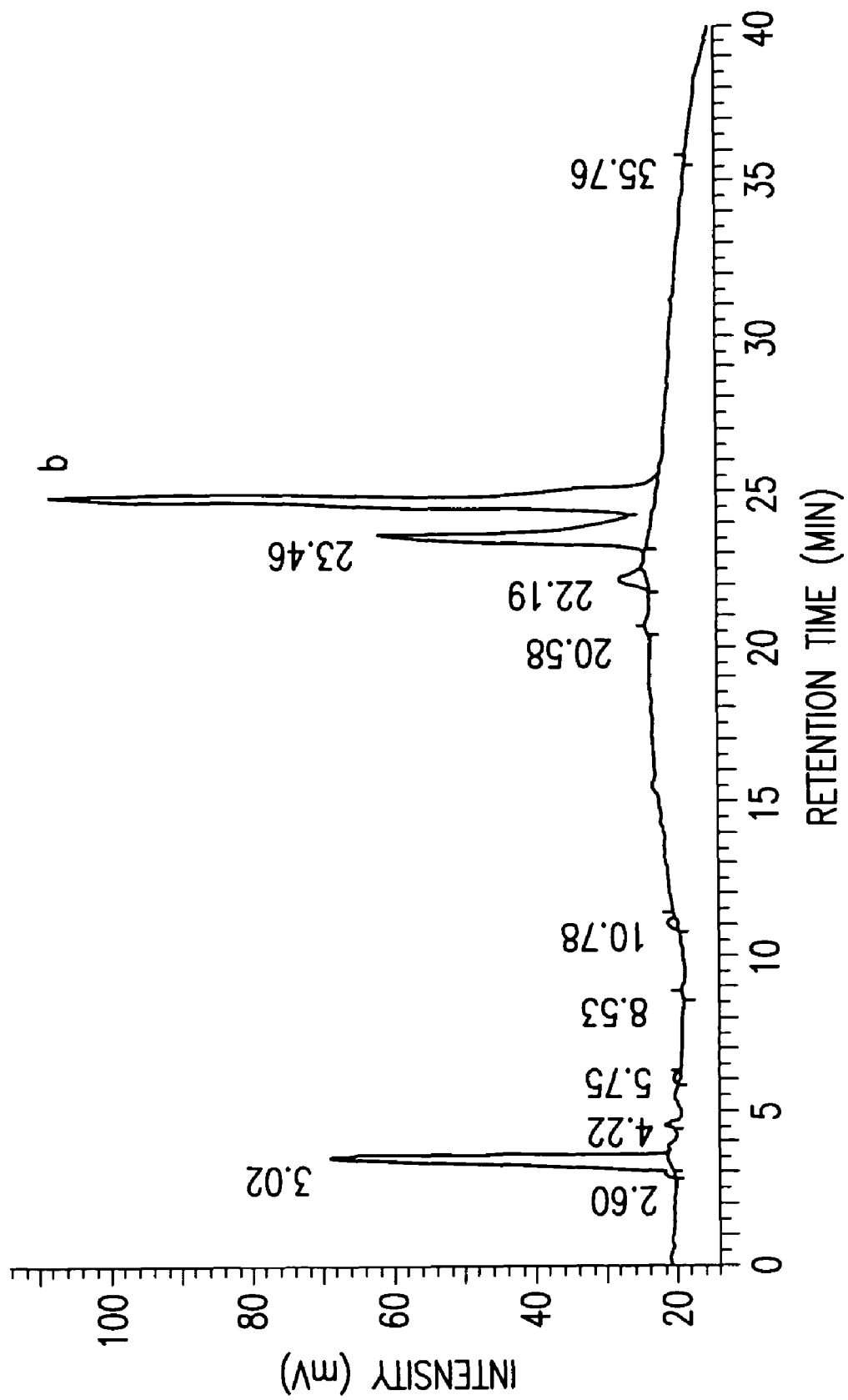
Figure 7B:
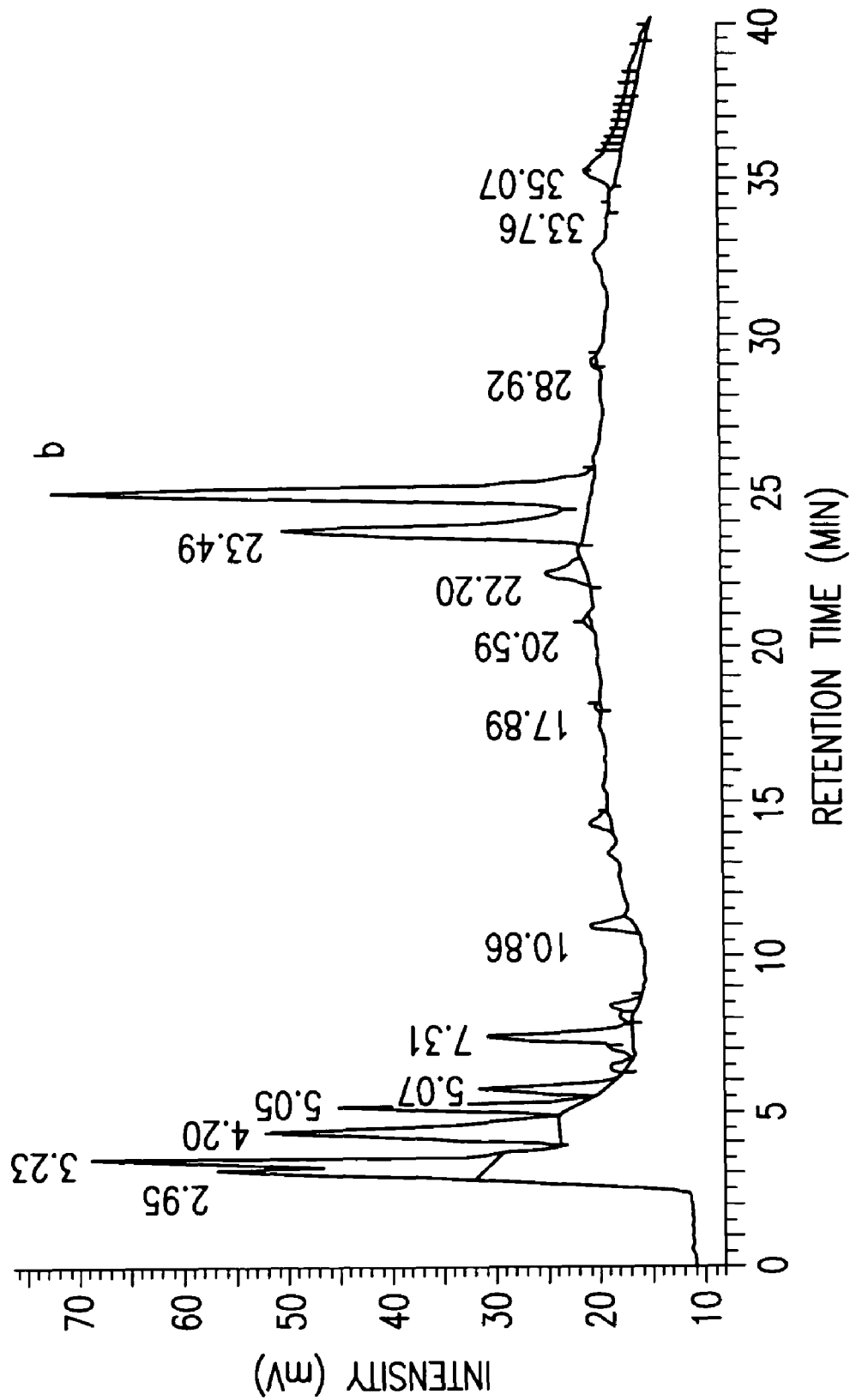

A representative example of a mannosidase fusion construct derived from a combinatorial DNA library of the invention is pFB8, which a truncated *Saccharomyces* SEC12(m) targeting peptide (988-1296 nucleotides of SEC12 from SwissProt P11655) ligated in-frame to a 187 N-terminal amino acid deletion of a mouse α-mannosidase IA (Genbank AN 6678787). The nomenclature used herein, thus, refers to the targeting peptide/catalytic domain region of a glycosylation enzyme as *Saccharomyces* SEC12 (m)/mouse mannosidase IA Δ187. The encoded fusion protein localizes in the ER by means of the SEC12 targeting peptide sequence while retaining its mannosidase catalytic domain activity and is capable of producing in vivo N-glycans having a $Man_5GlcNAc_2$ structure (Example 11; FIG. 6F, FIG. 7B).

Figure 5C:
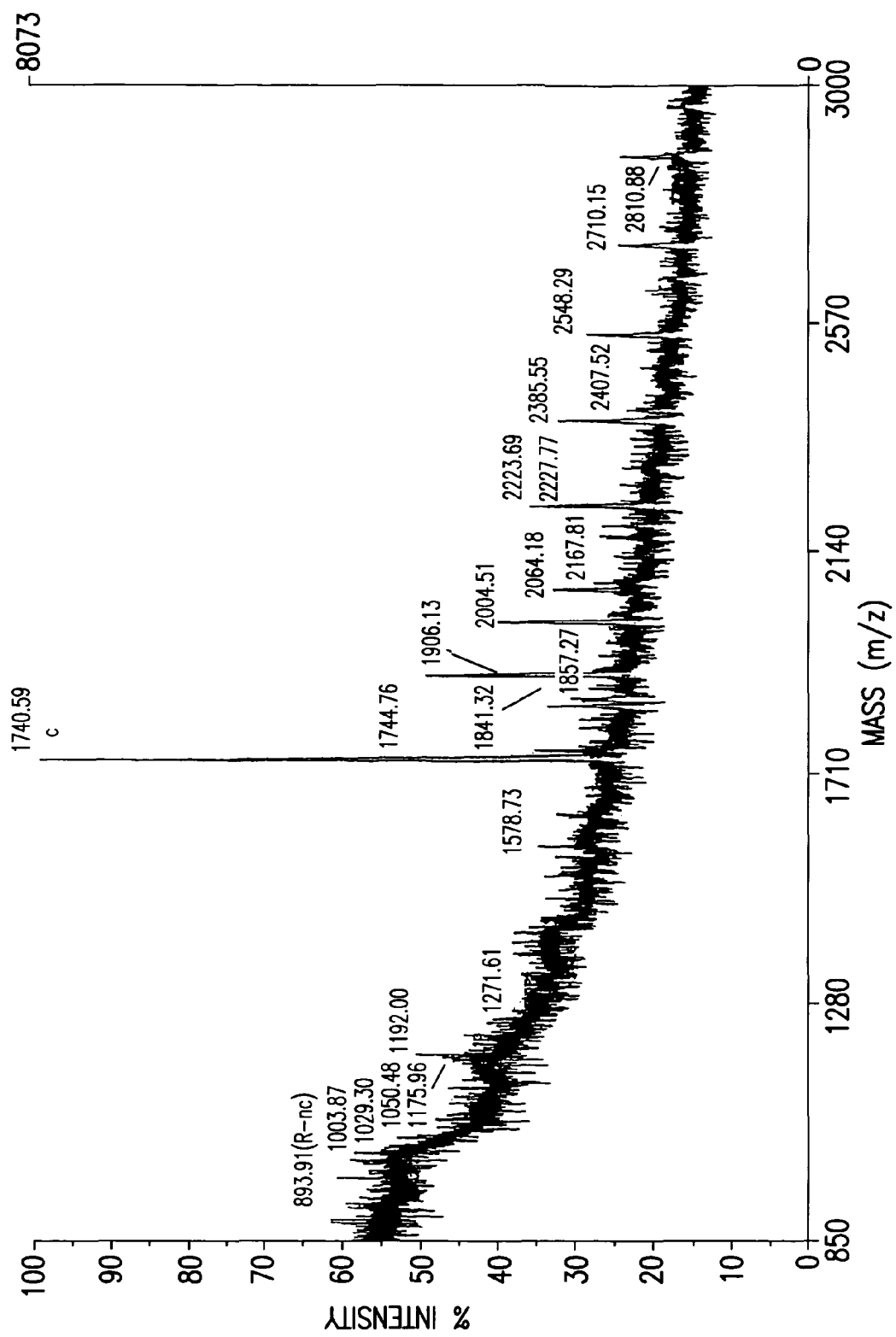
Figure 5D:
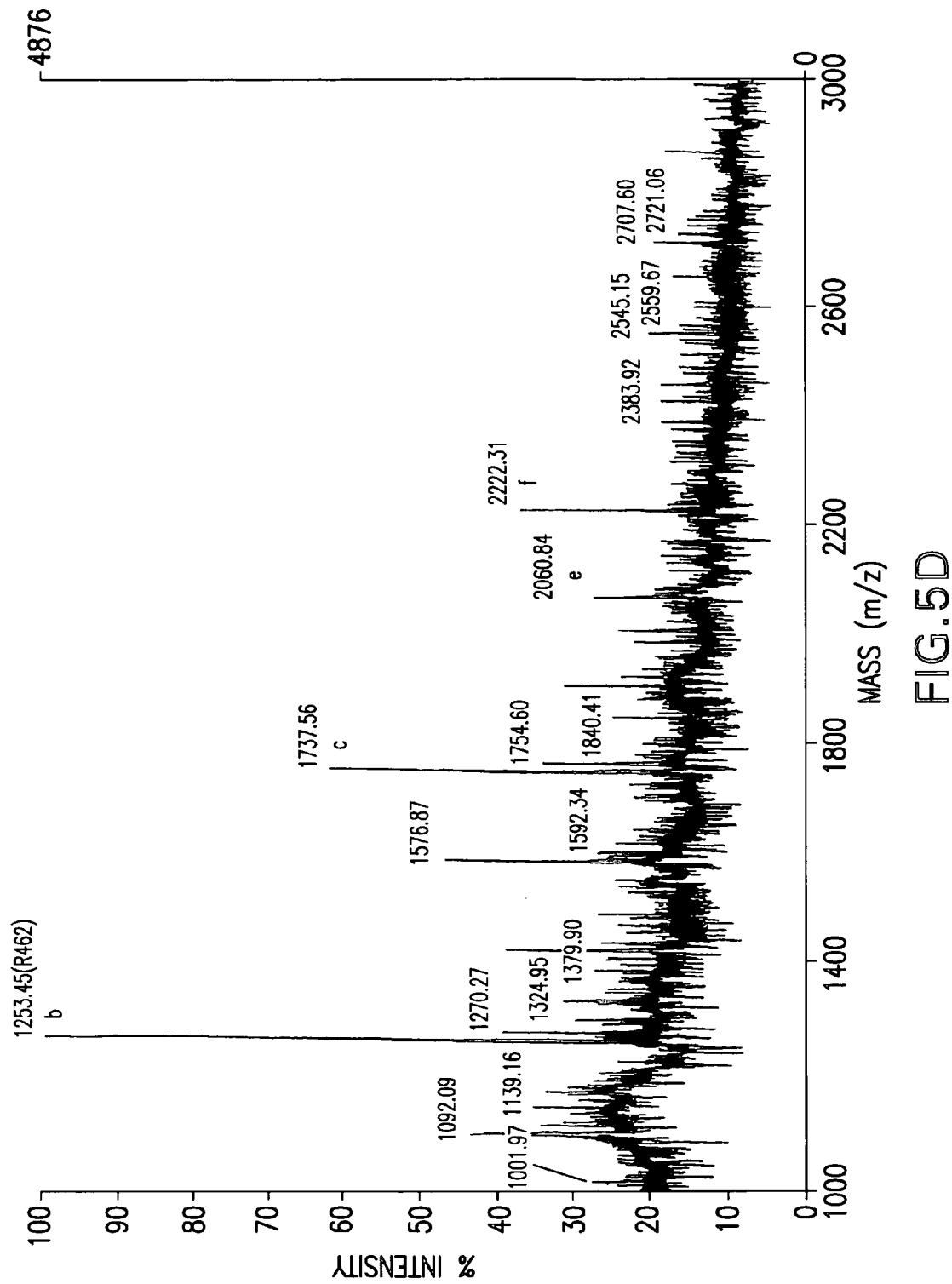
Figure 8:
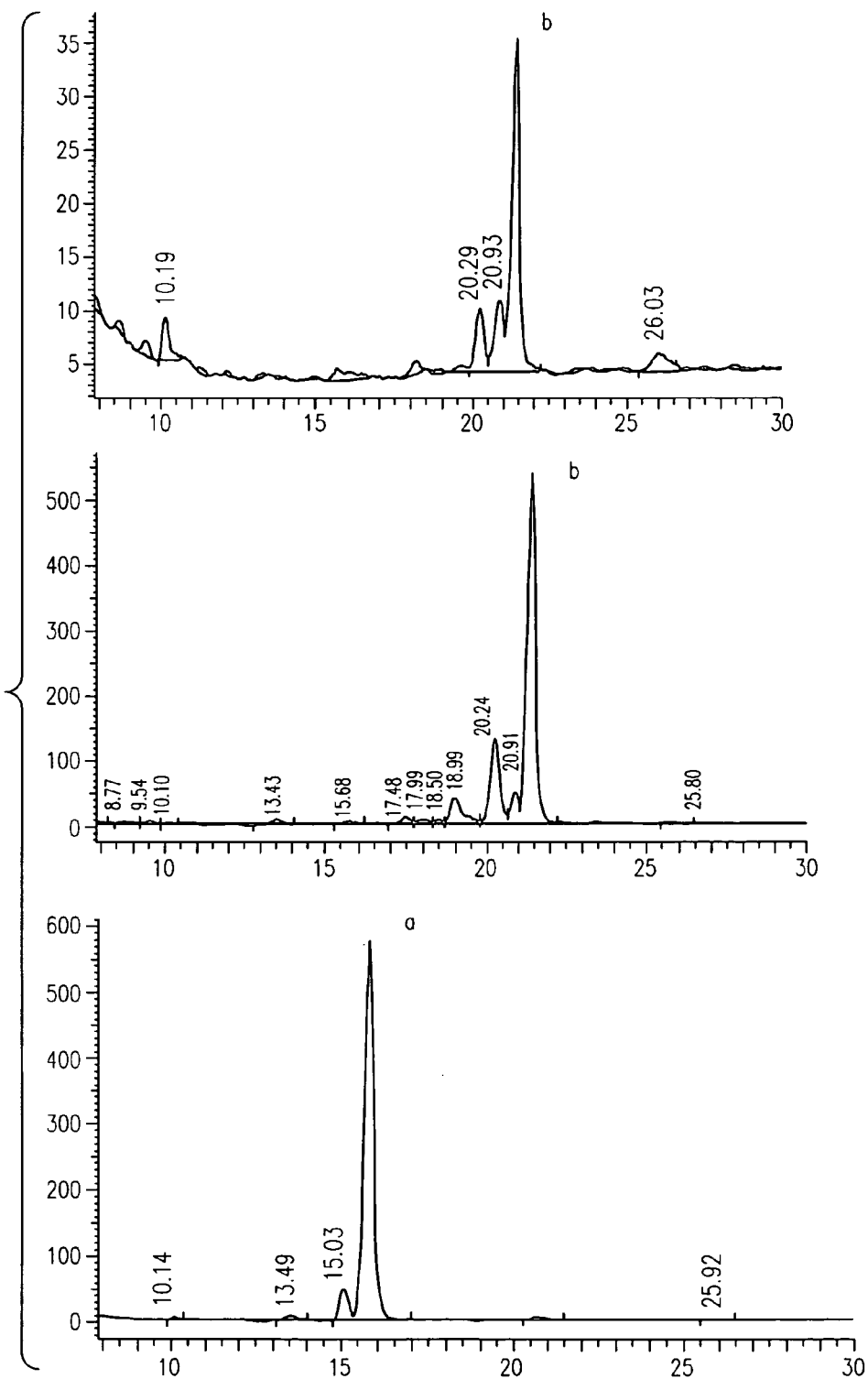
FIG. 8 shows a high performance liquid chromatogram for: (A) $Man_9GlcNAc_2$ standard labeled with 2-AB (negative control); (B) supernatant of medium P. pastoris, Δoch1 transformed with pGC5 mannosidase, which demonstrates a lack of extracellular mannosidase activity in the supernatant; and (C) $Man_9GlcNAc_2$ standard labeled with 2-AB after exposure to T. reesei mannosidase (positive control).
Figure 8B:
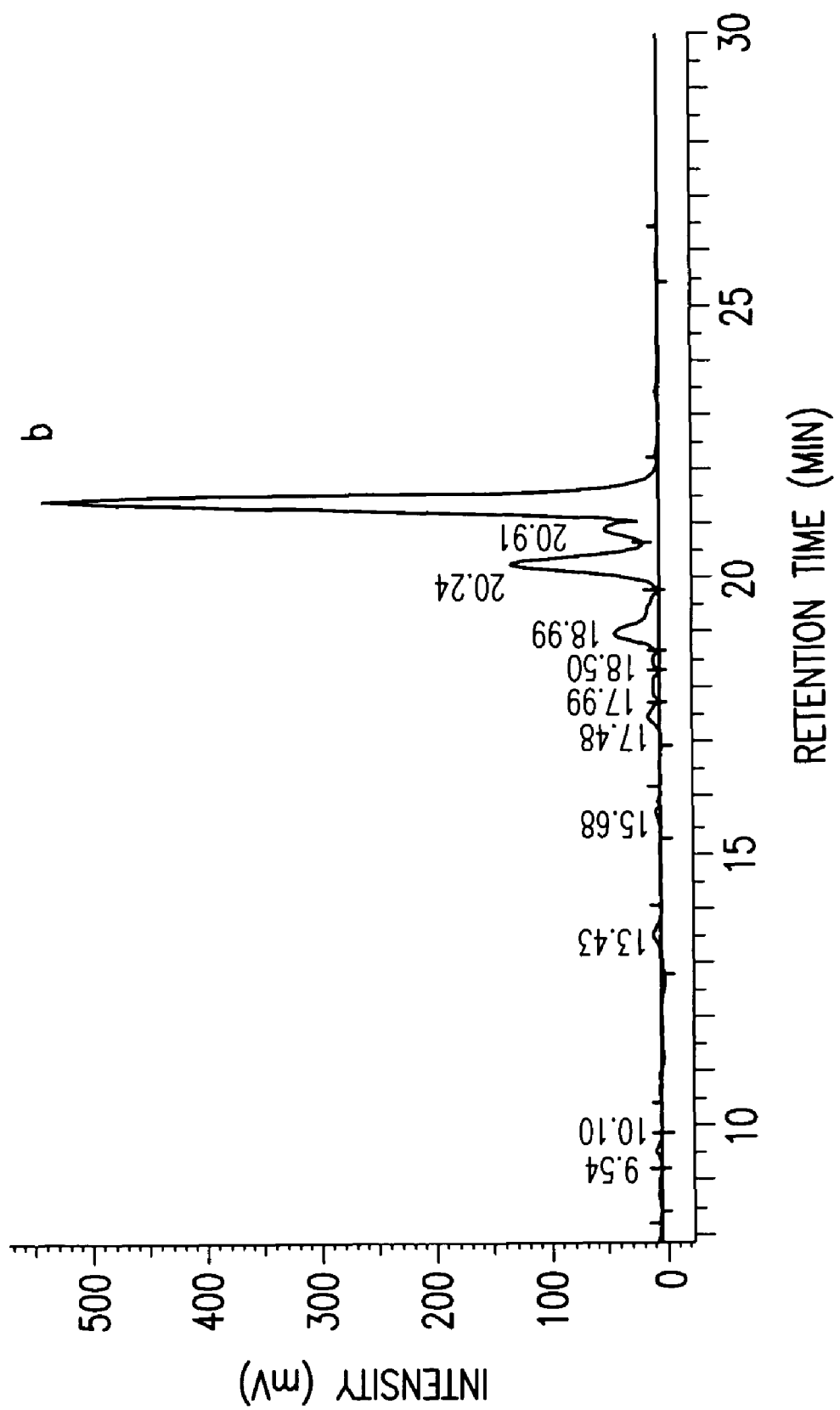

The fusion construct pGC5, *Saccharomyces* MNS1(m)/mouse mannosidase IB Δ99, is another example of a fusion construct having intracellular mannosidase trimming activity (Example 11; FIG. 5D, FIG. 8B). Fusion construct pBC18-5 (*Saccharomyces* VAN1(s)/*C. elegans* mannosidase IB Δ80) is yet another example of an efficient fusion construct capable of producing N-glycans having a $Man_5GlcNAc_2$ structure in vivo. By creating a combinatorial DNA library of these and other such mannosidase fusion constructs according to the invention, a skilled artisan may distinguish and select those constructs having optimal intracellular trimming activity from those having relatively low or no activity. Methods using combinatorial DNA libraries of the invention are advantageous because only a select few mannosidase fusion constructs may produce a particularly desired N-glycan in vivo.

In addition, mannosidase trimming activity may be specific to a particular protein of interest. Thus, it is to be further understood that not all targeting peptide/mannosidase catalytic domain fusion constructs may function equally well to produce the proper glycosylation on a glycoprotein of interest. Accordingly, a protein of interest may be introduced into a host cell transfected with a combinatorial DNA library to identify one or more fusion constructs which express a mannosidase activity optimal for the protein of interest. One skilled in the art will be able to produce and select optimal fusion construct(s) using the combinatorial DNA library approach described herein.

It is apparent, moreover, that other such fusion constructs exhibiting localized active mannosidase catalytic domains (or more generally, domains of any enzyme) may be made using techniques such as those exemplified in Example 11 and described herein. It will be a matter of routine experimentation for one skilled in the art to make and use the combinatorial DNA library of the present invention to optimize, for example, $Man_5GlcNAc_2$ production from a library of fusion constructs in a particular expression vector introduced into a particular host cell.

Glycosyltransferase Fusion Constructs

Similarly, a glycosyltransferase combinatorial DNA library was made using the methods of the invention. A combinatorial DNA library of sequences derived from glycosyltransferase I (GnTI) activities were assembled with targeting peptides and screened for efficient production in a lower eukaryotic host cell of a $GlcNAcMan_5GlcNAc_2$ N-glycan structure on a marker glycoprotein. A fusion construct shown to produce $GlcNAcMan_5GlcNAc_2$ (pPB104), *Saccharomyces* MNN9(s)/human GnTI Δ38 was identified (Example 15). A wide variety of such GnTI fusion constructs were assembled (Example 15, Table 10). Other combinations of targeting peptide/GnTI catalytic domains can readily be assembled by making a combinatorial DNA library. It is also apparent to one skilled in the art that other such fusion constructs exhibiting glycosyltransferase activity may be made as demonstrated in Example 15. It will be a matter of routine experimentation for one skilled in the art to use the combinatorial DNA library method described herein to optimize $GlcNAcMan_5GlcNAc_2$ production using a selected fusion construct in a particular expression vector and host cell line.

As stated above for mannosidase fusion constructs, not all targeting peptide/GnTI catalytic domain fusion constructs will function equally well to produce the proper glycosylation on a glycoprotein of interest as described herein. However, one skilled in the art will be able to produce and select optimal fusion construct(s) using a DNA library approach as described herein. Example 15 illustrates a preferred embodiment of a combinatorial DNA library comprising targeting peptides and GnTI catalytic domain fusion constructs involved in producing glycoproteins with predominantly $GlcNAcMan_5GlcNAc_2$ structure.

Using Multiple Fusion Constructs to Alter Host Cell Glycosylation

Figure 10:
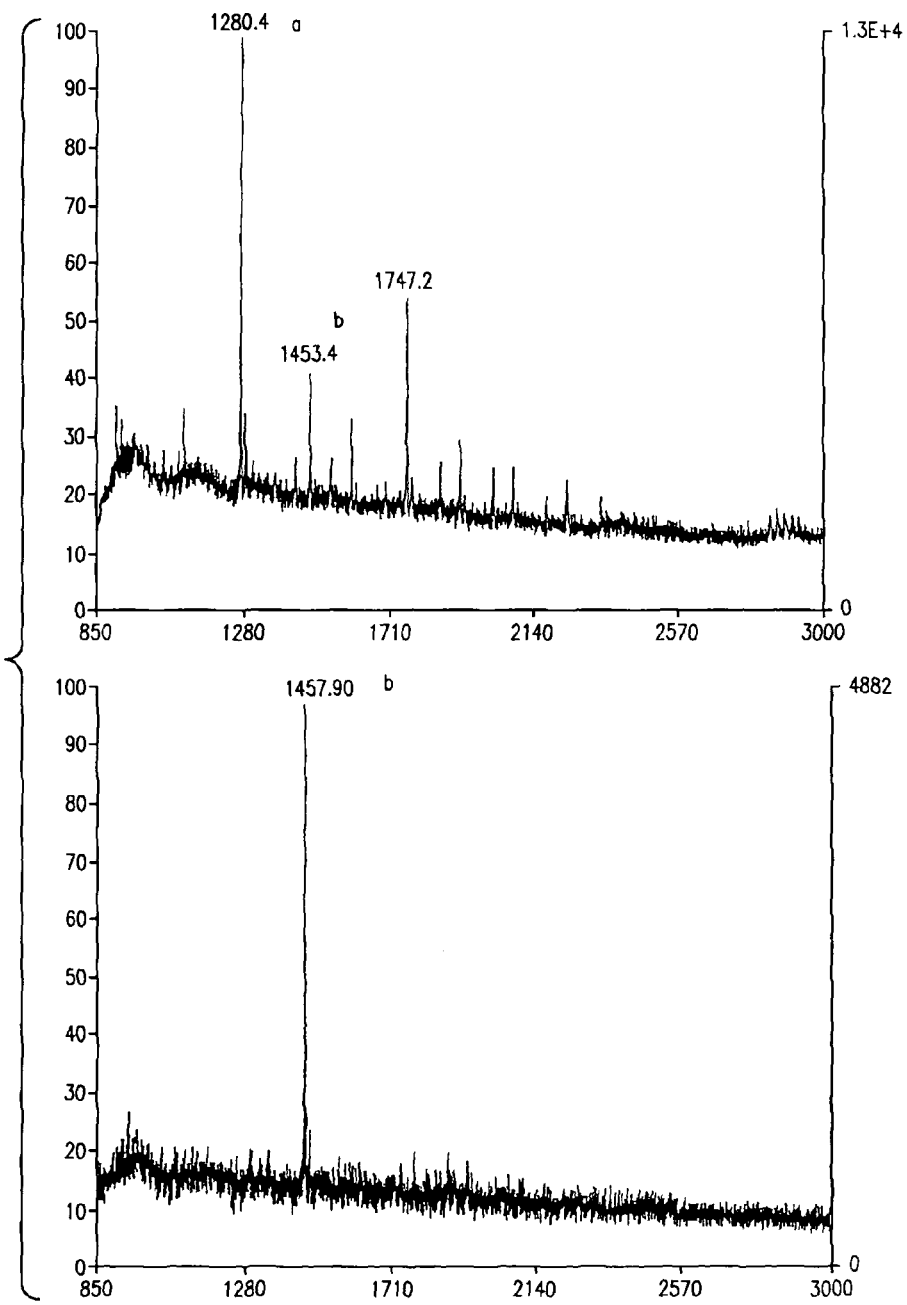
FIGS. 10A-10B demonstrate the activity of an UDP-GlcNAc transporter in the production of $GlcNAcMan_5GlcNAc_2$ in P. pastoris.
Figure 10A:
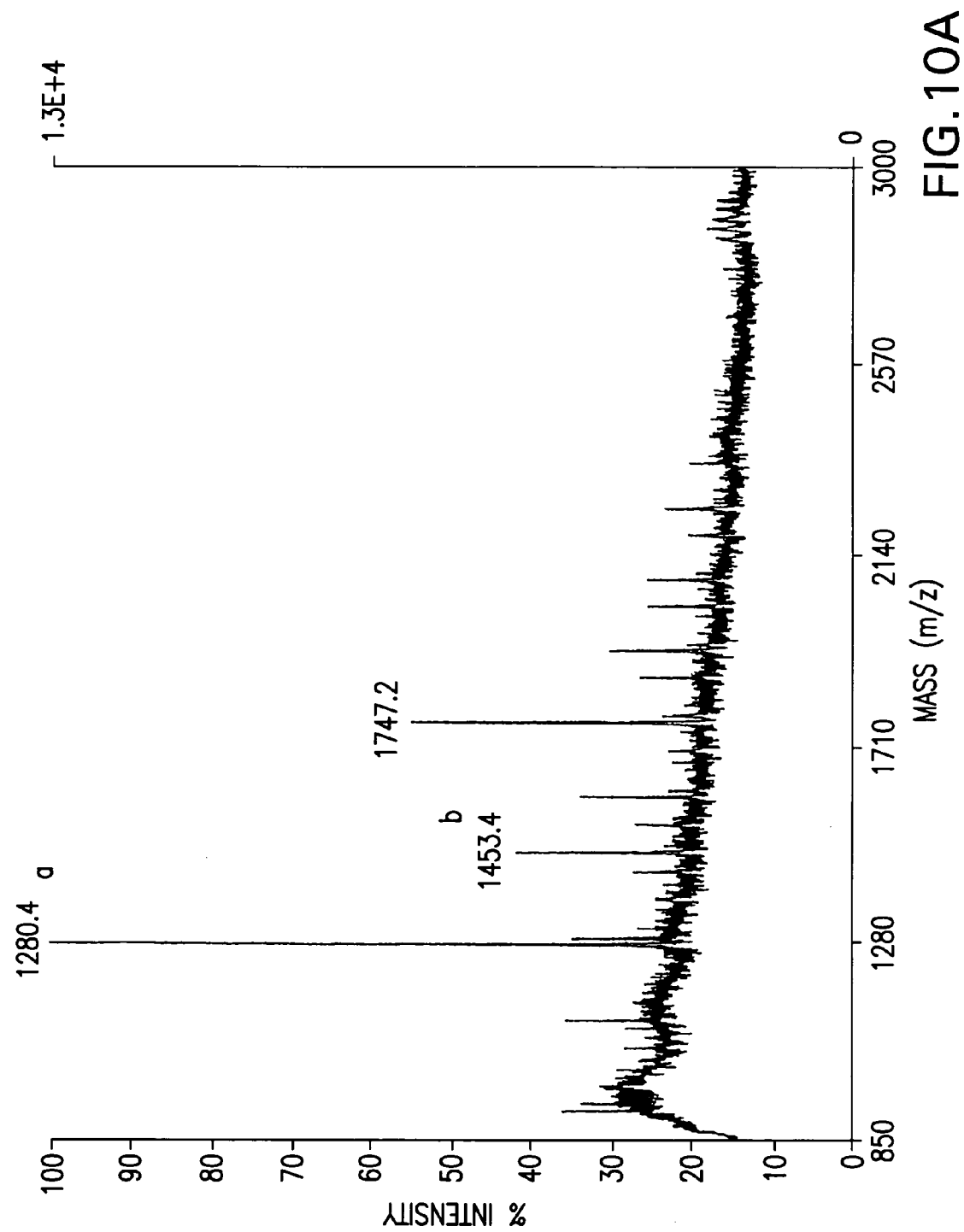
Figure 10B:
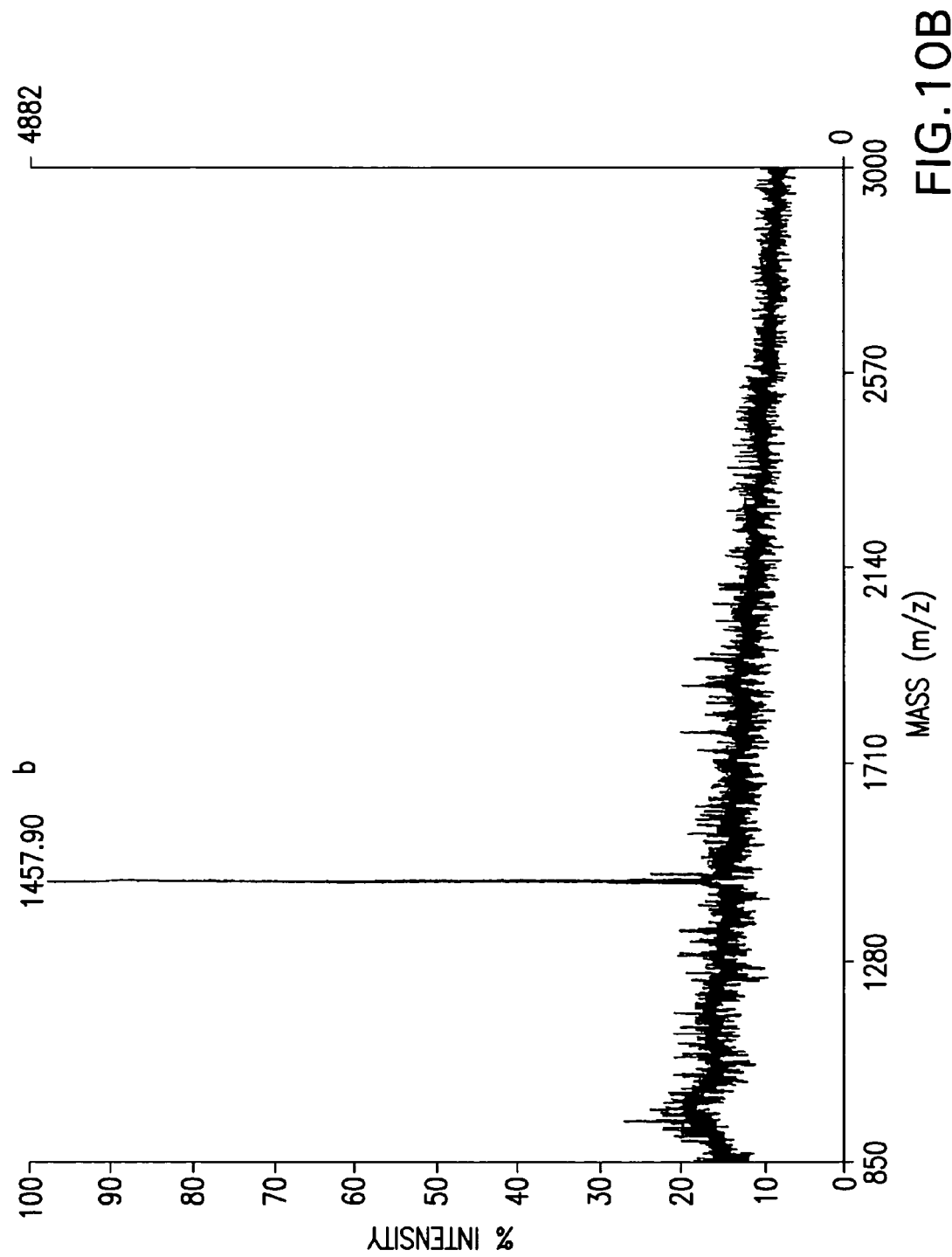

In another example of using the methods and libraries of the invention to alter host cell glycosylation, a *P. pastoris* strain with an OCH1 deletion that expresses a reporter protein (K3) was transformed with multiple fusion constructs isolated from combinatorial libraries of the invention to convert high mannose N-glycans to human-like N-glycans (Example 15). First, the mannosidase fusion construct pFB8 (*Saccharomyces* SEC12 (m)/mouse mannosidase IA Δ187) was transformed into a *P. pastoris* strain lacking 1,6 initiating mannosyltransferases activity (i.e. och1 deletion; Example 1). Second, pPB103 comprising a *K. lactis* MNN2-2 gene (Genbank AN AF106080) encoding an UDP-GlcNAc transporter was constructed to increase further production of $GlcNAcMan_5GlcNAc_2$. The addition of the UDP-GlcNAc transporter increased production of $GlcNAcMan_5GlcNAc_2$ significantly in the *P. pastoris* strain as illustrated in FIG. 10B. Third, pPB104 comprising *Saccharomyces* MNN9 (s)/human GnTI Δ38 was introduced into the strain. This *P. pastoris* strain is referred to as "PBP-3."

It is understood by one skilled in the art that host cells such as the above-described yeast strains can be sequentially transformed and/or co-transformed with one or more expression vectors. It is also understood that the order of transformation is not particularly relevant in producing the glycoprotein of interest. The skilled artisan recognizes the routine modifications of the procedures disclosed herein may provide improved results in the production of the glycoprotein of interest.

Figure 5E:
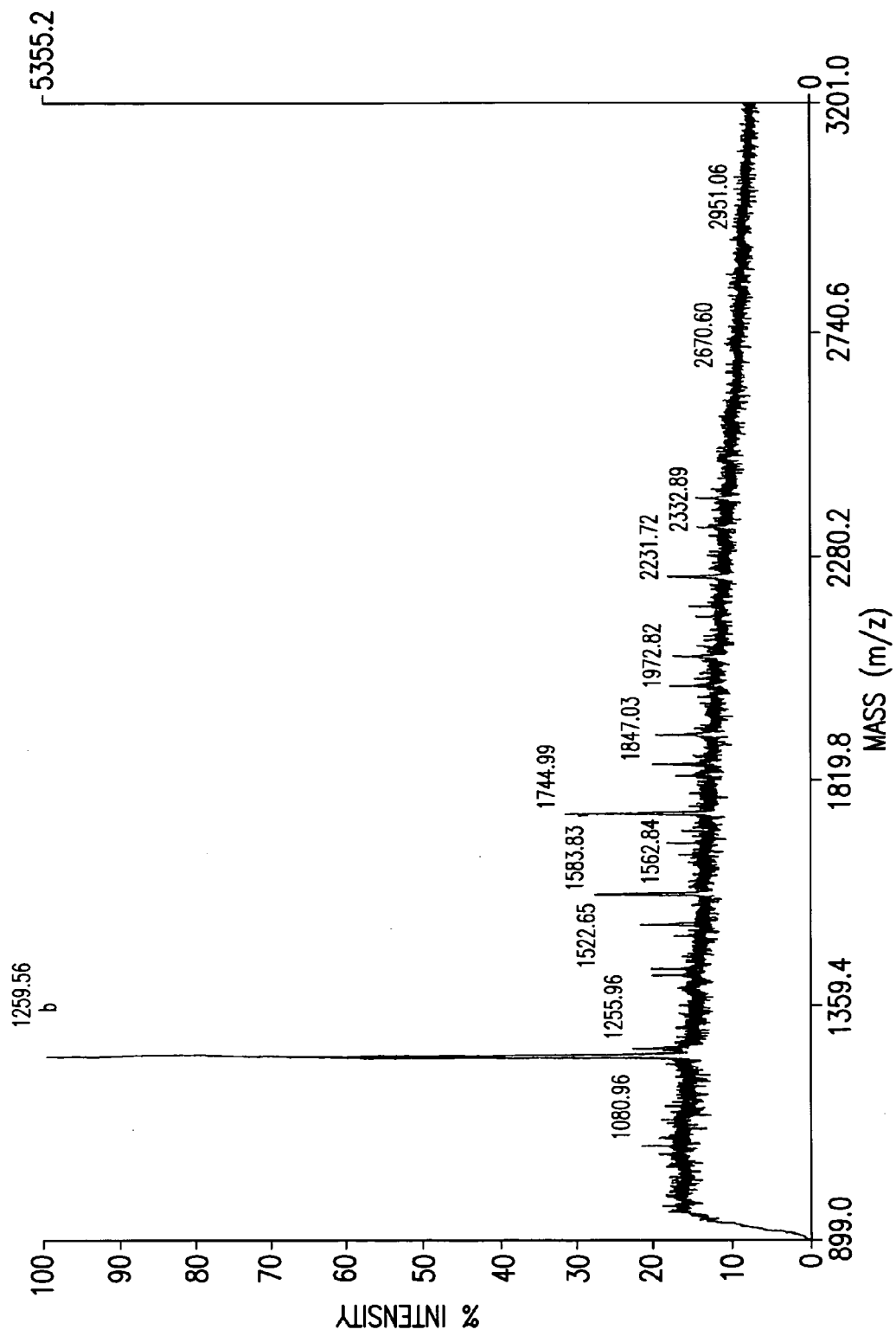

The importance of using a particular targeting peptide sequence with a particular catalytic domain sequence becomes readily apparent from the experiments described herein. The combinatorial DNA library provides a tool for constructing enzyme fusions that are involved in modifying N-glycans on a glycoprotein of interest, which is especially useful in producing human-like glycoproteins. (Any enzyme fusion, however, may be selected using libraries and methods of the invention.) Desired transformants expressing appropriately targeted, active α-1,2-mannosidase produce K3 with N-glycans of the structure $Man_5GlcNAc_2$ as shown in FIGS. 5D and 5E. This confers a reduced molecular mass to the cleaved glycan compared to the K3 of the parent OCH1 deletion strain, as was detected by MALDI-TOF mass spectrometry in FIG. 5C.

Similarly, the same approach was used to produce another secreted glycoprotein: IFN-β comprising predominantly $Man_5GlcNAc_2$. The $Man_5GlcNAc_2$ was removed by PNGase digestion (Papac et al. 1998 *Glycobiology* 8, 445-454) and subjected to MALDI-TOF as shown in FIG. 6A-6F. A single prominent peak at 1254 (m/z) confirms $Man_5GlcNA_2$ production on IFN-β in FIGS. 6E (pGC5) (*Saccharomyces* MNS1 (m)/mouse mannosidase IB Δ99) and 6F (pFB8) (*Saccharomyces* SEC12 (m)/mouse mannosidase IA Δ187). Furthermore, in the *P. pastoris* strain PBP-3 comprising pFB8 (*Saccharomyces* SEC12 (m)/mouse mannosidase IA Δ187), pPB104 (*Saccharomyces* MNN9 (s)/human GnTI Δ38) and pPB103 (*K. lactis* MNN2-2 gene), the hybrid N-glycan $GlcNAcMan_5GlcNAc_2$ [b] was detected by MALDI-TOF (FIG. 10).

Figure 9:
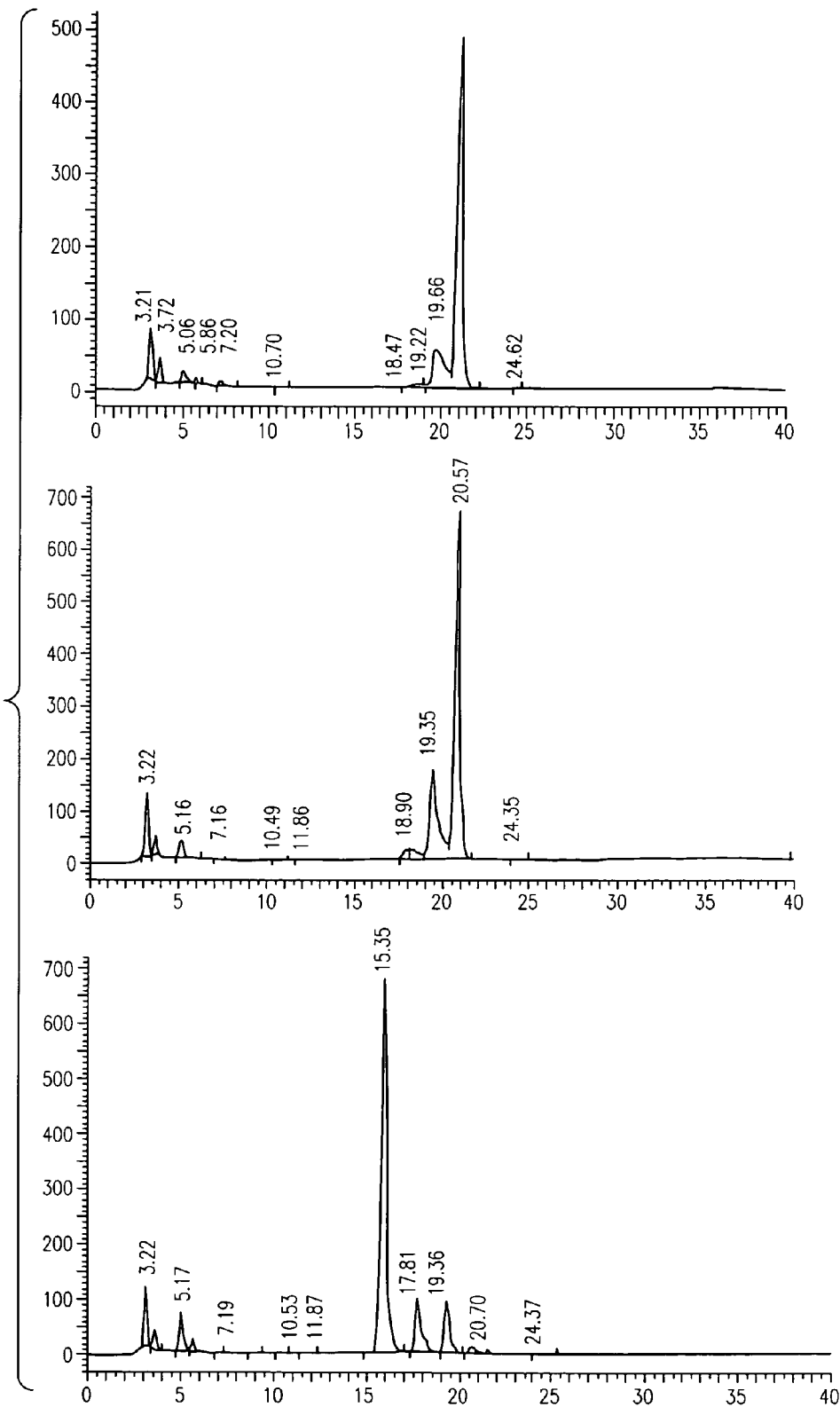
FIG. 9 shows a high performance liquid chromatogram for: (A) $Man_9GlcNAc_2$ standard labeled with 2-AB (negative control); (B) supernatant of medium P. pastoris, Δoch1 transformed with pBC18-5 mannosidase, which demonstrates lack of extracellular mannosidase activity in the supernatant; and (C) supernatant of medium P. pastoris, Δoch1 transformed with pDD28-3, which demonstrates activity in the supernatant (positive control).

After identifying transformants with a high degree of mannose trimming, additional experiments were performed to confirm that mannosidase (trimming) activity occurred in vivo and was not predominantly the result of extracellular activity in the growth medium (Example 13; FIGS. 7-9).

Host Cells

Figure 12:
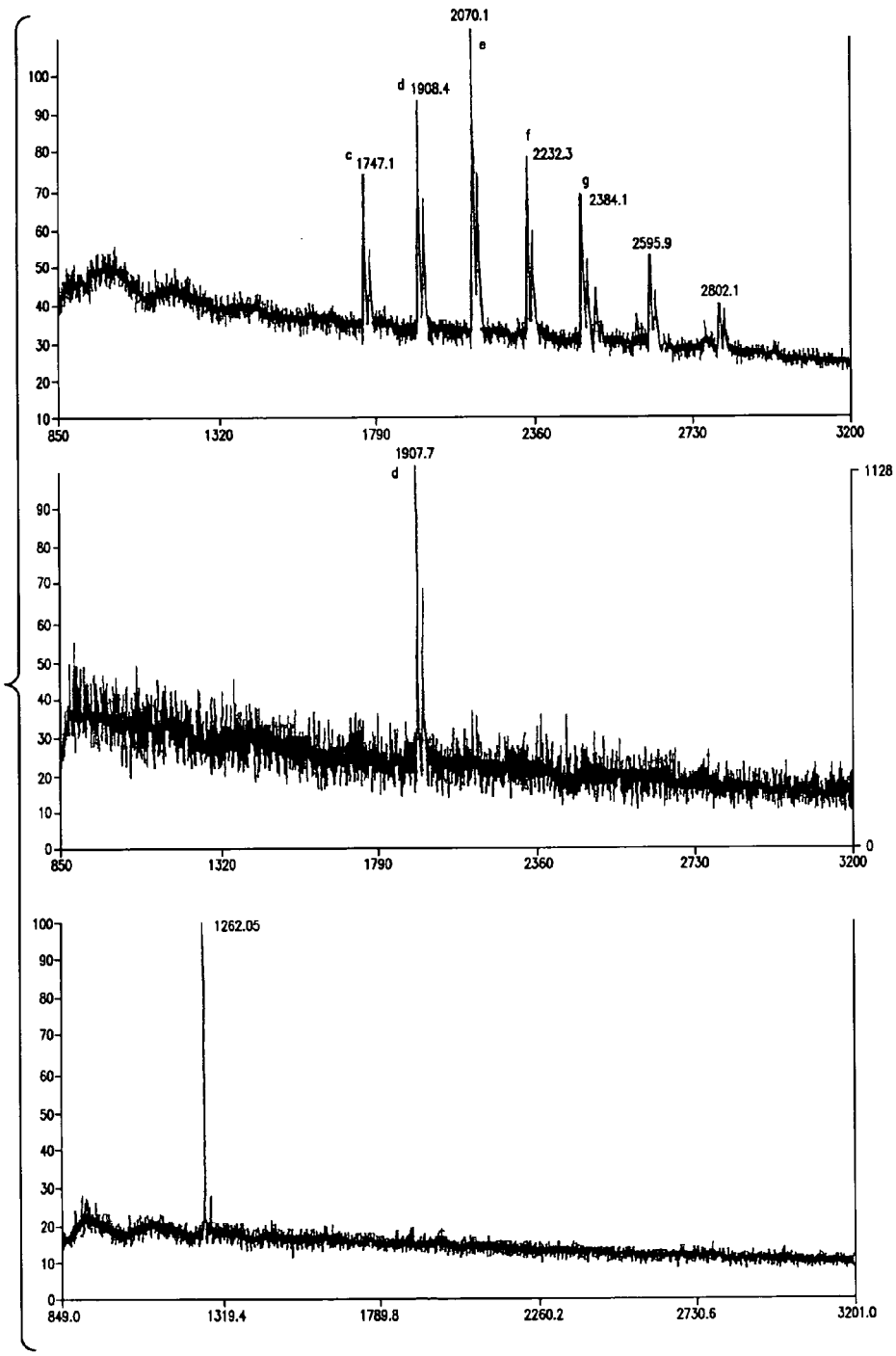
FIGS. 12A-12C show MALDI-TOF analysis of N-glycans released from a cell free extract of *K. lactis*.
Figure 12A:
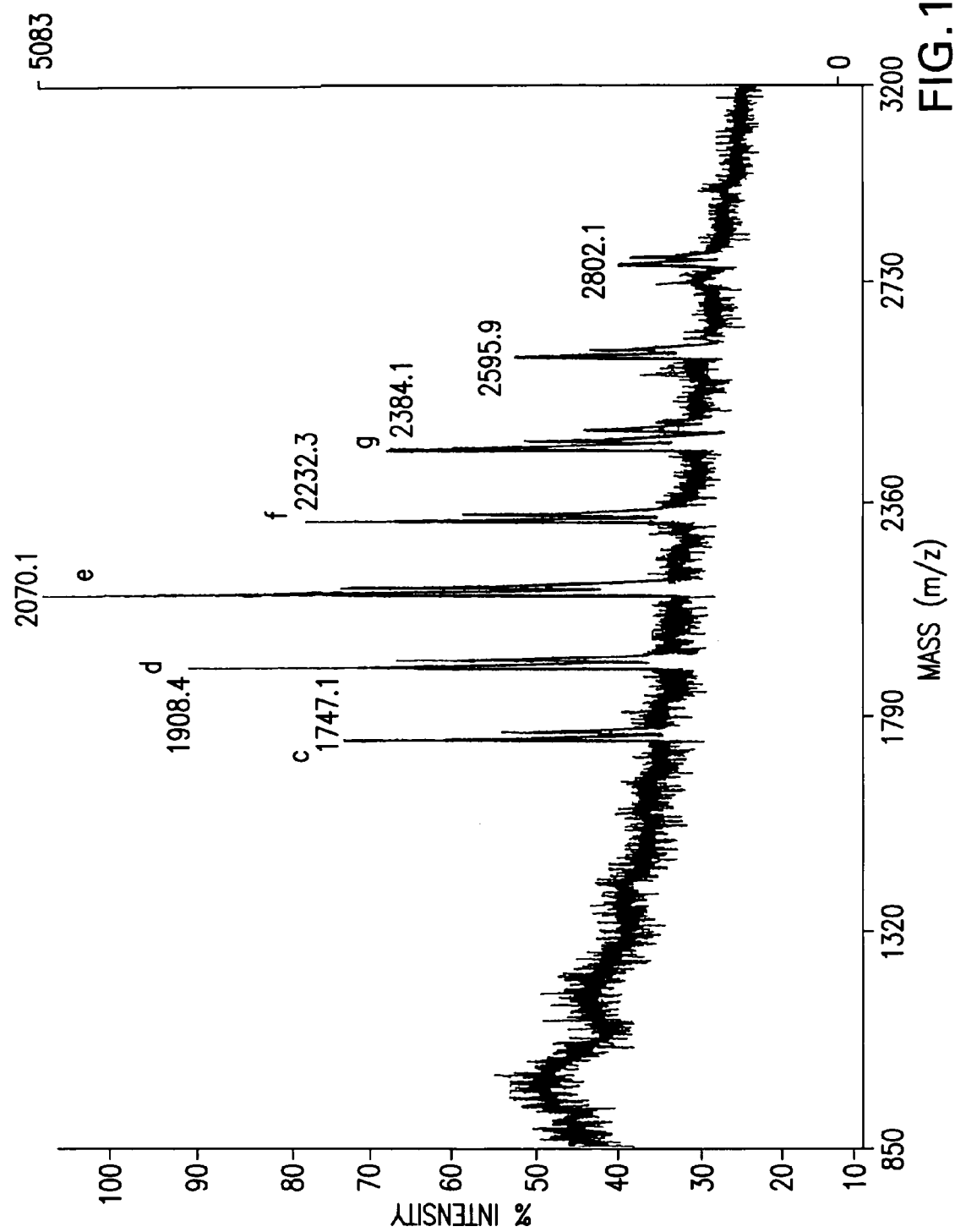

Although the present invention is exemplified using a *P. pastoris* host organism, it is understood by those skilled in the art that other eukaryotic host cells, including other species of yeast and fungal hosts, may be altered as described herein to produce human-like glycoproteins. The techniques described herein for identification and disruption of undesirable host cell glycosylation genes, e.g. OCH1, is understood to be applicable for these and/or other homologous or functionally related genes in other eukaryotic host cells such as other yeast and fungal strains. As described in Example 16, och1 mnn1 genes were deleted from *K. lactis* to engineer a host cell leading to N-glycans that are completely converted to $Man_5GlcNAc_2$ by 1,2-mannosidase (FIG. 12C).

The MNN1 gene was cloned from *K. lactis* as described in Example 16. The nucleic acid and deduced amino acid sequences of the *K. lactis* MNN1 gene are shown in SEQ ID NOS: 43 and 44, respectively. Using gene-specific primers, a construct was made to delete the MNN1 gene from the genome of *K. lactis* (Example 16). Host cells depleted in och1 and mnn1 activities produce N-glycans having a $Man_9GlcNAc_2$ carbohydrate structure (see, e.g., FIG. 10). Such host cells may be engineered further using, e.g., methods and libraries of the invention, to produce mammalian- or human-like glycoproteins.

Thus, in another embodiment, the invention provides an isolated nucleic acid molecule having a nucleic acid sequence comprising or consisting of at least forty-five, preferably at least 50, more preferably at least 60 and most preferably 75 or more nucleotide residues of the *K. lactis* MNN1 gene (SEQ ID NO: 43), and homologs, variants and derivatives thereof. The invention also provides nucleic acid molecules that hybridize under stringent conditions to the above-described nucleic acid molecules. Similarly, isolated polypeptides (including muteins, allelic variants, fragments, derivatives, and analogs) encoded by the nucleic acid molecules of the invention are provided. In addition, also provided are vectors, including expression vectors, which comprise a nucleic acid molecule of the invention, as described further herein. Similarly host cells transformed with the nucleic acid molecules or vectors of the invention are provided.

Another aspect of the present invention thus relates to a non-human eukaryotic host strain expressing glycoproteins comprising modified N-glycans that resemble those made by human-cells. Performing the methods of the invention in species other than yeast and fungal cells is thus contemplated and encompassed by this invention. It is contemplated that a combinatorial nucleic acid library of the present invention may be used to select constructs that modify the glycosylation pathway in any eukaryotic host cell system. For example, the combinatorial libraries of the invention may also be used in plants, algae and insects, and in other eukaryotic host cells, including mammalian and human cells, to localize proteins, including glycosylation enzymes or catalytic domains thereof, in a desired location along a host cell secretory pathway. Preferably, glycosylation enzymes or catalytic domains and the like are targeted to a subcellular location along the host cell secretory pathway where they are capable of functioning, and preferably, where they are designed or selected to function most efficiently.

As described in Examples 17 and 18, plant and insect cells may be engineered to alter the glycosylation of expressed proteins using the combinatorial library and methods of the invention. Furthermore, glycosylation in mammalian cells, including human cells, may also be modified using the combinatorial library and methods of the invention. It may be possible, for example, to optimize a particular enzymatic activity or to otherwise modify the relative proportions of various N-glycans made in a mammalian host cell using the combinatorial library and methods of the invention.

Examples of modifications to glycosylation which can be affected using a method according to this embodiment of the invention are: (1) engineering a eukaryotic host cell to trim mannose residues from $Man_8GlcNAc_2$ to yield a $Man_5GlcNAc_2$ N-glycan; (2) engineering eukaryotic host cell to add an N-acetylglucosamine (GlcNAc) residue to $Man_5GlcNAc_2$ by action of GlcNAc transferase I; (3) engineering a eukaryotic host cell to functionally express an enzyme such as an N-acetylglucosaminyl Transferase (GnTI, GnTII, GnTIII, GnTIV, GnTV, GnTVI), mannosidase II, fucosyltransferase (FT), galactosyl tranferase (GalT) or a sialyltransferase (ST).

By repeating the method, increasingly complex glycosylation pathways can be engineered into a target host, such as a lower eukaryotic microorganism. In one preferred embodiment, the host organism is transformed two or more times with DNA libraries including sequences encoding glycosylation activities. Selection of desired phenotypes may be performed after each round of transformation or alternatively after several transformations have occurred. Complex glycosylation pathways can be rapidly engineered in this manner.

Sequential Glycosylation Reactions

In a preferred embodiment, such targeting peptide/catalytic domain libraries are designed to incorporate existing information on the sequential nature of glycosylation reactions in higher eukaryotes. Reactions known to occur early in the course of glycoprotein processing require the targeting of enzymes that catalyze such reactions to an early part of the Golgi or the ER. For example, the trimming of $Man_8GlcNAc_2$ to $Man_5GlcNAc_2$ by mannosidases is an early step in complex N-glycan formation. Because protein processing is initiated in the ER and then proceeds through the early, medial and late Golgi, it is desirable to have this reaction occur in the ER or early Golgi. When designing a library for mannosidase I localization, for example, one thus attempts to match ER and early Golgi targeting signals with the catalytic domain of mannosidase I.

Integration Sites

As one ultimate goal of this genetic engineering effort is a robust protein production strain that is able to perform well in an industrial fermentation process, the integration of multiple genes into the host (e.g., fungal) chromosome preferably involves careful planning. The engineered strain may likely have to be transformed with a range of different genes, and these genes will have to be transformed in a stable fashion to ensure that the desired activity is maintained throughout the fermentation process. As described herein, any combination of various desired enzyme activities may be engineered into the fungal protein expression host, e.g., sialyltransferases, mannosidases, fucosyltransferases, galactosyltransferases, glucosyltransferases, GlcNAc transferases, ER and Golgi specific transporters (e.g. syn and antiport transporters for UDP-galactose and other precursors), other enzymes involved in the processing of oligosaccharides, and enzymes involved in the synthesis of activated oligosaccharide precursors such as UDP-galactose, CMP-N-acetylneuraminic acid. Examples of preferred methods for modifying glycosylation in a lower eukaryotic host cell, such as *Pichia pastoris*, are shown in Table 6. (The HDEL and KDEL signal peptides in the second row of the third column are shown in SEQ ID NOS 5 and 6, respectively).

TABLE 6

Some preferred embodiments for modifying glycosylation in a lower eukaroytic microorganism

| Desired Structure | Suitable Catalytic Activities | Suitable Sources of Localization Sequences | Suitable Gene Deletions | Suitable Transporters and/or Phosphatases |
| --- | --- | --- | --- | --- |
| $Man_5GlcNAc_2$ | α-1,2-mannosidase (murine, human, *Bacillus* sp., *A. nidulans*) | Mns1 (N-terminus, *S. cerevisiae*) Och1 (N-terminus, *S. cerevisiae*, *P. pastoris*) Ktr1 Mnn9 Mnt1 (*S. cerevisiae*) KDEL, HDEL (C-terminus) | OCH1 MNN4 MNN6 | none |
| $GlcNAcMan_5GlcNAc_2$ | GlcNAc Transferase I, (human, murine, rat etc.) | Och1 (N-terminus, *S. cerevisiae*, *P. pastoris*) KTR1 (N-terminus) Mnn1 (N-terminus, *S. cerevisiae*) Mnt1 (N-terminus, *S. cerevisiae*) GDPase (N-terminus, *S. cerevisiae*) | OCH1 MNN4 MNN6 | UDP-GlcNAc transporter (human, murine, *K. lactis*) UDPase (human) |
| $GlcNAcMan_3GlcNAc_2$ | mannosidase II | Ktr1 Mnn1 (N-terminus, *S. cerevisiae*) Mnt1 (N-terminus, *S. cerevisiae*) Kre2/Mnt1 (*S. cerevisiae*) Kre2 (*P. pastoris*) Ktr1 (*S. cerevisiae*) Ktr1 (*P. pastoris*) Mnn1 (*S. cerevisiae*) | OCH1 MNN4 MNN6 | UDP-GlcNAc transporter (human, murine, K. lactis) UDPase (human) |
| $GlcNAc_{(2-4)}Man_3GlcNAc_2$ | GlcNAc Transferase II, III, IV, V (human, murine) | Mnn1 (N-terminus, *S. cerevisiae*) Mnt1 (N-terminus, *S. cerevisiae*) Kre2/Mnt1 (*S. cerevisiae*) | OCH1 MNN4 MNN6 | UDP-GlcNAc transporter (human, murine, K. lactis) UDPase (human) |

TABLE 6-continued

Some preferred embodiments for modifying glycosylation in a lower eukaroytic microorganism

| Desired Structure | Suitable Catalytic Activities | Suitable Sources of Localization Sequences | Suitable Gene Deletions | Suitable Transporters and/or Phosphatases |
|---|---|---|---|---|
| $Gal_{(1-4)}GlcNAc_{(2-4)}-Man_3GlcNAc_2$ | β-1,4-Galactosyl transferase (human) | Kre2 (P. pastoris)<br>Ktr1 (S. cerevisiae)<br>Ktr1 (P. pastoris)<br>Mnn1 (S. cerevisiae)<br>Mnn1 (N-terminus, S. cerevisiae)<br>Mnt1 (N-terminus, S. cerevisiae)<br>Kre2/Mnt1 (S. cerevisiae)<br>Kre2 (P. pastoris)<br>Ktr1 (S. cerevisiae)<br>Ktr1 (P. pastoris)<br>Mnn1 (S. cerevisiae) | OCH1<br>MNN4<br>MNN6 | UDP-Galactose transporter (human, S. pombe) |
| $NANA_{(1-4)}-Gal_{(1-4)}GlcNAc_{(2-4)}-Man_3GlcNAc_2$ | α-2,6-Sialyltransferase (human)<br>α-2,3-Sialyltransferase | KTR1<br>MNN1 (N-terminus, S. cerevisiae)<br>MNT1 (N-terminus, S. cerevisiae)<br>Kre2/Mnt1 (S. cerevisiae)<br>Kre2 (P. pastoris)<br>Ktr1 (S. cerevisiae)<br>Ktr1 (P. pastoris)<br>MNN1 (S. cerevisiae) | OCH1<br>MNN4<br>MNN6 | CMP-Sialic acid transporter (human) |

As any strategy to engineer the formation of complex N-glycans into a host cell such as a lower eukaryote involves both the elimination as well as the addition of particular glycosyltransferase activities, a comprehensive scheme will attempt to coordinate both requirements. Genes that encode enzymes that are undesirable serve as potential integration sites for genes that are desirable. For example, 1,6 mannosyltransferase activity is a hallmark of glycosylation in many known lower eukaryotes. The gene encoding alpha-1,6 mannosyltransferase (OCH1) has been cloned from S. cerevisiae and mutations in the gene give rise to a viable phenotype with reduced mannosylation. The gene locus encoding alpha-1,6 mannosyltransferase activity therefore is a prime target for the integration of genes encoding glycosyltransferase activity. In a similar manner, one can choose a range of other chromosomal integration sites that, based on a gene disruption event in that locus, are expected to: (1) improve the cells ability to glycosylate in a more human-like fashion, (2) improve the cells ability to secrete proteins, (3) reduce proteolysis of foreign proteins and (4) improve other characteristics of the process that facilitate purification or the fermentation process itself.

Target Glycoproteins

The methods described herein are useful for producing glycoproteins, especially glycoproteins used therapeutically in humans. Glycoproteins having specific glycoforms may be especially useful, for example, in the targeting of therapeutic proteins. For example, mannose-6-phosphate has been shown to direct proteins to the lysosome, which may be essential for the proper function of several enzymes related to lysosomal storage disorders such as Gaucher's, Hunter's, Hurler's, Scheie's, Fabry's and Tay-Sachs disease, to mention just a few. Likewise, the addition of one or more sialic acid residues to a glycan side chain may increase the lifetime of a therapeutic glycoprotein in vivo after administration. Accordingly, host cells (e.g., lower eukaryotic or mammalian) may be genetically engineered to increase the extent of terminal sialic acid in glycoproteins expressed in the cells. Alternatively, sialic acid may be conjugated to the protein of interest in vitro prior to administration using a sialic acid transferase and an appropriate substrate. Changes in growth medium composition may be employed in addition to the expression of enzyme activities involved in human-like glycosylation to produce glycoproteins more closely resembling human forms (S. Weikert, et al., Nature Biotechnology, 1999, 17, 1116-1121; Werner, Noe, et al 1998 Arzneimittelforschung 48(8):870-880; Weikert, Papac et al., 1999; Andersen and Goochee 1994 Cur. Opin. Biotechnol. 5: 546-549; Yang and Butler 2000 Biotechnol. Bioengin. 68(4): 370-380). Specific glycan modifications to monoclonal antibodies (e.g. the addition of a bisecting GlcNAc) have been shown to improve antibody dependent cell cytotoxicity (Umana P., et al. 1999), which may be desirable for the production of antibodies or other therapeutic proteins.

Therapeutic proteins are typically administered by injection, orally, pulmonary, or other means. Examples of suitable target glycoproteins which may be produced according to the invention include, without limitation: erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin and α-feto proteins.

The following are examples which illustrate the compositions and methods of this invention. These examples should not be construed as limiting: the examples are included for the purposes of illustration only.

EXAMPLE 1

Cloning and Disruption of the OCH1 Gene in *P. pastoria*

Generation of an OCH1 Mutant of *P. pastoris*:
A 1215 bp ORF of the *P. pastoris* OCH1 gene encoding a putative α-1,6 mannosyltransferase was amplified from *P. pastoris* genomic DNA (strain X-33, Invitrogen, Carlsbad, Calif.) using the oligonucleotides 5'-ATGGCGAAGGCA-GATGGCAGT-3' (SEQ ID NO:7) and 5'-TTAGTCCTTC-CAACTTCCTTC-3' (SEQ ID NO:8) which were designed based on the *P. pastoris* OCH1 sequence (Japanese Patent Application Publication No. 8-336387). Subsequently, 2685 bp upstream and 1175 bp downstream of the ORF of the OCH1 gene were amplified from a *P. pastoris* genomic DNA library (Boehm, T. et al. Yeast 1999 May; 15(7):563-72) using the internal oligonucleotides 5'-ACTGCCATCTGCCT-TCGCCAT-3' (SEQ ID NO:9) in the OCH1 gene, and 5'-GTAATACGACTCACTATAGGGC-3' T7 (SEQ ID NO:10) and 5'-AATTAACCCTCACTAAAGGG-3' T3 (SEQ ID NO:11) oligonucleotides in the backbone of the library bearing plasmid lambda ZAP II (Stratagene, La Jolla, Calif.). The resulting 5075 bp fragment was cloned into the pCR2.1-TOPO vector (Invitrogen, Carlsbad, Calif.) and designated pBK9.

After assembling a gene knockout construct that substituted the OCH1 reading frame with a HIS4 resistance gene, *P. pastoris* was transformed and colonies were screened for temperature sensitivity at 37° C. OCH1 mutants of *S. cerevisiae* are temperature sensitive and are slow growers at elevated temperatures. One can thus identify functional homologs of OCH1 in *P. pastoris* by complementing an OCH1 mutant of *S. cerevisiae* with a *P. pastoris* DNA or cDNA library. About 20 temperature sensitive strains were further subjected to a colony PCR screen to identify colonies with a deleted och1 gene. Several och1 deletions were obtained.

The linearized pBK9.1, which has 2.1 kb upstream sequence and 1.5 kb down stream sequence of OCH1 gene cassette carrying *Pichia* HIS4 gene, was transformed into *P. pastoris* BK1 [GS115 (his4 Invitrogen Corp., San Diego, Calif.) carrying the human IFN-β gene in the AOX1 locus] to knock out the wild-type OCH1 gene. The initial screening of transformants was performed using histidine drop-out medium followed by replica plating to select the temperature sensitive colonies. Twenty out of two hundred histidine-positive colonies showed a temperature sensitive phenotype at 37° C. To exclude random integration of pBK9.1 into the *Pichia* genome, the 20 temperature-sensitive isolates were subjected to colony PCR using primers specific to the upstream sequence of the integration site and to HIS4 ORF. Two out of twenty colonies were och1 defective and further analyzed using a Southern blot and a Western blot indicating the functional och1 disruption by the och1 knock-out construct. Genomic DNA were digested using two separate restriction enzymes BglII and ClaI to confirm the och1 knock-out and to confirm integration at the open reading frame. The Western Blot showed och1 mutants lacking a discrete band produced in the GS115 wild type at 46.2 kDa.

EXAMPLE 2

Engineering of *P. pastoris* with α-1,2-Mannosidase to Produce $Man_5GlcNAc_2$-Containing IFN-β Precursors An α-1,2-mannosidase is required for the trimming of $Man_8GlcNAc_2$ to yield $Man_5GlcNAc_2$, an essential intermediate for complex N-glycan formation. While the production of a $Man_5GlcNAc_2$ precursor is essential, it is not necessarily sufficient for the production of hybrid and complex glycans because the specific isomer of $Man_5GlcNAc_2$ may or may not be a substrate for GnTI. An och1 mutant of *P. pastoris* is engineered to express secreted human interferon-β under the control of an aox promoter. A DNA library is constructed by the in-frame ligation of the catalytic domain of human mannosidase IB (an α-1,2-mannosidase) with a sub-library including sequences encoding early Golgi and ER localization peptides. The DNA library is then transformed into the host organism, resulting in a genetically mixed population wherein individual transformants each express interferon-β as well as a synthetic mannosidase gene from the library. Individual transformant colonies are cultured and the production of interferon is induced by addition of methanol. Under these conditions, over 90% of the secreted protein is glycosylated interferon-β.

Supernatants are purified to remove salts and low-molecular weight contaminants by $C_{18}$ silica reversed-phase chromatography. Desired transformants expressing appropriately targeted, active α-1,2-mannosidase produce interferon-β including N-glycans of the structure $Man_5GlcNAc_2$, which has a reduced molecular mass compared to the interferon-β of the parent strain. The purified interferon-β is analyzed by MALDI-TOF mass spectroscopy and colonies expressing the desired form of interferon-β are identified.

EXAMPLE 3

Generation of an och1 Mutant Strain Expressing an α-1,2-Mannosidase, GnTI and GnTII for Production of a Human-Like Glycoprotein The 1215 bp open reading frame of the *P. pastoris* OCH1 gene as well as 2685 bp upstream and 1175 bp downstream was amplified by PCR (see also WO 02/00879), cloned into the pCR2.1-TOPO vector (Invitrogen) and designated pBK9. To create an och1 knockout strain containing multiple auxotrophic markers, 100 μg of pJN329, a plasmid containing an och1::URA3 mutant allele flanked with SfiI restriction sites was digested with SfiI and used to transform *P. pastoris* strain JC308 (Cereghino et al. *Gene* 263 (2001) 159-169) by electroporation. Following incubation on defined medium lacking uracil for 10 days at room temperature, 1000 colonies were picked and re-streaked. URA+ clones that were unable to grow at 37° C., but grew at room temperature, were subjected to colony PCR to test for the correct integration of the och1::URA3 mutant allele. One clone that exhibited the expected PCR pattern was designated YJN153. The Kringle 3 domain of human plasminogen (K3) was used as a model protein. A $Neo^R$ marked plasmid containing the K3 gene was transformed into strain YJN153 and a resulting strain, expressing K3, was named BK64-1.

Plasmid pPB103, containing the *Kluyveromyces lactis* MNN2-2 gene which encodes a Golgi UDP-N-acetylglucosamine transporter was constructed by cloning a blunt BglII-HindIII fragment from vector pDL02 (Abeijon et al. (1996) *Proc. Natl. Acad. Sci. U.S.A.* 93:5963-5968) into BglII and BamHI digested and blunt ended pBLADE-SX containing the *P. pastoris* ADE1 gene (Cereghino et al. (2001) *Gene* 263:159-169). This plasmid was linearized with EcoNI and transformed into strain BK64-1 by electroporation and one strain confirmed to contain the MNN2-2 by PCR analysis was named PBP1.

A library of mannosidase constructs was generated, comprising in-frame fusions of the leader domains of several type I or type II membrane proteins from *S. cerevisiae* and *P. pastoris* fused with the catalytic domains of several α-1,2-mannosidase genes from human, mouse, fly, worm and yeast sources (see, e.g., WO02/00879, incorporated herein by reference). This library was created in a *P. pastoris* HIS4 integration vector and screened by linearizing with SalI, transforming by electroporation into strain PBP1, and analyzing the glycans released from the K3 reporter protein. One active construct chosen was a chimera of the 988-1296 nucleotides (C-terminus) of the yeast SEC12 gene fused with a N-terminal deletion of the mouse α-1,2-mannosidase IA gene (FIG. 3), which was missing the 187 nucleotides. A *P. pastoris* strain expressing this construct was named PBP2.

A library of GnTI constructs was generated, comprising in-frame fusions of the same leader library with the catalytic domains of GnTI genes from human, worm, frog and fly sources (WO 02/00879). This library was created in a *P. pastoris* ARG4 integration vector and screened by linearizing with AatII, transforming by electroporation into strain PBP2, and analyzing the glycans released from K3. One active construct chosen was a chimera of the first 120 bp of the *S. cerevisiae* MNN9 gene fused to a deletion of the human GnTI gene, which was missing the first 154 bp. A *P. pastoris* strain expressing this construct was named PBP3.

A library of GnTII constructs was generated, which comprised in-frame fusions of the leader library with the catalytic domains of GnTII genes from human and rat sources (WO 02/00879). This library was created in a *P. pastoris* integration vector containing the NST$^R$ gene conferring resistance to the drug nourseothricin. The library plasmids were linearized with EcoRI, transformed into strain RDP27 by electroporation, and the resulting strains were screened by analysis of the released glycans from purified K3.

Materials for the Following Reactions

MOPS, sodium cacodylate, manganese chloride, UDP-galactose and CMP-N-acetylneuraminic acid were from Sigma. Trifluoroacetic acid (TFA) was from Sigma/Aldrich, Saint Louis, Mo. Recombinant rat α2,6-sialyltransferase from *Spodoptera frugiperda* and β1,4-galactosyltransferase from bovine milk were from Calbiochem (San Diego, Calif.). Protein N-glycosidase F, mannosidases, and oligosaccharides were from Glyko (San Rafael, Calif.). DEAE ToyoPearl resin was from TosoHaas. Metal chelating "HisBind" resin was from Novagen (Madison, Wis.). 96-well lysate-clearing plates were from Promega (Madison, Wis.). Protein-binding 96-well plates were from Millipore (Bedford, Mass.). Salts and buffering agents were from Sigma (St. Louis, Mo.). MALDI matrices were from Aldrich (Milwaukee, Wis.).

Protein Purification

Kringle 3 was purified using a 96-well format on a Beckman BioMek 2000 sample-handling robot (Beckman/Coulter Ranch Cucamonga, Calif.). Kringle 3 was purified from expression media using a C-terminal hexa-histidine tag. The robotic purification is an adaptation of the protocol provided by Novagen for their HisBind resin. Briefly, a 150 uL (μL) settled volume of resin is poured into the wells of a 96-well lysate-binding plate, washed with 3 volumes of water and charged with 5 volumes of 50 mM NiSO4 and washed with 3 volumes of binding buffer (5 mM imidazole, 0.5M NaCl, 20 mM Tris-HCL pH7.9). The protein expression media is diluted 3:2, media/PBS (60 mM PO4, 16 mM KCl, 822 mM NaCl pH7.4) and loaded onto the columns. After draining, the columns are washed with 10 volumes of binding buffer and 6 volumes of wash buffer (30 mM imidazole, 0.5M NaCl, 20 mM Tris-HCl pH7.9) and the protein is eluted with 6 volumes of elution buffer (1M imidazole, 0.5M NaCl, 20 mM Tris-HCl pH7.9). The eluted glycoproteins are evaporated to dryness by lyophilyzation.

Release of N-Linked Glycans

The glycans are released and separated from the glycoproteins by a modification of a previously reported method (Papac, et al. A. J. S. (1998) *Glycobiology* 8, 445-454). The wells of a 96-well Multi Screen IP (Immobilon-P membrane) plate (Millipore) are wetted with 100 uL of methanol, washed with 3×150 uL of water and 50 uL of RCM buffer (8M urea, 360 mM Tris, 3.2 mM EDTA pH8.6), draining with gentle vacuum after each addition. The dried protein samples are dissolved in 30 uL of RCM buffer and transferred to the wells containing 10 uL of RCM buffer. The wells are drained and washed twice with RCM buffer. The proteins are reduced by addition of 60 uL of 0.1M DTT in RCM buffer for 1 hr at 37° C. The wells are washed three times with 300 uL of water and carboxymethylated by addition of 60 uL of 0.1M iodoacetic acid for 30 min in the dark at room temperature. The wells are again washed three times with water and the membranes blocked by the addition of 100 uL of 1% PVP 360 in water for 1 hr at room temperature. The wells are drained and washed three times with 300 uL of water and deglycosylated by the addition of 30 uL of 10 mM NH$_4$HCO$_3$ pH 8.3 containing one milliunit of N-glycanase (Glyko). After 16 hours at 37° C., the solution containing the glycans was removed by centrifugation and evaporated to dryness.

Matrix Assisted Laser Desorption Ionization Time of Flight Mass Spectrometry

Molecular weights of the glycans were determined using a Voyager DE PRO linear MALDI-TOF (Applied Biosciences) mass spectrometer using delayed extraction. The dried glycans from each well were dissolved in 15 uL of water and 0.5 uL spotted on stainless steel sample plates and mixed with 0.5 uL of S-DHB matrix (9 mg/mL of dihydroxybenzoic acid, 1 mg/mL of 5-methoxysalicilic acid in 1:1 water/acetonitrile 0.1% TFA) and allowed to dry.

Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.10%, the internal pressure was less than 5×10-7 torr, and the low mass gate was 875Da. Spectra were generated from the sum of 100-200 laser pulses and acquired with a 2 GHz digitizer. Man$_5$GlcNAc$_2$ oligosaccharide was used as an external molecular weight standard. All spectra were generated with the instrument in the positive ion mode. The estimated mass accuracy of the spectra was 0.5%.

EXAMPLE 4

Engineering a Strain to Produce Galactosyltransferase

Galactosyltransferase Reaction

Approximately 2 mg of protein (r-K3:hPg [PBP6-5]) was purified by nickel-affinity chromatography, extensively dialyzed against 0.1% TFA, and lyophilized to dryness. The protein was redissolved in 150 μL of 50 mM MOPS, 20 mM MnCl2, pH7.4. After addition of 32.5 μg (533 nmol) of UDP-galactose and 4mU of β1,4-galactosyltransferase, the sample was incubated at 37° C. for 18 hours. The samples were then dialyzed against 0.1% TFA for analysis by MALDI-TOF mass spectrometry.

The spectrum of the protein reacted with galactosyltransferase showed an increase in mass consistent with the addition of two galactose moieties when compared with the spectrum of a similar protein sample incubated without enzyme. Protein samples were next reduced, carboxymethylated and deglycosylated with PNGase F. The recovered N-glycans were analyzed by MALDI-TOF mass spectrometry. The mass of the predominant glycan from the galactosyltransferase reacted protein was greater than that of the control glycan by a mass consistent with the addition of two galactose moieties (325.4 Da).

EXAMPLE 5

Engineering a Strain to Express Functional and Active Mannosidase II

To generate a human-like glycoform, a microorganism is engineered to express a mannosidase II enzyme which removes the two remaining terminal mannoses from the structure $GlcNAcMan_5GlcNAc_2$ (see FIG. 1B). A DNA library including sequences encoding cis and medial Golgi localization signals is fused in-frame to a library encoding mannosidase II catalytic domains. The host organism is a strain, e.g. a yeast, that is deficient in hypermannosylation (e.g. an och1 mutant) and provides N-glycans having the structure $GlcNAcMan_5GlcNAc_2$ in the Golgi and/or ER. After transformation, organisms having the desired glycosylation phenotype are selected. An in vitro assay is used in one method. The desired structure $GlcNAcMan_3GlcNAc_2$ (but not the undesired $GlcNAcMan_5GlcNAc_2$) is a substrate for the enzyme GlcNAc Transferase II (see FIG. 1B). Accordingly, single colonies may be assayed using this enzyme in vitro in the presence of the substrate, UDP-GlcNAc. The release of UDP is determined either by HPLC or an enzymatic assay for UDP. Alternatively, radioactively labeled UDP-GlcNAc or MALDI-TOF may be used.

The foregoing in vitro assays are conveniently performed on individual colonies using high-throughput screening equipment. Alternatively a lectin binding assay is used. In this case the reduced binding of lectins specific for terminal mannoses allows the selection of transformants having the desired phenotype. For example, *Galantus nivalis* lectin binds specifically to terminal α-1,3-mannose, the concentration of which is reduced in the presence of operatively expressed mannosidase II activity. In one suitable method, *G. nivalis* lectin attached to a solid agarose support (available from Sigma Chemical, St. Louis, Mo.) is used to deplete the transformed population of cells having high levels of terminal α-1,3-mannose.

EXAMPLE 6

Engineering a Strain to Express Sialyltransferase

The enzymes α2,3-sialyltransferase and α2,6-sialyltransferase add terminal sialic acid to galactose residues in nascent human N-glycans, leading to mature glycoproteins (see "α2,3 ST; α2,6 ST" in FIG. 1B). In human cells, the reactions occur in the trans Golgi or TGN. Accordingly, a DNA library is constructed by the in-frame fusion of sequences encoding sialyltransferase catalytic domains with sequences encoding trans Golgi or TGN localization signals (Malissard et al. *Biochem Biophys Res Commun* 2000 Jan. 7; 267(1):169-73; Borsig et al. *Biochem Biophys Res Commun* 1995 May 5; 210(1):14-20). The host organism is a strain, e.g. a yeast, that is deficient in hypermannosylation (e.g., an och1 mutant), which provides N-glycans having terminal galactose residues in the late Golgi or TGN, and provides a sufficient concentration of CMP-sialic acid in the late Golgi or TGN. Following transformation, transformants having the desired phenotype are selected, e.g., using a fluorescent antibody specific for N-glycans having a terminal sialic acid. In addition, the strains are engineered to produce the CMP-NANA precursors.

Sialyltransferase Reaction

After resuspending the (galactosyltransferase reacted) (Example 4) proteins in 10 μL of 50 mM sodium cacodylate buffer pH6.0, 300 μg (488 nmol) of CMP-N-acetylneuraminic acid (CMP-NANA) dissolved in 15 μL of the same buffer, and 5 μL (2mU) of recombinant α-2,6 sialyltransferase were added. After incubation at 37° C. for 15 hours, an additional 200 μg of CMP-NANA and 1 mU of sialyltransferase were added. The protein samples were incubated for an additional 8 hours and then dialyzed and analyzed by MALDI-TOF-MS as above. The spectrum of the glycoprotein reacted with sialyltransferase showed an increase in mass when compared with that of the starting material (the protein after galactosyltransferase reaction). The N-glycans were released and analyzed as above. The increase in mass of the two ion-adducts of the predominant glycan was consistent with the addition of two sialic acid residues (580 and 583Da).

EXAMPLE 7

Engineering a Strain to Express UDP-GlcNAc Transporter

The cDNA of human Golgi UDP-GlcNAc transporter has been cloned by Ishida and coworkers. (Ishida, N., et al. 1999 *J. Biochem.* 126(1): 68-77). Guillen and coworkers have cloned the canine kidney Golgi UDP-GlcNAc transporter by phenotypic correction of a *Kluyveromyces lactis* mutant deficient in Golgi UDP-GlcNAc transport. (Guillen, E., et al. 1998). Thus a mammalian Golgi UDP-GlcNAc transporter gene has all of the necessary information for the protein to be expressed and targeted functionally to the Golgi apparatus of yeast. These or other cloned transporter genes may be engineered into a host organism to provide UDP-GlcNAc substrates for efficient GnT reactions in the Golgi and/or ER of the host. FIG. 10B demonstrates the effect of a strain expressing a *K. lactis* UDP-GlcNAc transporter. In comparison to FIG. 10A, which lacks a UDP-GlcNAc transporter, the effect of adding a UDP-GlcNAc transporter shows a dramatic increase in the production of $GlcNAcMan_5GlcNAc_2$.

EXAMPLE 8

Engineering a Strain to Express GDP-Fucose Transporter

The rat liver Golgi membrane GDP-fucose transporter has been identified and purified by Puglielli, L. and C. B. Hirschberg 1999 *J. Biol. Chem.* 274(50):35596-35600. The corresponding gene can be identified using standard techniques, such as N-terminal sequencing and Southern blotting using a degenerate DNA probe. The intact gene is then expressed in a host microorganism that also expresses a fucosyltransferase.

EXAMPLE 9

Engineering a Strain to Express UDP-Galactose Transporter

Human UDP-galactose (UDP-Gal) transporter has been cloned and shown to be active in *S. cerevisiae*. (Kainuma, M., et al. 1999 *Glycobiology* 9(2): 133-141). A second human UDP-galactose transporter (hUGT1) has been cloned and functionally expressed in Chinese Hamster Ovary Cells. Aoki, K., et al. 1999 *J. Biochem.* 126(5): 940-950. Likewise, Segawa and coworkers have cloned a UDP-galactose transporter from *Schizosaccharomyces pombe* (Segawa, H., et al. 1999 *Febs Letters* 451(3): 295-298). These or other sequences encoding UDP-galactose transporter activities may be introduced into a host cell directly or may be used as a component of a sub-library of the invention to engineer a strain having increased UDP-galactose transporter activity.

EXAMPLE 10

Engineering a Strain to Express CMP-Sialic Acid Transporter

Human CMP-sialic acid transporter (hCST) has been cloned and expressed in Lec 8 CHO cells by Aoki and coworkers (1999). Molecular cloning of the hamster CMP-sialic acid transporter has also been achieved (Eckhardt and Gerardy Schahn 1997 *Eur. J. Biochem.* 248(1): 187-192). The functional expression of the murine CMP-sialic acid transporter was achieved in *Saccharomyces cerevisiae* by Beminsone, P., et al. 1997 *J. Biol. Chem.* 272 (19):12616-12619. These or other sequences encoding CMP-sialic acid transporter activities may be introduced into a host cell directly or may be used as a component of a sub-library of the invention to engineer a strain having increased CMP-sialic acid transporter activity.

EXAMPLE 11

Engineering of *P. pastoris* to Produce $Man_5GlcNA_2$ as the Predominant N-Glycan Structure Using a Combinatorial DNA Library An och1 mutant of *P. pastoris* (see Examples 1 and 3) was engineered to express and secrete proteins such as the kringle 3 domain of human plasminogen (K3) under the control of the inducible AOXI promoter. The Kringle 3 domain of human plasminogen (K3) was used as a model protein. A DNA fragment encoding the K3 was amplified using Pfu turbo polymerase (Strategene, La Jolla, Calif.) and cloned into EcoRI and XbaI sites of pPICZαA (Invitrogen, Carlsbad, Calif.), resulting in a C-terminal 6-His tag. In order to improve the N-linked glycosylation efficiency of K3 (Hayes et al. 1975 *J. Arch. Biochem. Biophys.* 171, 651-655), $Pro_{46}$ was replaced with $Ser_{46}$ using site-directed mutagenesis. The resulting plasmid was designated pBK64. The correct sequence of the PCR construct was confirmed by DNA sequencing.

A combinatorial DNA library was constructed by the in-frame ligation of murine α-1,2-mannosidase IB (Genbank AN 6678787) and IA (Genbank AN 6754619) catalytic domains with a sub-library including sequences encoding Cop II vesicle, ER, and early Golgi localization peptides according to Table 6. The combined DNA library was used to generate individual fusion constructs, which were then transformed into the K3 expressing host organism, resulting in a genetically mixed population wherein individual transformants each express K3 as well as a localization signal/mannosidase fusion gene from the library. Individual transformants were cultured and the production of K3 was induced by transfer to a methanol containing medium. Under these conditions, after 24 hours of induction, over 90% of the protein in the medium was K3. The K3 reporter protein was purified from the supernatant to remove salts and low-molecular weight contaminants by Ni-affinity chromatography. Following affinity purification, the protein was desalted by size exclusion chromatography on a Sephadex G10 resin (Sigma, St. Louis, Mo.) and either directly subjected to MALDI-TOF analysis described below or the N-glycans were removed by PNGase digestion as described below (Release of N-glycans) and subjected to MALDI-TOF analysis Miele et al. 1997 *Biotechnol. Appl. Biochem.* 25, 151-157.

Following this approach, a diverse set of transformants were obtained; some showed no modification of the N-glycans compared to the och1 knockout strain; and others showed a high degree of mannose trimming (FIG. 5D, 5E). Desired transformants expressing appropriately targeted, active α-1,2-mannosidase produced K3 with N-glycans of the structure $Man_5GlcNAc_2$. This confers a reduced molecular mass to the glycoprotein compared to the K3 of the parent och1 deletion strain, a difference which was readily detected by MALDI-TOF mass spectrometry (FIG. 5). Table 7 indicates the relative $Man_5GlcNAc_2$ production levels.

TABLE 7

A representative combinatorial DNA library of localization sequences/catalytic domains exhibiting relative levels of $Man_5GlcNAc_2$ production.

| | | Targeting peptide sequences | | | | |
|---|---|---|---|---|---|---|
| | | MNS1(s) | MNS1(m) | MNS1(l) | SEC12(s) | SEC12(m) |
| Catalytic Domains | Mouse mannosidase 1A Δ187 | FB4 ++ | FB5 + | FB6 − | FB7 ++ | FB8 ++++ |
| | Mouse mannosidase 1B Δ58 | GB4 ++ | GB5 + | GB6 + | GB7 ++ | GB8 + |
| | Mouse mannosidase 1B Δ99 | GC4 − | GC5 +++ | GC6 + | GC7 + | GC8 + |
| | Mouse mannosidase 1B Δ170 | GD4 − | GD5 − | GD6 − | GD7 + | GD8 + |

TABLE 8

Another combinatorial DNA library of localization sequences/catalytic domains exhibiting relative levels of Man$_5$GlcNAc$_2$ production.

| | | Targeting peptide sequences | | | | | |
|---|---|---|---|---|---|---|---|
| | | VAN1(s) | VAN1(m) | VAN1(l) | MNN10(s) | MNN10(m) | MNN10(l) |
| Catalytic Domains | C. elegans mannosidase 1B Δ80 | BC18-5 +++++ | BC19 ++++ | BC20 +++ | BC27 +++++ | BC28 +++++ | BC29 +++ |
| | C. elegans mannosidase 1B Δ31 | BB18 +++++ | BB19 +++++ | BB20 ++++ | BB18 +++++ | BB19 +++++ | BB20 ++++ |

Targeting peptides were selected from MNS I (SwissProt P32906) in S. cerevisiae (long, medium and short) (see supra Nucleic Acid Libraries; Combinatorial DNA Library of Fusion Constructs) and SEC12 (SwissProt P11655) in S. cerevisiae (988-1140 nucleotides: short) and (988-1296: medium). Although majority of the targeting peptide sequences were N-terminal deletions, some targeting peptide sequences, such as SEC12 were C-terminal deletions. Catalytic domains used in this experiment were selected from mouse mannosidase 1A with a 187 amino acid N-terminal deletion; and mouse mannosidase 1B with a 58, 99 and 170 amino acid deletion. The number of (+)s, as used herein, indicates the relative levels of Man$_5$GlcNA$_2$ production. The notation (−) indicates no apparent production of Man$_5$GlcNA$_2$. The notation (+) indicates less than 10% production of Man$_5$GlcNA$_2$. The notation (++) indicates about 10-20% production of Man$_5$GlcNA$_2$. The notation with (+++) indicates about 20-40% production of Man$_5$GlcNA$_2$. The notation with (++++) indicates about 50% production of Man$_5$GlcNA$_2$. The notation with (+++++) indicates greater than 50% production of Man$_5$GlcNA$_2$.

Table 9 shows relative amount of Man$_5$GlcNAc$_2$ on secreted K3. Six hundred and eight (608) different strains of P. pastoris, Δoch1 were generated by transforming them with a single construct of a combinatorial genetic library that was generated by fusing nineteen (19) α-1,2 mannosidase catalytic domains to thirty-two (32) fungal ER, and cis-Golgi leaders.

TABLE 9

| Amount of Man$_5$GlcNAc$_2$ on secreted K3 (% of total glycans) | Number of constructs (%) |
|---|---|
| N.D.* | 19 (3.1) |
| 0-10% | 341 (56.1) |
| 10-20% | 50 (8.2) |
| 20-40& | 75 (12.3) |
| 40-60% | 72 (11.8) |
| More than 60% | 51 (8.4)† |
| Total | 608 (100) |

*Several fusion constructs were not tested because the corresponding plasmids could not be propagated in E. coli prior to transformation into P. pastoris.
†Clones with the highest degree of Man$_5$GlcNAc$_2$ trimming (30/51) were further analyzed for mannosidase activity in the supernatant of the medium. The majority (28/30) displayed detectable mannosidase activity in the supernatant (e.g. FIG. 4B). Only two constructs displayed high Man$_5$GlcNAc$_2$ levels, while lacking mannosidase activity in the medium (e.g. FIG. 4C).

Table 7 shows two constructs pFB8 and pGC5, among others, displaying Man$_5$GlcNA$_2$. Table 8 shows a more preferred construct, pBC18-5, a S. cerevisiae VAN1(s) targeting peptide sequence (from SwissProt 23642) ligated in-frame to a C. elegans mannosidase IB (Genbank AN CAA98114) 80 amino acid N-terminal deletion (Saccharomyces Van1(s)/C. elegans mannosidase IB Δ80). This fusion construct also produces a predominant Man$_5$GlcNA$_2$ structure, as shown in FIG. 5E. This construct was shown to produce greater than 50% Man$_5$GlcNA$_2$ (+++++).

Generation of a Combinatorial Localization/Mannosidase Library:

Generating a combinatorial DNA library of α-1,2-mannosidase catalytic domains fused to targeting peptides required the amplification of mannosidase domains with varying lengths of N-terminal deletions from a number of organisms. To approach this goal, the full length open reading frames (ORFs) of α-1,2-mannosidases were PCR amplified from either cDNA or genomic DNA obtained from the following sources: Homo sapiens, Mus musculus, Drosophila melanogaster, Caenorhabditis elegans, Aspergillus nidulans and Penicillium citrinum. In each case, DNA was incubated in the presence of oligonucleotide primers specific for the desired mannosidase sequence in addition to reagents required to perform the PCR reaction. For example, to amplify the ORF of the M. musculus α-1,2-mannosidase IA, the 5'-primer ATGCCCGTGGGGGGCCTGTTGC-CGCTCTTCAGTAGC (SEQ ID NO: 12) and the 3'-primer TCATTTCTCTTTGCCATCAATTTCCT-TCTTCTGTTCACGG (SEQ ID NO: 13) were incubated in the presence of Pfu DNA polymerase (Stratagene, La Jolla, Calif.) and amplified under the conditions recommended by Stratagene using the cycling parameters: 94° C. for 1 min (1 cycle); 94° C. for 30 sec, 68° C. for 30 sec, 72° C. for 3 min (30 cycles). Following amplification the DNA sequence encoding the ORF was incubated at 72° C. for 5 min with 1U Taq DNA polymerase (Promega, Madison, Wis.) prior to ligation into pCR2.1-TOPO (Invitrogen, Carlsbad, Calif.) and transformed into TOP10 chemically competent E. coli, as recommended by Invitrogen. The cloned PCR product was confirmed by ABI sequencing using primers specific for the mannosidase ORF.

To generate the desired N-terminal truncations of each mannosidase, the complete ORF of each mannosidase was used as the template in a subsequent round of PCR reactions wherein the annealing position of the 5'-primer was specific to the 5'-terminus of the desired truncation and the 3'-primer remained specific for the original 3'-terminus of the ORF. To facilitate subcloning of the truncated mannosidase fragment into the yeast expression vector, pJN347 (FIG. 2C) AscI and PacI restriction sites were engineered onto each truncation product, at the 5'- and 3'-termini respectively. The number and position of the N-terminal truncations generated for each mannosidase ORF depended on the position of the transmembrane (TM) region in relation to the catalytic domain (CD).

For instance, if the stem region located between the TM and CD was less than 150 bp, then only one truncation for that protein was generated. If, however, the stem region was longer than 150 bp then either one or two more truncations were generated depending on the length of the stem region.

An example of how truncations for the *M. musculus* mannosidase IA (Genbank AN 6678787) were generated is described herein, with a similar approach being used for the other mannosidases. FIG. 3 illustrates the ORF of the *M. musculus* α-1,2-mannosidase IA with the predicted transmembrane and catalytic domains being highlighted in bold. Based on this structure, three 5'-primers were designed (annealing positions underlined in FIG. 3) to generate the Δ65-, Δ105- and Δ187-N-terminal deletions. Using the Δ65 N-terminal deletion as an example the 5'-primer used was 5'-GGCGCGCCGACTCCTCCAAGCTGCT-CAGCGGGGTCCTGTTCCAC-3' (SEQ ID NO:14) (with the AscI restriction site highlighted in bold) in conjunction with the 3'-primer 5'-CCTTAATTAATCATTTCTCTTTGC-CATCAATTTCCTTCTTCTGTTCACGG-3' (SEQ ID NO: 15) (with the PacI restriction site highlighted in bold). Both of these primers were used to amplify a 1561 bp fragment under the conditions outlined above for amplifying the full length *M. musculus* mannosidase 1A ORF. Furthermore, like the product obtained for the full length ORF, the truncated product was also incubated with Taq DNA polymerase, ligated into pCR2.1-TOPO (Invitrogen, Carlsbad, Calif.), transformed into TOP10 and ABI sequenced. After having amplified and confirmed the sequence of the truncated mannosidase fragment, the resulting plasmid, pCR2.1-Δ65 mMannIA, was digested with AscI and PacI in New England Biolabs buffer #4 (Beverly, Mass.) for 16 h at 37° C. In parallel, the pJN347 (FIG. 2C) was digested with the same enzymes and incubated as described above. Post-digestion, both the pJN347 (FIG. 2C) back-bone and the truncated catalytic domain were gel extracted and ligated using the Quick Ligation Kit (New England Biolabs, Beverly, Mass.), as recommended by the manufacturers, and transformed into chemically competent DH5α cells (Invitrogen, Carlsbad, Calif.). Colony PCR was used to confirm the generation of the pJN347-mouse Mannosidase IAΔ65 construct.

Having generated a library of truncated α-1,2-mannosidase catalytic domains in the yeast expression vector pJN347 (FIG. 2C) the remaining step in generating the targeting peptide/catalytic domain library was to clone in-frame the targeting peptide sequences (FIG. 2). Both the pJN347-mannosidase constructs (FIG. 2D) and the pCR2.1TOPO-targeting peptide constructs (FIG. 2B) such as were incubated overnight at 37° C. in New England Biolabs buffer #4 in the presence of the restriction enzymes NotI and AscI. Following digestion, both the pJN347-mannosidase back-bone and the targeting peptide regions were gel-extracted and ligated using the Quick Ligation Kit (New England Biolabs, Beverly, Mass.), as recommended by the manufacturers, and transformed into chemically competent DH5α cells (Invitrogen, Carlsbad, Calif.). Subsequently, the pJN347-targeting peptide/mannosidase constructs were ABI sequenced to confirm that the generated fusions were in-frame. The estimated size of the final targeting peptide/alpha-1,2-mannosidase library contains over 1300 constructs generated by the approach described above. FIG. 2 illustrates construction of the combinatorial DNA library.

Engineering a *P. pastoris* OCH1 Knock-Out Strain with Multiple Auxotrophic Markers.

Figure 4A:
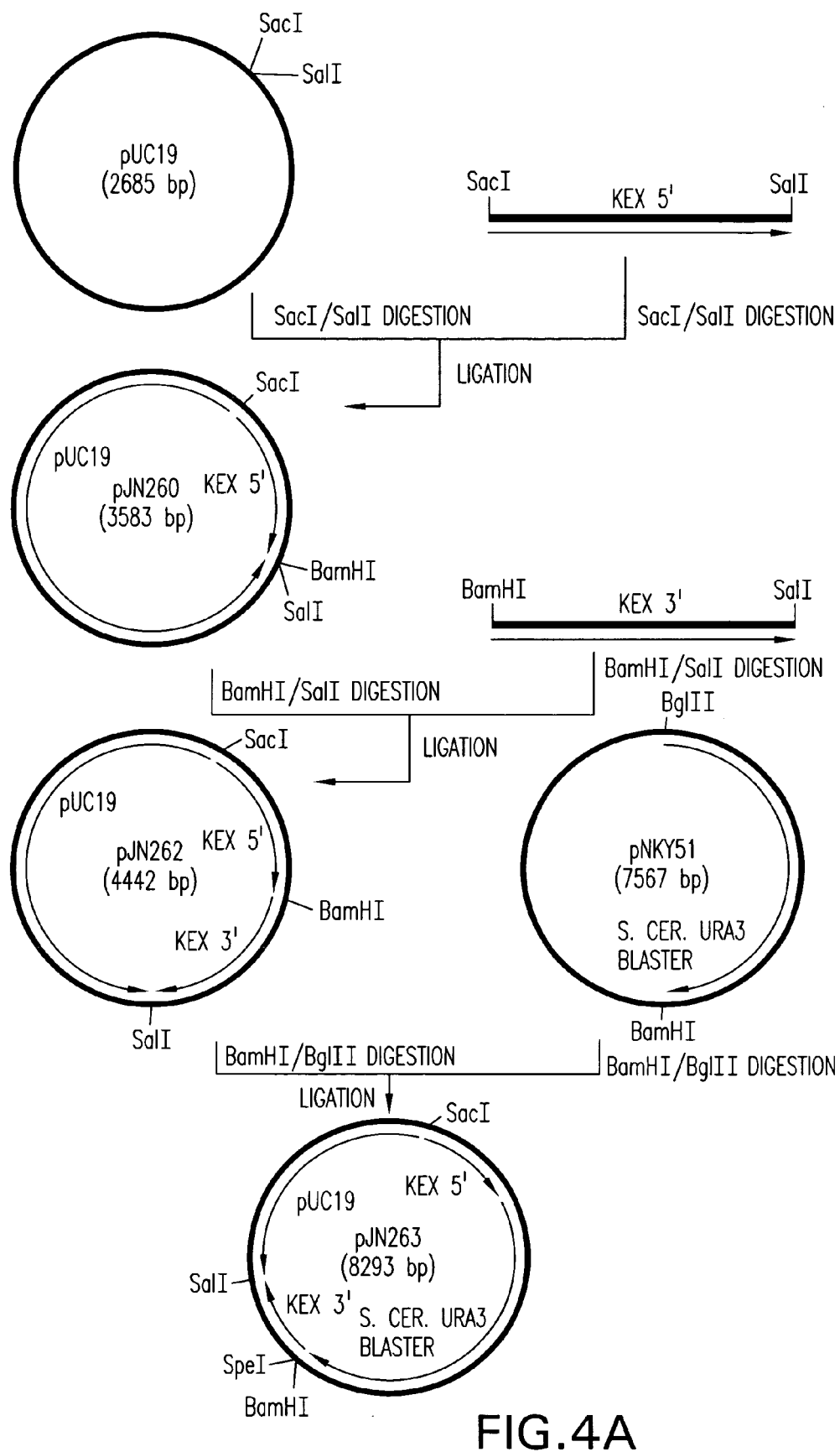
FIG. 4 illustrates engineering of vectors with multiple auxotrophic markers and genetic integration of target proteins in the P. pastoris OCH1 locus.
Figure 4B:
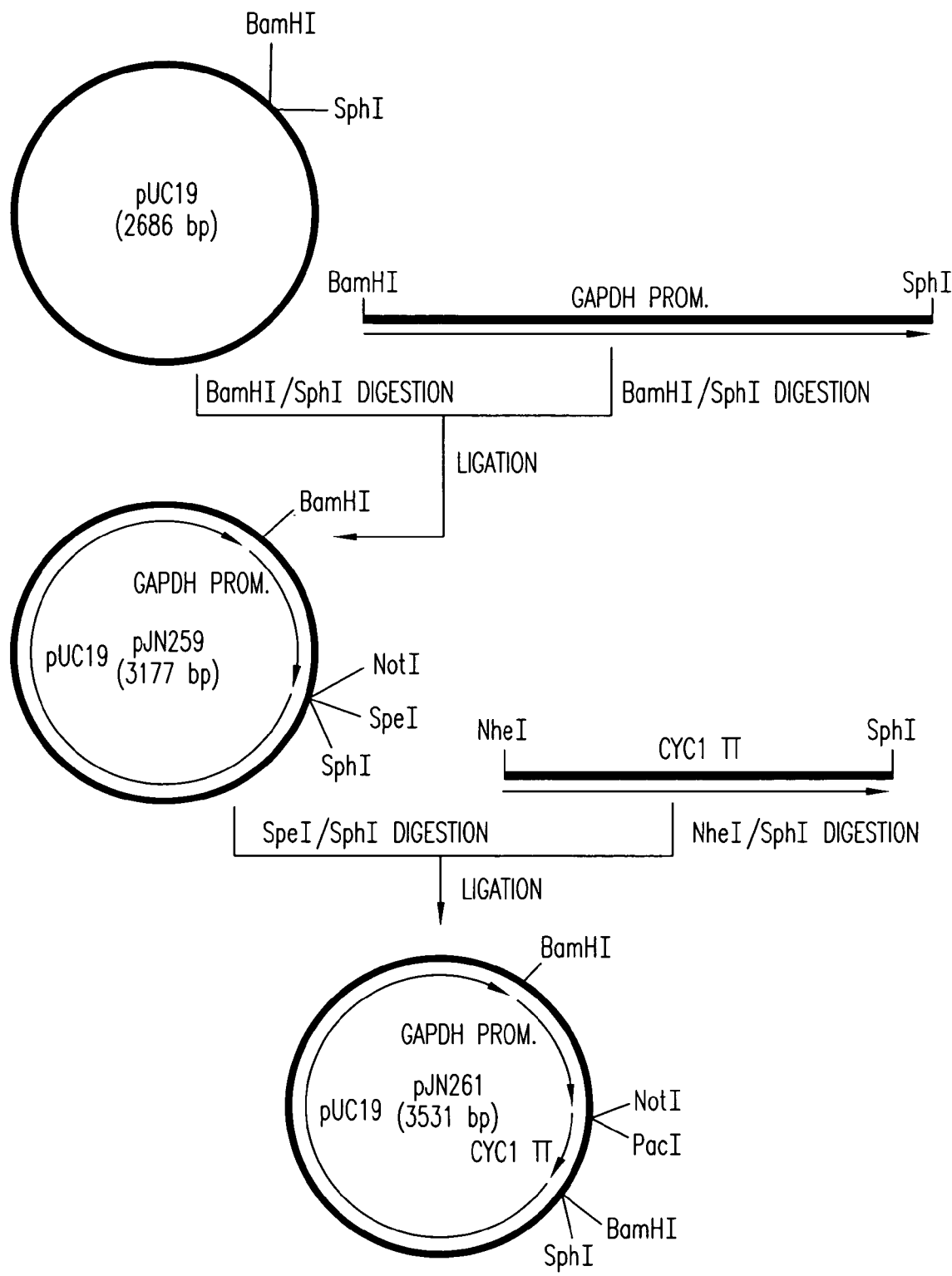

The first step in plasmid construction involved creating a set of universal plasmids containing DNA regions of the KEX1 gene of *P. pastoris* (Boehm et al. Yeast 1999 May; 15(7):563-72) as space holders for the 5' and 3' regions of the genes to be knocked out. The plasmids also contained the *S. cerevisiae* Ura-blaster (Alani et al., *Genetics* 116, 541-545. 1987) as a space holder for the auxotrophic markers, and an expression cassette with a multiple cloning site for insertion of a foreign gene. A 0.9-kb fragment of the *P. pastoris* KEX1-5' region was amplified by PCR using primers GGC GAGCTCGGCCTACCCGGCCAAGGCTGAGATCATTT-GTCCAGCTTCA GA (SEQ ID NO:16) and GCCCA-CGTCGACGGATCCGTTTAAACATCGATTGGAGAG-GCTGACACC GCTACTA (SEQ ID NO: 17) and *P. pastoris* genomic DNA as a template and cloned into the SacI, SalI sites of pUC19 (New England Biolabs, Beverly, Mass.). The resulting plasmid was cut with BamHI and SalI, and a 0.8-kb fragment of the KEX1-3' region that had been amplified using primers CGGGATCCACTAGTATTTAAATCATATGTGC-GAGTGTACAACTCTTCCC ACATGG (SEQ ID NO: 18) and GGACGCGTCGACGGCCTACCCGGCCGTAC-GAGGAATTTCTCGG ATGACTCTTTTC (SEQ ID NO: 19) was cloned into the open sites creating pJN262. This plasmid was cut with BamHI and the 3.8-kb BamHI, BglII fragment of pNKY51 (Alani et al. 1987) was inserted in both possible orientations resulting in plasmids pJN263 (FIG. 4A) and pJN284 (FIG. 4B).

An expression cassette was created with NotI and PacI as cloning sites. The GAPDH promoter of *P. pastoris* was amplified using primers CGGGATCCCTCGAGAGATCT-TTTTTGTAGAAATGTCTTGGTGCCT (SEQ ID NO:20) and GGACATGCATGCACTAGTGCGGCCGCCACGTG-ATAGTTGTTCA ATTGATTGAAATAGGGACAA (SEQ ID NO:21) and plasmid pGAPZ-A (Invitrogen) as template and cloned into the BamHI, SphI sites of pUC19 (New England Biolabs, Beverly, Mass.) (FIG. 4B). The resulting plasmid was cut with SpeI and SphI and the CYC1 transcriptional terminator region ("TT") that had been amplified using primers CCTTGCTAGCTTAATTAACCGCGG- CACGTC-CGACGGCGGCCCA CGGGTCCCA (SEQ ID NO:22) and GGACATGCATGCGGATCCCTTAAGAGCCGGC-AGCTTGCAAATT AAAGCCTTCGAGCGTCCC (SEQ ID NO:23) and plasmid pPICZ-A (Invitrogen) as a template was cloned into the open sites creating pJN261 (FIG. 4B).

Figure 4C:
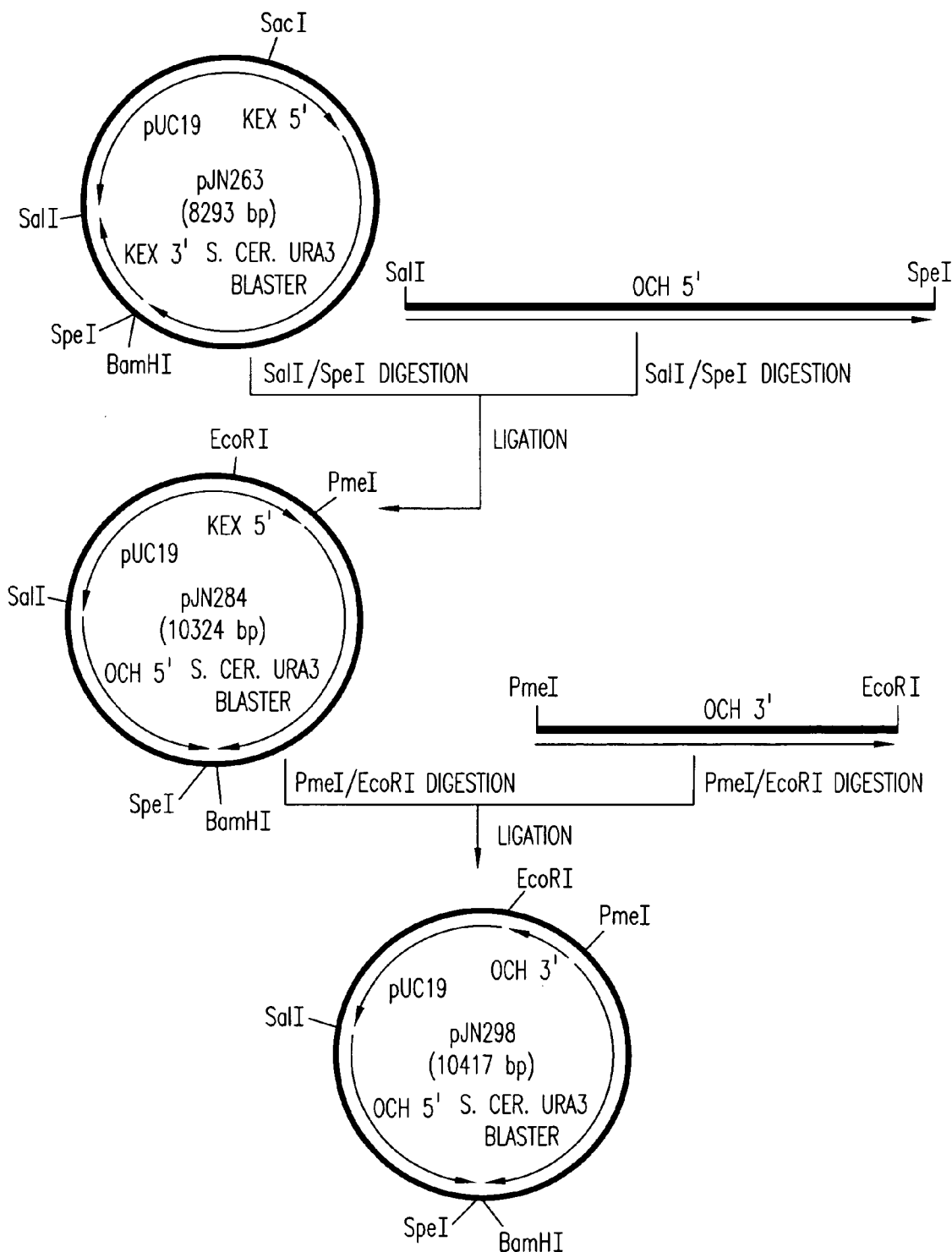
Figure 4D:
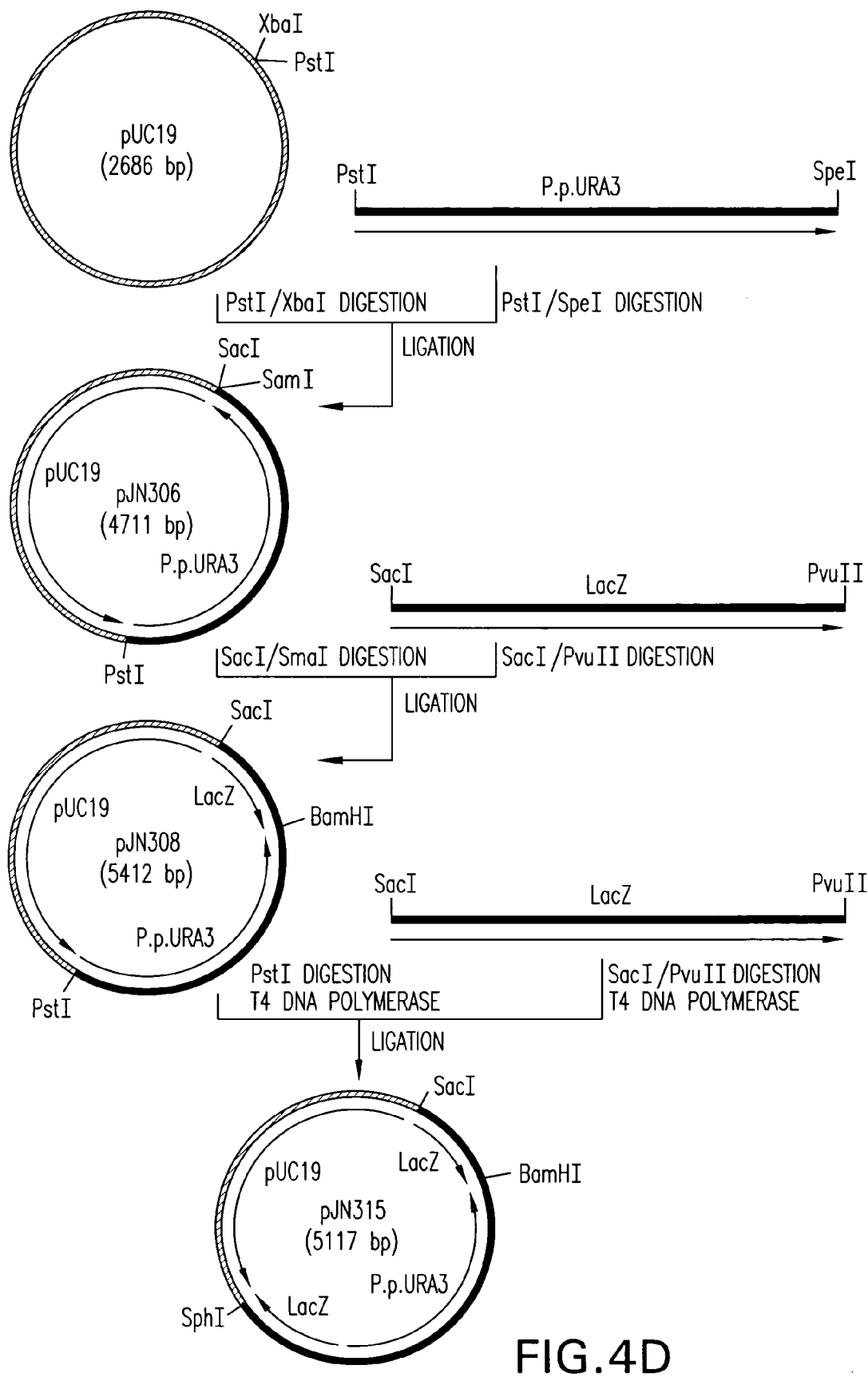
Figure 4E:
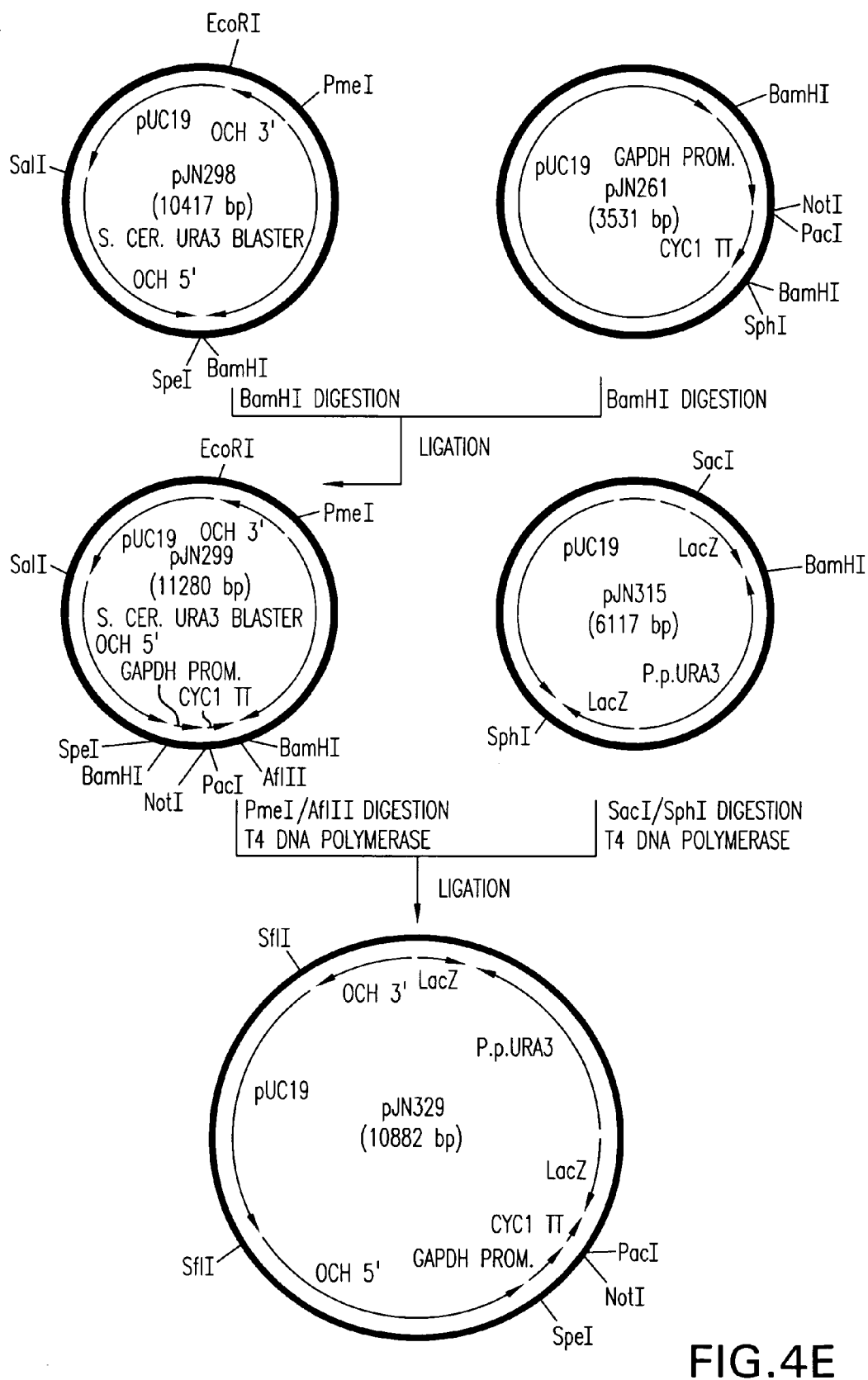

A knockout plasmid for the *P. pastoris* OCH1 gene was created by digesting pJN263 with SalI and SpeI and a 2.9-kb DNA fragment of the OCH1-5' region, which had been amplified using the primers GAACCAC GTCGACGGCCATTGCGGCCAAAACCTTTTTTCCTAT-T CAAACACAAGGCATTGC (SEQ ID NO:24) and CTC-CAATACTAGTCGAAGATTATCTTCTACGGTGCCTG-GACTC (SEQ ID NO:25) and *P. pastoris* genomic DNA as a template, was cloned into the open sites (FIG. 4C). The resulting plasmid was cut with EcoRI and PmeI and a 1.0-kb DNA fragment of the OCH1-3' region that had been generated using the primers TGGAAGGTTTAAAC- AAAGCTAGAG-TAAAATAGATATAGCGAG ATTAGAGAATG (SEQ ID NO:26) and AAGAATTCGGCTGGAAGGCCTTGT-ACCTTGATGTAGTTCCCGTT TTCATC (SEQ ID NO:27) was inserted to generate pJN298 (FIG. 4C). To allow for the possibility to simultaneously use the plasmid to introduce a new gene, the BamHI expression cassette of pJN261 (FIG. 4B) was cloned into the unique BamHI site of pJN298 (FIG. 4C) to create pJN299 (FIG. 4E).

The *P. pastoris* Ura3-blaster cassette was constructed using a similar strategy as described in Lu. P., et al. 1998 (Cloning and disruption of the β-isopropylmalate dehydrogenase gene (Leu2) of *Pichia stipidis* with URA3 and recovery of the double auxotroph. Appl. Microbiol. Biotechnol. 49, 141-146.) A 2.0-kb PstI, SpeI fragment of *P. pastoris* URA3 was inserted into the PstI, XbaI sites of pUC19 (New England Biolabs, Beverly, Mass.) to create pJN306 (FIG. 4D). Then a 0.7-kb SacI, PvuII DNA fragment of the lacZ open reading frame was cloned into the SacI, SmaI sites to yield pJN308 (FIG. 4D). Following digestion of pJN308 (FIG. 4D) with PstI, and treatment with T4 DNA polymerase, the SacI-PvuII fragment from lacZ that had been blunt-ended with T4 DNA polymerase was inserted generating pJN315 (FIG. 4D). The lacZ/URA3 cassette was released by digestion with SacI and SphI, blunt ended with T4 DNA polymerase and cloned into the backbone of pJN299 that had been digested with PmeI and AflII and blunt ended with T4 DNA polymerase. The resulting plasmid was named pJN329 (FIG. 4E).

Figure 4F:
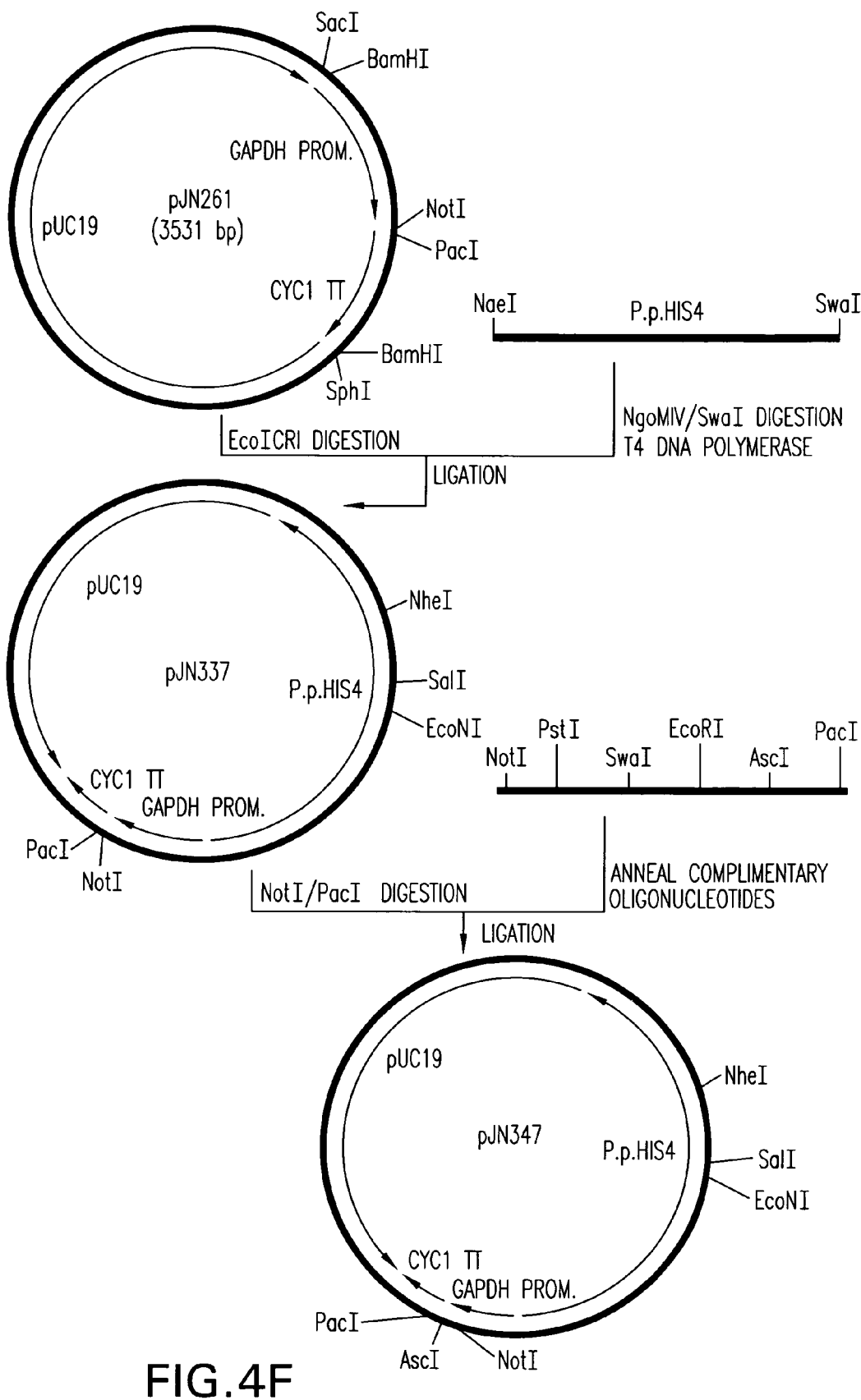

A HIS4 marked expression plasmid was created by cutting pJN261 (FIG. 4F) with EcoICRI (FIG. 4F). A 2.7 kb fragment of the *Pichia pastoris* HIS4 gene that had been amplified using the primers GCCCAAGCCGGCCTTAAG-GGATCTCCTGATGACTGACTCACTGATAATA AAAATACGG (SEQ ID NO:28) and GGGCGCGT ATTTAAATACTAGTGGATCTATCGAATCTAAATGTAA-GTTA AAATCTCTAA (SEQ ID NO:29) cut with NgoMIV and SwaI and then blunt-ended using T4 DNA polymerase, was then ligated into the open site. This plasmid was named pJN337 (FIG. 4F). To construct a plasmid with a multiple cloning site suitable for fusion library construction, pJN337 was cut with NotI and PacI and the two oligonucleotides GGCCGCCTGCAGATTTAAATGAATTCGGCGCGCCT-TAAT (SEQ ID NO:30) and TAAGGCGCGCCGAATTCATTTAAATCTGCAGGGC (SEQ ID NO:31), that had been annealed in vitro were ligated into the open sites, creating pJN347 (FIG. 4F).

To create an och1 knockout strain containing multiple auxotrophic markers, 100 μg of pJN329 was digested with SfiI and used to transform *P. pastoris* strain JC308 (Cereghino et al. *Gene* 263 (2001) 159-169) by electroporation. Following transformation, the URA dropout plates were incubated at room temperature for 10 days. One thousand (1000) colonies were picked and restreaked. All 1000 clones were then streaked onto 2 sets of URA dropout plates. One set was incubated at room temperature, whereas the second set was incubated at 37° C. The clones that were unable to grow at 37° C., but grew at room temperature, were subjected to colony PCR to test for the correct OCH1 knockout. One clone that showed the expected PCR signal (about 4.5 kb) was designated YJN153.

EXAMPLE 12

Characterization of the Combinatorial DNA Library

Positive transformants screened by colony PCR confirming integration of the mannosidase construct into the *P. pastoris* genome were subsequently grown at room temperature in 50 ml BMGY buffered methanol-complex medium consisting of 1% yeast extract, 2% peptone, 100 mM potassium phosphate buffer, pH 6.0, 1.34% yeast nitrogen base, $4 \times 10^{-5}$% biotin, and 1% glycerol as a growth medium) until $OD_{600}$ nm 2-6 at which point they were washed with 10 ml BMMY (buffered methanol-complex medium consisting of 1% yeast extract, 2% peptone, 100 mM potassium phosphate buffer, pH 6.0, 1.34% yeast nitrogen base, $4 \times 10^{-5}$% biotin, and 1.5% methanol as a growth medium) media prior to induction of the reporter protein for 24 hours at room temperature in 5 ml BMMY. Consequently, the reporter protein was isolated and analyzed by mass spectrophotometry and HPLC to characterize its glycan structure. Using the targeting peptides in Table 6, mannosidase catalytic domains localized to either the ER or the Golgi showed significant level of trimming of a glycan predominantly containing $Man_8GlcNAc_2$ to a glycan predominantly containing $Man_5GlcNAc_2$. This is evident when the glycan structure of the reporter glycoprotein is compared between that of *P. pastoris* och1 knock-out in FIGS. 5C, 6C and the same strain transformed with *M. musculus* mannosidase constructs as shown in FIGS. 5D, 5E, 6D-6F. FIGS. 5 and 6 show expression of constructs generated from the combinatorial DNA library which show significant mannosidase activity in *P. pastoris*. Expression of pGC5 (*Saccharomyces* MNS1(m)/mouse mannosidase IB Δ99) (FIG. 5D, 6E) produced a protein which has approximately 30% of all glycans trimmed to $Man_5GlcNAc_2$, while expression of pFB8 (*Saccharomyces* SEC12(m)/mouse mannosidase IA Δ187) (FIG. 6F) produced approximately 50% $Man_5GlcNAc_2$ and expression of pBC18-5 (*Saccharomyces* VAN1(s)/*C. elegans* mannosidase IB Δ80) (FIG. 5E) produced 70% $Man_5GlcNAc_2$.

Release of N-Glycans

The glycans were released and separated from the glycoproteins by a modification of a previously reported method (Papac et al. 1998 *Glycobiology* 8, 445-454). After the proteins were reduced and carboxymethylated and the membranes blocked, the wells were washed three time with water. The protein was deglycosylated by the addition of 30 μl of 10 mM $NH_4HCO_3$ pH 8.3 containing one milliunit of N-glycanase (Glyko, Novato, Calif.). After 16 hr at 37° C., the solution containing the glycans was removed by centrifugation and evaporated to dryness.

Matrix Assisted Laser Desorption Ionization Time of Flight Mass Spectrometry

After the N-glycans were released by PNGase digestion, they were analyzed by Matrix Assisted Laser Desorption Ionization Time of Flight Mass Spectrometry. Molecular weights of the glycans were determined using a Voyager DE PRO linear MALDI-TOF (Applied Biosciences) mass spectrometer using delayed extraction. The dried glycans from each well were dissolved in 15 μl of water and 0.5 μl was spotted on stainless steel sample plates and mixed with 0.5 μl of S-DHB matrix (9 mg/ml of dihydroxybenzoic acid, 1 mg/ml of 5-methoxysalicilic acid in 1:1 water/acetonitrile 0.1% TFA) and allowed to dry. Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.1%, the internal pressure was less than $5 \times 10^{-7}$ torr, and the low mass gate was 875 Da. Spectra were generated from the sum of 100-200 laser pulses and acquired with a 500 MHz digitizer. $Man_5GlcNAc_2$ oligosaccharide was used as an external molecular weight standard. All spectra were generated with the instrument in the positive ion mode.

EXAMPLE 13

Trimming In Vivo by Alpha-1,2-Mannosidase

To ensure that the novel engineered strains of Example 11 in fact produced the desired $Man_5GlcNAc_2$ structure in vivo, cell supernatants were tested for mannosidase activity (see FIGS. 7-9). For each construct/host strain described below, HPLC was performed at 30° C. with a 4.0 mm×250 mm column of Altech (Avondale, Pa., USA) Econosil-$NH_2$ resin (5 μm) at a flow rate of 1.0 ml/min for 40 min. In FIGS. 7 and 8, degradation of the standard Man$_9$GlcNAc$_2$ [b] was shown to occur resulting in a peak which correlates to Man$_8$GlcNAc$_2$. In FIG. 7, the Man$_9$GlcNAc$_2$ [b] standard eluted at 24.61 min and Man$_5$GlcNAc$_2$ [a] eluted at 18.59 min. In FIG. 8, Man$_9$GlcNAc$_2$ eluted at 21.37 min and Man$_5$GlcNAc$_2$ at 15.67 min. In FIG. 9, the standard Man$_8$GlcNAc$_2$ [b] was shown to elute at 20.88 min.

Figure 7C:
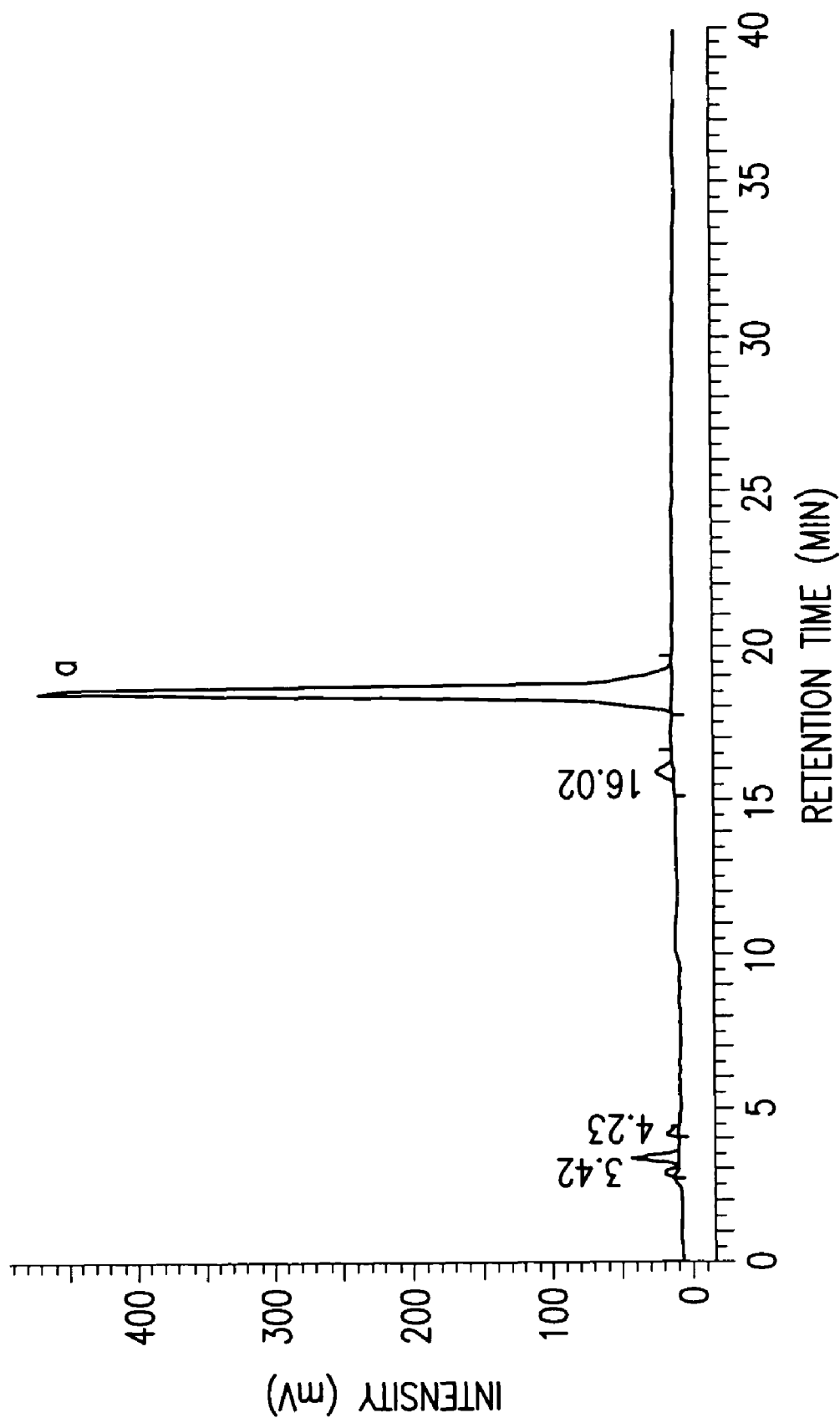

P. pastoris cells comprising plasmid pFB8 (Saccharomyces SEC12 (m)/mouse mannosidase IA Δ187) were grown at 30° C. in BMGY to an OD600 of about 10. Cells were harvested by centrifugation and transferred to BMMY to induce the production of K3 (kringle 3 from human plasminogen) under control of an AOX1 promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient of 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 6F. The earlier removed aliquot of the supernatant was further tested for the presence of secreted mannosidase activity. A commercially available standard of 2-aminobenzamide-labeled N-linked-type oligomannose 9 (Man9-2-AB) (Glyko, Novato, Calif.) was added to: BMMY (FIG. 7A), the supernatant from the above aliquot (FIG. 7B), and BMMY containing 10 ng of 75mU/mL of α-1,2-mannosidase from Trichoderma reesei (obtained from Contreras et al., WO 02/00856 A2) (FIG. 7C). After incubation for 24 hours at room temperature, samples were analyzed by amino silica HPLC to determine the extent of mannosidase trimming.

Figure 8C:
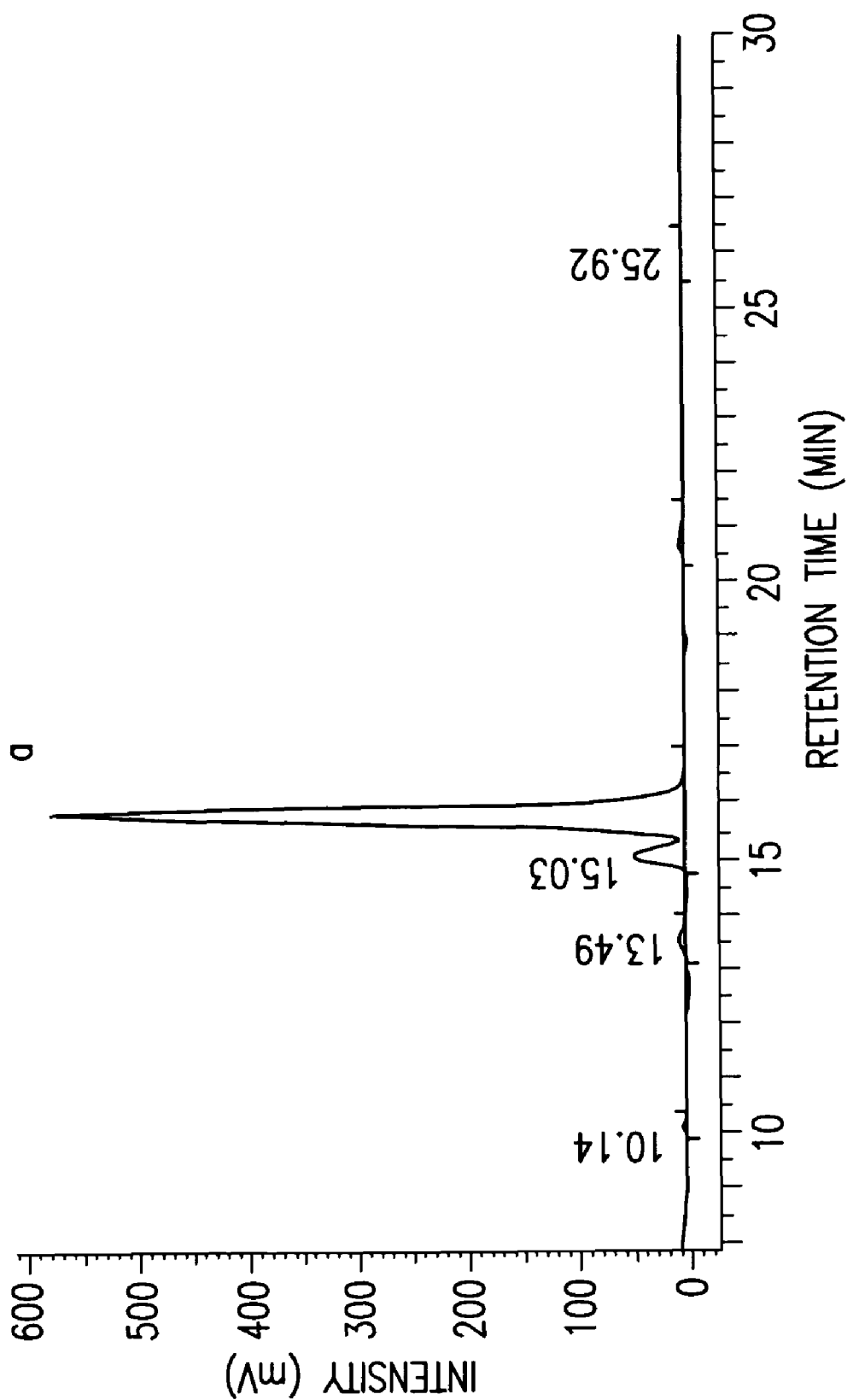

P. pastoris cells comprising plasmid pGC5 (Saccharomyces MNS1(m)/mouse mannosidase IB Δ99) were similarly grown and assayed. Cells were grown at room temperature in BMGY to an OD600 of about 10. Cells were harvested by centrifugation and transferred to BMMY to induce the production of K3 under control of an AOX1 promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient of 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 5D. The earlier removed aliquot of the supernatant was further tested for the presence of secreted mannosidase activity as shown in FIG. 8B. A commercially available standard of Man9-2-AB (Glyko, Novato, Calif.) were added to: BMMY (FIG. 8A), supernatant from the above aliquot (FIG. 8B), and BMMY containing 10 ng of 75mU/mL of α-1,2-mannosidase from Trichoderma reesei (obtained from Contreras et al., WO 02/00856 A2) (FIG. 8C). After incubation for 24 hours at room temperature, samples were analyzed by amino silica HPLC to determine the extent of mannosidase trimming.

Man9-2-AB was used as a substrate and it is evident that after 24 hours of incubation, mannosidase activity was virtually absent in the supernatant of the pFB8 (Saccharomyces SEC12 (m)/mouse mannosidase IA Δ187) strain digest (FIG. 7B) and pGC5 (Saccharomyces MNS1(m)/mouse mannosidase IB Δ99) strain digest (FIG. 8B) whereas the positive control (purified α-1,2-mannosidase from T. reesei obtained from Contreras) leads to complete conversion of Man$_9$GlcNAc$_2$ to Man$_5$GlcNAc$_2$ under the same conditions, as shown in FIGS. 7C and 8C. This is conclusive data showing in vivo mannosidase trimming in P. pastoris pGC5 strain; and pFB8 strain, which is distinctly different from what has been reported to date (Contreras et al., WO 02/00856 A2).

Figure 9A:
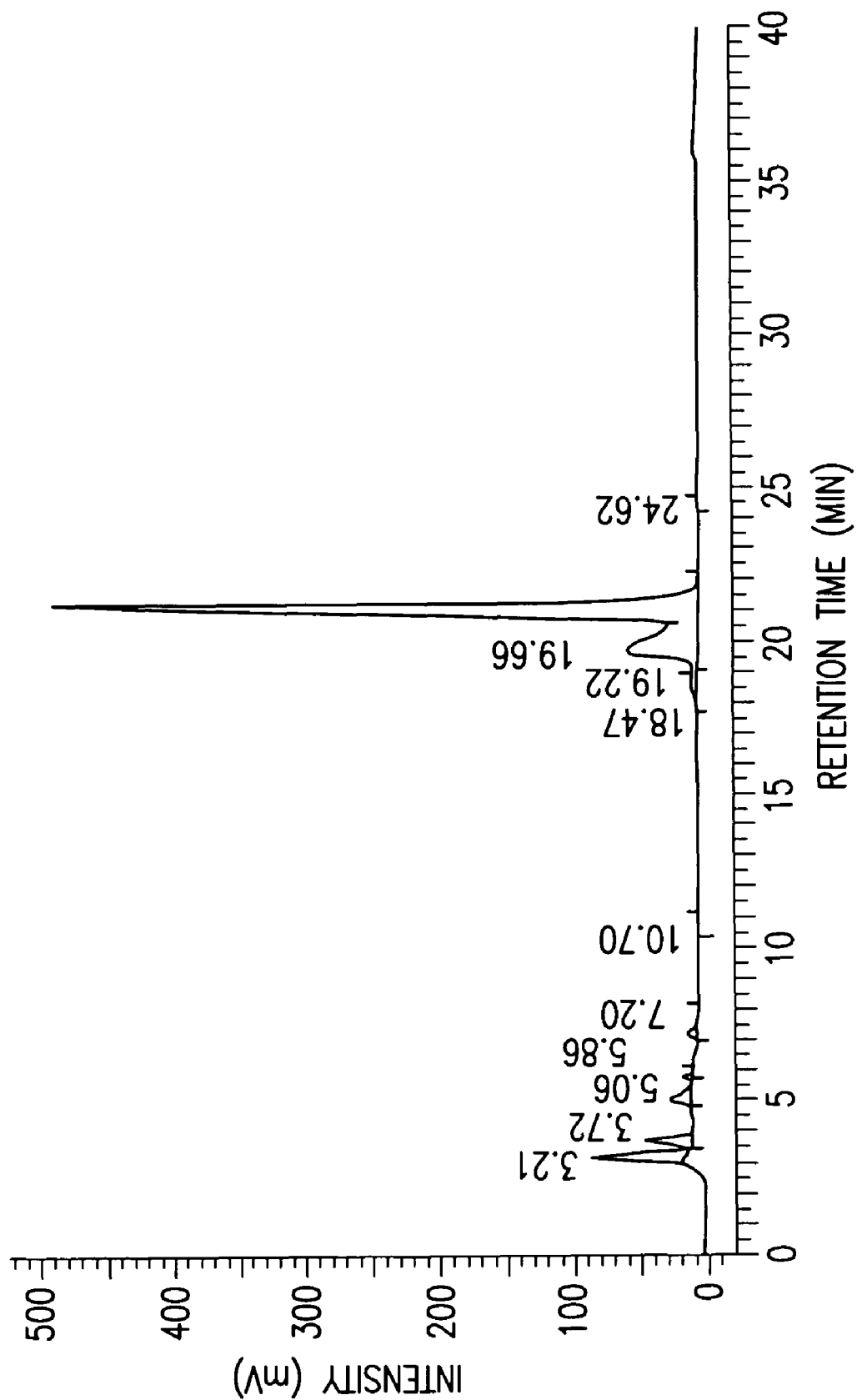
Figure 9B:
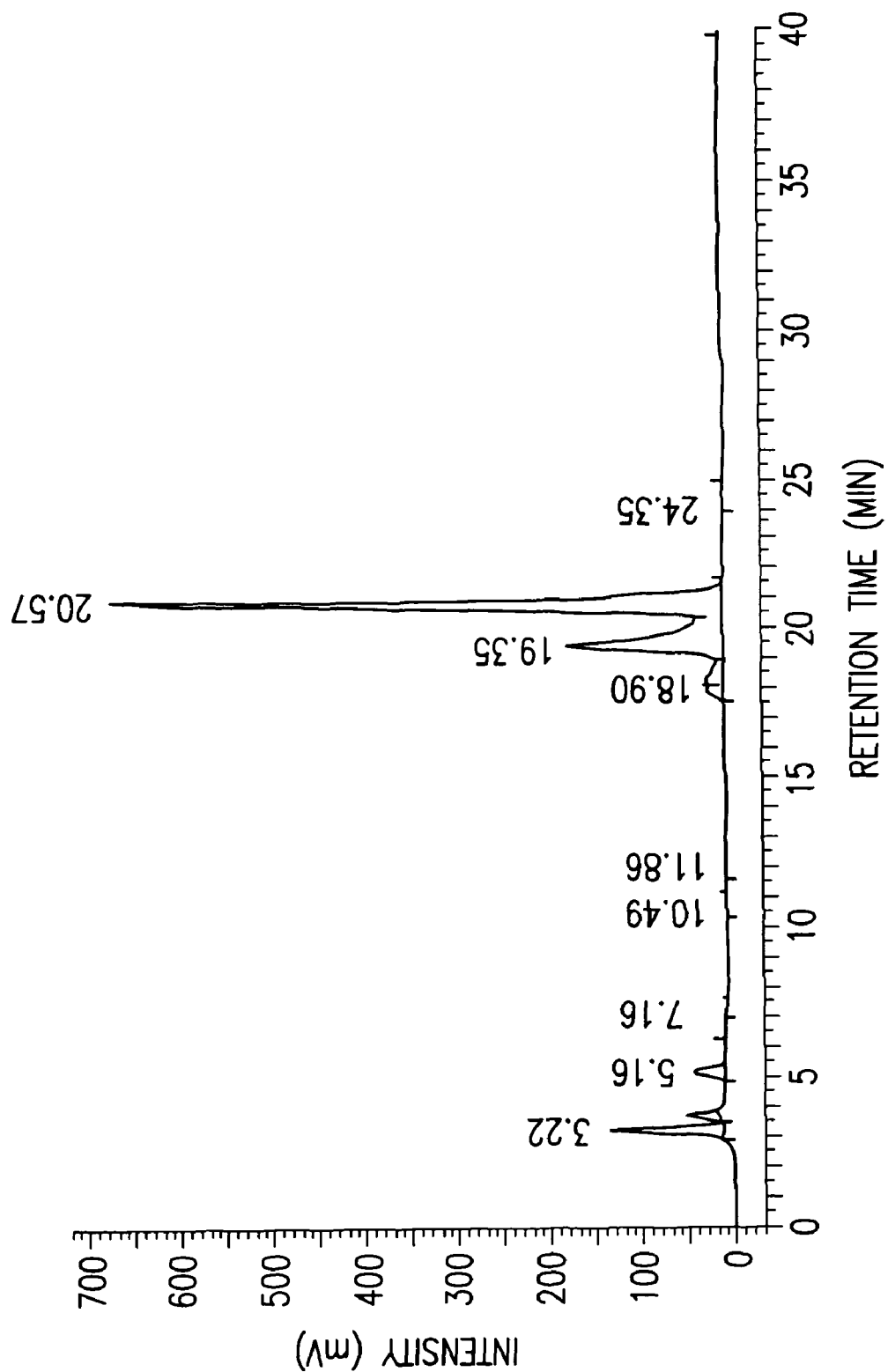
Figure 9C:
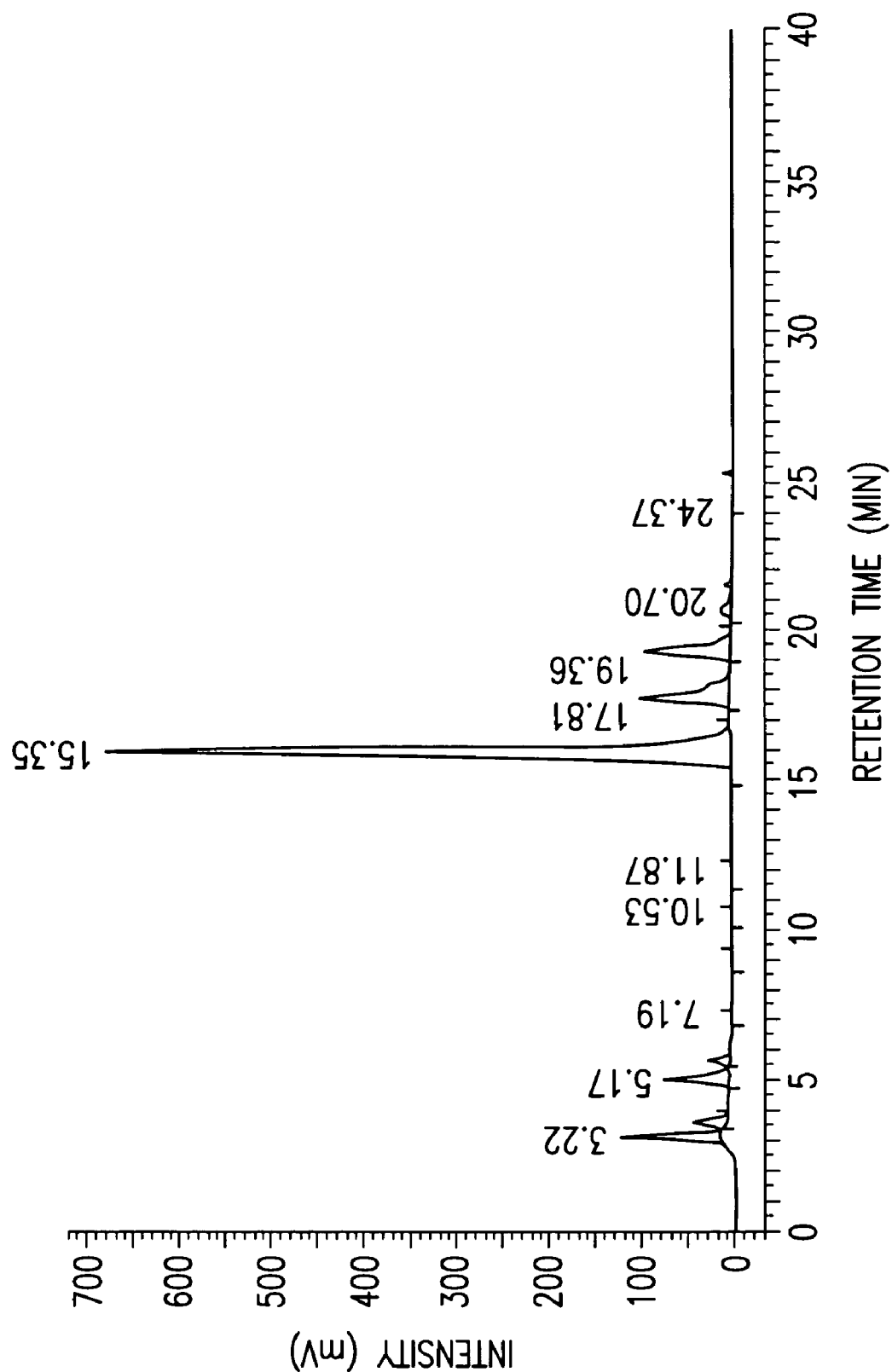

FIG. 9 further substantiates localization and activity of the mannosidase enzyme. P. pastoris comprising pBC18-5 (Saccharomyces VAN1(s)/C. elegans mannosidase IB Δ80) was grown at room temperature in BMGY to an OD600 of about 10. Cells were harvested by centrifugation and transferred to BMMY to induce the production of K3 under control of an AOX1 promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient 25 mM NaAc, pH5.0 to 25 mM NaAc, pH5.0, 1M NaCl, resulted in a 95% pure K3 eluting between 300-500mM NaCl. N-glycan analysis of the K3 derived glycans is shown in FIG. 5E. The earlier removed aliquot of the supernatant was further tested for the presence of secreted mannosidase activity as shown in FIG. 9B. A commercially available standard of Man8-2-AB (Glyko, Novato, Calif.) was added to: BMMY (FIG. 9A), supernatant from the above aliquot pBC18-5 (Saccharomyces VAN1(s)/C. elegans mannosidase IB Δ80) (FIG. 9B), and BMMY containing media from a different fusion construct pDD28-3 (Saccharomyces MNN10(m) (from SwissProt 50108)/H. sapiens mannosidase IB Δ99) (FIG. 9C). After incubation for 24 hours at room temperature, samples were analyzed by amino silica HPLC to determine the extent of mannosidase trimming. FIG. 9B demonstrates intracellular mannosidase activity in comparison to a fusion construct pDD28-3 (Saccharomyces MNN10(m) H. sapiens mannosidase IB Δ99) exhibiting a negative result (FIG. 9C).

EXAMPLE 14 pH Optimum Assay of Engineered α-1,2-Mannosidase

P. pastoris cells comprising plasmid pBB27-2 (Saccharomyces MNN10 (s) (from SwissProt 50108)/C. elegans mannosidase IB Δ31) were grown at room temperature in BMGY to an OD600 of about 17. About 80 µL of these cells were inoculated into 600 µL BMGY and were grown overnight. Subsequently, cells were harvested by centrifugation and transferred to BMMY to induce the production of K3 (kringle 3 from human plasminogen) under control of an AOX1 promoter. After 24 hours of induction, cells were removed by centrifugation to yield an essentially clear supernatant (pH 6.43). The supernatant was removed for mannosidase pH optimum assays. Fluorescence-labeled Man$_8$GlcNAc$_2$ (0.5 µg) was added to 20 µL of supernatant adjusted to various pH (FIG. 11) and incubated for 8 hours at room temperature. Following incubation the sample was analyzed by HPLC using an Econosil NH2 4.6×250 mm, 5 micron bead, amino-bound silica column (Altech, Avondale, Pa.). The flow rate was 1.0 ml/min for 40 min and the column was maintained to 30° C. After eluting isocratically (68% A:32% B) for 3 min, a linear solvent gradient (68% A:32% B to 40% A:60% B) was employed over 27 min to elute the glycans (18). Solvent A (acetonitrile) and solvent B (ammonium formate, 50 mM, pH 4.5. The column was equilibrated with solvent (68% A:32% B) for 20 min between runs.

EXAMPLE 15

Engineering of *P. pastoris* to Produce N-Glycans with the Structure GlcNAcMan$_5$GlcNAc$_2$ GlcNAc Transferase I activity is required for the maturation of complex and hybrid N-glycans (U.S. Pat. No. 5,834,251). Man$_5$GlcNAc$_2$ may only be trimmed by mannosidase II, a necessary step in the formation of human glycoforms, after the addition of N-acetylglucosamine to the terminal α-1,3 mannose residue of the trimannose stem by GlcNAc Transferase I (Schachter, 1991 Glycobiology 1(5):453-461). Accordingly, a combinatorial DNA library was prepared including DNA fragments encoding suitably targeted catalytic domains of GlcNAc Transferase I genes from *C. elegans* and *Homo sapiens*; and localization sequences from GLS, MNS, SEC, MNN9, VAN1, ANP1, HOC1, MNN10, MNN11, MNT1, KTR1, KTR2, MNN2, MNN5, YUR1, MNN1, and MNN6 from *S. cerevisiae* and *P. pastoris* putative α-1,2-mannosyltransferases based on the homology from *S. cerevisiae*: D2, D9 and J3, which are KTR homologs. Table 10 includes but does not limit targeting peptide sequences such as SEC and OCH1, from *P. pastoris* and *K. lactis* GnTI, (See Table 6 and Table 10)

TABLE 10

A representative combinatorial library of targeting peptide sequences/catalytic domain for UDP-N-Acetylglucosaminyl Transferase I (GnTI)

| | | Targeting peptide | | | | |
|---|---|---|---|---|---|---|
| | | OCHI(s) | OCHI(m) | OCHI(l) | MNN9(s) | MNN9(m) |
| Catalytic | Human, GnTI, Δ38 | PB105 | PB106 | PB107 | PB104 | N/A |
| Domain | Human, GnTI, Δ86 | NB12 | NB13 | NB14 | NB15 | NB |
| | *C. elegans*, GnTI, Δ88 | OA12 | OA13 | OA14 | OA15 | OA16 |
| | *C. elegans*, GnTI, Δ35 | PA12 | PA13 | PA14 | PA15 | PA16 |
| | *C. elegans*, GnTI, Δ63 | PB12 | PB13 | PB14 | PB15 | PB16 |
| | *X. leavis*, GnTI, Δ33 | QA12 | QA13 | QA14 | QA15 | QA16 |
| | *X. leavis*, GnTI, Δ103 | QB12 | QB13 | QB14 | QB15 | QB16 |

Targeting peptide sequences were selected from OCH1 in *P. pastoris* (long, medium and short) (see Example 11) and MNN9 (SwissProt P39107) in *S. cerevisiae* short, and medium. Catalytic domains were selected from human GnTI with a 38 and 86 amino acid N-terminal deletion, *C. elegans* (gly-12) GnTI with a 35 and 63 amino acid deletion as well as *C. elegans* (gly-14) GnTI with a 88 amino acid N-terminal deletion and *X. leavis* GnTI with a 33 and 103 amino acid N-terminal deletion, respectively.

A portion of the gene encoding human N-acetylglucosaminyl Transferase I (MGATI, Accession# NM002406), lacking the first 154 bp, was amplified by PCR using oligonucleotides 5'-TGGCAGGCGCGCCTCAGTCAGCGCTCTCG-3' (SEQ ID NO:32) and 5'-AGGTTAATTA AGTGCTAATTC-CAGCTAGG-3' (SEQ ID NO:33) and vector pHG4.5 (ATCC#79003) as template. The resulting PCR product was cloned into pCR2.1-TOPO and the correct sequence was confirmed. Following digestion with AscI and PacI the truncated GnTI was inserted into plasmid pJN346 to create pNA. After digestion of pJN271 with NotI and AscI, the 120 bp insert was ligated into pNA to generate an in-frame fusion of the MNN9 transmembrane domain with the GnTI, creating pNA 15.

The host organism is a strain of *P. pastoris* that is deficient in hypermannosylation (e.g. an och1 mutant), provides the substrate UDP-GlcNAc in the Golgi and/or ER (i.e. contains a functional UDP-GlcNAc transporter), and provides N-glycans of the structure Man$_5$GlcNAc$_2$ in the Golgi and/or ER (e.g. *P. pastoris* pFB8 (*Saccharomyces* SEC12 (m)/mouse mannosidase IA Δ187) from above). First, *P. pastoris* pFB8 was transformed with pPB103 containing the *Kluyveromyces lactis* MNN2-2 gene (Genbank AN AF106080) (encoding UDP-GlcNAc transporter) cloned into BamHI and BglII site of pBLADE-SX plasmid (Cereghino et al. Gene 263 (2001) 159-169). Then the aforementioned combinatorial DNA library encoding a combination of exogenous or endogenous GnTI/localization genes was transformed and colonies were selected and analyzed for the presence of the GnTI construct by colony PCR. Our transformation and integration efficiency was generally above 80% and PCR screening can be omitted once robust transformation parameters have been established.

Protein Purification

K3 was purified from the medium by Ni-affinity chromatography utilizing a 96-well format on a Beckman BioMek 2000 laboratory robot. The robotic purification is an adaptation of the protocol provided by Novagen for their HisBind resin. Another screening method may be performed using a specific terminal GlcNAc binding antibody, or a lectin such as the GSII lectin from *Griffonia simplificolia*, which binds terminal GlcNAc (EY Laboratories, San Mateo, Calif.). These screens can be automated by using lectins or antibodies that have been modified with fluorescent labels such as FITC or analyzed by MALDI-TOF.

Secreted K3 can be purified by Ni-affinity chromatography, quantified and equal amounts of protein can be bound to a high protein binding 96-well plate. After blocking with BSA, plates can be probed with a GSII-FACS lectin and screened for maximum fluorescent response. A preferred method of detecting the above glycosylated proteins involves the screening by MALDI-TOF mass spectrometry following the affinity purification of secreted K3 from the supernatant of 96-well cultured transformants. Transformed colonies were picked and grown to an OD600 of 10 in a 2 ml, 96-well plate in BMGY at 30° C. Cells were harvested by centrifugation, washed in BMMY and resuspended in 250 ul of BMMY. Following 24 hours of induction, cells were removed by centrifugation, the supernatant was recovered and K3 was purified from the supernatant by Ni affinity chromatography. The N-glycans were released and analyzed by MALDI-TOF delayed extraction mass spectrometry as described herein.

In summary, the methods of the invention yield strains of *P. pastoris* that produce GlcNAcMan$_5$GlcNAc$_2$ in high yield, as shown in FIG. 10B. At least 60% of the N-glycans are GlcNAcMan$_5$GlcNAc$_2$. To date, no report exists that describes the formation of GlcNAcMan$_5$GlcNAc$_2$ on secreted soluble glycoproteins in any yeast. Results presented herein show that addition of the UDP-GlcNAc transporter along with GnTI activity produces a predominant GlcNAcMan$_5$GlcNAc$_2$ structure, which is confirmed by the peak at 1457 (m/z) (FIG. 10B).

Construction of Strain PBP-3:

The *P. pastoris* strain expressing K3, (Δoch1, arg-, ade-, his-) was transformed successively with the following vectors. First, pFB8 (*Saccharomyces* SEC12 (m)/mouse mannosidase IA Δ187) was transformed in the *P. pastoris* strain by electroporation. Second, pPB103 containing *Kluyveromyces lactis* MNN2-2 gene (Genbank AN AF106080) (encoding UDP-GlcNAc transporter) cloned into pBLADE-SX plasmid (Cereghino et al. Gene 263 (2001) 159-169) digested with BamHI and BglII enzymes was transformed in the *P. pastoris* strain. Third, pPB104 containing *Saccharomyces* MNN9(s)/human GnTI Δ38 encoding gene cloned as NotI-PacI fragment into pJN336 was transformed into the *P. pastoris* strain.

EXAMPLE 16

Engineering *K. lactis* Cells to Produce N-Glycans with the Structure Man$_5$GlcNAc$_2$ Identification and Disruption of the *K. lactis* OCH1 Gene The OCH1 gene of the budding yeast *S. cerevisiae* encodes a 1,6-mannosyltransferase that is responsible for the first Golgi localized mannose addition to the Man$_8$GlcNAc$_2$ N-glycan structure on secreted proteins (Nakayama et al, *J Biol. Chem.;* 268(35):26338-45 (Dec. 15, 1993)). This mannose transfer is generally recognized as the key initial step in the fungal specific polymannosylation of N-glycan structures (Nakanishi-Shindo et al, 1993; Nakayama et al, 1992; Morin-Ganet et al, *Traffic* 1(1):56-68. (January 2000)). Deletion of this gene in *S. cerevisiae* results in a significantly shorter N-glycan structure that does not include this typical polymannosylation or a growth defect at elevated temperatures (Nakayama et al, *EMBO J.;* 11(7):2511-9 (July 1992)).

The Och1p sequence from *S. cerevisiae* was aligned with known homologs from *Candida albicans* (Genbank accession #AAL49987), and *P. pastoris* (B. K. Choi et al. in prep) along with the Hoc1 proteins of *S. cerevisiae* (Neiman et al, *Genetics,* 145(3):637-45 (March 1997) and *K. lactis* (PENDANT EST database) which are related but distinct mannosyltransferases. Regions of high homology that were in common among Och1p homologs but distinct from the Hoc1p homologs were used to design pairs of degenerate primers that were directed against genomic DNA from the *K. lactis* strain MG1/2 (Bianchi et al, *Current Genetics* 12, 185-192 (1987)). PCR amplification with primers RCD33 (CCAGAAGAATTCAATTYTGYCARTGG) (SEQ ID NO:34) and RCD34 (CAGTGAAAATACCTGGNCCNGTCCA) (SEQ ID NO:35) resulted in a 302 bp product that was cloned and sequenced and the predicted translation was shown to have a high degree of homology to Och1 proteins (>55% to *S. cerevisiae* Och1p).

The 302 bp PCR product was used to probe a Southern blot of genomic DNA from *K. lactis* strain (MG1/2) with high stringency (Sambrook et al, 1989). Hybridization was observed in a pattern consistent with a single gene indicating that this 302 bp segment corresponds to a portion of the *K. lactis* genome and *K. lactis* (K1OCH1) contains a single copy of the gene. To clone the entire K1OCH1 gene, the Southern blot was used to map the genomic locus. Accordingly, a 5.2 kb BamHI/PstI fragment was cloned by digesting genomic DNA and ligating those fragments in the range of 5.2 kb into pUC19 (New England Biolabs, Beverly, Mass.) to create a *K. lactis* subgenomic library. This subgenomic library was transformed into *E. coli* and several hundred clones were tested by colony PCR using RCD 33/34. The 5.2 kb clone containing the predicted K1OCH1 gene was sequenced and an open reading frame of 1362 bp encoding a predicted protein that is 46.5% identical to the *S. cerevisiae* OCH1 gene. The 5.2 kb sequence was used to make primers for construction of an och1::KAN$^R$ deletion allele using a PCR overlap method (Davidson et al, *Microbiology.* 148(Pt 8):2607-15. August 2002). This deletion allele was transformed into two *K. lactis* strains and G418 resistant colonies selected. These colonies were screened by both PCR and for temperature sensitivity to obtain a strain deleted for the OCH1 ORF. The results of the experiment show strains which reveal a mutant PCR pattern, which were characterized by analysis of growth at various temperatures and N-glycan carbohydrate analysis of secreted and cell wall proteins following PNGase digestion. The och1 mutation conferred a temperature sensitivity which allowed strains to grow at 30° C. but not at 35° C. FIG. 12A shows a MALDI-TOF analysis of a wild type *K. lactis* strain producing N-glycans of Man$_8$GlcNAc$_2$ [c] and higher.

Identification, Cloning, and Disruption of the *K. lactis* MNN1 Gene

*S. cerevisiae* MNN1 is the structural gene for the Golgi α-1,3-mannosyltransferase. The product of MNN1 is a 762-amino acid type II membrane protein (Yip et al., *Proc Natl Acad Sci USA.* 91(7):2723-7. (1994)). Both N-linked and O-linked oligosaccharides isolated from mnn1 mutants lack α-1,3-mannose linkages (Raschke et al., *J Biol. Chem.,* 248 (13):4660-6. (Jul. 10, 1973).

The Mnn1p sequence from *S. cerevisiae* was used to search the *K. lactis* translated genomic sequences (PEDANT). One 405 bp DNA sequence encoding a putative protein fragment of significant similarity to Mnn1p was identified. An internal segment of this sequence was subsequently PCR amplified with primers KMN1 (TGCCATCTTTTAGGTCCAGGC-CCGTTC) (SEQ ID NO:36) and KMN2 (GATCCCAC-GACGCATCGTATTTCTTTC), (SEQ ID NO:37) and used to probe a Southern blot of genomic DNA from *K. lactis* strain (MG1/2). Based on the Southern hybridization data a 4.2 Kb BamHI-PstI fragment was cloned by generating a size-selected library as described herein. A single clone containing the *K. lactis* MNN1 gene was identified by whole colony PCR using primers KMN1 (SEQ ID NO:36) and KMN2 (SEQ ID NO:37) and sequenced. Within this clone a 2241 bp ORF was identified encoding a predicted protein that was 34% identical to the *S. cerevisiae* MNN1 gene. Primers were designed for construction of a mnn1::NAT$^R$ deletion allele using the PCR overlap method (Davidson et al. 2002).

This disruption allele was transformed into a strain of *K. lactis* by electroporation and Noursethoicin resistant transformants were selected and PCR amplified for homologous insertion of the disruption allele. Strains that reveal a mutant PCR pattern may be subjected to N-glycan carbohydrate analysis of a known reporter gene.

Figure 12B:
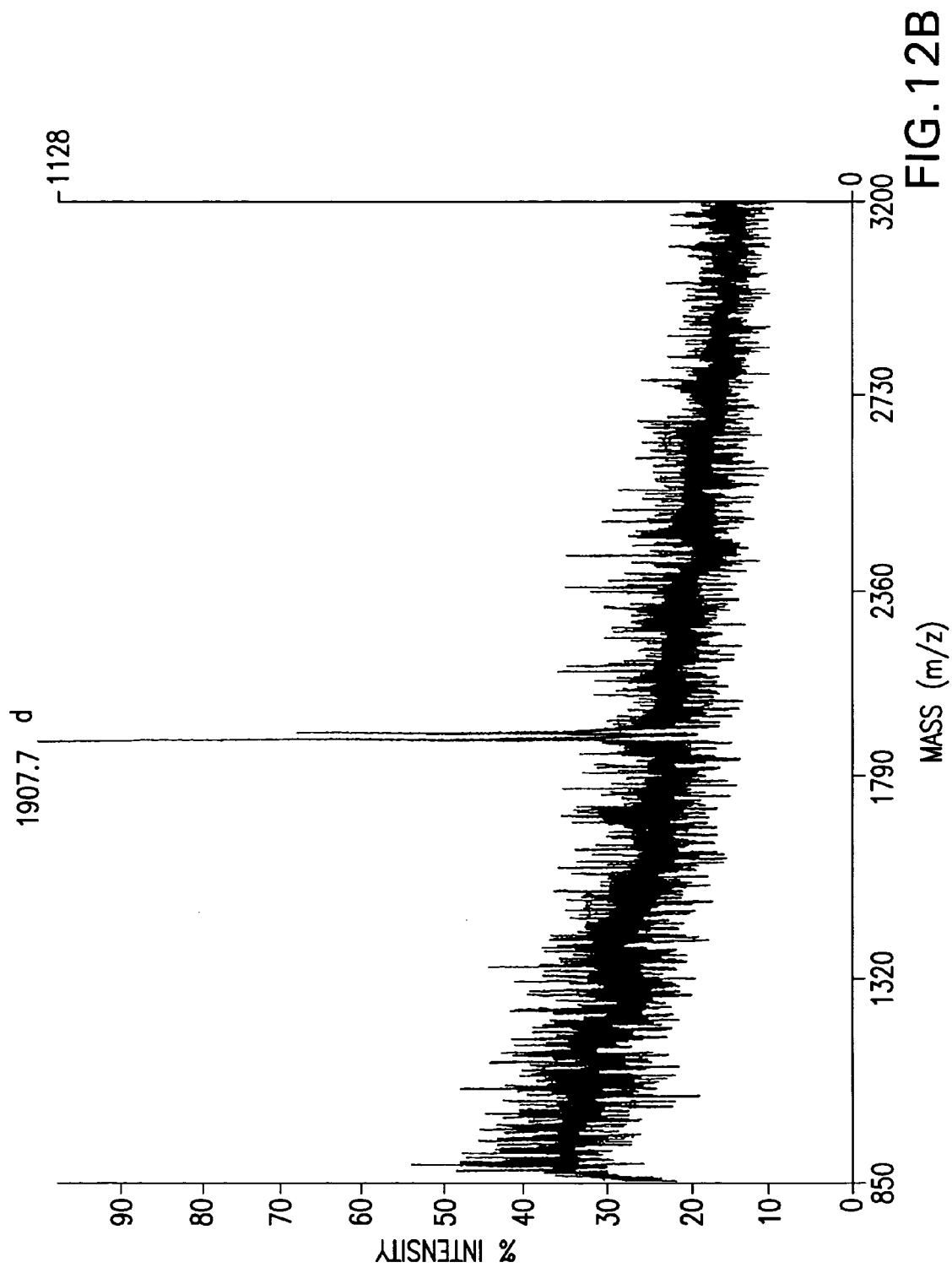
Figure 12C:
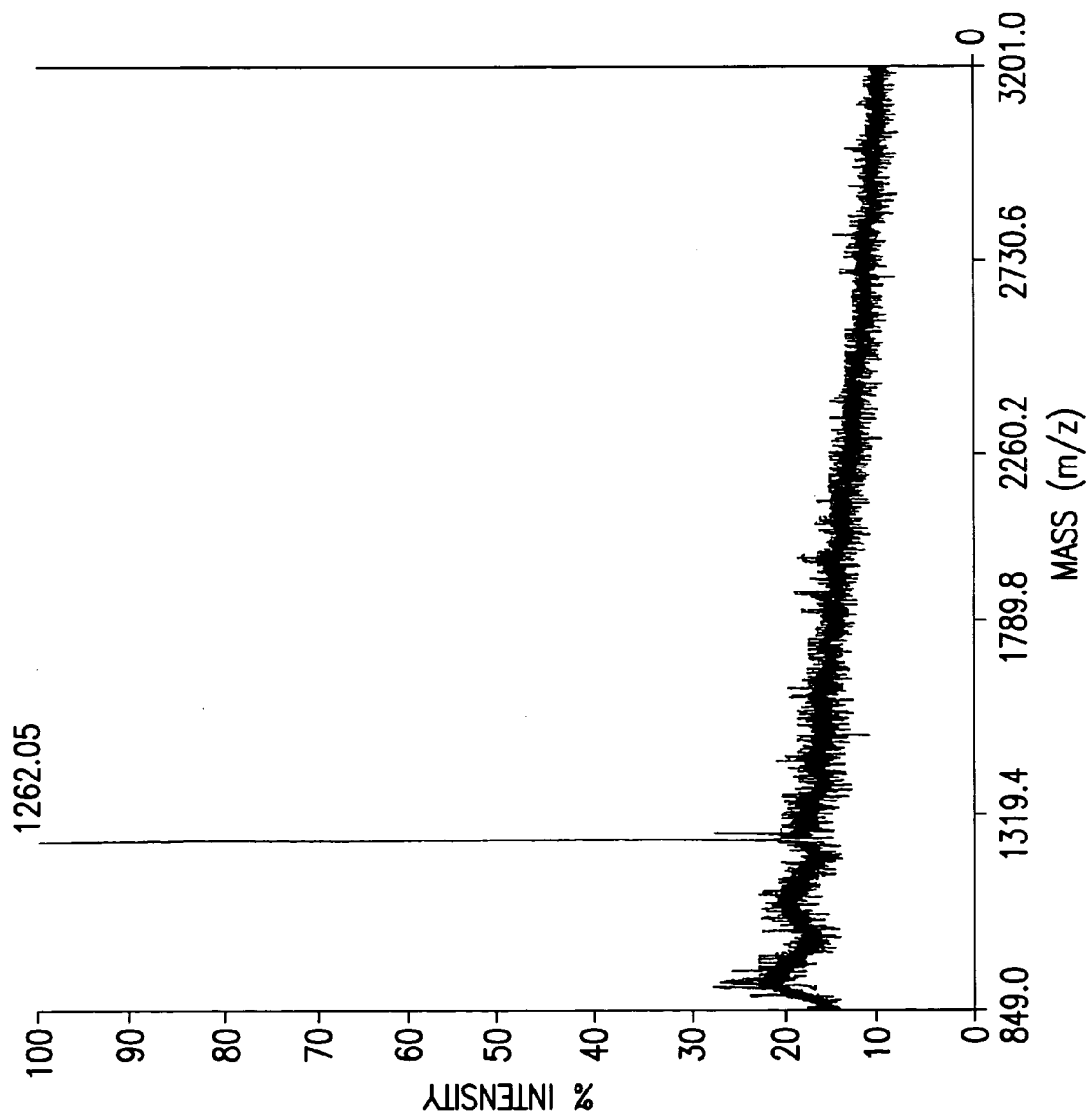

FIG. 12B depicts the N-glycans from the *K. lactis* och1 mnn1 deletion strain observed following PNGase digestion the MALDI-TOF as described herein. The predominant peak at 1908 (m/z) indicated as [d] is consistent with the mass of Man$_9$GlcNAc$_2$.

EXAMPLE 17

Engineering Plant Cells to Express GlcNAc Transferases or Galactosyltransferases GlcNAc transferase IV is required for the addition of β1,4 GlcNAc to the α-1,6 mannose residue and the α-1,3 mannose residues in complex N-glycans in humans. So far GlcNAc transferase IV has not been detected in or isolated from plants. A transgenic plant that is capable of adding human-like N-glycans must therefore be engineered to express GlcNAc transferase IV. Thus, the plant host cell or transgenic plant must also localize an expressed GlcNAc transferase IV to the correct intracellular compartment in the host so that the enzyme can add the β1,4 GlcNAc to the appropriate mannose residues.

There is some evidence that glycosyltransferases from mammals and plants have similar targeting signals. For example, a full-length rat α-2,6-sialyltransferase has been shown to correctly localize to the trans Golgi network in transgenic *arabidopsis* though not necessarily active (Wee E et al. *Plant Cell* 1998 October; 10(10):1759-68). A fusion construct having fifty-two N-terminal amino acids from α-2,6-sialyltransferase fused to a green fluorescent reporter protein (GFP) was also shown to correctly localize to the plant Golgi (Boevink et al. *Plant J* 1998 August; 15(3):441-7). Two mammalian proteins—TGN30 and furin—and AtELP, an *arabidopsis* integral membrane protein (Sanderfoot et al. *Proc Natl Acad Sci USA* 1998 Aug. 18; 95(17):9920-5), which localize to the trans Golgi network, each contain a tyrosine tetrapeptide motif which targets them to the Golgi, probably by a recycling mechanism via the plasma membrane. Although mammals and plants appear to share some common mechanisms related to protein targeting, exogenous glycosylases may nonetheless not target correctly in a plant cell, however, localization does not necessarily equal enzyme activity. It therefore becomes essential to devise means to correctly target in a plant cell these enzymes and/or other enzymes which participate in forming complex, human-like N-glycans.

Glycosylation enzymes are integral membrane proteins which reside in the endoplasmic reticulum and Golgi apparatus. The targeting and localization signals are normally contained in the cytoplasmic and/or transmembrane domains and in some cases are contained in some lumenal amino acids. For example, fifty-two amino acids that make up the transmembrane domain, nine cytoplasmic amino acids and twenty-six lumenal amino acids of α-2,6-sialyltransferase are required to target GFP to the trans Golgi network (Boevink et al. *Plant J* 1998 Aug; 15(3):441-7).

Figure 13:
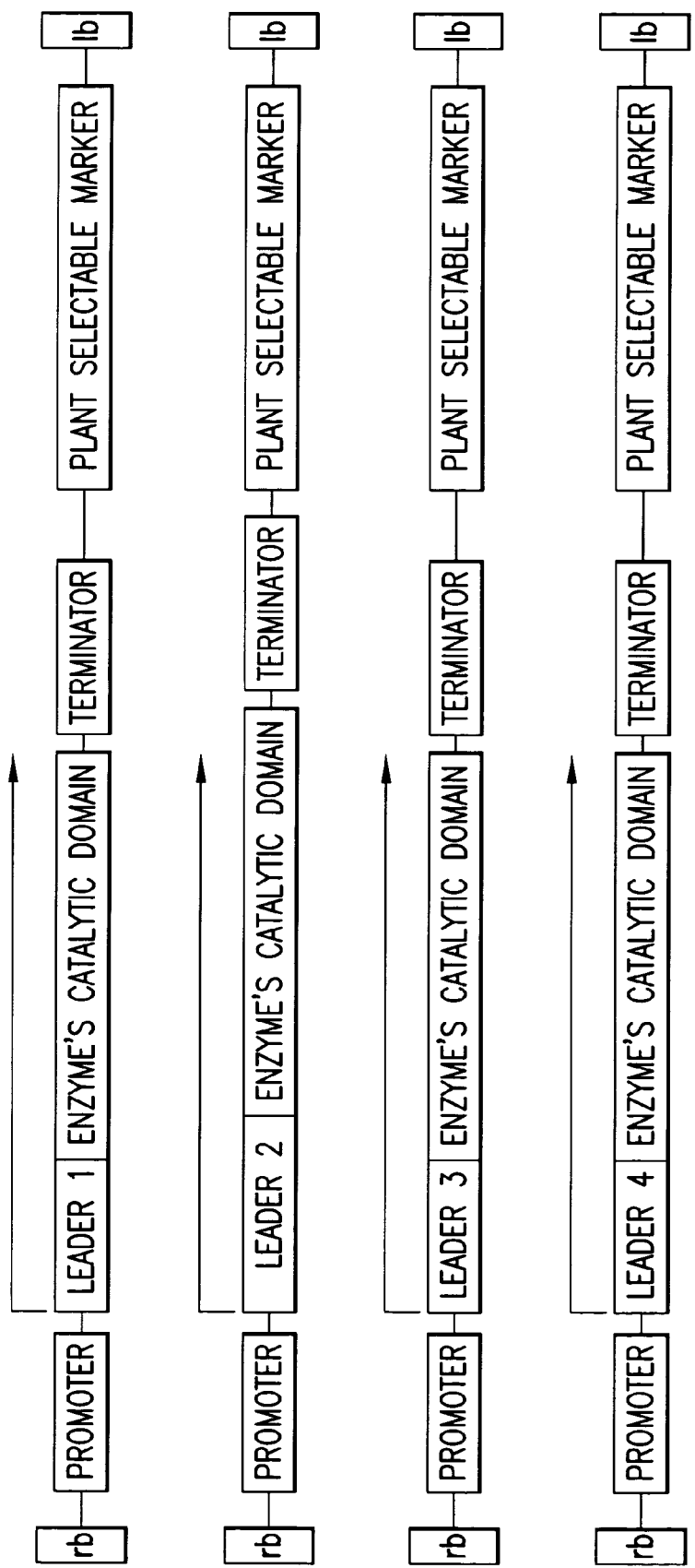
FIG. 13 represents T-DNA cassettes with catalytic domain(s) of glycosylation enzymes fused in-frame to different leader sequences. The ends of the T-DNA are marked by the right (rb) and left borders (lb). Various promoters and terminators may also be used. The plant selectable marker can also be varied. The right and left borders are required only for *agrobacterium*-mediated transformation and not for particle bombardment or electroporation.

Thus, a library of sequences encoding cellular targeting signal peptides comprising of either just the cytoplasmic and transmembrane domains or the cytoplasmic, transmembrane and lumenal domains of endoplasmic reticulum and Golgi specific proteins is generated, as described in Example 11. The targeting peptide sequences maybe chosen from ER and Golgi-resident plant, yeast or animal proteins. A glycosylation related protein, e.g., an enzyme (or catalytic domain thereof) such as a glycosylase or integral membrane enzyme can be fused in-frame to the library of targeting peptide sequences and introduced into plants (FIG. 13). Plant targeting peptide sequences may be most efficient in localizing the chimeric enzymes to the ER and Golgi, although targeting peptide sequences from fungi and mammals may also be effective. For example, the N-terminal 77 amino acids from tobacco N-acetylglucosaminyl Transferase I have been shown to correctly target a reporter protein to the Golgi (Essl D. et al., *FEBS Lett* 1999 Jun. 18; 453(1-2):169-73). In one embodiment, one or more N-terminal fragments comprising these 77 amino acids (or subsets of these amino acids) is fused to one or more fragments comprising a catalytic domain of GlcNAc transferase IV. At least one resulting fusion protein correctly localizes a functional GlcNAc transferase IV to the Golgi apparatus in a plant cell, as evidenced by monitoring the glycosylation state of a reporter glycoprotein resident or introduced into the plant host cell using techniques described herein.

Another plant enzyme shown to localize to the Golgi is *Arabidopsis* GlcNAc transferase II (Strasser R et al., *Glycoconj J* 1999 December; 16(12):787-91). Thus, in another embodiment, one or more different fragments of the *arabidopsis* GlcNAc transferase II targeting peptide are fused to a GlcNAc transferase IV catalytic domain and fusion constructs produced and tested as described above. The plant specific β1,2-xylosyltransferase from *Arabidopsis thaliana* is another protein that localizes to the Golgi and its localization and retention in the Golgi is dependent on its cytoplasmic and transmembrane sequences (Dimberger et al., *Plant Mol Biol* 2002 September; 50(2):273-81). Thus, in another embodiment, one or more fragments comprising the cytoplasmic and transmembrane sequences of β1,2-xylosyltransferase are fused to one or more fragments comprising a GlcNAc transferase IV catalytic domain and resulting fusion constructs are transformed into plant cells and tested for their ability to produce a human-like N-glycan and to otherwise modulate glycosylation in the plant host cell.

Because GlcNAc transferase IV or Galactosyltransferase from one organism may function more efficiently in a specific plant host than one from another organism, fragments comprising GlcNAc transferase IVs (or catalytic domains) from various eukaryotic organisms are fused in-frame to the library of endoplasmic reticulum (ER) and Golgi targeting peptide sequences and are then introduced into plants. The use of a library of nucleic acids encoding enzyme domains isolated or derived from different species increases the chances of efficient glycosylation—in addition to correct localization and glycosylation by GlcNAc transferase IV.

The methods and combinatorial nucleic acid libraries of the invention may be used to introduce and localize, sequentially or en masse, multiple enzymes required to glycosylate proteins in a plant cell with human-like N-glycans. As different plant species may require different growth conditions, protocols for transformation may vary depending on the species being transformed (Potrykus, "Gene transfer methods for plants and cell cultures." *Ciba Found Symp* 1990; 154:198-208; discussion 208-12). The commonly used methods for generating transgenic plants include *Agrobacterium* mediated transformation, particle bombardment (Sanford, J. C. et al, Biolistic plant transformation. *Physiol. Plant.* 1990, 79: 206-209) and electroporation.

*Agrobacterium* Method

The catalytic domains of GlcNAc transferase IVs are fused in-frame to multiple different targeting peptide sequences known to target proteins to the ER and Golgi in plants. Each of these fusion constructs is introduced under the control of the ubiquitously expressed promoters like the 35S CaMV, ubiquitin or actin promoters, tissue specific promoters or inducible promoters. A plant specific terminator region is also used. This cassette (Promoter::targeting peptide-GlcNAc transferase IV::terminator) is cloned into a vector suitable for *Agrobacterium* mediated transformation (FIG. 13). The vector also contains a selectable marker that allows one to select for transformed plants. The common selectable markers used include those resulting in kanamycin, hygromycin and basta resistance. The construct is introduced into *Agrobacterium* via well-established transformation methods, which are available in the art. An *Agrobacterium* library of Golgi-targeted GlcNAc transferase IVs is thereby generated.

Embryonic and meristematic tissue may be transformed and can regenerate transgenic plants. To transform tissue, tissue explants (these could be plumules and radicals from germinated seeds) are first soaked and coated with an *Agrobacterium* innoculum. They are then cultured on plates containing the innoculum to form an undifferentiated mass of cells termed the callus. Transformed plant cells are selected for by adding to the medium the relevant kanamycin, hygromycin or basta (depending on the selectable marker used on the construct). The transformed plant cells can either be grown in culture and remain undifferentiated or they are treated with shoot regenerating and shoot elongation medium. Explants that differentiate are transferred onto rooting medium to generate transgenic plants. Some plants like *Arabidopsis* can be transformed by dipping flowers into an *Agrobacterium* solution. Seeds from the transformed plants are germinated on plates containing the relevant herbicide or antibiotic selection. Transgenic plants are those that grow on the selection media. The transgenic plants are then screened for those with properly glycosylated proteins (i.e., those which have complex, human-like N-glycans) by isolating glycoproteins from plant extracts and analyzing glycoprotein patterns as described elsewhere herein, e.g., by using a specific antibody or lectin. Although the *Agrobacterium* method is economical and simple, it is limited to certain species of plants. Accordingly, plants that cannot be transformed using *Agrobacterium* can be transformed by ballistics or electroporation.

Particle Bombardment Method and Electroporation

Compared to *Agrobacterium* mediated transformation, these methods have a greater tendency to insert multiple copies of the transgene into the genome. This could result in gene silencing and cosuppression. However, unlike *Agrobacterium* mediated transformation, these methods are not species limited and are therefore useful when an *Agrobacterium* method cannot be employed to generate transgenic plants. In the particle bombardment method, cultured plant cells are bombarded with very small tungsten or gold particle that have been coated with DNA (Promoter::targeting peptide-GlcNAc transferase IV-terminator::selectable marker) (FIG. 13) (rb and lb not required) while in the electroporation method, plant cells in a DNA (Promoter::targeting peptide-GlcNAc transferase IV-terminator::selectable marker) solution are treated with an electric pulse that perforates the cell, allowing it to take up DNA. The cells are then cultured and allowed to recover. Stable transformants are selected for by culturing and regenerating plants on appropriate selection medium.

Engineering Soybeans to Express GlcNAc Transferase IV Using a Soybean Cotyledonary Node *Agrobacterium* Mediated Transformation System An *Agrobacterium* library of Golgi-targeted GlcNAc transferase IV is generated as described above. Soybean explants are transformed with the library using a protocol described by Hinchee et al (*Bio/Technology* 1988. 6:915). A reporter protein is expressed with a His tag, purified and then analyzed. Transgenic plants are assayed for proteins with the α-1,6 mannose and the α-1,3 mannose residues using, e.g., mass spectroscopy.

Engineering Pea to Express GlcNAc Transferase IV Using Particle Bombardment

A GlcNAc transferase IV plasmid library is coated onto tungsten or gold particles and used as microprojectiles to bombard calli derived from pea embryonic tissue as described (Molnar et al., *Symposium on Recent Advances in Plant Biotechnology*, Sep. 4-11, 1999, Stara Lesna, Slovak Republic). A reporter protein is expressed with a His tag, purified and then analyzed. Transgenic plants are assayed for proteins with the α-1,6 mannose and the α-1,3 mannose residues using, e.g., MALDI.

Engineering Plants to Express GlcNAc Transferase I

GlcNAc transferase I is involved in the addition of GlcNAc to the terminal α-1,3 mannose residue to form $Man_5GlcNAc_2$, an essential step in the maturation of complex N-glycans. Although GlcNAc transferase I has been isolated from plants and appears to have the same function as its mammalian homolog, it may not be the most efficient enzyme for glycosylation of mammalian or exogenous proteins and may not be found in every plant species. As the addition of GlcNAc to the terminal α-1,3 mannose residue is a controlling step in the mammalian glycosylation pathway, it is advantageous to have transgenic plants that can carry out this step efficiently. To create transgenic plants that express GlcNAc transferase I that can function efficiently to promote the formation of complex N-glycans, a library of GlcNAc transferase I isolated or derived from various organisms is fused in-frame to multiple plant Golgi targeting peptide sequences according to the methods described herein. The combinatorial library thus created is introduced into a plant cell or organism as described above for GlcNAc transferase IV.

Engineering Maize to Express GlcNAc Transferase I Using Particle Bombardment

Transgenic maize can be obtained using a protocol similar to the one used to generate peas that express GlcNAc transferase IV. Here the GlcNAc transferase I plasmid library is coated onto tungsten or gold particles and used to bombard calli derived from maize embryonic tissue, e.g., using a protocol specific for the generation of transgenic maize (Gordon-Kamm W J et al., *Plant Cell* 1990 July; 2(7):603-618)). Transgenic plants are assayed for proteins having GlcNAc on the terminal α-1,3 mannose residue, e.g., using specific antibodies or by assaying reduced binding of the N-glycans to certain lectins or by using MALDI-TOF. Other useful references for using plant host cells according to the invention include: Christou P. *Plant Mol Biol* 1997 September; 35(1-2):197-203; Chowrira G M et al. *Mol Biotechnol* 1995 February; 3(1):17-23; Dimberger et al., *Plant Mol Biol* 2002 September; 50(2):273-81; Frame B R et al. *Plant Physiol* 2002 May; 129(1):13-22; Gomord V et al. *Biochimie* 1999 June; 81(6): 607-18; Laursen C M et al. *Plant Mol Biol* 1994 January; 24(1):51-61; Orci L et al. *J Cell Biol* 2000 Sep. 18; 150(6): 1263-70; Newell C A. *Mol Biotechnol* 2000 September; 16(1):53-65; Pawlowski Wp et al. *Mol Biotechnol* 1996 August; 6(1):17-30; Schroeder H E et al. *Plant Physiol* 1993 March; 101(3):751-757; Sorokin, A P et al. *Plant Sci.* 2000 Jul. 28; 156(2):227-233; Strasser R et al. *Glycoconj J* 1999 December; 16(12):787-91; and Tomes D T et al. *Plant Mol Biol* 1990 February; 14(2):261-8.

Engineering Plant Cells to Produce β1,4-Galactosyltransferases

β1,4-galactosyltransferase is an important human glycosyltransferase that is absent in plants. Lerouge P et al. *Plant Mol Biol* 1998 September; 38(1-2):31-48. In mammals, β1,4-galactosyltransferase is localized in the Golgi and is responsible for the transfer of galactose residues to the terminal N-acetylglucosamine of the core $Man_3GlcNAc_2$ of complex N-glycans. In plants, the $Man_3GlcNAc_2$ core contains β1,2-xylose and α1,3-fucose residues and lacks the β1,4-galactose. The xylose and fucose modifications are implicated in allergies and act as antigenic epitopes and are therefore not desirable modifications of therapeutic proteins.

The galactose modifications carried out by β1,4-galactosyltransferase can be important for the proper functioning of the therapeutic proteins. In mammals, β1,4-galactosyltransferase acts after N-acetylglucosaminyltransferase I and N-acetylglucosaminyltransferase II and has been shown to initiate branching of the complex N-glycan. Lerouge P et al. *Plant Mol Biol* 1998 September; 38(1-2):31-48. Palacpac N et al. *Proc Natl Acad Sci USA* 1999 Apr. 13; 96(8):4692-7. In tobacco cells, expression of human β1,4-galactosyltransferase has been shown to result in galactosylated N-glycans with reduced fucose and xylose modifications. Bakker H et al. *Proc Natl Acad Sci USA* 2001 Feb. 27; 98(5):2899-904 Fujiyama K et al. *Biochem Biophys Res Commun* 2001 Nov. 30; 289(2):553-7. Palacpac N et al. *Proc Natl Acad Sci USA* 1999 Apr. 13; 96(8):4692-7. In these studies, a 1.2 kb fragment of human β1,4-galactosyltransferase was cloned downstream of the cauliflower mosaic virus promoter (35SCaMV), introduced into the binary vector pGA482, and finally into tobacco cells. Palacpac N et al. *Proc Natl Acad Sci USA* 1999 Apr. 13; 96(8):4692-7.

Tobacco cells were transformed using the *agrobacterium* method described by Rempel et al. (Rempel, H. C. et al. 1995. *Transgenic Res.* 4(3):199-207.) Transformation of tobacco cells has also been described (An, G 1985. *Plant Physiol.* 79:568-570). Expression of β1,4-galactosyltransferase under the 35SCaMV resulted in ubiquitous expression of the gene in tobacco cells. Tobacco cells expressing human β1,4-galactosyltransferase showed the presence of galactosylated N-glycans. (Palacpac N et al. *Proc Natl Acad Sci USA* 1999 Apr. 13; 96(8):4692-7). Bakker et al. showed that crossing tobacco plants expressing human β1,4-galactosyltransferase with plants expressing the heavy and light chain of a mouse antibody resulted in plants in which the antibody showed 30% galactosylation (Bakker H et al. *Proc Natl Acad Sci USA* 2001 Feb. 27; 98(5):2899-904).

A combinatorial DNA library can be constructed to obtain a β1,4-galactosyltransferase line for the addition of galactose residues. The combinatorial DNA library can effectively produce lines which are more efficient in the addition of galactose residues. Once such a line is made it can be easily crossed to lines expressing other glycosylation enzymes and to those expressing therapeutic proteins to produce therapeutic proteins with human-like glycosylation. The final line can then be grown as plants and harvested to extract proteins or can be cultured as plant cells in suspension cultures to produce proteins in bioreactors. By expressing the therapeutic proteins using the library of signal peptides, it is possible to retain the therapeutic protein within the cells or have them secreted into the medium. Tobacco cells expressing β1,4-galactosyltransferase secrete galactosylated N-glycans (Ryo Misaki et al. *Glycobiology* 2002 Dec. 17; 10:1093). While horseradish peroxidase isozyme C expressed in tobacco plants expressing β1,4-galactosyltransferase contained xylose and fucose modifications, no xylose or fucose modification could be detected in horseradish peroxidase isozyme C expressed in tobacco cells expressing β1,4-galactosyltransferase (GT6 cells). (Fujiyama K et al. *Biochem Biophys Res Commun* 2001 Nov. 30; 289(2):553-7). This indicates that it may be advantageous to express therapeutic proteins in cell lines instead of whole plants.

Engineering Plants to Produce Sialyltransferase

In mammals, sialyltransferase is a trans golgi enzyme that adds terminal sialic acid residues to glycosylated polypeptides. Thus far, terminal sialic acid residues have not been detected in plants (Wee E et al. *Plant Cell* 1998 October; 10(10):1759-68). Wee et al. expressed the rat α-2,6-sialyltransferase in transgenic *arabidopsis* and showed that the enzyme properly localized to the golgi and was functional. Wee et al. demonstrated that membranes isolated from transgenic *arabidopsis*, when incubated with CMP-3H-sialic acid and asialofetuin acceptor, resulted in the addition of sialic acid residues while membrane isolated from wild-type *arabidopsis* did not. While expressing the rat α-2,6-sialyltransferase in *arabidopsis* resulted in a functional enzyme that was able to incorporate sialic acid residues, fusing the mammalian enzymes α-2,3-sialyltransferase and α-2,6-sialyltransferase to a variety of transit peptides using the library approach of the present invention described earlier can result in more efficient sialylation in other plant species. Wee E et al had to isolate membranes and incubate them with CMP-3H-sialic acid and asialofetuin acceptor since *arabidopsis* does not have CMP-sialic acid or its transporter. In order to overcome this additional step and obtain sialic acid addition in the plant, CMP-sialic acid biosynthetic pathway and the CMP-sialic acid transporter can be co-expressed in transgenic plants expressing α-2,3-sialyltransferase and α-2,6-sialyltransferase. As an alternative the CMP-sialic acid transporter can be co-expressed α-2,3-sialyltransferase and α-2,6-sialyltransferase in plant cells grown in suspension culture, and CMP-sialic acid or other precursors of CMP-sialic acid supplied in the medium.

Expressing α-2,3-Sialyltransferase and α-2,6-Sialyltransferase in Lemna

As described in the U.S. Pat. No. 6,040,498, lemna (duckweed) can be transformed using both *agrobacterium* and ballistic methods. Using protocols described in the patent, lemna will be transformed with a library of golgi targeted α-2,3-sialyltransferase and/or α-2,6-sialyltransferase and a library of mammalian CMP-sialic acid transporters. Transgenic plants can be assayed for proteins with terminal sialic acid residues.

Expressing α-2,3-Sialyltransferase and α-2,6-Sialyltransferase in Tobacco Cells

Alpha-2,3-sialyltransferase and/or α-2,6-sialyltransferase and/or a library of mammalian CMP-sialic acid transporters can also be introduced into tobacco cells grown in suspension culture as described for β1,4-galactosyltransferases. CMP-sialic acid can be added to the medium. Both the cells and the culture medium (secreted proteins) can be assayed for proteins with terminal sialic acid residues.

EXAMPLE 18

Engineering Insect Cells to Produce Glycosyltransferases

Insect cells provide another mechanism for producing glycoproteins but the resulting glycoproteins are not complex human-like glycoproteins. Marz et al. 1995 *Glycoproteins*, 29:543-563; Jarvis 1997 *The Baculoviruses* 389-431. It is another feature of the present invention to provide enzymes in insect cells, which are targeted to the organelles in the secretory pathway. In a preferred embodiment, enzymes such as glycosyltransferases, galactosyltransferases and sialyltransferases are targeted to the ER, Golgi or the trans Golgi network in lepidopteran insect cells (Sf9). Expression of mammalian β1,4-galactosyltransferase has been shown in Sf9 cells. Hollister et al. *Glycobiology*. 1998 8(5):473-480. These enzymes are targeted by means of a chimeric protein comprising a cellular targeting signal peptide not normally associated with the enzyme. The chimeric proteins are made by constructing a nucleic acid library comprising targeting sequences as described herein and the glycosylation enzymes. Baculovirus expression in insect cells is commonly used for stable transformation for adding mammalian glycosyltransferases in insect cells. Hollister et al. *Glycobiology*. 2001 11(1):1-9.

TABLE 11

| DNA and Protein Sequence Resources |
| --- |

1. European Bioinformatics Institute (EBI) is a centre for research and services in bioinformatics: http://www.ebi.ac.uk/
2. Swissprot database: http://www.expasy.ch/spr
3. List of known glycosyltransferases and their origin.
4. human cDNA, Kumar et al (1990) Proc. Natl. Acad. Sci. USA 87: 9948-9952
5. human gene, Hull et al (1991) Biochem. Biophys. Res. Commun. 176: 608-615
6. mouse cDNA, Kumar et al (1992) Glycobiology 2: 383-393
7. mouse gene, Pownall et al (1992) Genomics 12: 699-704
8. murine gene (5' flanking, non-coding), Yang et al (1994) Glycobiology 5: 703-712
9. rabbit cDNA, Sarkar et al (1991) Proc. Natl. Acad. Sci. USA 88: 234-238
10. rat cDNA, Fukada et al (1994) Biosci.Biotechnol.Biochem. 58: 200-201
   1,2 (GnTII) EC 2.4.1.143
11. human gene, Tan et al (1995) Eur. J. Biochem. 231: 317-328
12. rat cDNA, D'Agostaro et al (1995) J. Biol. Chem. 270: 15211-15221
13. β1,4 (GnTIII) EC 2.4.1.144
14. human cDNA, Ihara et al (1993) J. Biochem.113: 692-698
15. murine gene, Bhaumik et al (1995) Gene 164: 295-300
16. rat cDNA, Nishikawa et al (1992) J. Biol. Chem. 267: 18199-18204
   β1,4 (GnTIV) EC 2.4.1.145
17. human cDNA, Yoshida et al (1998) Glycoconjugate Journal 15: 1115-1123
18. bovine cDNA, Minowa et al., European Patent EP 0 905 232
   β1,6 (GnT V) EC 2.4.1.155
19. human cDNA, Saito et al (1994) Biochem. Biophys. Res. Commun. 198: 318-327
20. rat cDNA, Shoreibah et al (1993) J. Biol. Chem. 268: 15381-15385 β1,4 Galactosyltransferase, EC 2.4.1.90 (LacNAc synthetase) EC 2.4.1.22 (lactose synthetase)
21. bovine cDNA, D'Agostaro et al (1989) Eur. J. Biochem. 183: 211-217
22. bovine cDNA (partial), Narimatsu et al (1986) Proc. Natl. Acad. Sci. USA 83: 4720-4724
23. bovine cDNA (partial), Masibay & Qasba (1989) Proc. Natl. Acad. Sci. USA 86: 5733-5377
24. bovine cDNA (5' end), Russo et al (1990) J. Biol. Chem. 265: 3324
25. chicken cDNA (partial), Ghosh et al (1992) Biochem. Biophys. Res. Commun. 1215-1222
26. human cDNA, Masri et al (1988) Biochem. Biophys. Res. Commun. 157: 657-663
27. human cDNA, (HeLa cells) Watzele & Berger (1990) Nucl. Acids Res. 18: 7174
28. human cDNA, (partial) Uejima et al (1992) Cancer Res. 52: 6158-6163
29. human cDNA, (carcinoma) Appert et al (1986) Biochem. Biophys. Res. Commun. 139: 163-168
30. human gene, Mengle-Gaw et al (1991) Biochem. Biophys. Res. Commun. 176: 1269-1276
31. murine cDNA, Nakazawa et al (1988) J. Biochem. 104: 165-168
32. murine cDNA, Shaper et al (1988) J. Biol. Chem. 263: 10420-10428
33. murine cDNA (novel), Uehara & Muramatsu unpublished
34. murine gene, Hollis et al (1989) Biochem. Biophys. Res. Commun. 162: 1069-1075
35. rat protein (partial), Bendiak et al (1993) Eur. J. Biochem. 216: 405-417
   2,3-Sialyltransferase, (ST3Gal II) (N-linked) (Gal-1,3/4-GlcNAc) EC 2.4.99.6
36. human cDNA, Kitagawa & Paulson (1993) Biochem. Biophys. Res. Commun. 194: 375-382
37. rat cDNA, Wen et al (1992) J. Biol. Chem. 267: 21011-21019
   2,6-Sialyltransferase, (ST6Gal I) EC 2.4.99.1
38. chicken, Kurosawa et al (1994) Eur. J. Biochem 219: 375-381
39. human cDNA (partial), Lance et al (1989) Biochem. Biophys. Res. Commun. 164: 225-232
40. human cDNA, Grundmann et al (1990) Nucl. Acids Res. 18: 667
41. human cDNA, Zettlmeisl et al (1992) Patent EPO475354-A/3
42. human cDNA, Stamenkovic et al (1990) J. Exp. Med. 172: 641-643 (CD75)
43. human cDNA, Bast et al (1992) J. Cell Biol. 116: 423-435
44. human gene (partial), Wang et al (1993) J. Biol. Chem. 268: 4355-4361
45. human gene (5' flank), Aasheim et al (1993) Eur. J. Biochem. 213: 467-475
46. human gene (promoter), Aas-Eng et al (1995) Biochim. Biophys. Acta 1261: 166-169
47. mouse cDNA, Hamamoto et al (1993) Bioorg. Med. Chem. 1: 141-145
48. rat cDNA, Weinstein et al (1987) J. Biol. Chem. 262: 17735-17743
49. rat cDNA (transcript fragments), Wang et al (1991) Glycobiology 1: 25-31, Wang et al (1990) J. Biol. Chem. 265: 17849-17853
50. rat cDNA (5' end), O'Hanlon et al (1989) J. Biol. Chem. 264: 17389-17394; Wang et al (1991) Glycobiology 1: 25-31
51. rat gene (promoter), Svensson et al (1990) J. Biol. Chem. 265: 20863-20688
52. rat mRNA (fragments), Wen et al (1992) J. Biol. Chem. 267: 2512-2518

Additional methods and reagents which can be used in the methods for modifying the glycosylation are described in the literature, such as U.S. Pat. Nos. 5,955,422, 4,775,622, 6,017,743, 4,925,796, 5,766,910, 5,834,251, 5,910,570, 5,849,904, 5,955,347, 5,962,294, 5,135,854, 4,935,349, 5,707,828, and 5,047,335. Appropriate yeast expression systems can be obtained from sources such as the American Type Culture Collection, Rockville, Md. Vectors are commercially available from a variety of sources.

---

What is claimed is:

1. A glycoprotein composition comprising a recombinant human glycoprotein wherein at least 60 % of the oligosaccharide structures on the glycoprotein consist of a GlcNAcMan$_5$GlcNAc$_2$ oligosaccharide structure.

2. A glycoprotein composition comprising a recombinant human glycoprotein wherein at least 60% of the oligosaccharide structures on the glycoprotein in consist of a GlcNAcMan$_5$GlcNAc$_2$ oligosaccharide structure, and wherein the glycoprotein is produced in a Pichia pastoris genetically engineered to lack OCH1 activity and to express
   (a) a chimeric mannosidase I comprising an alpha-1,2 mannosidase catalytic domain fused to a cellular targeting signal peptide not normally associated with the catalytic domain and selected to target the enzyme to the ER or Golgi apparatus of the host cell;
   (b) a chimeric N-acetylglucosamine transferase I (GnT I) comprising a GnT I catalytic domain fused to a cellular targeting signal peptide not normally associated with the catalytic domain and selected to target the catalytic domain to the ER or Golgi apparatus of the host cell; and
   (c) a uridine diphosphate-N-acetylglucosamine (UDP-GlcNAc) transporter.

3. The glycoprotein composition of claim 2, wherein the chimeric mannosidase I comprises the *Saccharomyces* SEC12 cellular targeting peptide and the mouse mannosidase IA lacking the first 187 amino acids.

4. The glycoprotein composition of claim 2, wherein the chimeric GnT I comprises the *Saccharomyces* MNN9 cellular targeting peptide and the human GnT I lacking the first 38 amino acids.

5. The glycoprotein composition of claim 2, wherein the UDP-GlcNAc transporter is encoded by the *Kluveromyces lactis* MNN2-2 gene.

6. A glycoprotein composition comprising a recombinant human glycoprotein wherein at least 50% to 70% of the oligosaccharide structures on the glycoprotein consist of a Man$_5$GlcNAc$_2$ oligosaccharide structure.

7. A glycoprotein composition comprising a recombinant human glycoprotein wherein at least 50% to 70% of the oligosaccharide structures on the glycoprotein consist of a Man$_5$GlcNAc$_2$ oligosaccharide structure, and wherein the glycoprotein is produced in a Pichia pastoris genetically engineered to lack OCH1 activity and to express
   (a) a chimeric mannosidase I comprising an alpha-1,2 mannosidase catalytic domain fused to a cellular targeting signal peptide not normally associated with the catalytic domain and selected to target the enzyme to the ER or Golgi apparatus of the host cell;
   (b) a chimeric N-acetylglucosamine transferase I (GnT I) comprising a GnT I catalytic domain fused to a cellular targeting signal peptide not normally associated with the catalytic domain and selected to target the catalytic domain to the ER or Golgi apparatus of the host cell; and
   (c) a uridine diphosphate-N-acetylglucosamine (UDP-GlcNAc) transporter.

8. The glycoprotein composition of claim 7, wherein the chimeric mannosidase I comprises the *Saccharomyces* SEC12 cellular targeting peptide and the mouse mannosidase IA lacking the first 187 amino acids.

9. The glycoprotein composition of claim 7, wherein the chimeric mannosidase I comprises the *Saccharomyces* VAN1 cellular targeting peptide and the C. elegans mannosidase IB lacking the first 80 amino acids.

10. The glycoprotein composition of claim 1, wherein the recombinant human glycoprotein is a therapeutic glycoprotein.

11. The glycoprotein composition of claim 1, wherein the recombinant human glycoprotein is selected from the group consisting of erythropoietin;
    interferon-α; interferon-β; interferon-γ; interferon-ω; granulocyte-CSF; factor VIII; factor IX;human protein C; soluble IgE receptor α-chain; IgG; IgG fragments; IgM; interleukins;
    urokinase; chymase; urea trypsin inhibitor; IGF-binding protein; epidermal growth factor;
    growth hormone-releasing factor; annexin V fusion protein; angiostatin; vascular endothelial growth factor-2; myeloid progenitor inhibitory factor-1; osteoprotegerin; α-1-antitrypsin; and,
    α-feto proteins.

12. The glycoprotein composition of claim 6, wherein the glycoprotein is a therapeutic glycoprotein.

13. The glycoprotein composition of claim 6, wherein the glycoprotein is selected from the group consisting of erythropoietin; interferon-α; interferon-β;
    interferon-γ; interferon-ω; granulocyte-CSF; factor VIII; factor IX; human protein C; soluble IgE receptor α-chain; IgG; IgG fragments; IgM; interleukins; urokinase; chymase; urea trypsin inhibitor; IGF-binding protein; epidermal growth factor; growth hormone-releasing factor;
    annexin V fusion protein; angiostatin; vascular endothelial growth factor-2; myeloid progenitor inhibitory factor-1; osteoprotegerin; α-1-antitrypsin; and, α-feto proteins.

14. The glycoprotein composition of claim 2, wherein the glycoprotein is a therapeutic glycoprotein.

15. The glycoprotein composition of claim 2, wherein the glycoprotein is selected from the group consisting of erythropoietin; interferon-α; interferon-β;
    interferon-γ; interferon-ω; granulocyte-CSF; factor VIII; factor IX; human protein C; soluble IgE receptor α-chain; IgG; IgG fragments; IgM; interleukins; urokinase; chymase; urea trypsin inhibitor; IGF-binding protein; epidermal growth factor; growth hormone-releasing factor;
    annexin V fusion protein; angiostatin; vascular endothelial growth factor-2; myeloid progenitor inhibitory factor-1; osteoprotegerin; α-1-antitrypsin; and, α-feto proteins.

16. The glycoprotein composition of claim 7, wherein the glycoprotein is a therapeutic glycoprotein.

17. The glycoprotein composition of claim 7, wherein the glycoprotein is selected from the group consisting of erythropoietin; interferon-α; interferon-β;
    interferon-γ; interferon-ω; granulocyte-CSF; factor VIII; factor IX; human protein C; soluble IgE receptor α-chain; IgG; IgG fragments; IgM; interleukins; urokinase; chymase; urea trypsin inhibitor; IGF-binding protein; epidermal growth factor; growth hormone-releasing factor;
    annexin V fusion protein; angiostatin; vascular endothelial growth factor-2; myeloid progenitor inhibitory factor-1; osteoprotegerin; α-1-antitrypsin; and, α-feto proteins.

* * * * *

SEQUENCE LISTING

<160> NUMBER OF SEQ ID NOS: 47

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
atggcgaagg cagatggcag t                                          21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ttagtccttc caacttcctt c                                          21

<210> SEQ ID NO 3
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 9
<223> OTHER INFORMATION: n is a, t, c, or g
<220> FEATURE:
<221> NAME/KEY: modified_base
<222> LOCATION: 12
<223> OTHER INFORMATION: n is a, t, c, or g
<220> FEATURE:
<221> NAME/KEY: modified_base
<222> LOCATION: 18
<223> OTHER INFORMATION: n is a, t, c, or g
<220> FEATURE:
<221> NAME/KEY: modified_base
<222> LOCATION: 24
<223> OTHER INFORMATION: n is a, t, c, or g

<400> SEQUENCE: 3
taytggmgng tngarcynga yatnaa                                     26

<210> SEQ ID NO 4
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 6
<223> OTHER INFORMATION: n is a, t, c, or g
<220> FEATURE:
<221> NAME/KEY: modified_base
<222> LOCATION: 12
<223> OTHER INFORMATION: n is a, t, c, or g

<400> SEQUENCE: 4

```
gcrtcnccccc anckytcrta                                              20

<210> SEQ ID NO 5
<211> LENGTH: 4
<212> TYPE: PRT
<213> ORGANISM: Artificial Sequence
<220> FEATURE:
<223> OTHER INFORMATION: Illustrative signal tetrapeptide

<400> SEQUENCE: 5

His Asp Glu Leu
1

<210> SEQ ID NO 6
<211> LENGTH: 4
<212> TYPE: PRT
<213> ORGANISM: Artificial Sequence
<220> FEATURE:
<223> OTHER INFORMATION: Illustrative signal tetrapeptide

<400> SEQUENCE: 6

Lys Asp Glu Leu
1

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
atggcgaagg cagatggcag t                                             21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ttagtccttc caacttcctt c                                             21

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
actgccatct gccttcgcca t                                             21

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
gtaatacgac tcactatagg gc                                            22

<210> SEQ ID NO 11
<211> LENGTH: 20
```

```
<212> TYPE: DNA
<213> ORGANISM: Artificial Sequence
<220> FEATURE:
<223> OTHER INFORMATION: primer

<400> SEQUENCE: 11
aattaaccct cactaaaggg                                          20

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
atgcccgtgg ggggcctgtt gccgctcttc agtagc                        36

<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13
tcatttctct ttgccatcaa tttccttctt ctgttcacgg                    40

<210> SEQ ID NO 14
<211> LENGTH: 44
<212> TYPE: DNA
<213> ORGANISM: Artificial Sequence
<220> FEATURE:
<223> OTHER INFORMATION: primer

<400> SEQUENCE: 14
ggcgcgccga ctcctccaag ctgctcagcg gggtcctgtt ccac               44

<210> SEQ ID NO 15
<211> LENGTH: 50
<212> TYPE: DNA
<213> ORGANISM: Artificial Sequence
<220> FEATURE:
<223> OTHER INFORMATION: primer

<400> SEQUENCE: 15
ccttaattaa tcatttctct ttgccatcaa tttccttctt ctgttcacgg         50

<210> SEQ ID NO 16
<211> LENGTH: 51
<212> TYPE: DNA
<213> ORGANISM: Artificial Sequence
<220> FEATURE:
<223> OTHER INFORMATION: primer

<400> SEQUENCE: 16
ggcgagctcg gcctacccgg ccaaggctga gatcatttgt ccagcttcag a       51

<210> SEQ ID NO 17
<211> LENGTH: 55
<212> TYPE: DNA
<213> ORGANISM: Artificial Sequence
<220> FEATURE:
<223> OTHER INFORMATION: primer

<400> SEQUENCE: 17
gcccacgtcg acggatccgt ttaaacatcg attggagagg ctgacaccgc tacta   55
```

<210> SEQ ID NO 18
<211> LENGTH: 54
<212> TYPE: DNA
<213> ORGANISM: Artificial Sequence
<220> FEATURE:
<223> OTHER INFORMATION: primer

<400> SEQUENCE: 18
cgggatccac tagtatttaa atcatatgtc gagtgtacaa ctcttcccac atgg        54

<210> SEQ ID NO 19
<211> LENGTH: 55
<212> TYPE: DNA
<213> ORGANISM: Artificial Sequence
<220> FEATURE:
<223> OTHER INFORMATION: primer

<400> SEQUENCE: 19
ggacgcgtcg acggcctacc cggccgtacg aggaatttct cggatgactc ttttc       55

<210> SEQ ID NO 20
<211> LENGTH: 45
<212> TYPE: DNA
<213> ORGANISM: Artificial Sequence
<220> FEATURE:
<223> OTHER INFORMATION: primer

<400> SEQUENCE: 20
cgggatccct cgagagatct tttttgtaga aatgtcttgg tgcct                  45

<210> SEQ ID NO 21
<211> LENGTH: 63
<212> TYPE: DNA
<213> ORGANISM: Artificial Sequence
<220> FEATURE:
<223> OTHER INFORMATION: primer

<400> SEQUENCE: 21
ggacatgcat gcactagtgc ggccgccacg tgatagttgt tcaattgatt gaaataggga  60
caa                                                                63

<210> SEQ ID NO 22
<211> LENGTH: 52
<212> TYPE: DNA
<213> ORGANISM: Artificial Sequence
<220> FEATURE:
<223> OTHER INFORMATION: primer

<400> SEQUENCE: 22
ccttgctagc ttaattaacc gcggcacgtc cgacggcggc ccacgggtcc ca          52

<210> SEQ ID NO 23
<211> LENGTH: 61
<212> TYPE: DNA
<213> ORGANISM: Artificial Sequence
<220> FEATURE:
<223> OTHER INFORMATION: primer

<400> SEQUENCE: 23
ggacatgcat gcggatccct taagagccgg cagcttgcaa attaaagcct tcgagcgtcc  60
c                                                                  61

<210> SEQ ID NO 24
<211> LENGTH: 61

```
<212> TYPE: DNA
<213> ORGANISM: Artificial Sequence
<220> FEATURE:
<223> OTHER INFORMATION: primer

<400> SEQUENCE: 24
gaaccacgtc gacggccatt gcggccaaaa ccttttttcc tattcaaaca caaggcattg    60
c                                                                    61

<210> SEQ ID NO 25
<211> LENGTH: 43
<212> TYPE: DNA
<213> ORGANISM: Artificial Sequence
<220> FEATURE:
<223> OTHER INFORMATION: primer

<400> SEQUENCE: 25
ctccaatact agtcgaagat tatcttctac ggtgcctgga ctc                       43

<210> SEQ ID NO 26
<211> LENGTH: 53
<212> TYPE: DNA
<213> ORGANISM: Artificial Sequence
<220> FEATURE:
<223> OTHER INFORMATION: primer

<400> SEQUENCE: 26
tggaaggttt aaacaaagct agagtaaaat agatatagcg agattagaga atg            53

<210> SEQ ID NO 27
<211> LENGTH: 50
<212> TYPE: DNA
<213> ORGANISM: Artificial Sequence
<220> FEATURE:
<223> OTHER INFORMATION: primer

<400> SEQUENCE: 27
aagaattcgg ctggaaggcc ttgtaccttg atgtagttcc cgttttcatc                50

<210> SEQ ID NO 28
<211> LENGTH: 58
<212> TYPE: DNA
<213> ORGANISM: Artificial Sequence
<220> FEATURE:
<223> OTHER INFORMATION: primer

<400> SEQUENCE: 28
gcccaagccg gccttaaggg atctcctgat gactgactca ctgataataa aaatacgg       58

<210> SEQ ID NO 29
<211> LENGTH: 59
<212> TYPE: DNA
<213> ORGANISM: Artificial Sequence
<220> FEATURE:
<223> OTHER INFORMATION: primer

<400> SEQUENCE: 29
gggcgcgtat ttaaatacta gtggatctat cgaatctaaa tgtaagttaa aatctctaa      59

<210> SEQ ID NO 30
<211> LENGTH: 39
<212> TYPE: DNA
<213> ORGANISM: Artificial Sequence
<220> FEATURE:
<223> OTHER INFORMATION: primer

<400> SEQUENCE: 30
```

```
ggccgcctgc agatttaaat gaattcggcg cgccttaat                                  39

<210> SEQ ID NO 31
<211> LENGTH: 34
<212> TYPE: DNA
<213> ORGANISM: Artificial Sequence
<220> FEATURE:
<223> OTHER INFORMATION: primer

<400> SEQUENCE: 31
taaggcgcgc cgaattcatt taaatctgca gggc                                       34

<210> SEQ ID NO 32
<211> LENGTH: 29
<212> TYPE: DNA
<213> ORGANISM: Artificial Sequence
<220> FEATURE:
<223> OTHER INFORMATION: primer

<400> SEQUENCE: 32
tggcaggcgc gcctcagtca gcgctctcg                                             29

<210> SEQ ID NO 33
<211> LENGTH: 29
<212> TYPE: DNA
<213> ORGANISM: Artificial Sequence
<220> FEATURE:
<223> OTHER INFORMATION: primer

<400> SEQUENCE: 33
aggttaatta agtgctaatt ccagctagg                                             29

<210> SEQ ID NO 34
<211> LENGTH: 26
<212> TYPE: DNA
<213> ORGANISM: Artificial Sequence
<220> FEATURE:
<223> OTHER INFORMATION: primer

<400> SEQUENCE: 34
ccagaagaat tcaattytgy cartgg                                                26

<210> SEQ ID NO 35
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: 17
<223> OTHER INFORMATION: n is a, t, c, or g
<220> FEATURE:
<221> NAME/KEY: modified_base
<222> LOCATION: 20
<223> OTHER INFORMATION: n is a, t, c, or g

<400> SEQUENCE: 35
cagtgaaaat acctggnccn gtcca                                                 25

<210> SEQ ID NO 36
<211> LENGTH: 27
<212> TYPE: DNA
<213> ORGANISM: Artificial Sequence
<220> FEATURE:
<223> OTHER INFORMATION: primer

<400> SEQUENCE: 36
```

```
tgccatcttt taggtccagg cccgttc                                           27
```

<210> SEQ ID NO 37
<211> LENGTH: 27
<212> TYPE: DNA
<213> ORGANISM: Artificial Sequence
<220> FEATURE:
<223> OTHER INFORMATION: primer

<400> SEQUENCE: 37

```
gatcccacga cgcatcgtat ttctttc                                           27
```

<210> SEQ ID NO 38
<211> LENGTH: 302
<212> TYPE: DNA
<213> ORGANISM: Kluveromyces lactis

<400> SEQUENCE: 38

```
gcccttcagt gaaatacct ggcccggtcc agttcataat atcggtacca tctgtatttt        60
tggcggtttt cttttgttga tgtttgtaat ttttgttgaa cttcttttta tccctcatgt      120
tgacattata atcatctgca atgtctttta atacttcagc atcatctaaa ggaatgctgc      180
ttttaacatt tgccacgctc tccaatgttg ttgcggtgat atttgtgatc aattcgcgca      240
ataatggatg gccagatttt gattgtattg tccactgaca aaattgaatt ctctggaagg      300
gc                                                                     302
```

<210> SEQ ID NO 39
<211> LENGTH: 80
<212> TYPE: PRT
<213> ORGANISM: Kluveromyces lactis

<400> SEQUENCE: 39

```
Thr Ile Gln Ser Lys Ser Gly His Pro Leu Leu Arg Glu Leu Ile Thr
  1               5                  10                  15

Asn Ile Thr Ala Thr Thr Leu Glu Ser Val Ala Asn Val Lys Ser Ser
             20                  25                  30

Ile Pro Leu Asp Asp Ala Glu Val Leu Lys Asp Ile Ala Asp Asp Tyr
         35                  40                  45

Asn Val Asn Met Arg Asp Lys Lys Lys Phe Asn Lys Asn Tyr Lys His
     50                  55                  60

Gln Gln Lys Lys Thr Ala Lys Asn Thr Asp Gly Thr Asp Ile Met Asn
 65                  70                  75                  80
```

<210> SEQ ID NO 40
<211> LENGTH: 404
<212> TYPE: DNA
<213> ORGANISM: Kluveromyces lactis

<400> SEQUENCE: 40

```
cccagcgtgc cattaccgta tttgccgccg tttgaaatac tcaatattca tgatggttgt       60
aaggcgtttt ttatcattcg cgatataata tgccatcttt taggtccagg cccgttctct     120
tagctatctt tggtgtctgt gctaccgtga tatggtacct attctttttc cagtctaatc     180
tgaagatggc agatttgaaa aaggtagcaa cttcaaggta tctttcacaa gaaccgtcgt     240
tatcagaact tatgtcaaat gtgaagatca agcctattga agaaacccccg gtttcgccat    300
tggagttgat tccagatatc gaaatatcga ctagaaagaa atacgatgcg tcgtgggatc     360
tgttgttccg tggtagaaaa tataaatcgt tcaacgatta tgat                      404
```

<210> SEQ ID NO 41
<211> LENGTH: 1363
<212> TYPE: DNA
<213> ORGANISM: Kluveromyces lactis

<400> SEQUENCE: 41

```
atggggttac caaagatttc aagaagaacg aggtacatta ttgtcattgt gctgatactg      60
tacttattgt tttctgtgca atggaatact gcgaaagtga atcaccattt ctataacagc     120
attggcacgg tgcttcccag tacagctcgc gtggatcact tgaacttgaa aaacttggac     180
ttagcaggta cgagcaataa cggtgatcat ttgatggatc tacgagttca attggctagt     240
caattcccct acgattctcg agtacccatc cccaaaaagg tatggcagac ctggaagatt     300
gatcccagtt caaagtcaca ggtttcttcc atttcaaaat gccagaatga ttggaaacat     360
ttcagtgcat ccgaggaacc gccatatcaa taccaattaa tcacagatga tcaaatgata     420
ccacttctag agcagctata tggtggggtc ccacaagtga taaaggcttt tgaatccttg     480
ccacttccaa ttcttaaagc agactttttc agatacttga tcctttatgc aagaggtggt     540
atatattctg acatggatac gttcccatta aagccattgt cgtcatggcc atcgacttct     600
cagtcctact tttctagttt aaagaatcca caaaggtata gaaattcctt ggacaacctt     660
gaaacgctag aagcttcaga acctggcttt gtcattggta tcgaggctga tccggataga     720
agcgattggg cagagtggta cgccaggaga atacaattct gtcagtggac aatacaatca     780
aaatctggcc atccattatt gcgcgaattg atcacaaata tcaccgcaac aacattggag     840
agcgtggcaa atgttaaaag cagcattcct ttagatgatg ctgaagtatt aaaagacatt     900
gcagatgatt ataatgtcaa catgagggat aaaaagaagt caacaaaaaa ttacaaacat     960
caacaaaaga aaaccgccaa aaatacagat ggtaccgata ttatgaactg gactggtcca    1020
ggtattttt cagatgttat tttccagtat cttaataacg ttatccagaa gaatgatgac    1080
atttaattt tcaatgataa tcttaatgtt atcaacaaac atggatccaa acatgataca    1140
actatgagat tctataaaga cattgttaaa aatttacaaa acgacaaacc cctcattgtt    1200
ctggggattc ttttcattga tgacagagcc tattctagtg gacgacatca tggtacttcc    1260
gattacttct ttctcaccag gtatcagaac aatgggcgct aaagaagaca acgacgagat    1320
ggcatttgtt aagcatattt ttgaaggaag ttggaaagac tga                      1363
```

<210> SEQ ID NO 42
<211> LENGTH: 453
<212> TYPE: PRT
<213> ORGANISM: Kluveromyces lactis

<400> SEQUENCE: 42

Met Gly Leu Pro Lys Ile Ser Arg Arg Thr Arg Tyr Ile Ile Val Ile
1               5                   10                  15

Val Leu Ile Leu Tyr Leu Leu Phe Ser Val Gln Trp Asn Thr Ala Lys
            20                  25                  30

Val Asn His His Phe Tyr Asn Ser Ile Gly Thr Val Leu Pro Ser Thr
        35                  40                  45

Ala Arg Val Asp His Leu Asn Leu Lys Asn Leu Asp Leu Ala Gly Thr
    50                  55                  60

Ser Asn Asn Gly Asp His Leu Met Asp Leu Arg Val Gln Leu Ala Ser
65                  70                  75                  80

Gln Phe Pro Tyr Asp Ser Arg Val Pro Ile Pro Lys Lys Val Trp Gln
                85                  90                  95

Thr Trp Lys Ile Asp Pro Ser Ser Lys Ser Gln Val Ser Ser Ile Ser
            100                 105                 110

Lys Cys Gln Asn Asp Trp Lys His Phe Ser Ala Ser Glu Glu Pro Pro
            115                 120                 125

Tyr Gln Tyr Gln Leu Ile Thr Asp Asp Gln Met Ile Pro Leu Leu Glu
        130                 135                 140

Gln Leu Tyr Gly Gly Val Pro Gln Val Ile Lys Ala Phe Glu Ser Leu
145                 150                 155                 160

Pro Leu Pro Ile Leu Lys Ala Asp Phe Phe Arg Tyr Leu Ile Leu Tyr
                165                 170                 175

Ala Arg Gly Gly Ile Tyr Ser Asp Met Asp Thr Phe Pro Leu Lys Pro
            180                 185                 190

Leu Ser Ser Trp Pro Ser Thr Ser Gln Ser Tyr Phe Ser Ser Leu Lys
        195                 200                 205

Asn Pro Gln Arg Tyr Arg Asn Ser Leu Asp Asn Leu Glu Thr Leu Glu
    210                 215                 220

Ala Ser Glu Pro Gly Phe Val Ile Gly Ile Glu Ala Asp Pro Asp Arg
225                 230                 235                 240

Ser Asp Trp Ala Glu Trp Tyr Ala Arg Arg Ile Gln Phe Cys Gln Trp
                245                 250                 255

Thr Ile Gln Ser Lys Ser Gly His Pro Leu Leu Arg Glu Leu Ile Thr
            260                 265                 270

Asn Ile Thr Ala Thr Thr Leu Glu Ser Val Ala Asn Val Lys Ser Ser
        275                 280                 285

Ile Pro Leu Asp Asp Ala Glu Val Leu Lys Asp Ile Ala Asp Asp Tyr
    290                 295                 300

Asn Val Asn Met Arg Asp Lys Lys Phe Asn Lys Asn Tyr Lys His
305                 310                 315                 320

Gln Gln Lys Lys Thr Ala Lys Asn Thr Asp Gly Thr Asp Ile Met Asn
                325                 330                 335

Trp Thr Gly Pro Gly Ile Phe Ser Asp Val Ile Phe Gln Tyr Leu Asn
            340                 345                 350

Asn Val Ile Gln Lys Asn Asp Asp Ile Leu Ile Phe Asn Asp Asn Leu
        355                 360                 365

Asn Val Ile Asn Lys His Gly Ser Lys His Asp Thr Thr Met Arg Phe
    370                 375                 380

Tyr Lys Asp Ile Val Lys Asn Leu Gln Asn Asp Lys Pro Ser Leu Phe
385                 390                 395                 400

Trp Gly Phe Phe Ser Leu Met Thr Glu Pro Ile Leu Val Asp Asp Ile
                405                 410                 415

Met Val Leu Pro Ile Thr Ser Phe Ser Pro Gly Ile Arg Thr Met Gly
            420                 425                 430

Ala Lys Glu Asp Asn Asp Glu Met Ala Phe Val Lys His Ile Phe Glu
        435                 440                 445

Gly Ser Trp Lys Asp
    450

<210> SEQ ID NO 43
<211> LENGTH: 2241
<212> TYPE: DNA
<213> ORGANISM: Kluveromyces lactis

<400> SEQUENCE: 43
atgatggttg taaggcgttt tttatcagct tcgcgatata atatgccatc ttttaggtcc      60
aggcccgttc tcttagctat ctttggtgtc tgtgctaccg tgatatggta cctattcttt     120

```
ttccagtcta atctgaagat ggcagatttg aaaaaggtag caacttcaag gtatctttca    180
caagaaccgt cgttatcaga acttatgtca aatgtgaaga tcaagcctat tgaagaaacc    240
ccggtttcgc cattggagtt gattccagat atcgaaatat cgactagaaa gaaatacgat    300
gcgtcgtggg atctgttgtt ccgtggtaga aaatataaat cgttcaacga ttatgatctt    360
catacgaaat gtgagtttta tttccagaat ttatacaatt tgaacgagga ttggaccaat    420
aatattcgga cgttcacttt cgatattaac gatgtagaca cgtctacgaa aattgacgct    480
cttaaagatt ccgatggggt tcaattggtg gacgagaagg ctatacgttt atacaagaga    540
acgcataacg ttgccttggc tacggaaagg ttacgtcttt atgataaatg ttttgtcaat    600
agtccaggtt caaacccatt gaaaatggat cacctttca gatcgaacaa gaagagtaag    660
actacggctt tggatgacga agtcactggg aaccgtgata cttttaccaa gacgaagaaa    720
acttcgttct taagcgatat ggacacgagt agtttccaga gtacgatca atgggatttc    780
gaacatagaa tgttccccat gatcccatat ttcgaggaac acaatttcac caacgtgatg    840
cctattttca ccggctcaaa cggtggggaa cctttacctc aagggaaatt cccggtatta    900
gatccaaaat ccggtgaatt gttacgtgta gagactttca gatatgataa atcgaaatcg    960
ctttggaaga actggaatga tatgtcctct gcttctggta acgtggtat tatcttggct   1020
gctggcgacg gccaagtgga ccaatgcatc cgtcttattg ctacgttgag agctcaagga   1080
aacgctctac ctattcaaat tatccacaac aaccaattga atgagaaatc tgtgaaactg   1140
ttatcggagg ccgctaaatc taccgaattc tcatccggta gagctcaatc tctttggtta   1200
gtgaatgtgg gccccacgtt ggaatcttca atgaagagca attttgggag atttaagaat   1260
aagtggttgt cagttatttt caacactttt gaagaattta tattcataga tacagatgcc   1320
atctcctaca ttaatatggc tgattatttc aacttcaagg agtacaaatc tactggaaca   1380
ctcttcttta aggataggtc tttggcaatt ggaactgaac agaaatgtgg tcctttgttc   1440
gaaactcttg aaccaagaat tcttgaaatg tactatttca atactttacc tatgatcaat   1500
ggtgattacg tggaacagca atgtatgggc atgctcaccc cagaggaaaa agtttacaaa   1560
cgtttctttg aagttggtca tcaacacaac ttggaaagtg gattattggc catcaacaaa   1620
aacgaacaca tcatgggatt ggttactgca acagtcttaa atatcgcacc aaaggtcgga   1680
ggttgcggtt ggggtgacaa agagtttttc tggcttggtt tgttggttgc tggccaacgc   1740
tactcgatct atgatataga tgcaagtgca attggtgttc ctcaacgaa gcaatctatc   1800
gctaacggag acgaatttga tgaatatagg atttgttctt tacaagtggc acatacttca   1860
tacgacggac atttactatg gataaatggt ggctctcagt actgtaagaa accagagact   1920
tttgaaggtg attggaccaa cattaaggag cttcgtgaat cgtattctga tgataaagaa   1980
aaggctctga aggcttatag tgatacagtt aaggtggaag cagcaatcgt gccagattcc   2040
agaagtaatg gttgggggtag agacgatcaa agatgtaaag gctacttctg gtgcggcaaa   2100
tttacttcaa agctgaaacc gtatacttat aacacggtgg taactaaagg tgatttgatc   2160
cgtttcggag acgaggaaat cgaaagtatc tccaagatta taagatctg gaatgatgct   2220
attattccag acggagctta a                                             2241
```

<210> SEQ ID NO 44
<211> LENGTH: 747
<212> TYPE: PRT
<213> ORGANISM: Kluveromyces lactis

<400> SEQUENCE: 44

```
Met Met Val Val Arg Arg Phe Leu Ser Ala Ser Arg Tyr Asn Met Pro
  1               5                  10                 15

Ser Phe Arg Ser Arg Pro Val Leu Leu Ala Ile Phe Gly Val Cys Ala
             20                  25                 30

Thr Val Ile Trp Tyr Leu Phe Phe Gln Ser Asn Leu Lys Met Ala
             35                  40                 45

Asp Leu Lys Lys Val Ala Thr Ser Arg Tyr Leu Ser Gln Glu Pro Ser
     50                  55                  60

Leu Ser Glu Leu Met Ser Asn Val Lys Ile Lys Pro Ile Glu Glu Thr
 65                  70                  75                  80

Pro Val Ser Pro Leu Glu Leu Ile Pro Asp Ile Glu Ile Ser Thr Arg
                 85                  90                  95

Lys Lys Tyr Asp Ala Ser Trp Asp Leu Leu Phe Arg Gly Arg Lys Tyr
            100                 105                 110

Lys Ser Phe Asn Asp Tyr Asp Leu His Thr Lys Cys Glu Phe Tyr Phe
            115                 120                 125

Gln Asn Leu Tyr Asn Leu Asn Glu Asp Trp Thr Asn Asn Ile Arg Thr
            130                 135                 140

Phe Thr Phe Asp Ile Asn Asp Val Asp Thr Ser Thr Lys Ile Asp Ala
145                 150                 155                 160

Leu Lys Asp Ser Asp Gly Val Gln Leu Val Asp Glu Lys Ala Ile Arg
                165                 170                 175

Leu Tyr Lys Arg Thr His Asn Val Ala Leu Ala Thr Glu Arg Leu Arg
                180                 185                 190

Leu Tyr Asp Lys Cys Phe Val Asn Ser Pro Gly Ser Asn Pro Leu Lys
            195                 200                 205

Met Asp His Leu Phe Arg Ser Asn Lys Ser Lys Thr Thr Ala Leu
            210                 215                 220

Asp Asp Glu Val Thr Gly Asn Arg Asp Thr Phe Thr Lys Thr Lys Lys
225                 230                 235                 240

Thr Ser Phe Leu Ser Asp Met Asp Thr Ser Ser Phe Gln Lys Tyr Asp
                245                 250                 255

Gln Trp Asp Phe Glu His Arg Met Phe Pro Met Ile Pro Tyr Phe Glu
            260                 265                 270

Glu His Asn Phe Thr Asn Val Met Pro Ile Phe Thr Gly Ser Asn Gly
            275                 280                 285

Gly Glu Pro Leu Pro Gln Gly Lys Phe Pro Val Leu Asp Pro Lys Ser
            290                 295                 300

Gly Glu Leu Leu Arg Val Glu Thr Phe Arg Tyr Asp Lys Ser Lys Ser
305                 310                 315                 320

Leu Trp Lys Asn Trp Asn Asp Met Ser Ser Ala Ser Gly Lys Arg Gly
            325                 330                 335

Ile Ile Leu Ala Ala Gly Asp Gly Gln Val Asp Gln Cys Ile Arg Leu
            340                 345                 350

Ile Ala Thr Leu Arg Ala Gln Gly Asn Ala Leu Pro Ile Gln Ile Ile
            355                 360                 365

His Asn Asn Gln Leu Asn Glu Lys Ser Val Lys Leu Leu Ser Glu Ala
            370                 375                 380

Ala Lys Ser Thr Glu Phe Ser Ser Gly Arg Ala Gln Ser Leu Trp Leu
385                 390                 395                 400

Val Asn Val Gly Pro Thr Leu Glu Ser Ser Met Lys Ser Asn Phe Gly
                405                 410                 415

Arg Phe Lys Asn Lys Trp Leu Ser Val Ile Phe Asn Thr Phe Glu Glu
```

```
                420             425             430
Phe Ile Phe Ile Asp Thr Asp Ala Ile Ser Tyr Ile Asn Met Ala Asp
            435                 440                 445

Tyr Phe Asn Phe Lys Glu Tyr Lys Ser Thr Gly Thr Leu Phe Phe Lys
    450                 455                 460

Asp Arg Ser Leu Ala Ile Gly Thr Glu Gln Lys Cys Gly Pro Leu Phe
465                 470                 475                 480

Glu Thr Leu Glu Pro Arg Ile Leu Glu Met Tyr Phe Asn Thr Leu
                485                 490                 495

Pro Met Ile Asn Gly Asp Tyr Val Gln Gln Cys Met Gly Met Leu
                500                 505                 510

Thr Pro Glu Glu Lys Val Tyr Lys Arg Phe Phe Glu Val Gly His Gln
                515                 520                 525

His Asn Leu Glu Ser Gly Leu Leu Ala Ile Asn Lys Asn Glu His Ile
                530                 535                 540

Met Gly Leu Val Thr Ala Thr Val Leu Asn Ile Ala Pro Lys Val Gly
545                 550                 555                 560

Gly Cys Gly Trp Gly Asp Lys Glu Phe Phe Trp Leu Gly Leu Leu Val
                565                 570                 575

Ala Gly Gln Arg Tyr Ser Ile Tyr Asp Ile Asp Ala Ser Ala Ile Gly
                580                 585                 590

Val Pro Gln Gln Lys Gln Ser Ile Ala Asn Gly Asp Glu Phe Asp Glu
                595                 600                 605

Tyr Arg Ile Cys Ser Leu Gln Val Ala His Thr Ser Tyr Asp Gly His
                610                 615                 620

Leu Leu Trp Ile Asn Gly Gly Ser Gln Tyr Cys Lys Ile Cys Pro Glu
625                 630                 635                 640

Thr Phe Glu Gly Asp Trp Thr Asn Ile Lys Glu Leu Arg Glu Ser Tyr
                645                 650                 655

Ser Asp Asp Lys Glu Lys Ala Leu Lys Ala Tyr Ser Asp Thr Val Lys
                660                 665                 670

Val Glu Ala Ala Ile Val Pro Asp Ser Arg Ser Asn Gly Trp Gly Arg
                675                 680                 685

Asp Asp Gln Arg Cys Lys Gly Tyr Phe Trp Cys Gly Lys Phe Thr Ser
690                 695                 700

Lys Leu Lys Pro Tyr Thr Tyr Asn Thr Val Val Thr Lys Gly Asp Leu
705                 710                 715                 720

Ile Arg Phe Gly Asp Glu Glu Ile Glu Ser Ile Ser Lys Ile Asn Lys
                725                 730                 735

Ile Trp Asn Asp Ala Ile Ile Pro Asp Gly Ala
                740                 745

<210> SEQ ID NO 45
<211> LENGTH: 1968
<212> TYPE: DNA
<213> ORGANISM: Mus musculus
<220> FEATURE:
<221> NAME/KEY: CDS
<222> LOCATION: (1)...(1965)

<400> SEQUENCE: 45 atg ccc gtg ggg ggc ctg ttg ccg ctc ttc agt agc cct ggg ggc ggc        48
Met Pro Val Gly Gly Leu Leu Pro Leu Phe Ser Ser Pro Gly Gly Gly
 1               5                   10                  15 ggc ctg ggc agt ggc ctg ggc ggg ggg ctt ggc ggc ggg agg aag ggg        96
Gly Leu Gly Ser Gly Leu Gly Gly Gly Leu Gly Gly Gly Arg Lys Gly
            20                  25                  30
```

| | | |
|---|---|---|
| tct ggc ccc gct gcc ttc cgc ctc acc gag aag ttc gtg ctg ctg ctg<br>Ser Gly Pro Ala Ala Phe Arg Leu Thr Glu Lys Phe Val Leu Leu Leu<br>     35                    40                    45 | | 144 |
| gtg ttc agc gcc ttc atc acg ctc tgc ttc ggg gca atc ttc ttc ctg<br>Val Phe Ser Ala Phe Ile Thr Leu Cys Phe Gly Ala Ile Phe Phe Leu<br> 50                    55                    60 | | 192 |
| cct gac tcc tcc aag ctg ctc agc ggg gtc ctg ttc cac tcc aac cct<br>Pro Asp Ser Ser Lys Leu Leu Ser Gly Val Leu Phe His Ser Asn Pro<br>65                   70                    75                    80 | | 240 |
| gcc ttg cag ccg ccg gcg gag cac aag ccc ggg ctc ggg gcg cgt gcg<br>Ala Leu Gln Pro Pro Ala Glu His Lys Pro Gly Leu Gly Ala Arg Ala<br>                  85                    90                    95 | | 288 |
| gag gat gcc gcc gag ggg aga gtc cgg cac cgc gag gaa ggc gcg cct<br>Glu Asp Ala Ala Glu Gly Arg Val Arg His Arg Glu Glu Gly Ala Pro<br>              100                    105                  110 | | 336 |
| ggg gac cct gga gct gga ctg gaa gac aac tta gcc agg atc cgc gaa<br>Gly Asp Pro Gly Ala Gly Leu Glu Asp Asn Leu Ala Arg Ile Arg Glu<br>          115                    120                  125 | | 384 |
| aac cac gag cgg gct ctc agg gaa gcc aag gag acc ctg cag aag ctg<br>Asn His Glu Arg Ala Leu Arg Glu Ala Lys Glu Thr Leu Gln Lys Leu<br>130                    135                    140 | | 432 |
| ccg gag gag atc caa aga gac att ctg ctg gag aag gaa aag gtg gcc<br>Pro Glu Glu Ile Gln Arg Asp Ile Leu Leu Glu Lys Glu Lys Val Ala<br>145                    150                    155                  160 | | 480 |
| cag gac cag ctg cgt gac aag gat ctg ttt agg ggc ttg ccc aag gtg<br>Gln Asp Gln Leu Arg Asp Lys Asp Leu Phe Arg Gly Leu Pro Lys Val<br>                  165                    170                  175 | | 528 |
| gac ttc ctg ccc ccc gtc ggg gta gag aac cgg gag ccc gct gac gcc<br>Asp Phe Leu Pro Pro Val Gly Val Glu Asn Arg Glu Pro Ala Asp Ala<br>              180                    185                  190 | | 576 |
| acc atc cgt gag aag agg gca aag atc aaa gag atg atg acc cat gct<br>Thr Ile Arg Glu Lys Arg Ala Lys Ile Lys Glu Met Met Thr His Ala<br>          195                    200                  205 | | 624 |
| tgg aat aat tat aaa cgc tat gcg tgg ggc ttg aac gaa ctg aaa cct<br>Trp Asn Asn Tyr Lys Arg Tyr Ala Trp Gly Leu Asn Glu Leu Lys Pro<br>210                    215                    220 | | 672 |
| ata tca aaa gaa ggc cat tca agc agt ttg ttt ggc aac atc aaa gga<br>Ile Ser Lys Glu Gly His Ser Ser Ser Leu Phe Gly Asn Ile Lys Gly<br>225                    230                    235                  240 | | 720 |
| gct aca ata gta gat gcc ctg gat acc ctt ttc att atg ggc atg aag<br>Ala Thr Ile Val Asp Ala Leu Asp Thr Leu Phe Ile Met Gly Met Lys<br>              245                    250                  255 | | 768 |
| act gaa ttt caa gaa gct aaa tcg tgg att aaa aaa tat tta gat ttt<br>Thr Glu Phe Gln Glu Ala Lys Ser Trp Ile Lys Lys Tyr Leu Asp Phe<br>          260                    265                  270 | | 816 |
| aat gtg aat gct gaa gtt tct gtt ttt gaa gtc aac ata cgc ttc gtc<br>Asn Val Asn Ala Glu Val Ser Val Phe Glu Val Asn Ile Arg Phe Val<br>275                    280                    285 | | 864 |
| ggt gga ctg ctg tca gcc tac tat ttg tcc gga gag gag ata ttt cga<br>Gly Gly Leu Leu Ser Ala Tyr Tyr Leu Ser Gly Glu Glu Ile Phe Arg<br>        290                    295                  300 | | 912 |
| aag aaa gca gtg gaa ctt ggg gta aaa ttg cta cct gca ttt cat act<br>Lys Lys Ala Val Glu Leu Gly Val Lys Leu Leu Pro Ala Phe His Thr<br>305                    310                    315                  320 | | 960 |
| ccc tct gga ata cct tgg gca ttg ctg aat atg aaa agt ggg atc ggg<br>Pro Ser Gly Ile Pro Trp Ala Leu Leu Asn Met Lys Ser Gly Ile Gly<br>              325                    330                  335 | | 1008 |
| cgg aac tgg ccc tgg gcc tct gga ggc agc agt atc ctg gcc gaa ttt<br>Arg Asn Trp Pro Trp Ala Ser Gly Gly Ser Ser Ile Leu Ala Glu Phe<br>          340                    345                  350 | | 1056 |

| | | |
|---|---|---|
| gga act ctg cat tta gag ttt atg cac ttg tcc cac tta tca gga gac<br>Gly Thr Leu His Leu Glu Phe Met His Leu Ser His Leu Ser Gly Asp<br>355 360 365 | | 1104 |
| cca gtc ttt gcc gaa aag gtt atg aaa att cga aca gtg ttg aac aaa<br>Pro Val Phe Ala Glu Lys Val Met Lys Ile Arg Thr Val Leu Asn Lys<br>370 375 380 | | 1152 |
| ctg gac aaa cca gaa ggc ctt tat cct aac tat ctg aac ccc agt agt<br>Leu Asp Lys Pro Glu Gly Leu Tyr Pro Asn Tyr Leu Asn Pro Ser Ser<br>385 390 395 400 | | 1200 |
| gga cag tgg ggt caa cat cat gtg tcg gtt gga gga ctt gga gac agc<br>Gly Gln Trp Gly Gln His His Val Ser Val Gly Gly Leu Gly Asp Ser<br>405 410 415 | | 1248 |
| ttt tat gaa tat ttg ctt aag gcg tgg tta atg tct gac aag aca gat<br>Phe Tyr Glu Tyr Leu Leu Lys Ala Trp Leu Met Ser Asp Lys Thr Asp<br>420 425 430 | | 1296 |
| ctc gaa gcc aag aag atg tat ttt gat gct gtt cag gcc atc gag act<br>Leu Glu Ala Lys Lys Met Tyr Phe Asp Ala Val Gln Ala Ile Glu Thr<br>435 440 445 | | 1344 |
| cac ttg atc cgc aag tca agt ggg gga cta acg tac atc gca gag tgg<br>His Leu Ile Arg Lys Ser Ser Gly Gly Leu Thr Tyr Ile Ala Glu Trp<br>450 455 460 | | 1392 |
| aag ggg ggc ctc ctg gaa cac aag atg ggc cac ctg acg tgc ttt gca<br>Lys Gly Gly Leu Leu Glu His Lys Met Gly His Leu Thr Cys Phe Ala<br>465 470 475 480 | | 1440 |
| gga ggc atg ttt gca ctt ggg gca gat gga gct ccg gaa gcc cgg gcc<br>Gly Gly Met Phe Ala Leu Gly Ala Asp Gly Ala Pro Glu Ala Arg Ala<br>485 490 495 | | 1488 |
| caa cac tac ctt gaa ctc gga gct gaa att gcc cgc act tgt cat gaa<br>Gln His Tyr Leu Glu Leu Gly Ala Glu Ile Ala Arg Thr Cys His Glu<br>500 505 510 | | 1536 |
| tct tat aat cgt aca tat gtg aag ttg gga ccg gaa gcg ttt cga ttt<br>Ser Tyr Asn Arg Thr Tyr Val Lys Leu Gly Pro Glu Ala Phe Arg Phe<br>515 520 525 | | 1584 |
| gat ggc ggt gtg gaa gct att gcc acg agg caa aat gaa aag tat tac<br>Asp Gly Gly Val Glu Ala Ile Ala Thr Arg Gln Asn Glu Lys Tyr Tyr<br>530 535 540 | | 1632 |
| atc tta cgg ccc gag gtc atc gag aca tac atg tac atg tgg cga ctg<br>Ile Leu Arg Pro Glu Val Ile Glu Thr Tyr Met Tyr Met Trp Arg Leu<br>545 550 555 560 | | 1680 |
| act cac gac ccc aag tac agg acc tgg gcc tgg gaa gcc gtg gag gct<br>Thr His Asp Pro Lys Tyr Arg Thr Trp Ala Trp Glu Ala Val Glu Ala<br>565 570 575 | | 1728 |
| cta gaa agt cac tgc aga gtg aac gga ggc tac tca ggc tta cgg gat<br>Leu Glu Ser His Cys Arg Val Asn Gly Gly Tyr Ser Gly Leu Arg Asp<br>580 585 590 | | 1776 |
| gtt tac att gcc cgt gag agt tat gac gat gtc cag caa agt ttc ttc<br>Val Tyr Ile Ala Arg Glu Ser Tyr Asp Asp Val Gln Gln Ser Phe Phe<br>595 600 605 | | 1824 |
| ctg gca gag aca ctg aag tat ttg tac ttg ata ttt tcc gat gat gac<br>Leu Ala Glu Thr Leu Lys Tyr Leu Tyr Leu Ile Phe Ser Asp Asp Asp<br>610 615 620 | | 1872 |
| ctt ctt cca cta gaa cac tgg atc ttc aac acc gag gct cat cct ttc<br>Leu Leu Pro Leu Glu His Trp Ile Phe Asn Thr Glu Ala His Pro Phe<br>625 630 635 640 | | 1920 |
| cct ata ctc cgt gaa cag aag aag gaa att gat ggc aaa gag aaa<br>Pro Ile Leu Arg Glu Gln Lys Lys Glu Ile Asp Gly Lys Glu Lys<br>645 650 655 | | 1965 |
| tga | | 1968 |

```
<210> SEQ ID NO 46
<211> LENGTH: 655
<212> TYPE: PRT
<213> ORGANISM: Mus musculus

<400> SEQUENCE: 46

Met Pro Val Gly Gly Leu Leu Pro Leu Phe Ser Pro Gly Gly Gly
 1               5                  10                  15

Gly Leu Gly Ser Gly Leu Gly Gly Leu Gly Gly Arg Lys Gly
             20                  25                  30

Ser Gly Pro Ala Ala Phe Arg Leu Thr Glu Lys Phe Val Leu Leu
             35                  40                  45

Val Phe Ser Ala Phe Ile Thr Leu Cys Phe Gly Ala Ile Phe Leu
 50                  55                  60

Pro Asp Ser Ser Lys Leu Leu Ser Gly Val Leu Phe His Ser Asn Pro
 65                  70                  75                  80

Ala Leu Gln Pro Pro Ala Glu His Lys Pro Gly Leu Gly Ala Arg Ala
                 85                  90                  95

Glu Asp Ala Ala Glu Gly Arg Val Arg His Arg Glu Gly Ala Pro
                100                 105                 110

Gly Asp Pro Gly Ala Gly Leu Glu Asp Asn Leu Ala Arg Ile Arg Glu
            115                 120                 125

Asn His Glu Arg Ala Leu Arg Glu Ala Lys Glu Thr Leu Gln Lys Leu
130                 135                 140

Pro Glu Glu Ile Gln Arg Asp Ile Leu Leu Lys Glu Lys Val Ala
145                 150                 155                 160

Gln Asp Gln Leu Arg Asp Lys Asp Leu Phe Arg Gly Leu Pro Lys Val
                165                 170                 175

Asp Phe Leu Pro Pro Val Gly Val Glu Asn Arg Glu Pro Ala Asp Ala
            180                 185                 190

Thr Ile Arg Glu Lys Arg Ala Lys Ile Lys Glu Met Met Thr His Ala
        195                 200                 205

Trp Asn Asn Tyr Lys Arg Tyr Ala Trp Gly Leu Asn Glu Leu Lys Pro
210                 215                 220

Ile Ser Lys Glu Gly His Ser Ser Ser Leu Phe Gly Asn Ile Lys Gly
225                 230                 235                 240

Ala Thr Ile Val Asp Ala Leu Asp Thr Leu Phe Ile Met Gly Met Lys
                245                 250                 255

Thr Glu Phe Gln Glu Ala Lys Ser Trp Ile Lys Lys Tyr Leu Asp Phe
            260                 265                 270

Asn Val Asn Ala Glu Val Ser Val Phe Glu Val Asn Ile Arg Phe Val
        275                 280                 285

Gly Gly Leu Leu Ser Ala Tyr Tyr Leu Ser Gly Glu Glu Ile Phe Arg
290                 295                 300

Lys Lys Ala Val Glu Leu Gly Val Lys Leu Leu Pro Ala Phe His Thr
305                 310                 315                 320

Pro Ser Gly Ile Pro Trp Ala Leu Leu Asn Met Lys Ser Gly Ile Gly
                325                 330                 335

Arg Asn Trp Pro Trp Ala Ser Gly Gly Ser Ser Ile Leu Ala Glu Phe
            340                 345                 350

Gly Thr Leu His Leu Glu Phe Met His Leu Ser His Leu Ser Gly Asp
        355                 360                 365

Pro Val Phe Ala Glu Lys Val Met Lys Ile Arg Thr Val Leu Asn Lys
370                 375                 380

Leu Asp Lys Pro Glu Gly Leu Tyr Pro Asn Tyr Leu Asn Pro Ser Ser
```

|   |   |   |   |   | 385 |   |   |   | 390 |   |   |   | 395 |   |   |   | 400 |
|---|---|---|---|---|---|---|---|---|---|---|---|---|---|---|---|---|---|

Gly Gln Trp Gly Gln His His Val Ser Val Gly Gly Leu Gly Asp Ser
              405                 410                 415

Phe Tyr Glu Tyr Leu Leu Lys Ala Trp Leu Met Ser Asp Lys Thr Asp
              420                 425                 430

Leu Glu Ala Lys Lys Met Tyr Phe Asp Ala Val Gln Ala Ile Glu Thr
              435                 440                 445

His Leu Ile Arg Lys Ser Ser Gly Gly Leu Thr Tyr Ile Ala Glu Trp
              450                 455                 460

Lys Gly Gly Leu Leu Glu His Lys Met Gly His Leu Thr Cys Phe Ala
465                 470                 475                 480

Gly Gly Met Phe Ala Leu Gly Ala Asp Gly Ala Pro Glu Ala Arg Ala
              485                 490                 495

Gln His Tyr Leu Glu Leu Gly Ala Glu Ile Ala Arg Thr Cys His Glu
              500                 505                 510

Ser Tyr Asn Arg Thr Tyr Val Lys Leu Gly Pro Glu Ala Phe Arg Phe
              515                 520                 525

Asp Gly Gly Val Glu Ala Ile Ala Thr Arg Gln Asn Glu Lys Tyr Tyr
              530                 535                 540

Ile Leu Arg Pro Glu Val Ile Glu Thr Tyr Met Tyr Met Trp Arg Leu
545                 550                 555                 560

Thr His Asp Pro Lys Tyr Arg Thr Trp Ala Trp Glu Ala Val Glu Ala
              565                 570                 575

Leu Glu Ser His Cys Arg Val Asn Gly Gly Tyr Ser Gly Leu Arg Asp
              580                 585                 590

Val Tyr Ile Ala Arg Glu Ser Tyr Asp Asp Val Gln Gln Ser Phe Phe
              595                 600                 605

Leu Ala Glu Thr Leu Lys Tyr Leu Tyr Leu Ile Phe Ser Asp Asp Asp
              610                 615                 620

Leu Leu Pro Leu Glu His Trp Ile Phe Asn Thr Glu Ala His Pro Phe
625                 630                 635                 640

Pro Ile Leu Arg Glu Gln Lys Lys Glu Ile Asp Gly Lys Glu Lys
              645                 650                 655

```
<210> SEQ ID NO 47
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: 9
<223> OTHER INFORMATION: n is a, t, c, or g
<220> FEATURE:
<221> NAME/KEY: modified_base
<222> LOCATION: 12
<223> OTHER INFORMATION: n is a, t, c, or g
<220> FEATURE:
<221> NAME/KEY: modified_base
<222> LOCATION: 18
<223> OTHER INFORMATION: n is a, t, c, or g

<400> SEQUENCE: 47
taytggmgng tngarcynga yathaa                                            26
```